(12) United States Patent
Edelman

(10) Patent No.: US 11,268,131 B2
(45) Date of Patent: *Mar. 8, 2022

(54) REAGENTS AND METHODS FOR THE ANALYSIS OF LINKED NUCLEIC ACIDS

(71) Applicant: CS Genetics Limited, Cambridge (GB)

(72) Inventor: Lucas Brandon Edelman, Cambridge (GB)

(73) Assignee: CS Genetics Limited, Cambridge (GB)

( * ) Notice: Subject to any disclaimer, the term of this patent is extended or adjusted under 35 U.S.C. 154(b) by 59 days.

This patent is subject to a terminal disclaimer.

(21) Appl. No.: 16/866,089

(22) Filed: May 4, 2020

(65) Prior Publication Data

US 2020/0299750 A1 Sep. 24, 2020

Related U.S. Application Data

(63) Continuation of application No. 16/277,794, filed on Feb. 15, 2019, now Pat. No. 10,640,811, which is a continuation of application No. 15/750,824, filed as application No. PCT/GB2017/053820 on Dec. 19, 2017, now Pat. No. 10,287,624.

(30) Foreign Application Priority Data

Dec. 23, 2016 (GB) ..................................... 1622226

(51) Int. Cl.
| | |
|---|---|
| C12Q 1/6806 | (2018.01) |
| C12Q 1/6809 | (2018.01) |
| C12Q 1/6827 | (2018.01) |
| C12Q 1/6832 | (2018.01) |
| C12Q 1/6834 | (2018.01) |
| C12Q 1/6869 | (2018.01) |

(52) U.S. Cl.
CPC ......... *C12Q 1/6806* (2013.01); *C12Q 1/6809* (2013.01); *C12Q 1/6827* (2013.01); *C12Q 1/6832* (2013.01); *C12Q 1/6834* (2013.01); *C12Q 1/6869* (2013.01)

(58) Field of Classification Search
None
See application file for complete search history.

(56) References Cited

U.S. PATENT DOCUMENTS

2012/0196754 A1* 8/2012 Quake et al. .......... G16B 20/10
506/2
2014/0178881 A1 6/2014 Booth et al.

FOREIGN PATENT DOCUMENTS

| GB | 2559319 | 1/2019 |
|---|---|---|
| WO | WO 2001036601 | 5/2001 |
| WO | WO 2012135730 | 4/2012 |
| WO | WO 2013117591 | 8/2013 |
| WO | WO 2015048173 | 4/2015 |
| WO | WO 2016172598 | 10/2016 |
| WO | WO 2016187234 | 11/2016 |

OTHER PUBLICATIONS

Search and Examination Report dated Feb. 7, 2017, Appl. No. GB1622226.7, 7pp.
European Search Report dated Dec. 13, 2018, Appl. No. EP 18180259.6, 9pp.
Examination Report dated May 31, 2017, Appl. No. GB1622226.7, 4 pp.
Examination Report dated Aug. 15, 2017, Appl. No. GB1622226.7, 4 pp.
Response to Examination Report filed Oct. 5, 2017, Appl. No. GB1622226.7, 62 pp.
Examination Report dated Oct. 10, 2017, Appl. No. GB1622226.7, 3 pp.
Response to Examination Report filed Dec. 7, 2017, Appl. No. GB1622226.7, 401 pp.
International Search Report dated Feb. 8, 2018, Appl. No. PCT/GB2017/053820, 16 pp.
International Search Report dated Feb. 4, 2019, Appl. No. PCT/GB2017/053820, 16 pp.
Response to Written Opinion filed Mar. 16, 2018, Appl. No. PCT/GB2017/053820, 12 pp.
Fang et al. (2016) "Construction of a Sequencing Library from Circulating Cell-Fee DNA," Current Protocols in Molecular Biology, 114:7.25.1-7.25.13. doi:10.1002/0471142727.mb0725s114.
Forshew et al. (2012) "Noninvasive Identification and Monitoring of Cancer Mutations by Targeted Deep Sequencing of Plasma DNA" Sci. Transl. Med. 4:136ra68.
Maheswaran et al. (2008) "Detection of Mutations in EGFR in Circulating Lung-Cancer Cells" N. Engl. J. Med. 359:366-377.
Neiman et al. (2011) "Decoding a Substantial Set of Samples in Parallel by Massive Sequencing" PLoS ONE, 6(3):e17785.
Orozco and Lewis (2010) "Flow Cytometric Analysis of Circulating Microparticles in Plasma," Cytometry Part A; 77A:502-514.
Stahlberg et al. (2016) "Simple multiplexed, PCR-based barcoding of DNA enables sensitive mutation detection in liquid biopsies using sequencing," Nucleic Acids Research, 44(11):e105.

(Continued)

*Primary Examiner* — Kaijiang Zhang
(74) *Attorney, Agent, or Firm* — Brian E. Davy; Bozicevic, Field & Francis LLP

(57) ABSTRACT

Reagents and methods for the analysis of nucleic acids (e.g. genomic DNA) of circulating microparticles (i.e. microparticles originating from blood) are provided. The methods comprise linking at least two fragments of a target nucleic acid of a circulating microparticle to produce a set of at least two linked fragments of the target nucleic acid. In the methods, fragments of a target nucleic acid may be linked by techniques such as barcoding, partitioning, ligation and/or separate sequencing. The sequencing of a set of linked fragments provides a set of informatically linked sequence reads corresponding to the sequences of fragments from a single microparticle.

21 Claims, 33 Drawing Sheets

Specification includes a Sequence Listing.

(56) References Cited

OTHER PUBLICATIONS

Examination Report dated May 25, 2020, Appl. No. EP17817860.4, 4 pp.
Office Action dated Apr. 2, 2020, Appl. No. CN201780087136.2, 12 pp.
Office Action dated Nov. 5, 2020, Appl. No. CN201780087136.2, 7 pp.
Office Action dated Apr. 25, 2021, Appl. No. CN201780087136.2, 5 pp.

* cited by examiner

FIGURE 15

| | Annealed to Genomic DNA Overnight | Annealed to Genomic DNA Overnight; Barcoding Reagents Denatured First | Annealed to Genomic DNA for 3 Hours | Annealed to Genomic DNA for 3 Hours; Barcoding Reagents Denatured First |
|---|---|---|---|---|
| HLA-A_Exon2 | 153 | 62 | 103 | 50 |
| HLA-A_Exon3 | 2548 | 341 | 818 | 106 |
| HLA-A_Exon4 | 489 | 235 | 400 | 108 |
| DQB1_Exon2 | 557 | 627 | 285 | 635 |
| DQB1_Exon3 | 2186 | 1614 | 1085 | 221 |
| BRCA1_US1 | 1771 | 941 | 1047 | 544 |
| BRCA1_SNP7 | 2524 | 1261 | 90 | 43 |
| BRCA1_SNP6 | 731 | 537 | 245 | 339 |
| BRCA1_SNP1 | 10033 | 5787 | 2905 | 1813 |
| BRCA1_DS1 | 4 | 103 | 5 | 0 |
| BRCA_AMP6 | 81 | 69 | 37 | 24 |
| BRCA_AMP7 | 731 | 391 | 40 | 472 |
| On-Target Fraction: | 81% | 76% | 82% | 70% |

Schematic of Sequence Read from Barcoding of genomic DNA loci
(In 5' to 3' Direction)

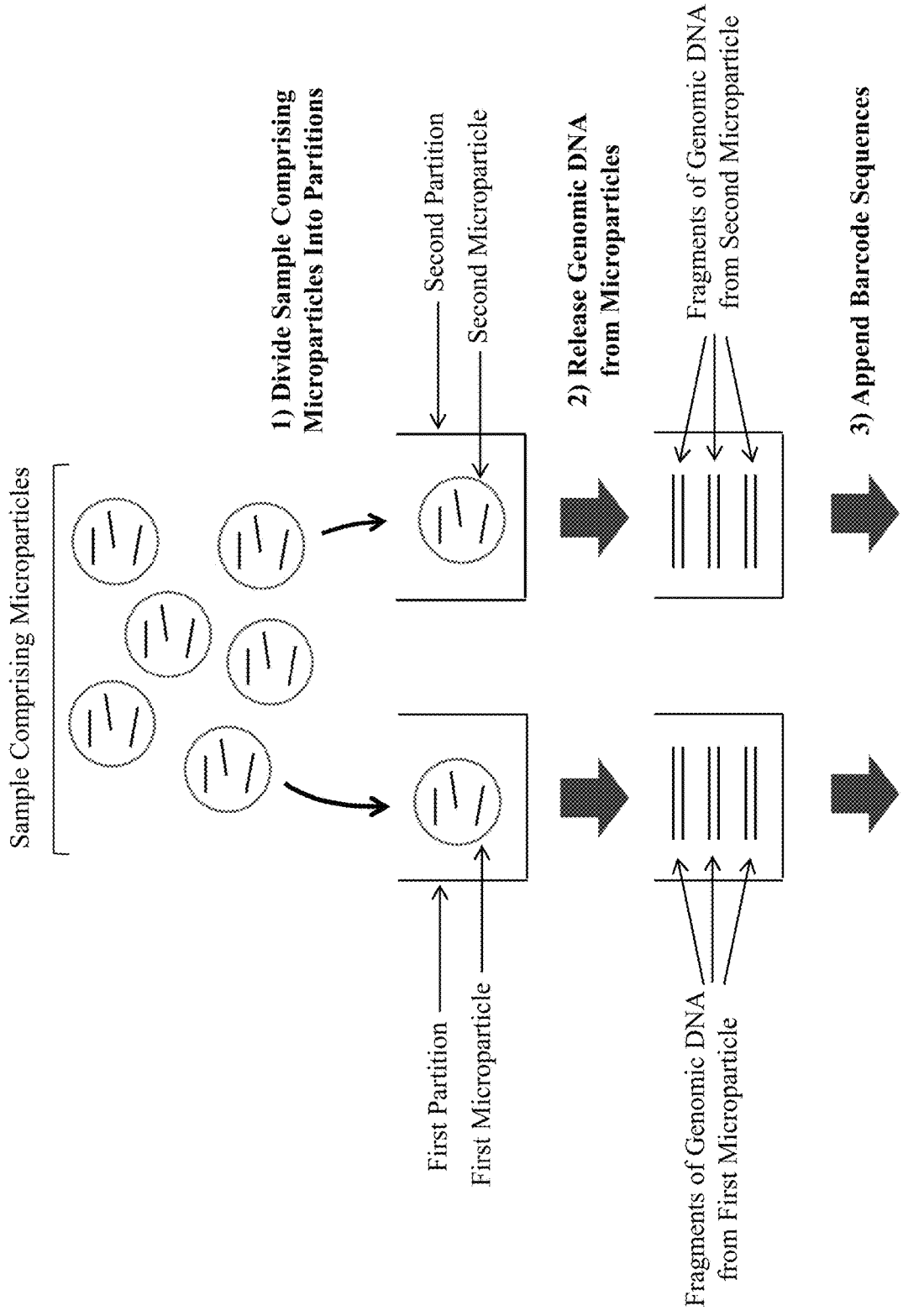

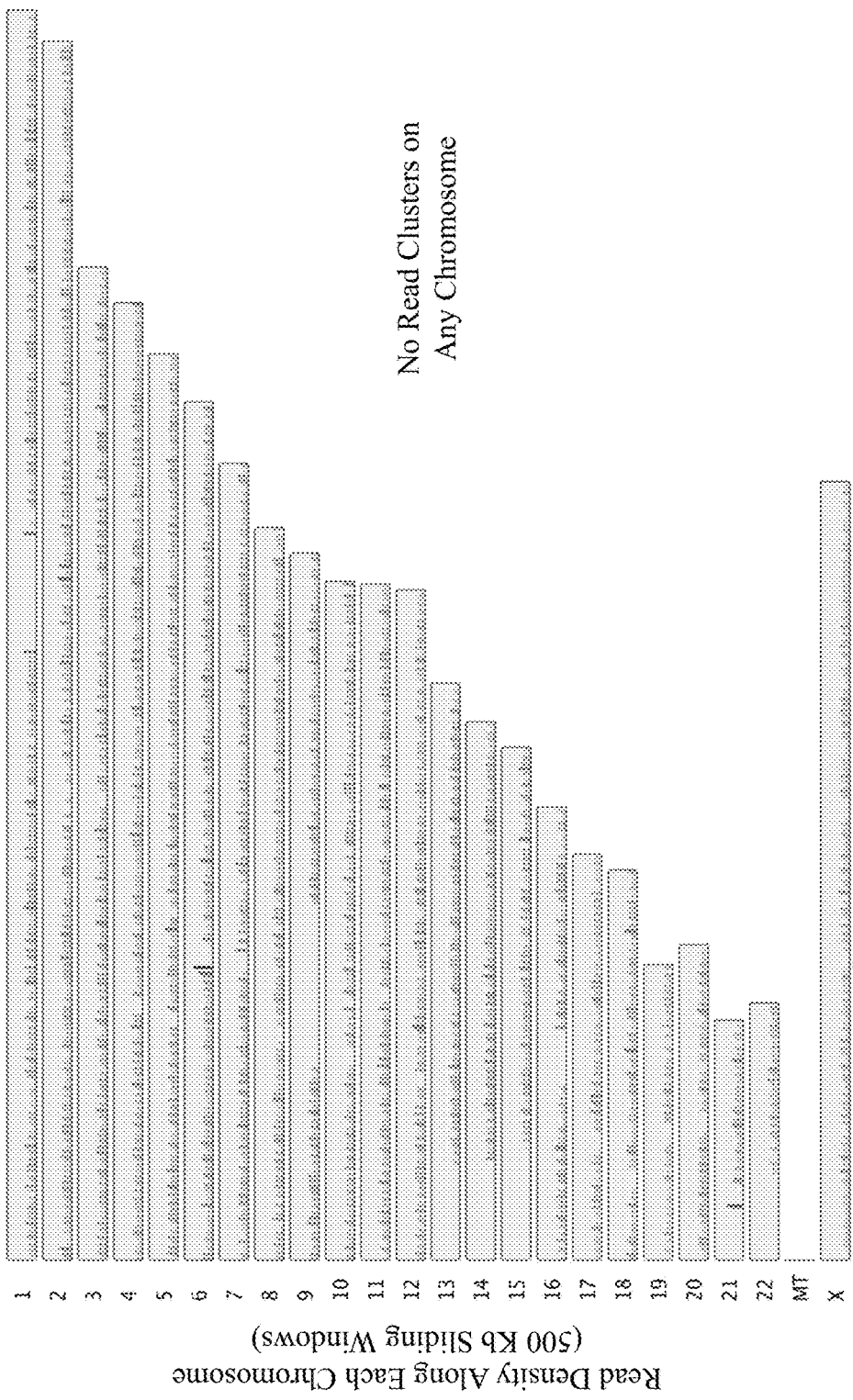

REAGENTS AND METHODS FOR THE ANALYSIS OF LINKED NUCLEIC ACIDS

CROSS-REFERENCE TO RELATED APPLICATIONS

The present application is a Continuation application and claims priority to U.S. patent application Ser. No. 15/750,824, filed on Feb. 6, 2018; which is a 371 National Phase patent application of PCT application Serial No. PCT/GB2017/053820, filed on Dec. 19, 2017; which claims the benefit of the earlier filed Great Britain Application No. GB1622226.7, filed on Dec. 23, 2016, which applications are incorporated by reference herein.

TECHNICAL FIELD

The present invention relates to the analysis of cell free nucleic acids (e.g. cell free DNA). In particular, it relates to the analysis of cell free DNA contained within microparticles originating from blood. Provided are reagents and methods for linking nucleic acids of single microparticles. Also provided are methods for analysing sets of linked nucleic acid fragments from single microparticles.

BACKGROUND

Cell-free DNA (cfDNA) in the circulation is typically fragmented (typically in the range of 100-200 base pairs in length), and thus methods for cfDNA analysis have traditionally focused upon biological signals that can be found with these short DNA fragments. For example, detecting single-nucleotide variants within individual molecules, or performing 'molecular counting' across a large number of sequenced fragments to indirectly infer the presence of large-scale chromosomal abnormalities e.g. tests for foetal chromosomal trisomies that assess foetal DNA within the maternal circulation (a form of so-called 'non-invasive prenatal testing', or NIPT).

A large variety of methods to analyse circulating cell-free DNA have been described previously. Depending upon the specific application area, these assays may employ different terminology for a broadly similar set of sample types and technical methods, such as circulating tumour DNA (ctDNA), cell-free foetal DNA (cffDNA), and/or liquid biopsy, or non-invasive prenatal testing. In general, these methods comprise a laboratory protocol to prepare samples of circulating cell-free DNA for sequencing, a sequencing reaction itself, and then an informatic framework to analyse the resulting sequences to detect a relevant biologic signal. The methods involve a DNA purification and isolation step prior to sequencing, which means that the subsequent analysis must rely solely on the information contained in the DNA itself. Following sequencing, such methods generally employ one or more informatic or statistical frameworks to analyse various aspects of the sequence data, such as detecting specific mutations therein, and/or detecting selective enrichment or selective depletion of particular chromosomes or sub-chromosomal regions (for example, which might be indicative of a chromosomal aneuploidy in a developing foetus).

Many of these methods are for use in NIPT (e.g. in U.S. Pat. Nos. 6,258,540 B1, 8,296,076 B2, 8318430 B2, 8195415 B2, 9447453 B2, and 8442774 B2). The most common methods for performing non-invasive prenatal testing for the detection of foetal chromosomal abnormalities (such as trisomies, and/or sub-chromosomal abnormalities such as microdeletions) involve sequencing a large number of molecules of cfDNA, mapping the resulting sequences to the genome (i.e. to determine which chromosome and/or which part of a given chromosome the sequence derive from), and then, for one or more such chromosomal or sub-chromosomal regions, determining the amount of sequence that maps thereto (e.g. in the form of absolute numbers of reads or relative numbers of reads) and then comparing this to one or more normal or abnormal threshold or cutoff values, and/or performing a statistical test, to determine whether said region(s) may be overrepresented in amount of sequence (which may, for example, correspond to a chromosomal trisomy) and/or whether said region(s) may be underrepresented in amount of sequence (which may, for example, correspond to a microdeletion).

A variety of additional or modified approaches to analyzing cell free DNA using data from unlinked, individual molecules have also been described (e.g. WO2016094853 A1, US2015344970 A1 and US20150105267 A1).

Despite the existence of such a wide range of methods, there remains a need for new methods of analysing cfDNA that would allow the reliable detection of long-range genetic information (e.g. phasing) and also for methods with greater sensitivity. For example, in the case of NIPT, foetal cfDNA only represents a minor fraction of the overall cfDNA in pregnant individuals (the majority of circulating DNA being normal maternal DNA). Therefore, a considerable technical challenge for NIPT revolves around differentiating foetal cfDNA from maternal DNA. Similarly, in a patient with cancer, cfDNA only represents a tiny fraction of the overall circulating DNA. Therefore, a similar technical challenge exists in relation to the use of cfDNA analysis for the diagnosis or monitoring of cancer.

DESCRIPTION

The invention provides methods for the analysis of nucleic acid fragments in circulating microparticles (or microparticles originating from blood). The invention is based on a linked-fragment approach in which fragments of nucleic acid from a single microparticle are linked together. This linkage enables the production of a set of linked sequence reads corresponding to the sequences of fragments from a single microparticle.

The linked-fragment approach provides highly sensitive cfDNA analysis and also enables the detection of long-range genetic information. The approach is based on a combination of insights. Firstly, the methods take advantage of the insight that individual circulating microparticles (for example, an individual circulating apoptotic body) will contain a number of fragments of genomic DNA that have been generated from the same individual cell (somewhere in the body) which has undergone apoptosis. Secondly, a fraction of such fragments of genomic DNA within an individual microparticle will preferentially comprise sequences from one or more specific chromosomal regions. Cumulatively, such circulating microparticles thus serve as a data-rich and multi-feature 'molecular stethoscope' to observe what may be quite complex genetic events occurring in a limited somatic tissue space somewhere in the body; importantly, since such microparticles in large part enter the circulation prior to clearance or metabolism, they may be detected noninvasively. The present invention describes experimental and informatic methods of using these 'stethoscopes' i.e. sets of linked fragments and linked sequence reads (either in the form of single, individual microparticles, or, in many embodiments, complex samples comprising a large number of single circulating microparticles) to perform analytic and diagnostic tasks.

The invention provides a method of analysing a sample comprising a microparticle originating from blood, wherein the microparticle contains at least two fragments of a target nucleic acid, and wherein the method comprises: (a) preparing the sample for sequencing comprising linking at least two of the at least two fragments of the target nucleic acid to produce a set of at least two linked fragments of the target nucleic acid; and (b) sequencing each of the linked fragments in the set to produce at least two (informatically) linked sequence reads.

The invention provides a method of analysing a sample comprising a circulating microparticle, wherein the circulating microparticle contains at least two fragments of a target nucleic acid, and wherein the method comprises: (a) preparing the sample for sequencing comprising linking at least two of the at least two fragments of the target nucleic acid to produce a set of at least two linked fragments of the target nucleic acid; and (b) sequencing each of the linked fragments in the set to produce at least two (informatically) linked sequence reads.

The invention provides a method of analysing a sample comprising a microparticle originating from blood, wherein the microparticle contains at least two fragments of genomic DNA, and wherein the method comprises: (a) preparing the sample for sequencing comprising linking at least two of the at least two fragments of genomic DNA to produce a set of at least two linked fragments of genomic DNA; and (b) sequencing each of the linked fragments in the set to produce at least two linked sequence reads.

The invention provides a method of analysing a sample comprising a circulating microparticle, wherein the circulating microparticle contains at least two fragments of genomic DNA, and wherein the method comprises: (a) preparing the sample for sequencing comprising linking at least two of the at least two fragments of genomic DNA to produce a set of at least two linked fragments of genomic DNA; and (b) sequencing each of the linked fragments in the set to produce at least two linked sequence reads.

In the methods, at least 3, at least 4, at least 5, at least 10, at least 50, at least 100, at least 500, at least 1000, at least 5000, at least 10,000, at least 100,000, or at least 1,000,000 fragments of the target nucleic acid of the microparticle may be linked as a set and then sequenced to produce at least 3, at least 4, at least 5, at least 10, at least 50, at least 100, at least 500, at least 1000, at least 5000, at least 10,000, at least 100,000, or at least 1,000,000 linked sequence reads. Preferably, at least 5 fragments of the target nucleic acid of the microparticle may be linked as a set and then sequenced to produce at least 5 linked sequence reads.

In the methods, each of the linked sequence reads may provide the sequence of at least 1 nucleotide, at least 5 nucleotides, at least 10 nucleotides, at least 20 nucleotides, at least 30 nucleotides, at least 50 nucleotides, at least 100 nucleotides, at least 200 nucleotides, at least 500 nucleotides, at least 1000 nucleotides, or at least 10,000 nucleotides of a linked fragment. Preferably, each of the linked sequence reads may provide the sequence of at least 20 nucleotides of a linked fragment.

In the methods, a total of at least 2, at least 10, at least 100, at least 1000, at least 10,000, at least 100,000, at least 1,000,000, at least 10,000,000, at least 100,000,000, at least 1,000,000,000, at least 10,000,000,000, at least 100,000,000,000, or at least 1,000,000,000,000 sequence reads may be produced. Preferably, a total of at least 500,000 sequence reads are produced.

A sequence read may comprise at least 5, at least 10, at least 25, at least 50, at least 100, at least 250, at least 500, at least 1000, at least 2000, at least 5000, or at least 10,000 nucleotides from the target nucleic acid (e.g. genomic DNA). Preferably, each sequence read comprises at least 5 nucleotides from the target nucleic acid.

A sequence read may comprise a raw sequence read, of portion thereof, generated from a sequencing instrument e.g. a 50-nucleotide long sequence raw sequence read generated from an Illumina sequence instrument. A sequence read may comprise a merged sequence from both reads of a paired-end sequencing run e.g. concatenated or merged sequences from both a first and second read of a paired-end sequencing run on an Illumina sequencing instrument. A sequence read may comprise a portion of a raw sequence read generated from a sequencing instrument e.g. 20 contiguous nucleotides within a raw sequence read of 150 nucleotides generated by an Illumina sequencing instrument. A single raw sequence read may comprise the at least two linked sequence reads produced by the methods of the invention.

Sequence reads may be produced by any method known in the art. For example, by chain-termination or Sanger sequencing. Preferably, sequencing is performed by a next-generation sequencing method such as sequencing by synthesis, sequencing by synthesis using reversible terminators (e.g. Illumina sequencing), pyrosequencing (e.g. 454 sequencing), sequencing by ligation (e.g. SOLiD sequencing), single-molecule sequencing (e.g. Single Molecule, Real-Time (SMRT) sequencing, Pacific Biosciences), or by nanopore sequencing (e.g. on the Minion or Promethion platforms, Oxford Nanopore Technologies). Most preferably, sequence reads are produced by sequencing by synthesis using reversible terminators (e.g. Illumina sequencing).

The methods may comprise a further step of mapping each of the linked sequence reads to a reference genomic sequence. The linked sequence reads may comprise sequences mapped to the same chromosome of the reference genomic sequence or sequences mapped to two or more different chromosomes of the reference genomic sequence.

The microparticle may have a diameter of at least 100 nm, at least 110 nm, at least 125 nm, at least 150 nm, at least 175 nm, at least 200 nm, at least 250 nm or at least 500 nm. Preferably, the microparticle has a diameter of at least 200 nm, The diameter of the microparticle may be 100-5000 nm. The diameter of the microparticle may be 10-10,000 nm (e.g. 100-10,000 nm, 110-10,000 nm), 50-5000 nm, 75-5,000 nm, 100-3,000 nm. The diameter of the microparticle may be 10-90 nm, 50-100 nm, 90-200 nm, 100-200 nm, 100-500 nm, 100-1000 nm, 1000-2000 nm, 90-5000 nm, or 2000-10,000 nm. Preferably, the microparticle diameter is between 100 and 5000 nm. Most preferably, the microparticle has a diameter that is between 200 and 5000 nm. The sample may include microparticles of at least two different sizes, or at least three different sizes, or a range of different sizes.

The linked fragments of genomic DNA may originate from a single genomic DNA molecule.

The methods may further comprise the step of estimating or determining the genomic sequence length of the linked fragments of genomic DNA. Optionally, this step may be performed by sequencing substantially an entire sequence of a linked fragment (i.e. from its approximate 5' end to its approximate 3' end) and counting the number of nucleotides sequenced therein. Optionally, this may be performed by sequencing a sufficient number of nucleotides at the 5' end of the sequence of the linked fragment to map said 5' end to a locus within a reference genome sequence (e.g. human genome sequence), and likewise sequencing a sufficient number of nucleotides at the 3' end of the linked fragment to map said 3' end to a locus within the reference genome sequence, and then determining the genomic sequence length of the linked fragment using the reference genome sequence (i.e. the number of nucleotides sequenced at the 3' end of the linked fragment+the number of nucleotides sequenced at the 5' end of the linked fragment+the number of nucleotides between these sequences in the reference genome (i.e. the unsequenced portion)).

Preferably the sample is isolated from blood, plasma or serum. The microparticle(s) may be isolated from blood, plasma or serum. The method may further comprise a step of isolating the microparticle(s) from blood, plasma or serum. This step may be performed prior to or during step (a).

The microparticle(s) may be isolated by centrifugation, size exclusion chromatography and/or filtering.

The step of isolating may comprise centrifugation. The microparticle(s) may be isolated by pelleting with a centrifugation step and/or an ultracentrifugation step, or a series of two or more centrifugation steps and/or ultracentrifugation steps at two or more different speeds, wherein the pellet and/or the supernatant from one centrifugation/ultracentrifugation step is further processed in a second centrifugation/ultracentrifugation step, and/or a differential centrifugation process The centrifugation or ultracentrifugation step(s) may be performed at a speed of 100-500,000 G, 100-1000 G, 1000-10,000 G, 10,000-100,000 G, 500-100,000 G, or 100,000-500,000 G. The centrifugation or ultracentrifugation step may be performed for a duration of at least 5 seconds, at least 10 seconds, at least 30 seconds, at least 60 seconds, at least 5 minutes, at least 10 minutes, at least 30 minutes, at least 60 minutes, or at least 3 hours The step of isolating may comprise size exclusion chromatography e.g. a column-based size exclusion chromatography process, such as one including a column comprising a sepharose-based matrix, or a sephacryl-based matrix.

The size exclusion chromatography may comprise using a matrix or filter comprising pore sizes at least 50 nanometers, at least 100 nanometers, at least 200 nanometers, at least 500 nanometers, at least 1.0 micrometer, at least 2.0 micrometers, or at least 5.0 micrometers in size or diameter.

The step of isolating may comprise filtering the sample. The filtrate may provide the microparticle(s) analysed in the methods. Optionally, the filter is used to isolate microparticles below a certain size, and wherein the filter preferentially or completely removes particles greater than 100 nanometers in size, greater than 200 nanometers in size, greater than 300 nanometers in size, greater than 500 nanometers in size, greater than 1.0 micrometer in size, greater than 2.0 micrometers in size, greater than 3.0 micrometers in size, greater than 5.0 micrometers in size, or greater than 10.0 micrometers in size. Optionally, two or more such filtering steps may be performed, using filters with the same size-filtering parameters, or with different size-filtering parameters. Optionally, the filtrate from one or more filtering steps comprises microparticles, and linked sequence reads are produced therefrom.

In the methods, the sample may comprise first and second microparticles originating from blood, wherein each microparticle contains at least two fragments of a target nucleic acid (e.g. genomic DNA), and wherein the method comprises performing step (a) to produce a first set of linked fragments of the target nucleic acid for the first microparticle and a second set of linked fragments of the target nucleic acid for the second microparticle, and performing step (b) to produce a first set of linked sequence reads for the first microparticle and a second set of linked sequence reads for the second microparticle.

In the methods, the set of linked sequence reads produced for the first microparticle may be distinguishable from the set of linked sequence reads produced for the second microparticle.

In the methods, the sample may comprise n microparticles originating from blood, wherein each microparticle contains at least two fragments of a target nucleic acid (e.g. genomic DNA), and wherein the method comprises performing step (a) to produce n sets of linked fragments of the target nucleic acid, one set for each of the n microparticles, and performing step (b) to produce n sets of linked sequence reads, one for each of the n microparticles.

In the methods, n may be at least 3, at least 5, at least 10, at least 50, at least 100, at least 1000, at least 10,000, at least 100,000, at least 1,000,000, at least 10,000,000, at least 100,000,000, at least 1,000,000,000, at least 10,000,000,000, or at least 100,000,000,000. Preferably, n is at least 100,000 microparticles.

In the methods, the nucleic acid sample may comprise at least 3, at least 5, at least 10, at least 50, at least 100, at least 1000, at least 10,000, at least 100,000, at least 1,000,000, at least 10,000,000, at least 100,000,000, at least 1,000,000,000, at least 10,000,000,000, or at least 100,000,000,000 microparticles, wherein said microparticles are comprised within a single contiguous aqueous volume during any step of the method, such as any step of contacting the sample with a library of multimeric barcoding reagents, and/or any step of appending barcode sequences to target nucleic acids, and/or any step of appending coupling sequences to target nucleic acids, and/or any step of crosslinking or permeabilising.

The set of linked sequence reads produced for each microparticle may be distinguishable from the sets of linked sequence reads produced for the other microparticles.

The methods may further comprise, prior to step (a), the step of partitioning the sample into at least two different reaction volumes.

In the present invention, two sequences or sequence reads (e.g. as determined by a sequencing reaction) may be linked informatically by any means that allows such sequences to be related or interrelated to each other in any way, within a computer system, within an algorithm, or within a dataset. Such linking may be comprised of, and/or established by, and/or represented by a discrete identifying link, or by a shared property, or by any indirect method linking, interrelating, or correlating two or more such sequences.

The linking may be comprised of, and/or established by, and/or represented by a sequence within a sequencing reaction itself (e.g. in the form of a barcode sequence determined through the sequencing reaction, or in the form of two different parts or segments of a single determined sequence which together comprise a first and a second linked sequence), or established, comprised, or represented independent of such sequences (such as established by merit of being comprised within the same flowcell, or within the same lane of a flowcell, or within the same compartment or region of a sequencing instrument, or comprised within the same sequencing run of a sequencing instrument, or comprised with a degree of spatial proximity within a biological sample, and/or with a degree of spatial proximity within a sequencing instrument or sequencing flowcell. Linking may be comprised of, and/or established by, and/or represented by a measure or parameter corresponding to a physical location or partition within a sequencing instrument, such as a pixel or pixel location within an image and/or within a multi-pixel camera or a multi-pixel charge-coupled device, and/or such as a nanopore or location of a nanopore within a nanopore sequencing instrument or nanopore membrane.

Linking may be absolute (i.e., two sequences are either linked or unlinked, with no quantitative, semi-quantitative, or qualitative/categorical relationships outside of this). Linking may also be relative, probabilistic, or established, comprised, or represented in terms of a degree, a probability, or an extent of linking, for example relative to (or represented by) one or more parameters that may hold one of a series of quantitative, semi-quantitative, or qualitative/categorical values. For example, two (or more) sequences may be linked informatically by a quantitative, semi-quantitative, or qualitative/categorical parameter, which represents, comprises, estimates, or embodies the proximity of said two (or more) sequences within a sequencing instrument, or the proximity of said two (or more) sequences within a biological sample.

For any analysis involving two or more sequences that are linked informatically by any such way, the existence (or lack thereof) of linking may be employed as a parameter in any analysis or evaluation step or any algorithm for performing same. For any analysis involving two or more sequences that are linked informatically by any such way, the degree, probability, or extent of linking may be employed as a parameter in any analysis or evaluation step or any algorithm for performing same.

In one version of such linking, a given set of two or more linked sequences may be associated with a specific identifier, such as an alphanumeric identifier, or a barcode, or a barcode sequence. In one further version a given set of two or more linked sequences may be associated with or a barcode, or a barcode sequence, wherein said barcode or barcode sequence is comprised within a sequence determined by the sequencing reaction. For example, each sequence determined in a sequencing reaction may comprise both a barcode sequence and a sequence corresponding to a genomic DNA sequence. Optionally, certain sequences or linked sequences may be represented by or associated with two or more barcodes or identifiers.

In another version of linking, two or more linked sequences may be kept within discrete partitions within a computer, or computer network, within a hard drive, or any sort of storage medium, or any other means of storing sequence data. Optionally, certain sequences or linked sequences may be kept in two or more partitions within such a computer or data medium.

Sequences that are linked informatically may comprise one or more sets of informatically linked sequences. Sequences in a linked set of sequences may all share the same linking function or representation thereof; for example, all sequences within a linked set may be associated with the same barcode or with the same identifier, or may be comprised within the same partition within a computer or storage medium; all sequences may share any other form of linking, interrelation, and/or correlation. One or more sequences in a linked set may be exclusive members of said set, and thus not members of any other set. Alternatively, one or more sequences in a linked set may be non-exclusive members of said set, and thus said sequences may be represented by and/or associated with two or more different linked sets of sequences.

1. Samples Containing Microparticles

Samples for use in the methods of the invention comprise at least one microparticle originating from blood (e.g.

human blood). The microparticle(s) may originate from maternal blood. The microparticle(s) may originate from the blood of a patient with a disease (e.g. cancer). The sample may, for example, be a blood sample, a plasma sample or a serum sample. The sample may be a mammalian sample. Preferably, the sample is a human sample.

A variety of cell-free microparticles have been found in blood, plasma, and/or serum from humans and other animals (Orozco et al, Cytometry Part A (2010). 77A: 502 514, 2010). These microparticles are diverse in the tissues and cells from which they originate, as well as the biophysical processes underlying their formation, as well as their respective sizes and molecular structures and compositions. Microparticles may comprise components from a cell membrane (e.g. incorporating phospholipid components) along with some spectrum of intracellular or cell-nuclear components. Microparticles include exosomes, apoptotic bodies (also known as apoptotic vesicles) and extracellular microvesicles.

A microparticle may be defined as a membranous vesicle containing at least two fragments of a target nucleic acid (e.g. genomic DNA). A microparticle may have a diameter of 100-5000 nm. Preferably, the microparticle has a diameter of 100-3000 nanometers.

Exosomes are amongst the smallest circulating microparticles, are typically in the range of 50 to 100 nanometers in diameter, and are thought derive from the cell membrane of viable, intact cells, and contain both protein and RNA components (including both mRNA molecules and/or degraded mRNA molecules, and small regulatory RNA molecules such as microRNA molecules) contained within an outer phospholipid component. Exosomes are thought to be formed by exocytosis of cytoplasmic multivesicular bodies (Gyorgy et al, Cell. Mol. Life Sci. (2011) 68:2667-2688). Exosomes are thought to play varied roles in cell-cell signaling as well as extracellular functions (Kanada et al, PNAS (2015) 1418401112). Techniques for quantitating or sequencing the microRNA and/or mRNA molecules found in exosomes have been described previously (e.g. U.S. patent application Ser. No. 13/456,121, European application EP2626433 A1).

Microparticles also include apoptotic bodies (also known as apoptotic vesicles) and extracellular microvesicles, which altogether can range up to 1 micron or even 2 to 5 microns in diameter, and are generally thought to be larger than 100 nanometers in diameter (Lichtenstein et al, Ann N Y Acad Sci. (2001); 945:239-49). All classes of circulating microparticles are thought to be generated by a large number and variety of cells in the body (Thierry et al, Cancer Metastasis Rev 35 (3), 347-376. 9 (2016)/s10555-016-9629-x).

Preferably, the microparticle is not an exosome e.g. the microparticle is any microparticle having a larger diameter than an exosome.

A large number of methods for isolating circulating microparticles (and/or particular subsets, categories, or fractions of circulating microparticles) have been described previously. European patent(s) ES2540255 (B1) and U.S. Pat. No. 9,005,888 B2 describe methods of isolating particular circulating microparticles such as apoptotic bodies based upon centrifugation procedures. A large number of methods for isolating different types of cell-free microparticles by centrifugation, ultracentrifugation, and other techniques have been well described and developed previously (Gyorgy et al, Cell. Mol. Life Sci. (2011) 68:2667-2688).

A microparticle contains at least two fragments of a target nucleic acid (e.g. molecules of fragmented genomic DNA).

These molecules of fragmented genomic DNA, and/or sequences comprised within these molecules of fragmented genomic DNA, may be linked by any method described herein.

The fragments of the target nucleic acid may be fragments of DNA (e.g. molecules of fragmented genomic DNA) or fragments of RNA (e.g. fragments of mRNA). Preferably, the fragments of the target nucleic acid are fragments of genomic DNA.

The fragments of DNA may be fragments of mitochondrial DNA. The fragments of DNA may be fragments of mitochondrial DNA from a maternal cell or tissue. The fragments of DNA may be fragments of mitochondrial DNA from a foetal or placental tissue. The fragments of DNA may be fragments of mitochondrial DNA from a diseased and/or cancer tissue.

A microparticle may comprise a platelet. A microparticle may comprise a tumour-educated platelet. A target nucleic acid may comprise platelet RNA (e.g., fragments of platelet RNA, and/or fragments of a tumour-educated platelet RNA). A sample comprising one or more platelets may comprise platelet-rich plasma (for example, platelet-rich plasma comprising tumour-educated platelets).

The fragments of the target nucleic acid may comprise double-stranded or single stranded nucleic acids. The fragments of genomic DNA may comprise double-stranded DNA or single-stranded DNA. The fragments of the target nucleic acid may comprise partially double-stranded nucleic acids. The fragments of genomic DNA may comprise partially double-stranded DNA.

The fragments of the target nucleic acid may be fragments originating from a single nucleic acid molecule, or fragments originating from two or more nucleic acid molecules. For example, the fragments of genomic DNA may originate from a single genomic DNA molecule.

As would be appreciated by the skilled person, as used herein the term fragments of a target nucleic acid refers to the original fragments present in the microparticle and to copies or amplicons thereof. For example, the term fragments of gDNA refers to the original gDNA fragments present in the microparticle and, for example, to DNA molecules that may be prepared from the original genomic DNA fragments by a primer-extension reaction. As a further example, the term fragments of mRNA refers to the original mRNA fragments present in the microparticle and, for example, to cDNA molecules that may be prepared from the original mRNA fragments by reverse transcription.

The fragments of the target nucleic acid (e.g. genomic DNA) may be at least 10 nucleotides, at least 15 nucleotides, at least 20 nucleotides, at least 25 nucleotides or at least 50 nucleotides. The fragments of the target nucleic acid (e.g. genomic DNA) may be 15 to 100,000 nucleotides, 20 to 50,000 nucleotides, 25 to 25,000 nucleotides, 30 to 10,000 nucleotides, 35-5,000 nucleotides, 40-1000 nucleotides or 50-500 nucleotides. The fragments of the target nucleic acid (e.g. genomic DNA) may be 20 to 200 nucleotides in length, 100 to 200 nucleotides in length, 200 to 1000 nucleotides in length, 50 to 250 nucleotides in length, 1000 to 10,000 nucleotides in length, 10,000 to 100,000 nucleotides in length, or 50 to 100,000 nucleotides in length. Preferably, the molecules of fragmented genomic DNA are 50 to 500 nucleotides in length.

In the sample, the microparticles may be at a concentration of less than 0.001 microparticles per microliter, less than 0.01 microparticles per microliter, less than 0.1 microparticles per microliter, less than 1.0 microparticles per microliter, less than 10 microparticles per microliter, less than 100 microparticles per microliter, less than 1000 microparticles per microliter, less than 10,000 microparticles per microliter, less than 100,000 microparticles per microliter, less than 1,000,000 microparticles per microliter, less than 10,000,000 microparticles per microliter, or less than 100,000,000 microparticles per microliter.

In the sample, the fragments of nucleic acid (e.g. genomic DNA) may be at a concentration of less than 1.0 picograms of DNA per microliter, less than 10 picograms of DNA per microliter, less than 100 picograms of DNA per microliter, less than 1.0 nanograms of DNA per microliter, less than 10 nanograms of DNA per microliter, less than 100 nanograms of DNA per microliter, or less than 1000 nanograms of DNA per microliter.

2. Linking by Barcoding

The invention provides a method of preparing a sample for sequencing, wherein the sample comprise a microparticle originating from blood, wherein the microparticle contains at least two fragments of a target nucleic acid (e.g. genomic DNA), and wherein the method comprises appending the at least two fragments of the target nucleic acid of the microparticle to a barcode sequence, or to different barcode sequences of a set of barcode sequences, to produce a set of linked fragments of the target nucleic acid.

The invention provides a method of preparing a sample for sequencing, wherein the sample comprise a circulating microparticle, wherein the circulating microparticle contains at least two fragments of a target nucleic acid (e.g. genomic DNA), and wherein the method comprises appending the at least two fragments of the target nucleic acid of the circulating microparticle to a barcode sequence, or to different barcode sequences of a set of barcode sequences, to produce a set of linked fragments of the target nucleic acid.

Prior to the step of appending the at least two fragments of the target nucleic acid of the microparticle to a barcode sequence, or to different barcode sequences of a set of barcode sequences, the method may comprise appending a coupling sequence to each of the fragments of the target nucleic acid (e.g. genomic DNA) of the microparticle, wherein the coupling sequences are then appended to the barcode sequence, or to different barcode sequences of a set of barcode sequences, to produce the set of linked fragments of the target nucleic acid.

In the method, the sample may comprise first and second microparticles originating from blood, wherein each microparticle contains at least two fragments of a target nucleic acid (e.g. genomic DNA), and wherein the method may comprise appending the at least two fragments of the target nucleic acid of the first microparticle to a first barcode sequence, or to different barcode sequences of a first set of barcode sequences, to produce a first set of linked fragments of the target nucleic acid and appending the at least two fragments of the target nucleic acid of the second microparticle to a second barcode sequence, or to different barcode sequences of a second set of barcode sequences, to produce a second set of linked fragments of the target nucleic acid.

The first barcode sequence may be different to the second barcode sequence. The barcode sequences of the first set of barcode sequences may be different to the barcode sequences of the second set of barcode sequences.

In the methods, the sample may comprise n microparticles originating from blood, wherein each microparticle contains at least two fragments of a target nucleic acid (e.g. genomic DNA), and wherein the method comprises performing step (a) to produce n sets of linked fragments of the target nucleic acid, one set for each of the n microparticles.

In the methods, n may be at least 3, at least 5, at least 10, at least 50, at least 100, at least 1000, at least 10,000, at least 100,000, at least 1,000,000, at least 10,000,000, at least 100,000,000, at least 1,000,000,000, at least 10,000,000,000, or at least 100,000,000,000. Preferably, n is at least 100,000 microparticles.

Preferably, each set of linked sequence reads is linked by a different barcode sequence or a different set of barcode sequences. Each barcode sequence of a set of barcode sequences may be different to the barcode sequences of at least 1, at least 4, at least 9, at least 49, at least 99, at least 999, at least 9,999, at least 99,999, at least 999,999, at least 9,999,999, at least 99,999,999, at least 999,999,999, at least 9,999,999,999, at least 99,999,999,999, or at least 999,999,999,999 other sets of barcode sequences in the library. Each barcode sequence of a set of barcode sequences may be different to the barcode sequences of all of the other sets of barcode sequences in the library. Preferably, each barcode sequence in a set of barcode sequences is different to the barcode sequences at least 9 other sets of barcode sequences in the library.

The invention provides a method of analysing a sample comprising a microparticle originating from blood, wherein the microparticle contains at least two fragments of a target nucleic acid, and wherein the method comprises: (a) preparing the sample for sequencing comprising appending the at least two fragments of a target nucleic acid (e.g. genomic DNA) of the microparticle to a barcode sequence to produce a set of linked fragments of the target nucleic acid; and (b) sequencing each of the linked fragments in the set to produce at least two linked sequence reads, wherein the at least two linked sequence reads are linked by the barcode sequence.

A barcode sequence may contain a unique sequence. Each barcode sequence may comprise at least 5, at least 10, at least 15, at least 20, at least 25, at least 50 or at least 100 nucleotides. Preferably, each barcode sequence comprises at least 5 nucleotides. Preferably each barcode sequence comprises deoxyribonucleotides, optionally all of the nucleotides in a barcode sequence are deoxyribonucleotides. One or more of the deoxyribonucleotides may be a modified deoxyribonucleotide (e.g. a deoxyribonucleotide modified with a biotin moiety or a deoxyuracil nucleotide). The barcode sequence may comprise one or more degenerate nucleotides or sequences. The barcode sequence may not comprise any degenerate nucleotides or sequences.

In the method, prior to the step of appending the at least two fragments of the target nucleic acid of the microparticle to a barcode sequence, the method may comprise appending a coupling sequence to each of the fragments of the nucleic acid of the microparticle, wherein the coupling sequences are then appended to the barcode sequence to produce the set of linked fragments.

In the methods, the sample may comprise first and second microparticles originating from blood, wherein each microparticle contains at least two fragments of a target nucleic acid (e.g. genomic DNA), and wherein the method comprises performing step (a) to produce a first set of linked fragments of the target nucleic acid for the first microparticle and a second set of linked fragments of the target nucleic acid for the second microparticle, and performing step (b) to produce a first set of linked sequence reads for the first microparticle and a second set of linked sequence reads for the second microparticle, wherein the at least two linked sequence reads for the first microparticle are linked by a different barcode sequence to the at least two linked sequence reads of the second microparticle.

The first set of linked fragments may be linked by a different barcode sequence to the second set of linked fragments.

In the methods, the sample may comprise n microparticles originating from blood, wherein each microparticle contains at least two fragments of a target nucleic acid (e.g. genomic DNA), and wherein the method comprises performing step (a) to produce n sets of linked fragments of the target nucleic acid, one set for each of the n microparticles, and performing step (b) to produce n sets of linked sequence reads, one for each of the n microparticles.

In the methods, n may be at least 3, at least 5, at least 10, at least 50, at least 100, at least 1000, at least 10,000, at least 100,000, at least 1,000,000, at least 10,000,000, at least 100,000,000, at least 1,000,000,000, at least 10,000,000,000, or at least 100,000,000,000. Preferably, n is at least 100,000 microparticles.

Preferably, each set of linked sequence reads is linked by a different barcode sequence.

In the methods, the different barcode sequences may be provided as a library of barcode sequences. The library used in the methods may comprise at least 2, at least 5, at least 10, at least 50, at least 100, at least 1000, at least 10,000, at least 100,000, at least 1,000,000, at least 10,000,000, at least 100,000,000, at least 1,000,000,000, at least 10,000,000,000, at least 100,000,000,000, or at least 1,000,000,000,000 different barcode sequences. Preferably, the library used in the methods comprises at least 1,000,000 different barcode sequences.

In the methods, each barcode sequence of the library may be appended only to fragments from a single microparticle.

The methods may be deterministic i.e. one barcode sequence may be used to identify sequence reads from a single microparticle or probabilistic i.e. one barcode sequence may be used to identify sequence reads likely to be from a single microparticle. In certain embodiments, one barcode sequence may be appended to fragments of genomic DNA from two or more microparticles.

The method may comprise: (a) preparing the sample for sequencing comprising appending each of the at least two fragments of a target nucleic acid (e.g. genomic DNA) of the microparticle to a different barcode sequence of a set of barcode sequences to produce a set of linked fragments of the target nucleic acid; and (b) sequencing each of the linked fragments in the set to produce at least two linked sequence reads, wherein the at least two linked sequence reads are linked by the set of barcode sequences.

In the methods, prior to the step of appending each of the at least two fragments of the target nucleic acid of the microparticle to a different barcode sequence, the method may comprise appending a coupling sequence to each of the fragments of the target nucleic acid of the microparticle, wherein each of the at least two fragments of the target nucleic acid of the microparticle is appended to a different barcode sequence of the set of barcode sequences by its coupling sequence.

In the methods, the sample may comprise first and second microparticles originating from blood, wherein each microparticle contains at least two fragments of a target nucleic acid (e.g. genomic DNA), and wherein the method may comprise performing step (a) to produce a first set of linked fragments of the target nucleic acid for the first microparticle and a second set of linked fragments of the target nucleic acid for the second microparticle, and performing step (b) to produce a first set of linked sequence reads for the first microparticle and a second set of linked sequence reads for the second microparticle, wherein the first set of linked sequence reads are linked by a different set of barcode sequences to the second set of linked sequence reads.

In the methods, the sample may comprise n microparticles originating from blood, wherein each microparticle contains at least two fragments of a target nucleic acid (e.g. genomic DNA), and wherein the method may comprise performing step (a) to produce n sets of linked fragments of the target nucleic acid, one set for each of the n microparticles, and performing step (b) to produce n sets of linked sequence reads, one for each of the n microparticles.

In the methods, n may be at least 3, at least 5, at least 10, at least 50, at least 100, at least 1000, at least 10,000, at least 100,000, at least 1,000,000, at least 10,000,000, at least 100,000,000, at least 1,000,000,000, at least 10,000,000,000, or at least 100,000,000,000. Preferably, n is at least 100,000 microparticles.

Preferably, each set of linked sequence reads is linked by a different set of barcode sequences.

In the methods, the different sets of barcode sequences may be provided as a library of sets of barcode sequences. The library used in the methods may comprise at least 2, at least 5, at least 10, at least 50, at least 100, at least 1000, at least 10,000, at least 100,000, at least 1,000,000, at least 10,000,000, at least 100,000,000, at least 1,000,000,000, at least 10,000,000,000, at least 100,000,000,000, or at least 1,000,000,000,000 different sets of barcode sequences. Preferably, the library used in the methods comprises at least 1,000,000 different sets of barcode sequences.

Each barcode sequence of a set of barcode sequences may be different to the barcode sequences of at least 1, at least 4, at least 9, at least 49, at least 99, at least 999, at least 9,999, at least 99,999, at least 999,999, at least 9,999,999, at least 99,999,999, at least 999,999,999, at least 9,999,999,999, at least 99,999,999,999, or at least 999,999,999,999 other sets of barcode sequences in the library. Each barcode sequence in a set of barcode sequences may be different to the barcode sequences of all of the other sets of barcode sequences in the library. Preferably, each barcode sequence in a set of barcode sequences is different to the barcode sequences at least 9 other sets of barcode sequences in the library.

In the methods, barcode sequences from a set of barcode sequences of the library may be appended only to fragments from a single microparticle.

The methods may be deterministic i.e. one set of barcode sequences may be used to identify sequence reads from a single microparticle or probabilistic i.e. one set of barcode sequences may be used to identify sequence reads likely to be from a single microparticle.

The method may comprise preparing first and second samples for sequencing, wherein each sample comprises at least one microparticle originating from blood, wherein each microparticle contains at least two fragments of a target nucleic acid (e.g. genomic DNA), and wherein the barcode sequences each comprise a sample identifier region, and wherein the method comprises: (i) performing step (a) for each sample, wherein the barcode sequence(s) appended to the fragments of the target nucleic acid from the first sample have a different sample identifier region to the barcode sequence(s) appended to the fragments of the target nucleic acid from the second sample; (ii) performing step (b) for each sample, wherein each linked sequence read comprises the sequence of the sample identifier region; and (iii) determining the sample from which each linked sequence read is derived by its sample identifier region.

In the methods, before, during, and/or after the step(s) of appending barcode sequences and/or coupling sequences, the method may comprise the step of cross-linking the fragments of genomic DNA in the microparticle(s).

In the methods, before, during, and/or after the step(s) of appending barcode sequences and/or coupling sequences, and/or optionally after the step of cross-linking the fragments of genomic DNA in the microparticle(s), the method may comprise the step of permeabilising the microparticle(s). prior to the step of transferring, and optionally after the step of cross-linking, the method comprises permeabilising the microparticle.

Barcode sequences may be comprised within barcoded oligonucleotides in a solution of barcoded oligonucleotides; such barcoded oligonucleotides may be single-stranded double-stranded, or single-stranded with one or more double-stranded regions. The barcoded oligonucleotides may be ligated to the fragments of the target nucleic acid in a single-stranded or double-stranded ligation reaction. The barcoded oligonucleotide may comprise a single-stranded 5' or 3' region capable of ligating to a fragment of the target nucleic acid. Each barcoded oligonucleotide may be ligated to a fragment of the target nucleic acid in a single-stranded ligation reaction. Alternatively, barcoded oligonucleotides may comprise a blunt, recessed, or overhanging 5' or 3' region capable of ligating to a fragment of the target nucleic acid. Each barcoded oligonucleotide may be ligated to a fragment of the target nucleic acid in a double-stranded ligation reaction.

In certain methods, the ends of fragments of the target nucleic acid may be converted into blunt double-stranded ends in a blunting reaction and the barcoded oligonucleotides may comprise a blunt double-stranded end. Each barcoded oligonucleotide may be ligated to a fragment of the target nucleic in a blunt-end ligation reaction. In certain methods, the ends of fragments of the target nucleic acid may have their ends converted into blunt double-stranded ends in a blunting reaction, and then have their ends converted into a form with single 3' adenosine overhangs, and wherein the barcoded oligonucleotides comprise a double-stranded end with a single 3' thymine overhang capable of annealing to the single 3' adenosine overhangs of the fragments of the target nucleic acid. Each barcoded oligonucleotide may be ligated to a fragment of the target nucleic acid in a double-stranded A/T ligation reaction.

In certain methods, barcoded oligonucleotides comprise a target region on their 3' or 5' end capable of annealing to a target region in a target nucleic acid and/or coupling sequence, and barcode sequences may be appended to target nucleic acids by annealing barcoded oligonucleotides to said target nucleic acid and/or coupling sequence, and optionally extending and/or ligating the barcoded oligonucleotide to a nucleic acid target and/or coupling sequence.

In certain methods, a coupling sequence may be appended to fragments of genomic DNA prior to appending a barcoded oligonucleotide.

The method may comprise, prior to the step of appending, the step of partitioning the nucleic acid sample into at least two different reaction volumes.

3. Linking by Barcoding Using Multimeric Barcoding Reagents

The invention provides a method of preparing a sample for sequencing, wherein the sample comprises a microparticle originating from blood, and wherein the microparticle contains at least two fragments of a target nucleic acid (e.g. genomic DNA), and wherein the method comprises the steps of: (a) contacting the sample with a library comprising a multimeric barcoding reagent, wherein the multimeric barcoding reagent comprises first and second barcode regions linked together, wherein each barcode region comprises a nucleic acid sequence; and (b) appending barcode sequences to each of first and second fragments of the target nucleic acid of the microparticle to produce first and second barcoded target nucleic acid molecules for the microparticle, wherein the first barcoded target nucleic acid molecule comprises the nucleic acid sequence of the first barcode region and the second barcoded target nucleic acid molecule comprises the nucleic acid sequence of the second barcode region.

The invention provides a method of preparing a sample for sequencing, wherein the sample comprises a microparticle originating from blood, and wherein the microparticle contains at least two fragments of a target nucleic acid (e.g. genomic DNA), and wherein the method comprises the steps of: (a) contacting the sample with the multimeric barcoding reagent, wherein the multimeric barcoding reagent comprises first and second barcoded oligonucleotides linked together, and wherein the barcoded oligonucleotides each comprise a barcode region; and (b) annealing or ligating the first and second barcoded oligonucleotides to first and second fragments of the target nucleic acid of the microparticle to produce first and second barcoded target nucleic acid molecules.

The invention provides a method of preparing a sample for sequencing, wherein the sample comprises first and second microparticles originating from blood, and wherein each microparticle contains at least two fragments of a target nucleic acid (e.g. genomic DNA), and wherein the method comprises the steps of: (a) contacting the sample with a library comprising at least two multimeric barcoding reagents, wherein each multimeric barcoding reagent comprises first and second barcode regions linked together, wherein each barcode region comprises a nucleic acid sequence and wherein the first and second barcode regions of a first multimeric barcoding reagent are different to the first and second barcode regions of a second multimeric barcoding reagent of the library; and (b) appending barcode sequences to each of first and second fragments of the target nucleic acid of the first microparticle to produce first and second barcoded target nucleic acid molecules for the first microparticle, wherein the first barcoded target nucleic acid molecule comprises the nucleic acid sequence of the first barcode region of the first multimeric barcoding reagent and the second barcoded target nucleic acid molecule comprises the nucleic acid sequence of the second barcode region of the first multimeric barcoding reagent, and appending barcode sequences to each of first and second fragments of the target nucleic acid of the second microparticle to produce first and second barcoded target nucleic acid molecules for the second microparticle, wherein the first barcoded target nucleic acid molecule comprises the nucleic acid sequence of the first barcode region of the second multimeric barcoding reagent and the second barcoded target nucleic acid molecule comprises the nucleic acid sequence of the second barcode region of the second multimeric barcoding reagent.

The invention provides a method of preparing a sample for sequencing, wherein the sample comprises first and second microparticles originating from blood, and wherein each microparticle contains at least two fragments of a target nucleic acid (e.g. genomic DNA), and wherein the method comprises the steps of: (a) contacting the sample with a library comprising at least two multimeric barcoding reagents, wherein each multimeric barcoding reagent comprises first and second barcoded oligonucleotides linked together, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library; and (b) annealing or ligating the first and second barcoded oligonucleotides of the first multimeric barcoding reagent to first and second fragments of the target nucleic acid of the first microparticle to produce first and second barcoded target nucleic acid molecules, and annealing or ligating the first and second barcoded oligonucleotides of the second multimeric barcoding reagent to first and second fragments of the target nucleic acid of the second microparticle to produce first and second barcoded target nucleic acid molecules.

The barcoded oligonucleotides may be ligated to the fragments of the target nucleic acid in a single-stranded or double-stranded ligation reaction.

In the methods, the barcoded oligonucleotide may comprise a single-stranded 5' or 3' region capable of ligating to a fragment of the target nucleic acid. Each barcoded oligonucleotide may be ligated to a fragment of the target nucleic acid in a single-stranded ligation reaction.

In the methods, the barcoded oligonucleotides may comprise a blunt, recessed, or overhanging 5' or 3' region capable of ligating to a fragment of the target nucleic acid. Each barcoded oligonucleotide may be ligated to a fragment of the target nucleic acid in a double-stranded ligation reaction.

In the methods, the ends of fragments of the target nucleic acid may be converted into blunt double-stranded ends in a blunting reaction and the barcoded oligonucleotides may comprise a blunt double-stranded end. Each barcoded oligonucleotide may be ligated to a fragment of the target nucleic in a blunt-end ligation reaction.

In the methods, the ends of fragments of the target nucleic acid may have their ends converted into blunt double-stranded ends in a blunting reaction, and then have their ends converted into a form with single 3' adenosine overhangs, and wherein the barcoded oligonucleotides comprise a double-stranded end with a single 3' thymine overhang capable of annealing to the single 3' adenosine overhangs of the fragments of the target nucleic acid. Each barcoded oligonucleotide may be ligated to a fragment of the target nucleic acid in a double-stranded A/T ligation reaction.

In the methods, the ends of fragments of the target nucleic acid may be contacted with a restriction enzyme, wherein the restriction enzyme digests each fragment at restriction sites to create ligation junctions at these restriction sites, and wherein the barcoded oligonucleotides comprise an end compatible with these ligation junctions. Each barcoded oligonucleotide may be ligated to a fragment of the target nucleic acid at said ligation junctions in a double-stranded ligation reaction. Optionally, said restriction enzyme may be EcoRI, HindIII, or BglII.

In the methods, prior to the step of annealing or ligating the first and second barcoded oligonucleotides to first and second fragments of the target nucleic acid, the method may comprise appending a coupling sequence to each of the fragments of the target nucleic acid, wherein the first and second barcoded oligonucleotides are then annealed or ligated to the coupling sequences of the first and second fragments of the target nucleic acid.

In the methods, step (b) may comprise: (i) annealing the first and second barcoded oligonucleotides of the first multimeric barcoding reagent to first and second fragments of the target nucleic acid of the first microparticle, and annealing the first and second barcoded oligonucleotides of the second multimeric barcoding reagent to first and second fragments of the target nucleic acid of the second microparticle; and (ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the fragments of the target nucleic acid as a template.

The method may comprise: (a) contacting the sample with a library comprising at least two multimeric barcoding reagents, wherein each multimeric barcoding reagent comprises first and second barcoded oligonucleotides linked together, wherein the barcoded oligonucleotides each comprise in the 5' to 3' direction a target region and a barcode region, wherein the barcode regions of the first and second barcoded oligonucleotides of a first multimeric barcoding reagent of the library are different to the barcode regions of the first and second barcoded oligonucleotides of a second multimeric barcoding reagent of the library, and wherein the sample is further contacted with first and second target primers for each multimeric barcoding reagent; and (b) performing the following steps for each microparticle (i) annealing the target region of the first barcoded oligonucleotide to a first sub-sequence of a first fragment of the target nucleic acid (e.g. genomic DNA) of the microparticle, and annealing the target region of the second barcoded oligonucleotide to a first sub-sequence of a second fragment of the target nucleic acid (e.g. genomic DNA) of the microparticle, (ii) annealing the first target primer to a second sub-sequence of the first fragment of the target nucleic acid of the microparticle, wherein the second sub-sequence is 3' of the first sub-sequence, and annealing the second target primer to a second sub-sequence of the second fragment of the target nucleic acid of the microparticle, wherein the second sub-sequence is 3' of the first sub-sequence, (iii) extending the first target primer using the first fragment of the target nucleic acid of the microparticle as template until it reaches the first sub-sequence to produce a first extended target primer, and extending the second target primer using the second fragment of the target nucleic acid of the microparticle until it reaches the first sub-sequence to produce a second extended target primer, and (iv) ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different and each comprises at least one nucleotide synthesised from the target nucleic acid as a template.

The multimeric barcoding reagents may each comprise: (i) first and second hybridization molecules linked together, wherein each of the hybridization molecules comprises a nucleic acid sequence comprising a hybridization region; and (ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule.

The multimeric barcoding reagents may each comprise: (i) first and second barcode molecules linked together, wherein each of the barcode molecules comprises a nucleic acid sequence comprising a barcode region; and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule.

In the methods, prior to step (b), the method may comprise a step of transferring the first and second barcoded oligonucleotides of the first multimeric barcoding reagent into the first microparticle of the sample and transferring the first and second barcoded oligonucleotides of the second multimeric barcoding reagent into the second microparticle of the sample. Optionally, prior to step (b), the method further comprises a step of transferring the target primers into the first and second microparticles. Optionally, prior to step (b), the method further comprises a step of transferring the first multimeric barcoding reagent into the first microparticle and transferring the second multimeric barcoding reagent into the second microparticle.

The invention provides a method of preparing a sample for sequencing, wherein the sample comprises at least two microparticles originating from blood, wherein each microparticle comprises at least two fragments of a target nucleic acid, and wherein the method comprises the steps of: (a) contacting the sample with a library comprising first and second multimeric barcoding reagents, wherein each multimeric barcoding reagent comprises first and second barcode molecules linked together, wherein each of the barcode molecules comprises a nucleic acid sequence comprising, optionally in the 5' to 3' direction, a barcode region and an adapter region; (b) appending a coupling sequence to first and second fragments of the target nucleic acid (e.g. genomic DNA) of first and second microparticles; (c) for each of the multimeric barcoding reagents, annealing the coupling sequence of the first fragment to the adapter region of the first barcode molecule, and annealing the coupling sequence of the second fragment to the adapter region of the second barcode molecule; and (d) for each of the multimeric barcoding reagents, appending barcode sequences to each of the at least two fragments of the target nucleic acid of the microparticle to produce first and second different barcoded target nucleic acid molecules, wherein the first barcoded target nucleic acid molecule comprises the nucleic acid sequence of the barcode region of the first barcode molecule and the second barcoded target nucleic acid molecule comprises the nucleic acid sequence of the barcode region of the second barcode molecule.

In the method, each of the barcode molecules may comprise a nucleic acid sequence comprising, in the 5' to 3' direction, a barcode region and an adapter region, and wherein step (d) comprises, for each of the multimeric barcoding reagents, extending the coupling sequence of the first fragment using the barcode region of the first barcode molecule as a template to produce a first barcoded target nucleic acid molecule, and extending the coupling sequence of the second fragment using the barcode region of the second barcode molecule as a template to produce a second barcoded target nucleic acid molecule, wherein the first barcoded target nucleic acid molecule comprises a sequence complementary to the barcode region of the first barcode molecule and the second barcoded target nucleic acid molecule comprises a sequence complementary to the barcode region of the second barcode molecule.

In the method, each of the barcode molecules may comprise a nucleic acid sequence comprising, in the 5' to 3' direction, an adapter region and a barcode region, wherein step (d) comprises, for each of the multimeric barcoding reagents, (i) annealing and extending a first extension primer using the barcode region of the first barcode molecule as a template to produce a first barcoded oligonucleotide, and annealing and extending a second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule, (ii) ligating the 3' end of the first barcoded oligonucleotide to the 5' end of the coupling sequence of the first fragment to produce a first barcoded target nucleic acid molecule and ligating the 3' end of the second barcoded oligonucleotide to the 5' end of the coupling sequence of the second fragment to produce a second barcoded target nucleic acid molecule.

In the method, each of the barcode molecules may comprise a nucleic acid sequence comprising, in the 5' to 3' direction, an adapter region, a barcode region and a priming region wherein step (d) comprises, for each of the multimeric barcoding reagents, (i) annealing a first extension primer to the priming region of the first barcode molecule and extending the first extension primer using the barcode region of the first barcode molecule as a template to produce a first barcoded oligonucleotide, and annealing a second extension primer to the priming region of the second barcode molecule and extending the second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule, and (ii) ligating the 3' end of the first barcoded oligonucleotide to the 5' end of the coupling sequence of the first fragment to produce a first barcoded target nucleic acid molecule and ligating the 3' end of the second barcoded oligonucleotide to the 5' end of the coupling sequence of the second fragment to produce a second barcoded target nucleic acid molecule.

Prior to step (b) or step (c), the method may comprise a step of transferring the first multimeric barcoding reagent, coupling sequences and/or extension primers into the first microparticle and transferring the second multimeric barcoding reagent, coupling sequences and/or extension primers into the second microparticle The method may comprise: (a) contacting the sample with a library comprising first and second multimeric barcoding reagents, wherein each multimeric barcoding reagent comprises first and second barcode molecules linked together, wherein each of the barcode molecules comprises a nucleic acid sequence comprising, in the 5' to 3' direction, a barcode region and an adapter region, and wherein the sample is further contacted with first and second adapter oligonucleotides for each of the multimeric barcoding reagents, wherein the first and second adapter oligonucleotides each comprise an adapter region, and; (b) ligating the first and second adapter oligonucleotides for the first multimeric barcoding reagent to first and second fragments of the target nucleic acid of the first microparticle, and ligating the first and second adapter oligonucleotides for the second multimeric barcoding reagent to first and second fragments of the target nucleic acid of the second microparticle; (c) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and (d) for each of the multimeric barcoding reagents, extending the first adapter oligonucleotide using the barcode region of the first barcode molecule as a template to produce a first barcoded target nucleic acid molecule, and extending the second adapter oligonucleotide using the barcode region of the second barcode molecule as a template to produce a second barcoded target nucleic acid molecule, wherein the first barcoded target nucleic acid molecule comprises a sequence complementary to the barcode region of the first barcode molecule and the second barcoded target nucleic acid molecule comprises a sequence complementary to the barcode region of the second barcode molecule.

The method may comprise the steps of: (a) contacting the sample with a library comprising first and second multimeric barcoding reagents, wherein each multimeric barcoding reagent comprises: (i) first and second barcode molecules linked together, wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule, wherein the second barcoded oligonucleotide comprises a barcode region annealed to the barcode region of the second barcode molecule, and wherein the barcode regions of the first and second barcoded oligonucleotides of the first multimeric barcoding reagent of the library are different to the barcode regions of the first and second barcoded oligonucleotides of the second multimeric barcoding reagent of the library; wherein the sample is further contacted with first and second adapter oligonucleotides for each of the multimeric barcoding reagents, wherein the first and second adapter oligonucleotides each comprise an adapter region; (b) annealing or ligating the first and second adapter oligonucleotides for the first multimeric barcoding reagent to first and second fragments of the target nucleic acid (e.g. genomic DNA) of the first microparticle, and annealing or ligating the first and second adapter oligonucleotides for the second multimeric barcoding reagent to first and second fragments of the target nucleic acid (e.g. genomic DNA) of the second microparticle; (c) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and (d) for each of the multimeric barcoding reagents, ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.

In the method, step (b) may comprise annealing the first and second adapter oligonucleotides for the first multimeric barcoding reagent to first and second fragments of the target nucleic acid (e.g. genomic DNA) of the first microparticle, and annealing the first and second adapter oligonucleotides for the second multimeric barcoding reagent to first and second fragments of the target nucleic acid (e.g. genomic DNA) of the second microparticle, and wherein either: (i) for each of the multimeric barcoding reagents, step (d) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the fragments of the target nucleic acid as a template, or (ii) for each of the multimeric barcoding reagents, before step (d), the method comprises extending the first and second adapter oligonucleotides to produce first and second different target nucleic acid molecules each of which comprises at least one nucleotide synthesised from the fragments of the target nucleic acid as a template.

In the methods, prior to the step of annealing or ligating the first and second adapter oligonucleotides to first and second fragments of the target nucleic acid, the method may comprise appending a coupling sequence to each of the fragments of the target nucleic acid, wherein the first and second adapter oligonucleotides are then annealed or ligated to the coupling sequences of the first and second fragments of the target nucleic acid.

In the methods, prior to step (b) or step (c), the method may comprise a step of transferring the first and second adapter oligonucleotides for the first multimeric barcoding reagent into the first microparticle and transferring the first and second adapter oligonucleotides for the second multimeric barcoding reagent into the second microparticle, optionally wherein the step further comprises transferring the first multimeric barcoding reagent into the first microparticle and transferring the second multimeric barcoding reagent into the second microparticle.

In any method described herein, the method may comprise a step of cross-linking the fragments of the target nucleic acid (e.g. genomic DNA) in the microparticle(s). The step may be performed with a chemical crosslinking agent e.g. formaldehyde, paraformaldehyde, glutaraldehyde, disuccinimidyl glutarate, ethylene glycol bis(succinimidyl succinate), a homobifunctional crosslinker, or a heterobifunctional crosslinker. This step may be performed before any permeabilisation step, after any permeabilisation step, before any partitioning step, before any step of appending coupling sequences, after any step of appending coupling sequences, before any step of appending barcode sequences (e.g. before a step (b)), after any step of appending barcode sequences (e.g. after a step (d)), whilst appending barcode sequences, or any combination thereof. For example, prior to contacting a sample comprising microparticles with a library of two or more multimeric barcoding reagents, the sample comprising microparticles may be crosslinked. Any such crosslinking step may further be ended by a quenching step, such as quenching a formaldehyde-crosslinking step by mixing with a solution of glycine. Any such crosslinks may be removed prior to specific subsequent steps of the protocol, such as prior to a primer-extension, PCR, or nucleic acid purification step.

In the methods, during step (b), (c) and/or (d) (i.e. the steps of appending the barcode sequences), the microparticles and/or fragments of the target nucleic acid may be contained within a gel or hydrogel, such as an agarose gel, a polyacrylamide gel, or any covalently crosslinked gel, such as a covalently crosslinked poly (ethylene glycol) gel, or a covalently crosslinked gel comprising a mixture of a thiol-functionalised poly (ethylene glycol) and an acrylate-functionalised poly (ethylene glycol).

In any method described herein, optionally after the step of cross-linking, the method may comprise permeabilising the microparticle(s). The microparticles may be permeabilised with an incubation step. The incubation step may be performed in the presence of a chemical surfactant. Optionally this permeabilisation step may take place before appending barcode sequences (e.g. before step (b)), after appending barcode sequences (e.g. after step (d)), or both before and after appending barcode sequences. The incubation step may be performed at a temperature of at least 20 degrees Celsius, at least 30 degrees Celsius, at least 37 degrees Celsius, at least 45 degrees Celsius, at least 50 degrees Celsius, at least 60 degrees Celsius, at least 65 degrees Celsius, at least 70 degrees Celsius, or at least 80 degrees Celsius. The incubation step may be at least 1 second long, at least 5 seconds long, at least 10 seconds long, at least 30 seconds long, at least 1 minute long, at least 5 minutes long, at least 10 minutes long, at least 30 minutes long, at least 60 minutes long, or at least 3 hours long. This step may be performed after any crosslinking step, before any permeabilisation step, after any permeabilisation step, before any partitioning step, before any step of appending coupling sequences, after any step of appending coupling sequences, before any step of appending barcode sequences (e.g. before step (b)), after any step of appending barcode sequences (e.g. after step (d)), whilst appending barcode sequences, or any combination thereof. For example, prior to contacting a sample comprising microparticles with a library of two or more multimeric barcoding reagents, the sample comprising microparticles may be crosslinked, and then permeabilised in the presence of a chemical surfactant.

In any of the methods described herein, the sample of microparticles may be digested with a proteinase digestion step, such as a digestion with a Proteinase K enzyme. Optionally, this proteinase digestion step may be at least 10 seconds long, at least 30 seconds long, at least 60 seconds long, at least 5 minutes long, at least 10 minutes long, at least 30 minutes long, at least 60 minutes long, at least 3 hours long, at least 6 hours long, at least 12 hours long, or at least 24 hours long. This step may be performed after any crosslinking step, before any permeabilisation step, after any permeabilisation step, before any partitioning step, before any step of appending coupling sequences, after any step of appending couplings sequences, before any step of appending barcode sequences (e.g. before step (b)), after any step of appending barcode sequences (e.g. after step (d)), whilst appending barcode sequences, or any combination thereof. For example, prior to contacting a sample comprising microparticles with a library of two or more multimeric barcoding reagents, the sample comprising microparticles may be crosslinked, and then partially digested with a Proteinase K digestion step.

In the methods, the barcoded oligonucleotides, adapter oligonucleotides and/or multimeric barcoding reagents may be transferred into the microparticles by complexation with a transfection reagent or lipid carrier (e.g. a liposome or a micelle).

The transfection reagent may be a lipid transfection reagent e.g. a cationic lipid transfection reagent. Optionally, said cationic lipid transfection reagent comprises at least two alkyl chains. Optionally, said cationic lipid transfection reagent may be a commercially available cationic lipid transfection reagent such as Lipofectamine.

In the methods, the barcoded oligonucleotides of the first multimeric barcoding reagent may be comprised within a first lipid carrier, and wherein the barcoded oligonucleotides of the second multimeric barcoding reagent may be comprised within a second lipid carrier. The lipid carrier may be a liposome or a micelle.

In the methods, steps (a) and (b), and optionally (c) and (d), may be performed on the at least two microparticles in a single reaction volume.

The method may further comprise, prior to step (b), the step of partitioning the nucleic acid sample into at least two different reaction volumes.

The invention provides a method of analysing a sample comprising a microparticle originating from blood, wherein the microparticle contains at least two fragments of a target nucleic acid (e.g. genomic DNA), and wherein the method comprises: (a) preparing the sample for sequencing comprising: (i) contacting the sample with a multimeric barcoding reagent comprising first and second barcode regions linked together, wherein each barcode region comprises a nucleic acid sequence, and (ii) appending barcode sequences to each of the at least two fragments of the target nucleic acid of the microparticle to produce first and second different barcoded target nucleic acid molecules, wherein the first barcoded target nucleic acid molecule comprises the nucleic acid sequence of the first barcode region and the second barcoded target nucleic acid molecule comprises the nucleic acid sequence of the second barcode region; and (b) sequencing each of the barcoded target nucleic acid molecules to produce at least two linked sequence reads.

In the methods, prior to the step of appending barcode sequences to each of the at least two fragments of genomic DNA of the microparticle, the method may comprise appending a coupling sequence to each of the fragments of genomic DNA of the microparticle, wherein a barcode sequence is then appended to the coupling sequence of each of the at least two fragments of genomic DNA of the microparticle to produce the first and second different barcoded target nucleic acid molecules.

The method may further comprise, optionally prior to step (a)(i) or (a)(ii), the step of transferring the first and second barcode regions of the multimeric barcoding reagent into the microparticle Any method described herein may further comprise, prior to the step of transferring, the step of cross-linking the fragments of genomic DNA in the microparticle. The cross-linking step may be performed with a chemical crosslinking agent e.g. formaldehyde, paraformaldehyde, glutaraldehyde, disuccinimidyl glutarate, ethylene glycol bis(succinimidyl succinate), a homobifunctional crosslinker, or a heterobifunctional crosslinker.

During step (a) the microparticles and/or fragments of the target nucleic acid may be contained within a gel or hydrogel, such as an agarose gel, a polyacrylamide gel, or any covalently crosslinked gel, such as a covalently crosslinked poly (ethylene glycol) gel, or a covalently crosslinked gel comprising a mixture of a thiol-functionalised poly (ethylene glycol) and an acrylate-functionalised poly (ethylene glycol).

Prior to the step of transferring, and optionally after the step of cross-linking, the method may further comprise the step of permeabilising the microparticle The microparticle(s) may be permeabilised with an incubation step. The incubation step may be performed in the presence of a chemical surfactant. Optionally this permeabilisation step may take place before appending barcode sequences (e.g. before step (a)(ii)), after appending barcode sequences (e.g. after step (a)(ii)), or both before and after appending barcode sequences. The incubation step may be performed at a temperature of at least 20 degrees Celsius, at least 30 degrees Celsius, at least 37 degrees Celsius, at least 45 degrees Celsius, at least 50 degrees Celsius, at least 60 degrees Celsius, at least 65 degrees Celsius, at least 70 degrees Celsius, or at least 80 degrees Celsius. The incubation step may be at least 1 second long, at least 5 seconds long, at least 10 seconds long, at least 30 seconds long, at least 1 minute long, at least 5 minutes long, at least 10 minutes long, at least 30 minutes long, at least 60 minutes long, or at least 3 hours long.

The sample of microparticles may be digested with a proteinase digestion step, such as a digestion with a Proteinase K enzyme. Optionally, this proteinase digestion step may be at least 10 seconds long, at least 30 seconds long, at least 60 seconds long, at least 5 minutes long, at least 10 minutes long, at least 30 minutes long, at least 60 minutes long, at least 3 hours long, at least 6 hours long, at least 12 hours long, or at least 24 hours long. This step may be performed before permeabilisation, after permeabilisation, before appending barcode sequences (e.g. before step (a) (ii)), after appending barcode sequences (e.g. after step (a)(ii)), whilst appending barcode sequences, or any combination thereof.

The first and second barcode regions of the multimeric barcoding reagent may transferred into the microparticle by complexation with a transfection reagent or lipid carrier (e.g. a liposome or a micelle).

The transfection reagent may be a lipid transfection reagent e.g. a cationic lipid transfection reagent. Optionally, said cationic lipid transfection reagent comprises at least two alkyl chains. Optionally, said cationic lipid transfection reagent may be a commercially available cationic lipid transfection reagent such as Lipofectamine.

Step (a) of the method may be performed by any of the methods of preparing a sample (or nucleic acid sample) for sequencing described herein.

The method may comprise preparing first and second samples for sequencing, wherein each sample comprises at least one microparticle originating from blood, wherein each microparticle contains at least two fragments of a target nucleic acid (e.g. genomic DNA), and wherein the barcode sequences each comprise a sample identifier region, and wherein the method comprises: (i) performing step (a) for each sample, wherein the barcode sequence(s) appended to the fragments of the nucleic acid from the first sample have a different sample identifier region to the barcode sequence(s) appended to the fragments of the target nucleic acid from the second sample; (ii) performing step (b) for each sample, wherein each sequence read comprises the sequence of the sample identifier region; and (iii) determining the sample from which each sequence read is derived by its sample identifier region.

The method may comprise analysing a sample comprising at least two microparticles originating from blood, wherein each microparticle contains at least two fragments of a target nucleic acid (e.g. genomic DNA), and wherein the method comprises the steps of: (a) preparing the sample for sequencing comprising: (i) contacting the sample with a library of multimeric barcoding reagents comprising a multimeric barcoding reagent for each of the two or more microparticles, wherein each multimeric barcoding reagent is as defined herein; and (ii) appending barcode sequences to each of the at least two fragments of the target nucleic acid of each microparticle, wherein at least two barcoded target nucleic acid molecules are produced from each of the at least two microparticles, and wherein the at least two barcoded target nucleic acid molecules produced from a single microparticle each comprise the nucleic acid sequence of a barcode region from the same multimeric barcoding reagent;

and (b) sequencing each of the barcoded target nucleic acid molecules to produce at least two linked sequence reads for each microparticle.

The barcode sequences may be appended to the fragments of genomic DNA of the microparticles in a single reaction volume i.e. step (a) of the method may be performed in a single reaction volume.

Prior to the step of appending (step (a)(ii)), the method may further comprise the step of partitioning the sample into at least two different reaction volumes.

In any of the methods, prior to the step of appending barcode sequences, the multimeric barcoding reagents may separate, fractionate, or dissolve into two or more constituent parts e.g. releasing barcoded oligonucleotides.

In any of the methods, the multimeric barcoding reagents may be at a concentration of less than 1.0 femtomolar, less than 10 femtomolar, less than 100 femtomolar, less than 1.0 picomolar, less than 10 picomolar, less than 100 picomolar, less than 1 nanomolar, less than 10 nanomolar, less than 100 nanomolar, or less than 1.0 micromolar.

4. Linking by Linking Fragments Together

The invention provides a method of analysing a sample comprising a microparticle originating from blood, wherein the microparticle contains at least two fragments of a target nucleic acid (e.g. genomic DNA), and wherein the method comprises: (a) preparing the sample for sequencing comprising linking together at least two fragments of the target nucleic acid of the microparticle to produce a single nucleic acid molecule comprising the sequences of the at least two fragments of the target nucleic acid; and (b) sequencing each of the fragments in the single nucleic acid molecule to produce at least two linked sequence reads.

The at least two fragments of the target nucleic acid (e.g. genomic DNA) may be contiguous in the single nucleic acid molecule.

The at least two linked sequence reads may be provided within a single raw sequence read.

The method may comprise, prior to the step of linking, appending a coupling sequence to at least one of the fragments of the target nucleic acid (e.g. genomic DNA) and then linking together the at least two fragments of the target nucleic acid by the coupling sequence.

The fragments of the target nucleic acid (e.g. genomic DNA) may be linked together by a solid support, wherein two or more fragments are linked to the same solid support (directly or indirectly e.g. via a coupling sequence). Optionally, the solid support is a bead, such as a Styrofoam bead, a superparamagnetic bead, or an agarose bead.

The fragments of the target nucleic acid (e.g. genomic DNA) may be linked together by a ligation reaction e.g. a double-stranded ligation reaction or a single-stranded ligation reaction The ends of fragments of a target nucleic acid may be converted into blunt, ligatable double-stranded ends in a blunting reaction, and the method may comprise ligating two or more of the fragments to each other by a blunt-end ligation reaction.

The ends of fragments of a target nucleic acid may be contacted with a restriction enzyme, wherein the restriction enzyme digests the fragments at restriction sites to create ligation junctions at these restriction sites, and wherein the method may comprise ligating two or more of the fragments to each other by a ligation reaction at the ligation junctions. Any target nucleic acid may be contacted with a restriction enzyme, wherein the restriction enzyme digests the fragments at restriction sites to create ligation junctions at these restriction sites, and wherein the method may comprise ligating two or more of the fragments to each other by a ligation reaction at the ligation junctions. Optionally, said restriction enzyme may be EcoRI, HindIII, or BglII.

A coupling sequence may be appended to two or more fragments of a target nucleic acid prior to linking together the fragments. Optionally, two or more different coupling sequences are appended to a population of fragments of the target nucleic acid.

The coupling sequence may comprise a ligation junction on at least one end, and wherein a first coupling sequence is appended to a first fragment of the target nucleic acid, and wherein a second coupling sequence is appended to a second fragment of the target nucleic acid, and wherein the two coupling sequences are ligated to each other, thus linking together the two fragments of the target nucleic acid.

The coupling sequence may comprise an annealing region on at least one 3' end, and wherein a first coupling sequence is appended to a first fragment of the target nucleic acid, and wherein a second coupling sequence is appended to a second fragment of the target nucleic acid, and wherein the two coupling sequences are complementary to and annealed to each other along a segment at least one nucleotide in length, and wherein a DNA polymerase is used to extend at least one of the 3' ends of a first coupling sequence at least one nucleotide into the sequence of the second fragment of the target nucleic acid, thus linking together the two fragments of the target nucleic acid (e.g. genomic DNA).

Prior to linking together the at least two fragments, the method may further comprise a step of cross-linking the microparticles e.g. with a chemical crosslinking agent, such as formaldehyde, paraformaldehyde, glutaraldehyde, disuccinimidyl glutarate, ethylene glycol bis(succinimidyl succinate), a homobifunctional crosslinker, or a heterobifunctional crosslinker.

Prior to linking together the at least two fragments, the method may further comprise partitioning the microparticles into two or more partitions.

The method may further comprise permeabilizing the microparticles during an incubation step. This step may be performed before partitioning (if performed), after partitioning (if performed), before linking together the fragments and/or after linking together the fragments.

The incubation step may be performed in the presence of a chemical surfactant, such as Triton X-100 ($C_{14}H_{22}O$ ($C_2H_4O)_n$ (n=9-10)), NP-40, Tween 20, Tween 80, Saponin, Digitonin, or Sodium dodecyl sulfate.

The incubation step is performed at a temperature of at least 20 degrees Celsius, at least 30 degrees Celsius, at least 37 degrees Celsius, at least 45 degrees Celsius, at least 50 degrees Celsius, at least 60 degrees Celsius, at least 65 degrees Celsius, at least 70 degrees Celsius, at least 80 degrees Celsius, at least 90 degrees Celsius, or at least 95 degrees Celsius.

The incubation step may be at least 1 second long, at least 5 seconds long, at least 10 seconds long, at least 30 seconds long, at least 1 minute long, at least 5 minutes long, at least 10 minutes long, at least 30 minutes long, at least 60 minutes long, or at least 3 hours long.

The method may comprise digesting the sample of microparticles with a proteinase digestion step, such as a digestion with a Proteinase K enzyme. Optionally, this proteinase digestion step may be at least 10 seconds long, at least 30 seconds long, at least 60 seconds long, at least 5 minutes long, at least 10 minutes long, at least 30 minutes long, at least 60 minutes long, at least 3 hours long, at least 6 hours long, at least 12 hours long, or at least 24 hours long. This step may be performed before partitioning (if performed), after partitioning (if performed), before linking together the fragments and/or after linking together the fragments.

The method may comprise amplifying (original) fragments of a target nucleic acid, and then linking together two or more of the resulting nucleic acid molecules.

The step of linking together the fragments may create a concatamerised nucleic acid molecule, comprising at least 3, at least 5, at least 10, at least 50, at least 100, at least 500, or at least 1000 nucleic acid molecules that have been appended to each other into single, contiguous nucleic acid molecules.

The method may be used to produce linked sequence reads for at least 3 microparticles, at least 5 microparticles, at least 10 microparticles, at least 50 microparticles, at least 100 microparticles, at least 1000 microparticles, at least 10,000 microparticles, at least 100,000 microparticles, at least 1,000,000 microparticles, at least 10,000,000 microparticles, at least 100,000,000 microparticles, at least 1,000,000,000 microparticles, at least 10,000,000,000 microparticles, or at least 100,000,000,000 microparticles.

The sample may comprise at least two microparticles originating from blood, wherein each microparticle contains at least two fragments of a target nucleic acid (e.g. genomic DNA), and wherein the method comprises performing step (a) to produce a single nucleic acid molecule comprising the sequences of the at least two fragments of the target nucleic acid for each microparticle, and performing step (b) to produce linked sequence reads for each microparticle.

Before, during, and/or after the step of linking together at least two fragments of the target nucleic acid (e.g. genomic DNA), the method may comprise the step of cross-linking the fragments of the target nucleic acid in the microparticle(s). The cross-linking step may be performed with a chemical crosslinking agent e.g. formaldehyde, paraformaldehyde, glutaraldehyde, disuccinimidyl glutarate, ethylene glycol bis(succinimidyl succinate), a homobifunctional crosslinker, or a heterobifunctional crosslinker.

Before, during, and/or after the step of linking together at least two fragments of the target nucleic acid (e.g. genomic DNA), and/or optionally after the step of cross-linking the fragments of the target nucleic acid in the microparticle(s), the method comprises the step of permeabilising the microparticle(s).

Prior to step (a), the method may further comprises the step of partitioning the nucleic acid sample into at least two different reaction volumes.

In one embodiment of a method of linking together at least two fragments of the target nucleic acid of a circulating microparticle to produce a single nucleic acid molecule comprising the sequences of at least two fragments of the target nucleic acid, a sample comprising at least one circulating microparticle (e.g. wherein said sample is obtained and/or purified by any method disclosed herein) is crosslinked at room temperature in a solution of 1% formaldehyde for 10 minutes, and then the formaldehyde crosslinking step is quenched with glycine. The microparticles are pelleted with a centrifugation step (e.g. at 3000×G for 5 minutes) and resuspended in 1× NEBuffer 2 (New England Biolabs) with 1.0% sodium dodecyl sulfate (SDS), and incubated at 45 degrees Celsius for 10 minutes to permeabilise the microparticle(s). The SDS is quenched by addition of Triton X-100, and the solution is incubated with AluI (New England Biolabs) at 37 degrees Celsius overnight to create blunt, ligatable ends. The enzyme is inactivated by addition of SDS to a final concentration of 1.0% and incubation at 65 degrees Celsius for 15 minutes. The SDS is quenched by addition of Triton X-100, and the solution is diluted at least 10-fold in 1× buffer for T4 DNA Ligase, and to a total concentration of DNA of at most 1.0 nanogram of DNA per microliter. The diluted solution is incubated with T4 DNA Ligase overnight at 16 degrees Celsius to ligate together fragments from circulating microparticles. Crosslinks are then reversed and protein components degraded by incubation overnight at 65 degrees Celsius in a solution of Proteinase K. Ligated DNA is then purified (e.g. with a Qiagen spin-column PCR Purification Kit, and/or Ampure XP beads). Illumina sequencing adapter sequences are then appended with a Nextera in vitro transposition method (Illumina; as per manufacturer's protocol), an appropriate number of PCR cycles are performed to amplify the ligated material; and then amplified and purified size-appropriate DNA is sequenced on an Illumina sequencer (e.g. an Illumina NextSeq 500, or a MiSeq) with paired-end reads of at least 50 bases each. Each end of the paired-end sequences is mapped independently to the reference human genome to elucidate linked sequence reads (e.g. reads wherein the two ends comprise sequences from different fragments of genomic DNA from a single circulating microparticle).

A method of linking together at least two fragments of the target nucleic acid of a microparticle to produce a single nucleic acid molecule comprising the sequences of the at least two fragments of the target nucleic acid may have a variety of unique properties and features that make it desirable as a method for linking sequences from one or more circulating microparticles. In one respect, such methods enable the linking of sequences from circulating microparticles without complex instrumentation (e.g. microfluidics for partitioning-based approaches). Furthermore, the approach is (broadly) able to be performed in single, individual reactions that could comprise a large number of circulating microparticles (e.g. hundreds, or thousands, or greater numbers), and thus is able to process a large number of circulating microparticles without the need for multiple reactions that may otherwise be necessary, for example, in a combinatorial indexing approach. Furthermore, since the method does not necessarily require the use of barcodes and/or multimeric barcoding reagents, it is not limited by the size of barcode libraries (and/or multimeric barcoding reagent libraries) to achieve useful molecular measurement of linked sequences from circulating microparticles.

5. Linking by Partitioning

The methods may be performed on a nucleic acid sample comprising at least two microparticles that has been partitioned into at least two different reaction volumes (or partitions).

In any of the methods, a nucleic acid sample comprising at least two microparticles may be partitioned into at least two different reaction volumes (or partitions). The different reaction volumes (or partitions) may be provided by different reaction vessels (or different physical reaction vessels). The different reaction volumes (or partitions) may be provided by different aqueous droplets e.g. different aqueous droplets within an emulsion or different aqueous droplets on a solid support (e.g. a slide).

For example, a nucleic acid sample may be partitioned prior to appending barcode sequences to fragments of the target nucleic acid of a microparticle. Alternatively, a nucleic acid sample may be partitioned prior to linking together at least two fragments of the target nucleic acid of a microparticle.

For any method involving a partitioning step, any steps of the method subsequent to said partitioning step may be performed independently upon each partition, such as any step of appending barcode sequences or appending coupling sequences, or any step of ligating, annealing, primer-extension, or PCR. Reagents (such as oligonucleotides, enzymes, and buffers) may be added directly to each partition. In methods wherein partitions comprise aqueous droplets in an emulsion, such addition steps may be performed via a process of merging aqueous droplets within the emulsion, such as with a microfluidic droplet-merger conduit, and optionally using a mechanical or thermal mixing step.

The partitions comprise different droplets of aqueous solution within an emulsion, and wherein the emulsion is a water-in-oil emulsion, and wherein droplets are generated by a physical shaking or a vortexing step, or wherein the droplets are generated by the merger of an aqueous solution with an oil solution within a microfluidic conduit or junction.

For methods wherein partitions comprise aqueous droplets within an emulsion, such a water-in-oil emulsion may be generated by any method or tool known in the art. Optionally, this may include commercially available microfluidic systems such as the Chromium system or other systems available from 10× Genomics Inc, digital droplet generators from Raindance Technologies or Bio-Rad, as well as component-based systems for microfluidic generation and manipulation such as Drop-Seq (Macosko et al., 2015, Cell 161, 1202-1214) and inDrop (Klein et al., 2015, Cell 161, 1187-1201).

The partitions may comprise different physically non-overlapping spatial volumes within a gel or hydrogel, such as an agarose gel, a polyacrylamide gel, or any covalently crosslinked gel, such as a covalently crosslinked poly (ethylene glycol) gel, or a covalently crosslinked gel comprising a mixture of thiol-functionalised poly (ethylene glycol) molecules and acrylate-functionalised poly (ethylene glycol) molecules.

The sample of microparticles may be separated into a total of at least 10, at least 100, at least 1000, at least 10,000, at least 100,000, at least 1,000,000, at least 10,000,000, at least 100,000,000, or at least 1,000,000,000 partitions. Preferably, the solution of microparticles is separated into a total of at least 1000 partitions.

The sample of microparticles may be separated into partitions such that an average of less than 0.0001 microparticles, less than 0.001 microparticles, less than 0.01 microparticles, less than 0.1 microparticles, less than 1.0 microparticle, less than 10 microparticles, less than 100 microparticles, less than 1000 microparticles, less than 10,000 microparticles, less than 100,000 microparticles, less than 1,000,000 microparticles, less than 10,000,000 microparticles, or less than 100,000,000 microparticles are present per partition. Preferably, an average of less than 1.0 microparticle is present per partition.

The solution of microparticles may be separated into partitions such that an average of less than 1.0 attogram of DNA, less than 10 attograms of DNA, less than 100 attograms of DNA, less than 1.0 femtogram of DNA, less than 10 femtograms of DNA, less than 100 femtograms of DNA, less than 1.0 picogram of DNA, less than 10 picograms of DNA, less than 100 picograms of DNA, or less than 1.0 nanogram of DNA is present per partition. Preferably, less than 10 picograms of DNA are present per partition.

The partitions may be less than 100 femtoliters, less than 1.0 picoliter, less than 10 picoliters, less than 100 picoliters, less than 1.0 nanoliter, less than 10 nanoliters, less than 100 nanoliters, less than 1.0 microliter, less than 10 microliters, less than 100 microliters, or less than 1.0 milliliter in volume.

Barcode sequences may be provided in each partition. For each of the two or more partitions comprising barcode sequences, the barcode sequences contained therein may comprise multiple copies of the same barcode sequence, or comprise different barcode sequences from the same set of barcode sequences.

After the microparticles have been separated into two or more partitions, the microparticles may permeabilised with an incubation step by any of the methods described herein.

The sample of microparticles may be digested with a proteinase digestion step, such as a digestion with a Proteinase K enzyme. Optionally, this proteinase digestion step may be at least 10 seconds long, at least 30 seconds long, at least 60 seconds long, at least 5 minutes long, at least 10 minutes long, at least 30 minutes long, at least 60 minutes long, at least 3 hours long, at least 6 hours long, at least 12 hours long, or at least 24 hours long. This step may be performed before partitioning, after partitioning, before appending barcode sequences, after appending barcode sequences and/or whilst appending barcode sequences.

Appending Sequences by Combinatorial Barcoding Processes

A method of appending barcode sequences may comprise at least two steps of a combinatorial barcoding process, wherein a first barcoding step is performed wherein a sample of microparticles is partitioned into two or more partitions, wherein each partition comprises a different barcode sequence or a different set of barcode sequences that are then appended to sequences from fragments of target nucleic acid (e.g. genomic DNA) of microparticles contained within that partition, and wherein the barcoded nucleic acid molecules of at least two partitions are then merged into a second sample mixture, and wherein this second sample mixture is then partitioned into two or more new partitions, wherein each new partition comprises a different barcode sequence or different set of barcode sequences that are then appended to sequences from fragments of the target nucleic acid (e.g. genomic DNA) of microparticles contained within the two or more new partitions.

Optionally, a combinatorial barcoding process may comprise a first barcoding step, wherein: A) a first sample mixture comprising at least first and second circulating microparticles is partitioned into at least first and second original partitions (for example, wherein at least a first circulating microparticle from the sample is partitioned into the first original partition, and wherein at least a second circulating microparticle from the sample is partitioned into the second original partition), wherein the first original partition comprises a barcode sequence (or a set of barcode sequences) different to a barcode sequence (or a set of barcode sequences) comprised within the second original partition, and wherein a barcode sequence (or barcode sequences from a set of barcode sequences) comprised within the first original partition is appended to at least first and second fragments of the target nucleic acid of the first circulating microparticle, and wherein a barcode sequence (or barcode sequences from a set of barcode sequences) comprised within the second original partition is appended to at least first and second fragments of the target nucleic acid of the second circulating microparticle; and wherein at least one circulating microparticle comprised within the first original partition and at least one circulating microparticle comprised within the second original partition are merged to produce a second sample mixture, and a second barcoding step, wherein: B) microparticles comprised within the second sample mixture are partitioned into at least first and second new partitions (for example, wherein at least a first circulating microparticle from the second sample mixture is partitioned into the first new partition, and wherein at least a second circulating microparticle from the second sample mixture is partitioned into the second new partition), wherein the first new partition comprises a barcode sequence (or a set of barcode sequences) different to a barcode sequence (or the set of barcode sequences) comprised within the second new partition, and wherein a barcode sequence (or barcode sequences from a set of barcode sequences) comprised within the first new partition is appended to at least first and second fragments of the target nucleic acid of the first circulating microparticle, and wherein a barcode sequence (or barcode sequences from a set of barcode sequences) comprised within the second new partition is appended to at least first and second fragments of the target nucleic acid of the second circulating microparticle.

Optionally, a combinatorial barcoding process may comprise a first barcoding step, wherein: A) a first sample mixture comprising at least first and second circulating microparticles is partitioned into at least first and second original partitions (for example, wherein at least a first circulating microparticle from the sample is partitioned into the first original partition, and wherein at least a second circulating microparticle from the sample is partitioned into the second original partition), wherein the first original partition comprises a barcode sequence (or a set of barcode sequences) comprised within barcoded oligonucleotides different to a barcode sequence (or a set of barcode sequences) comprised within barcoded oligonucleotides comprised within the second original partition, and wherein barcoded oligonucleotides comprised within the first original partition are appended to at least first and second fragments of the target nucleic acid of the first circulating microparticle, and wherein barcoded oligonucleotides comprised within the second original partition are appended to at least first and second fragments of the target nucleic acid of the second circulating microparticle; and wherein at least one circulating microparticle comprised within the first original partition and at least one circulating microparticle comprised within the second original partition are merged to produce a second sample mixture, and a second barcoding step, wherein: B) microparticles comprised within the second sample mixture are partitioned into at least first and second new partitions (for example, wherein at least a first circulating microparticle from the second sample mixture is partitioned into the first new partition, and wherein at least a second circulating microparticle from the second sample mixture is partitioned into the second new partition), wherein the first new partition comprises a barcode sequence (or a set of barcode sequences) comprised within barcoded oligonucleotides different to a barcode sequence (or a set of barcode sequences) comprised within barcoded oligonucleotides comprised within the second new partition, and wherein barcoded oligonucleotides comprised within the first new partition are appended to at least first and second fragments of the target nucleic acid of the first circulating microparticle, and wherein barcoded oligonucleotides comprised within the second new partition are appended to at least first and second fragments of the target nucleic acid of the second circulating microparticle.

Optionally, a combinatorial barcoding process may comprise a first barcoding step, wherein: A) a first sample mixture comprising at least first and second circulating microparticles is partitioned into at least first and second original partitions (for example, wherein at least a first circulating microparticle from the sample is partitioned into the first original partition, and wherein at least a second circulating microparticle from the sample is partitioned into the second original partition), wherein the first original partition comprises a barcode sequence (or a set of barcode sequences) comprised within barcoded oligonucleotides different to a barcode sequence (or a set of barcode sequences) comprised within barcoded oligonucleotides comprised within the second original partition, and wherein barcoded oligonucleotides comprised within the first original partition are ligated to at least first and second fragments of the target nucleic acid of the first circulating microparticle, and wherein barcoded oligonucleotides comprised within the second original partition are ligated to at least first and second fragments of the target nucleic acid of the second circulating microparticle; and wherein at least one circulating microparticle comprised within the first original partition and at least one circulating microparticle comprised within the second original partition are merged to produce a second sample mixture, and a second barcoding step, wherein: B) microparticles comprised within the second sample mixture are partitioned into at least first and second new partitions (for example, wherein at least a first circulating microparticle from the second sample mixture is partitioned into the first new partition, and wherein at least a second circulating microparticle from the second sample mixture is partitioned into the second new partition), wherein the first new partition comprises a barcode sequence (or a set of barcode sequences) comprised within barcoded oligonucleotides different to a barcode sequence (or a set of barcode sequences) comprised within barcoded oligonucleotides comprised within the second new partition, and wherein barcoded oligonucleotides comprised within the first new partition are ligated to at least first and second fragments of the target nucleic acid of the first circulating microparticle, and wherein barcoded oligonucleotides comprised within the second new partition are ligated to at least first and second fragments of the target nucleic acid of the second circulating microparticle.

Optionally, a combinatorial barcoding process may comprise A) a chemical crosslinking step, wherein a sample comprising at least first and second circulating microparticles is crosslinked with a chemical crosslinking agent (such as formaldehyde), and then optionally wherein the crosslinking step is ended by a quenching step, such as quenching a formaldehyde-crosslinking step by mixing the sample with a solution of glycine, and/or then optionally permeabilising the crosslinked microparticles (i.e., such that fragments of genomic DNA (and/or other target nucleic acids) are made physically accessible such that they can then be further manipulated; for example such that they may be barcoded in a barcoding step); optionally wherein any such permeabilisation is performed by incubation with a chemical surfactant such as a non-ionic detergent; and B) a first barcoding step, wherein a first sample mixture comprising at least first and second circulating microparticles is partitioned into at least first and second original partitions (for example, wherein at least a first circulating microparticle from the sample is partitioned into the first original partition, and wherein at least a second circulating microparticle from the sample is partitioned into the second original partition), wherein the first original partition comprises a barcode sequence (or a set of barcode sequences) comprised within barcoded oligonucleotides different to a barcode sequence (or a set of barcode sequences) comprised within barcoded oligonucleotides comprised within the second original partition, and wherein barcoded oligonucleotides comprised within the first original partition are ligated to at least first and second fragments of the target nucleic acid of the first circulating microparticle, and wherein barcoded oligonucleotides comprised within the second original partition are ligated to at least first and second fragments of the target nucleic acid of the second circulating microparticle; and wherein at least one circulating microparticle comprised within the first original partition and at least one circulating microparticle comprised within the second original partition are merged to produce a second sample mixture, and C) a second barcoding step, wherein microparticles comprised within the second sample mixture are partitioned into at least first and second new partitions (for example, wherein at least a first circulating microparticle from the second sample mixture is partitioned into the first new partition, and wherein at least a second circulating microparticle from the second sample mixture is partitioned into the second new partition), wherein the first new partition comprises a barcode sequence (or a set of barcode sequences) comprised within barcoded oligonucleotides different to a barcode sequence (or a set of barcode sequences) comprised within barcoded oligonucleotides comprised within the second new partition, and wherein barcoded oligonucleotides comprised within the first new partition are ligated to at least first and second fragments of the target nucleic acid of the first circulating microparticle, and wherein barcoded oligonucleotides comprised within the second new partition are ligated to at least first and second fragments of the target nucleic acid of the second circulating microparticle.

Optionally, in any combinatorial barcoding process, the method may comprise a step of cross-linking the circulating microparticles and/or fragments of a target nucleic acid (e.g. fragments of genomic DNA) in one or more circulating microparticle(s) prior to a first and/or second (and/or additional) barcoding step. The step may be performed with a chemical crosslinking agent e.g. formaldehyde, paraformaldehyde, glutaraldehyde, disuccinimidyl glutarate, ethylene glycol bis(succinimidyl succinate), a homobifunctional crosslinker, or a heterobifunctional crosslinker. This step may be performed before any permeabilisation step, after any permeabilisation step, before any partitioning step, before any step of appending barcode sequences, after any step of appending barcode sequences, whilst appending barcode sequences, or any combination thereof. Any such crosslinking step may further be ended by a quenching step, such as quenching a formaldehyde-crosslinking step by mixing with a solution of glycine. Any such crosslinks may further be removed prior to any subsequent steps of a laboratory protocol, such as prior to any primer-extension, and/or PCR, and/or purification step. A step of crosslinking by a chemical crosslinking agent serves the purpose of holding fragments of genomic DNA (and/or other target nucleic acids) within each microparticle in physical proximity to each other, such that the sample may be manipulated and processed whilst retaining the basic structural nature of the microparticles (i.e., whilst retaining physical proximity of genomic DNA fragments derived from the same microparticle).

Optionally, in any combinatorial barcoding process, in a step following a chemical crosslinking step, crosslinked microparticles may be permeabilised (i.e., such that fragments of genomic DNA (and/or other target nucleic acids) are made physically accessible such that they can then be further manipulated; for example such that they may be barcoded in a barcoding step); this permeabilisation may for example be performed by incubation with a chemical surfactant such as a non-ionic detergent. Optionally, a chemical surfactant for such a permeabilisation step may comprise Triton X-100 ($C_{14}H_{22}O(C_2H_4O)_n$ (n=9-10)), NP-40, Tween 20, Tween 80, Saponin, Digitonin, and/or Sodium dodecyl sulfate.

Optionally, in any combinatorial barcoding process, in any one or more step(s) following a chemical crosslinking step, the crosslinks may be partially or fully reversed (e.g., such that fragments of genomic DNA (and/or other target nucleic acids) are made more physically accessible such that they can then be further manipulated; for example such that they may be barcoded in a barcoding step); this crosslink-reversal may for example be performed by incubation at a high temperature, such as at least at least 45° C., at least 50° C., at least 55° C., at least 60° C., at least 65° C., at least 70° C., at least 75° C., at least 80° C., at least 85° C., or at least 90° C.; further, this crosslink-reversal may for example be performed for a certain duration of time, such as at least 1 minute, at least 5 minutes, at least 10 minutes, at least 20 minutes, at least 30 minutes, at least 60 minutes, at least 2 hours, at least 3 hours, at least 5 hours, or at least 24 hours.

Optionally, in any combinatorial barcoding process, following any one or more steps of appending barcode sequences (such as any step of appending and/or ligating barcoded oligonucleotides), and/or any one or more steps of partitioning one or more samples (e.g, circulating microparticles) into different partitions, and/or any one or more steps of merging two or more circulating microparticles into a single partition, and/or any one or more steps of chemical crosslinking, and/or any one or more other step(s), a purification process may be employed, in which microparticles are preferentially purified and isolated relative to other constituents within a solution employed within said step(s). Any one or more such purification steps may comprise a size-exclusion chromatography process. Any one or more such purification steps may comprise a size-centrifugation (e.g. differential centrifugation) process.

Optionally, in any combinatorial barcoding process, barcode sequences may be appended by any one or more methods described herein (such as single-stranded ligation, double-stranded ligation, blunt-ended ligation, A-tailed ligation, sticky-end-mediated ligation, hybridisation, hybridisation and extension, hybridisation and extension and ligation, and/or transposition).

Optionally, during any step of any combinatorial barcoding process, at least 2, at least 3, at least 5, at least 10, at least 20, at least 50, at least 100, at least 200, at least 500, at least 1000, at least 2000, at least 5000, at least 10,000, at least 50,000, at least 100,000, at least 500,000, or at least 1,000,000 circulating microparticles may be comprised within a partition (and/or within each of at least first and second partitions; and/or within any larger number of partitions). Preferably, at least 50 circulating microparticles may be comprised within a partition (and/or within each of at least first and second partitions; and/or within any larger number of partitions).

Optionally, during any step of any combinatorial barcoding process, at least 2, at least 3, at least 5, at least 10, at least 20, at least 50, at least 100, at least 200, at least 500, at least 1000, at least 2000, at least 5000, at least 10,000, at least 50,000, at least 100,000, at least 500,000, at least 1,000,000, at least 10,000,000, or at least 100,000,000 partitions may be employed (e.g. circulating microparticles may be partitioned into said number(s) of partitions). Preferably, during any step of any combinatorial barcoding process, at least 24 partitions may be employed (e.g. circulating microparticles may be partitioned into said number(s) of partitions).

Optionally, during any step of any combinatorial barcoding process, a sample of microparticles may be separated into partitions such that an average of less than 0.0001 microparticles, less than 0.001 microparticles, less than 0.01 microparticles, less than 0.1 microparticles, less than 1.0 microparticle, less than 10 microparticles, less than 100 microparticles, less than 1000 microparticles, less than 10,000 microparticles, less than 100,000 microparticles, less than 1,000,000 microparticles, less than 10,000,000 microparticles, or less than 100,000,000 microparticles are present per partition. Preferably, an average of less than 1.0 microparticle is present per partition.

Optionally, during any step of any combinatorial barcoding process, a solution of microparticles may be separated into partitions such that an average of less than 1.0 attogram of DNA, less than 10 attograms of DNA, less than 100 attograms of DNA, less than 1.0 femtogram of DNA, less than 10 femtograms of DNA, less than 100 femtograms of DNA, less than 1.0 picogram of DNA, less than 10 picograms of DNA, less than 100 picograms of DNA, or less than 1.0 nanogram of DNA is present per partition. Preferably, less than 10 picograms of DNA are present per partition.

Optionally, during any step of any combinatorial barcoding process, partitions may be less than 100 femtoliters, less than 1.0 picoliter, less than 10 picoliters, less than 100 picoliters, less than 1.0 nanoliter, less than 10 nanoliters, less than 100 nanoliters, less than 1.0 microliter, less than 10 microliters, less than 100 microliters, or less than 1.0 milliliter in volume.

Optionally, any combinatorial barcoding process may comprise at least 2, at least 3, at least 4, at least 5, at least 10, at least 20, at least 30, at least 40, at least 50, at least 100, at least 500, or at least 1000 different barcoding steps. Each of the barcoding steps may be as described herein for the first and second barcoding steps.

Optionally, in any combinatorial barcoding process, any one or more partitioning step may comprise stochastic character—for example, an estimated number (rather than an exact or precise number) of circulating microparticles may be partitioned into one or more partitions; i.e., said number(s) of circulating microparticles per partition may be subject to statistical or probabilistic uncertainty (such as subject to Poisson loading and/or distribution statistics).

Optionally, in any combinatorial barcoding process, the set of barcodes appended to a particular sequence (e.g. appended to a sequence of a fragment of genomic DNA; e.g. a set comprising a first barcode appended to said sequence during a first barcoding step and a second barcode appended to said sequence during a second barcoding step) may be employed to link sequences from a single microparticle and/or to link sequences from a set of two or more microparticles. Optionally, in any combinatorial barcoding process, the same set of two (or more than two) barcodes may be appended to a particular sequence (e.g. appended to a sequence of a fragment of genomic DNA) from two or more circulating microparticles (e.g., wherein said two or more circulating microparticles are partitioned into the same series of first and second partitions during the first and second barcoding steps respectively). Optionally, in any combinatorial barcoding process, the same set of two (or more than two) barcodes may be appended to a particular sequence (e.g. appended to a sequence of a fragment of genomic DNA) from only one circulating microparticle (e.g., wherein only one circulating microparticle is partitioned into a specific series of first and second partitions during the first and second barcoding steps respectively).

Optionally, in any combinatorial barcoding process, the number of partitions employed in any one or more barcoding steps, and the number of different barcoding steps, may combinatorically combine such that, on average, each set of two (or more) barcodes is appended to sequences from only one circulating microparticle. For example, for a sample comprising 1000 circulating microparticles, 100 partitions (and associated barcodes comprised therein) may be employed for each of first and second barcoding steps; the total number of different barcode sets will then equate to (100×100=) 10,000 different barcode sets; compared with the 1000 circulating microparticles comprised within the original sample, each barcode set will therefore on average by appended to sequences from only one (or, conceptually, less than one) circulating microparticle. The number of partitions employed at any one or more barcoding steps, and/or the number of different barcoding steps, may be increased and/or decreased in different embodiments of any combinatorial barcoding process to achieve a desired level of resolution and/or sensitivity (e.g. given the desire to analyse samples comprising different numbers of circulating microparticles, and/or different barcoding-specificity requirements for different applications). Optionally, in certain applications, having an imperfect and/or inefficient barcoding process (e.g., wherein only a small fraction of sequences from a particular microparticle are appended to barcodes in one or more barcoding steps; and/or e.g. wherein the same set(s) of barcode sequences are appended to sequences from two or more circulating microparticles) may enable sufficient molecular and/or informatic resolution to achieve a desired signal and/or sequencing readout.

A combinatorial barcoding process could provide advantages over alternative barcoding processes in the form of reducing the requirement for sophisticated and/or complex equipment to achieve a high number of potential identifying barcode sets for the purposes of appending barcodes to sequences (e.g. from fragments of genomic DNA) from circulating microparticles. For example, a combinatorial barcoding process employing 96 different partitions (as, for example, would be easily implemented with standard 96-well plates used broadly within molecular biology) across two different barcoding steps could achieve a net of (96×96=) 9216 different barcode sets; which considerably reduces the amount of partitions that would be required to perform such indexing compared with alternative, non-combinatoric approaches. Considerably higher levels of combinatoric indexing resolution could furthermore be achieved by increasing the number of barcoding steps, and/or increasing the number of partitions employed at one or more such barcoding steps. Furthermore, combinatorial barcoding processes may obviate the need for complex instrumentation—such as, for example, microfluidic instrumentation (such as the 10× Genomics Chromium System)—that is employed for alternative barcoding processes.

6. Linking by Spatial Sequencing or In-Situ Sequencing or In-Situ Library Construction The invention provides a method of preparing a sample for sequencing, wherein the sample comprises a microparticle originating from blood, and wherein the microparticle contains at least two fragments of a target nucleic acid (e.g. genomic DNA), and wherein the method comprises: (a) preparing the sample for sequencing, wherein the at least two fragments of the target nucleic acid of the microparticle are linked by their proximity to each other on a sequencing apparatus to produce a set of at least two linked fragments of the target nucleic acid; and (b) sequencing each of the linked fragments of the target nucleic acid using the sequencing apparatus to produce at least two linked sequence reads.

The nucleic acid sample may comprise at least two microparticles originating from blood, wherein each microparticle contains at least two fragments of a target nucleic acid (e.g. genomic DNA), and wherein the method comprises performing step (a) to produce a set of linked fragments of the target nucleic acid for each microparticle and wherein the fragments of the target nucleic acid of each microparticle are spatially distinct on the sequencing apparatus, and performing step (b) to produce linked sequence reads for each microparticle.

The at least two fragments from a microparticle may hold physical proximity to each other within or on the sequencing apparatus itself, and wherein this physical proximity is known or can be determined or observed by the sequencing apparatus or by or during its operation, and wherein this measure of physical proximity serves to link the at least two sequences.

The methods may comprise sequencing using an in situ library construction process. In the methods, intact or partially intact microparticles from a sample may be placed onto the sequencer, and wherein two or more fragments of the target nucleic acid (e.g. genomic DNA) are processed into sequencing-ready templates within the sequencer i.e. sequencing using an in situ library construction process. In situ library construction is described in Schwartz et al (2012) PNAS 109(46):18749-54).

The methods may comprise in situ sequencing. In the methods, the sample may remain intact (e.g. largely or partially intact), and fragments of the target nucleic acid (e.g. genomic DNA) within microparticles are sequenced directly e.g. using 'FISSEQ' fluorescent in situ sequencing technique method as described in Lee et al. (2014) Science, 343, 6177, 1360-1363).)

Optionally, samples of microparticles may be crosslinked with a chemical crosslinker, and then placed within or upon the sequencing apparatus, and then retained in physical proximity to each other. Optionally, two or more fragments of target nucleic acid (e.g. genomic DNA) from a microparticle placed within or upon the sequencing apparatus may then have all or part of their sequence determined by a sequencing process. Optionally, such fragments may be sequenced by a fluorescent in situ sequencing technique, wherein sequences of said fragments are determined by an optical sequencing process. Optionally, one or more coupling, adapter, or amplification sequence may be appended to said fragments of the target nucleic acid. Optionally, said fragments may be amplified in an amplification process, wherein the amplified products remain in physical proximity or in physical contact of the fragments from which they were amplified. Optionally, these amplified products are then sequenced by an optical sequencing process. Optionally, said amplified products are appended to a planar surface, such as a sequencing flowcell. Optionally, said amplified products generated from single fragments each make up a single cluster within a flowcell. Optionally, in any method as above, the distance between any two or more sequenced molecules is known a priori by configuration within the sequencing apparatus, or may be determined or observed during the sequencing process. Optionally, each sequenced molecule is mapped within a field of clusters, or within an array of pixels, wherein the distance between any two or more sequenced molecules is determined by the distance between said clusters or pixels. Optionally, any measure or estimation of distance or proximity may be used to link any two or more determined sequences.

Optionally, sequences determined by any method as above may be further evaluated, wherein a measure of distance or proximity between two or more sequenced molecules is compared to one or more cutoff or threshold values, and only molecules within a particular range, or above or below a particular threshold or cutoff value, are determined to be linked informatically. Optionally, a set of two or more such cutoff or threshold values or ranges thereof may be employed, such that different degrees and/or classes and/or categories of linking for any two or more sequenced molecules may be determined.

7. Linking by Separate Sequencing Processes

The invention provides a method of preparing a sample for sequencing, wherein the sample comprises a microparticle originating from blood, and wherein the microparticle contains at least two fragments of a target nucleic acid (e.g. genomic DNA), and wherein the method comprises: (a) preparing the sample for sequencing, wherein the at least two fragments of a target nucleic acid (e.g. genomic DNA) of each microparticle are linked by being loaded into a separate sequencing process to produce a set of at least two linked fragments the target nucleic acid; and (b) sequencing each of the linked fragments of the target nucleic acid using the sequencing apparatus to produce a set of at least two linked sequence reads.

The sample may comprise at least two microparticles originating blood, wherein each microparticle contains at least two fragments of a target nucleic acid (e.g. genomic DNA), and the method may comprise performing step (a) to produce linked fragments of the target nucleic acid for each microparticle wherein the at least two fragments of the target nucleic acid of each microparticle are linked by being loaded into a separate sequencing process, and performing step (b) for each sequencing process to produce linked sequence reads for each microparticle.

In the methods, fragments of a first single microparticle (or group of microparticles) may be sequenced independently of the fragments of other microparticles, and the resulting sequence reads are linked informatically; fragments contained within a second single microparticle (or group of microparticles) are sequenced independently of the first microparticle or group of microparticles, and the resulting sequence reads are linked informatically.

Optionally, first and the second sequencing processes (of all sequencing processes) are conducted with different sequencing instruments, and/or conducted with the same sequencing instrument but at two different times or within two different sequencing processes. Optionally, the first and the second sequencing processes are conducted with the same sequencing instrument but within two different regions, partitions, compartments, conduits, flowcells, lanes, nanopores, microscaffold, array of microscaffolds, or integrated circuit of the sequencing instrument. Optionally, 3 or more, 10 or more, 1000 or more, 1,000,000 or more, or 1,000,000,000 or more microparticles or groups of microparticles may be linked by the above method.

8. Amplifying Original Fragments Prior to Linking

As would be appreciated by the skilled person, as used herein the term 'fragments' (e.g. 'fragments of genomic DNA', or 'fragments of a target nucleic acid', or 'fragments of genomic DNA of/from a microparticle') refers to the original fragments present in the microparticle, as well as to portions, copies, or amplicons thereof, including copies of only a part of an original fragment (e.g. an amplicon thereof), as well as to modified fragments or copies (e.g. fragments to which a coupling sequence has been appended). For example, the term fragments of genomic DNA refers to the original genomic DNA fragments present in the microparticle and, for example, to DNA molecules that may be prepared from the original genomic DNA fragments by a primer-extension reaction. As a further example, the term fragments of mRNA refers to the original mRNA fragments present in the microparticle and, for example, to cDNA molecules that may be prepared from the original mRNA fragments by reverse transcription.

The methods may, prior to the step of appending barcode sequences, further comprise a step of amplifying the original fragments of the target nucleic of a microparticle e.g. by a primer-extension step or a polymerase chain reaction step. Barcode sequences may then be appended to the amplicons or copies of the original fragments of the target nucleic acid using any of the methods described herein.

The primer-extension step or polymerase chain reaction step may be performed using one or more primers that contain a segment of one or more degenerate bases.

The primer-extension step or polymerase chain reaction step may be performed using one or more primers that are specific for a particular target nucleic acid sequence (e.g. a particular target genomic DNA sequence).

The amplification step may be performed by a strand displacing polymerase, such as Phi29 DNA polymerase, or a Bst polymerase or a Bsm polymerase, or modified derivatives of phi29, Bst, or Bsm polymerases. The amplification may be performed by a multiple-displacement amplification reaction and a set of primers containing a region of one or more degenerate bases. Optionally, random hexamer, random heptamer, random octamer, random nonamer, or random decamer primers are used.

The amplification step may comprise extension by a DNA polymerase of a single-stranded nick in a fragment of an original target nucleic acid. The nick may be generated by an enzyme with single-stranded DNA cleavage behaviour, or by a sequence-specific nicking restriction endonuclease.

The amplification step may comprise incorporating at least one or more dUTP nucleotides into a DNA strand synthesized by replicating or amplifying at least a portion of one or more fragments of genomic DNA by a DNA polymerase, and wherein a nick is generated by a uracil-excising enzyme such as a uracil DNA glycosylase enzyme.

The amplification step may comprise the generation of priming sequences upon a nucleic acid comprising a fragment of genomic DNA, wherein the priming sequences are generated by a primase enzyme, such as a *Thermus Thermophilus* PrimPol polymerase or a TthPrimPol polymerase, and wherein a DNA polymerase is used to copy at least one nucleotide of a sequence of a fragment of genomic DNA using this priming sequence as a primer.

The amplification step may be performed by a linear amplification reaction, such as an RNA amplification process performed through an in vitro transcription process.

The amplification step may be performed by a primer-extension step or a polymerase chain reaction step, and wherein the primer or primers used therefor are universal primers corresponding to one or more universal priming sequence(s). The universal priming sequence(s) may be appended to fragments of genomic DNA by a ligation reaction, by a primer-extension or polymerase chain reaction, or by an in vitro transposition reaction.

9. Appending Coupling Sequences to Fragments Prior to Linking

In any of the methods, barcode sequences may be appended directly or indirectly (e.g. by annealing or ligation) to fragments of a target nucleic acid (e.g. gDNA) of a microparticle. The barcode sequences may be appended to coupling sequences (e.g. synthetic sequences) that are appended to the fragments.

In methods comprising linking together at least two fragments of the target nucleic acid of the microparticle to produce a single nucleic acid molecule, a coupling sequence may first be appended to each of the at least two fragments and the fragments may then be linked together by the coupling sequence.

A coupling sequence may be appended to an original fragment of target nucleic acid of a microparticle or to a copy or amplicon thereof.

A coupling sequence may be added to the 5' end or 3' end of two or more fragments of the nucleic acid sample. In this method, the target regions (of the barcoded oligonucleotides) may comprise a sequence that is complementary to the coupling sequence.

A coupling sequence may be comprised within a double-stranded coupling oligonucleotide or within a single-stranded coupling oligonucleotide. A coupling oligonucleotide may be appended to the target nucleic acid by a double-stranded ligation reaction or a single-stranded ligation reaction. A coupling oligonucleotide may comprise a single-stranded 5' or 3' region capable of ligating to a target nucleic acid and the coupling sequence may be appended to the target nucleic acid by a single-stranded ligation reaction.

A coupling oligonucleotide may comprise a blunt, recessed, or overhanging 5' or 3' region capable of ligating to a target nucleic acid and the coupling sequence may be appended to the target nucleic acid a double-stranded ligation reaction.

The end(s) of a target nucleic acid may be converted into blunt double-stranded end(s) in a blunting reaction, and the coupling oligonucleotide may comprise a blunt double-stranded end, and wherein the coupling oligonucleotide may be ligated to the target nucleic acid in a blunt-end ligation reaction.

The end(s) of a target nucleic acid may be converted into blunt double-stranded end(s) in a blunting reaction, and then converted into a form with (a) single 3' adenosine overhang(s), and wherein the coupling oligonucleotide may comprise a double-stranded end with a single 3' thymine overhang capable of annealing to the single 3' adenosine overhang of the target nucleic acid, and wherein the coupling oligonucleotide is ligated to the target nucleic acid in a double-stranded A/T ligation reaction The target nucleic acid may be contacted with a restriction enzyme, wherein the restriction enzyme digests the target nucleic acid at restriction sites to create (a) ligation junction(s) at the restriction site(s), and wherein the coupling oligonucleotide comprises an end compatible with the ligation junction, and wherein the coupling oligonucleotide is then ligated to the target nucleic acid in a double-stranded ligation reaction.

A coupling oligonucleotide may be appended via a primer-extension or polymerase chain reaction step.

A coupling oligonucleotide may be appended via a primer-extension or polymerase chain reaction step, using one or more oligonucleotide(s) that comprise a priming segment including one or more degenerate bases.

A coupling oligonucleotide may be appended via a primer-extension or polymerase chain reaction step, using one or more oligonucleotide(s) that further comprise a priming or hybridisation segment specific for a particular target nucleic acid sequence.

A coupling sequence may be added by a polynucleotide tailing reaction. A coupling sequence may be added by a terminal transferase enzyme (e.g. a terminal deoxynucleotidyl transferase enzyme). A coupling sequence may be appended via a polynucleotide tailing reaction performed with a terminal deoxynucleotidyl transferase enzyme, and wherein the coupling sequence comprises at least two contiguous nucleotides of a homopolymeric sequence.

A coupling sequence may comprise a homopolymeric 3' tail (e.g. a poly(A) tail). Optionally, in such methods, the target regions (of the barcoded oligonucleotides) comprise a complementary homopolymeric 3' tail (e.g. a poly(T) tail).

A coupling sequence may be comprised within a synthetic transposome, and may be appended via an in vitro transposition reaction.

A coupling sequence may be appended to a target nucleic acid, and wherein a barcode oligonucleotide is appended to the target nucleic acid by at least one primer-extension step or polymerase chain reaction step, and wherein said barcode oligonucleotide comprises a region of at least one nucleotide in length that is complementary to said coupling sequence. Optionally, this region of complementarity is at the 3' end of the barcode oligonucleotide. Optionally, this region of complementarity is at least 2 nucleotides in length, at least 5 nucleotides in length, at least 10 nucleotides in length, at least 20 nucleotides in length, or at least 50 nucleotides in length.

10. Optional Additional Steps of the Methods

The methods may comprise determining the presence or absence of at least one modified nucleotide or nucleobase in one or more fragments of genomic DNA from a sample comprising one or more circulating microparticles. The methods may comprise measurement of the modified nucleotide or nucleobase (e.g. measuring the modified nucleotide or nucleobase) in fragments of genomic DNA of a circulating microparticle. The measured value may be a total value of the analysed fragments of genomic DNA (i.e. linked fragments of genomic DNA) of a circulating microparticle and/or the measured value may be a value for each analysed fragment of genomic DNA. The modified nucleotide or nucleobase may be 5-methylcytosine or 5-hydroxy-methylcytosine.

Measurement(s) of modified nucleotides or nucleobases in one or more fragments of genomic DNA from circulating microparticles enables a variety of molecular and informatic analyses that may complement measurement of the sequence of said fragments themselves. In one respect, measurement of so-called 'epigenetic' marks (i.e. measurement of the 'epigenome') within fragments of genomic DNA from circulating microparticles enables comparison to (and/or mapping against) reference epigenetic sequences and/or lists of reference epigenetic sequences. This enables an 'orthogonal' form of analysing sequences from fragments of genomic DNA from circulating microparticles in comparison to measurement only of the standard 4 (unmodified) bases and/or their traditional 'genetic' sequences. Furthermore, measurement of modified nucleotides and/or nucleobases may enable more precision determination and/or estimation of the types of cells and/or tissues from which one or more circulating microparticles have arisen. Since different cell types within the body exhibit different epigenetic signatures, measurement of the epigenome of fragments of genomic DNA from circulating microparticles may therefore allow more precise such microparticle-to-cell type mapping. In the methods, epigenetic measurements from fragments of genomic DNA from circulating microparticles may be compared with (e.g. mapped to) a list (or lists) of reference epigenetic sequences corresponding to methylation and/or hydroxymethylation within particular specific tissues. This may enable the elucidation of and/or enrichment for microparticles (e.g. linked sets of sequences from particular microparticles) from a particular tissue type and/or a particular healthy and/or diseased tissue (e.g. cancer tissue). For example, the measurement of a modified nucleotide or nucleobase in fragments of genomic DNA of a circulating microparticle may enable the identification of linked sequences (or linked sequence reads) of fragments of genomic DNA originating from cancer cells. In a further example, the measurement of a modified nucleotide or nucleobase in fragments of genomic DNA of a circulating microparticle may enable the identification of linked sequences (or linked sequence reads) of fragments of genomic DNA originating from foetal cells. The absolute amount of a particular modified nucleotide or nucleobase may correlate with health and/or disease within a particular tissue. For example, the level of 5-hydroxy-methylcytosine is strongly altered in cancerous tissue compared with normal healthy tissues; measurement of 5-hydroxy-methylcytosine in fragments of genomic DNA from circulating microparticles may therefore enable more precise detection and/or analysis of circulating microparticles originating from cancer cells.

The methods may comprise measurement of 5-methylcytosine in fragments of genomic DNA of a circulating microparticle (e.g., measuring 5-methylcytosine in fragments of genomic DNA of a circulating microparticle). The methods may comprise measurement of 5-hydroxy-methylcytosine in fragments of genomic DNA of a circulating microparticle (e.g., measuring 5-hydroxy-methylcytosine in fragments of genomic DNA of a circulating microparticle).

The methods may comprise measurement of 5-methylcytosine in fragments of genomic DNA of a circulating microparticle (e.g., measuring 5-methylcytosine in fragments of genomic DNA of a circulating microparticle), wherein said measurement is performed using an enrichment probe that is specific for or preferentially binds 5-methylcytosine in fragments of genomic DNA compared with other modified or unmodified bases. The methods may comprise measurement of 5-hydroxy-methylcytosine in fragments of genomic DNA of a circulating microparticle (e.g., measuring 5-hydroxy-methylcytosine in fragments of genomic DNA of a circulating microparticle), wherein said measurement is performed using an enrichment probe that is specific for or preferentially binds 5-hydroxy-methylcytosine in fragments of genomic DNA compared with other modified or unmodified bases.

The methods may comprise measurement of 5-methylcytosine in fragments of genomic DNA of two or more circulating microparticles (e.g., measuring 5-methylcytosine in fragments of genomic DNA of a first circulating microparticle and measuring 5-methylcytosine in fragments of genomic DNA of a second circulating microparticle). The methods may comprise measurement of 5-hydroxy-methylcytosine in fragments of genomic DNA of two or more circulating microparticles (e.g., measuring 5-hydroxy-methylcytosine in fragments of genomic DNA of a first circulating microparticle and measuring 5-hydroxy-methylcytosine in fragments of genomic DNA of a second circulating microparticle).

The methods may comprise measurement of 5-methylcytosine in fragments of genomic DNA of two or more circulating microparticles (e.g., measuring 5-methylcytosine in fragments of genomic DNA of a first circulating microparticle and measuring 5-methylcytosine in fragments of genomic DNA of a second circulating microparticle), wherein said measurement is performed using an enrichment probe that is specific for or preferentially binds 5-methylcytosine in fragments of genomic DNA compared with other modified or unmodified bases. The methods may comprise measurement of 5-hydroxy-methylcytosine in fragments of genomic DNA of two or more circulating microparticles (e.g., measuring 5-hydroxy-methylcytosine in fragments of genomic DNA of a first circulating microparticle and measuring 5-hydroxy-methylcytosine in fragments of genomic DNA of a second circulating microparticle), wherein said measurement is performed using an enrichment probe that is specific for or preferentially binds 5-hydroxy-methylcytosine in fragments of genomic DNA compared with other modified or unmodified bases.

The methods may comprise measurement of 5-methylcytosine in fragments of genomic DNA of a circulating microparticle (e.g., measuring 5-methylcytosine in fragments of genomic DNA of a circulating microparticle), wherein said measurement is performed using a bisulfite conversion process or an oxidative bisulfite conversion process. The methods may comprise measurement of 5-hydroxy-methylcytosine in fragments of genomic DNA of a circulating microparticle (e.g., measuring 5-hydroxy-methylcytosine in fragments of genomic DNA of a circulating microparticle), wherein said measurement is performed using a bisulfite conversion process or an oxidative bisulfite conversion process.

The methods may comprise measurement of 5-methylcytosine in fragments of genomic DNA of two or more circulating microparticles (e.g., measuring 5-methylcytosine in fragments of genomic DNA of a first circulating microparticle and measuring 5-methylcytosine in fragments of genomic DNA of a second circulating microparticle), wherein said measurement is performed using a bisulfite conversion process or an oxidative bisulfite conversion process. The methods may comprise measurement of 5-hydroxy-methylcytosine in fragments of genomic DNA of two or more circulating microparticles (e.g., measuring 5-hydroxy-methylcytosine in fragments of genomic DNA of a first circulating microparticle and measuring 5-hydroxy-methylcytosine in fragments of genomic DNA of a second circulating microparticle), wherein said measurement is performed using a bisulfite conversion process or an oxidative bisulfite conversion process.

Optionally, sequences from two or more constituent parts of a sample comprising one or more circulating microparticles may be determined as relates to determining the presence or absence of at least one modified nucleotide or nucleobase in one or more fragments of genomic DNA from said sample. For example, an enrichment step may be performed to enrich for fragments of genomic DNA within a sample containing a modified base (such as 5-methylcytosine, or 5-hydroxy-methylcytosine), wherein a first constituent part of the sample comprising fragments of genomic DNA that have been enriched by said enrichment step may be sequenced, and a second constituent part of the sample comprising fragments of genomic DNA that have not been enriched by said enrichment step may also be sequenced (e.g. sequenced in a separate sequencing reaction). Optionally said second constituent part of the sample may comprise a non-enriched and/or supernatant fraction (e.g. a fraction not bound by an enrichment probe or affinity probe during an enrichment process) produced during the enrichment process. Optionally the original sample may be divided into first and second sub-samples, wherein the first sub-sample is employed to perform an enrichment step of produce the first constituent part of the sample, and wherein the said second constituent part of the sample may comprise the second, non-enriched sub-sample. Any combination of two or more enriched and/or unenriched and/or converted (e.g. bisulfite-converted, and/or oxidative bisulfite-converted) and/or unconverted constituent parts of a sample may be sequenced. For example, a sample comprising one or more circulating microparticles maybe be used to produce three constituent parts, such as a constituent part enriched for 5-methylcytosine DNA (or alternatively, a constituent part that has been bisulfite-converted), a constituent part enriched for 5-hydroxy-methylcytosine (or alternatively, a constituent part that has been oxidative-bisulfite-converted), and an unenriched (and/or unconverted) constituent part. Optionally, any such two or more constituent parts of a sample may be sequenced individually in separate sequencing reactions (such as within separate flowcells, or within separate lanes of a single flowcell). Optionally, any such two or more parts of a sample may be appended to identifying barcode sequences (e.g. which identify a given sequence as being within an enriched or unenriched constituent part of a sample) and then sequenced within the same sequencing process (such as within the same flowcell or lane of a flowcell).

Optionally, any method of linking sequences as described herein (for example, by appending barcode sequences, such as by appending barcode sequences from a multimeric barcoding reagent or by appending barcode sequences from a library of two or more multimeric barcoding reagents) may be performed before any such enrichment and/or molecular conversion step (for example, wherein such a linking process is performed on the original sample comprising at least one circulating microparticle, or at least two circulating microparticles, wherein the linked sequences are then used as input sequences for an enrichment or molecular conversion process).

For example, a sample comprising two or more circulating microparticles may be appended to barcode sequences from a library of two or more multimeric barcoding reagents, wherein first and second barcode sequences from a first multimeric barcoding reagent are appended to first and second fragments of genomic DNA from a first circulating microparticle, and wherein first and second barcode sequences from a second multimeric barcoding reagent are appended to first and second fragments of genomic DNA from a second circulating microparticle, and wherein the resulting barcode-appended fragments of genomic DNA are enriched for 5-methylcytosine (and/or 5-hydroxy-methylcytosine), and wherein the enriched fragments of genomic DNA are then sequenced, wherein the barcode sequences are then used to determine which enriched fragments were appended to barcodes from the same multimeric barcoding reagent(s), and thereby predict (or determine) which enriched fragments were comprised within the same circulating microparticle(s). In this example, a second sequencing reaction may also be performed on unenriched fragments of genomic DNA (for example, by sequencing fragments of genomic DNA within the supernatant fraction (i.e. the non-captured, non-enriched fraction) of the enrichment step, wherein the barcode sequences are then used to determine which unenriched fragments were appended to barcodes from the same multimeric barcoding reagent(s), and thereby predict (or determine) which unenriched fragments were comprised within the same circulating microparticle(s). In this example, if both enriched and unenriched fragments of genomic DNA are so sequenced, it may therefore be predicted (or determined) both which enriched and which unenriched fragments were appended to barcodes from the same multimeric barcoding reagent(s), and thereby be predicted (or determined) both which enriched and which unenriched fragments were comprised within the same circulating microparticle(s). Methods similar to this example may also be employed, for example by employing one or more molecular conversion methods, and/or for example by preparing, analysing, or sequencing three or more constituent parts of a sample (for example, a constituent part enriched for 5-methylcytosine, a constituent part enriched for 5-hydroxy-methylcytosine, and an unenriched constituent part).

Optionally, any method of linking sequences as described herein (for example, by appending barcode sequences, such as by appending barcode sequences from a multimeric barcoding reagent or a library of two or more multimeric barcoding reagents) may be performed after any such enrichment and/or molecular conversion step (for example, wherein an enrichment step is performed to enrich for fragments of genomic DNA containing 5-methylcytosine, or containing 5-hydroxy-methylcytosine, and wherein the fragments of genomic DNA enriched through this process are then linked by any method described herein).

The methods may comprise determining the presence or absence of at least one modified nucleotide or nucleobase in the fragments of genomic DNA, wherein an enrichment step is performed to enrich for fragments of genomic DNA containing said modified base. Such modified base may comprise one or more of 5-methylcytosine, or 5-hydroxy-methylcytosine, or any other modified base. Such an enrichment step may be performed by an enrichment probe, such as an antibody, enzyme, enzyme fragment, or other protein, or an aptamer, or any other probe, that is specific for or preferentially binds with said modified base compared with other modified or unmodified bases. Such an enrichment step may be performed by an enzyme capable of enzymatically modifying DNA molecules containing a modified base, such as a glucosyltransferase enzyme, such as a 5-hydroxymethylcytosine glucosyltransferase enzyme. Optionally, the presence of 5-hydroxymethylcytosine within a fragment of genomic DNA may be determined with a 5-hydroxymethylcytosine glucosyltransferase enzyme, wherein the 5-hydroxymethylcytosine glucosyltransferase enzyme is used to transfer a glucose moiety from uridine diphosphoglucose to the modified base within the fragment of genomic DNA to produce a glucosyl-5-hydroxymethyl-cytosine base, optionally wherein said glucosyl-5-hydroxymethylcytosine base is then detected, such as being detected with a glucosyl-5-hydroxymethylcytosine-sensitive restriction enzyme, wherein fragments of genomic DNA resistant to digestion by said glucosyl-5-hydroxymethylcytosine-sensitive restriction enzyme are considered to contain a modified 5-hydroxymethylcytosine base; optionally, said fragments of genomic DNA resistant to digestion may be sequenced to determine their sequence(s) by any method described herein. Optionally, if barcode sequences are appended, this enrichment step may be performed before the step of appending barcode sequences or after the step of appending barcode sequences. Optionally, if two or more sequences of fragments of genomic DNA from a microparticle are appended to each other, this enrichment step may be performed before the step of appending such sequences to each other or after the step of appending such sequences to each other. Any method of measuring at least one modified nucleotide or nucleobase in the fragments of genomic DNA using an enrichment probe may be performed with commercially available enrichment probes or other products such as commercially available antibodies, such as the anti-5-hydroxy-methylcytosine antibody ab178771 (Abcam), or such as the anti-5-methylcytosine antibody ab10805 (Abcam). Furthermore, commercially available products and/or kits may also be used for additional step(s) of such methods, such as Protein A or Protein G Dynabeads (ThermoFisher) for binding, recovery, and processing/washing of antibodies and/or fragments bound thereto.

The methods may comprise determining the presence or absence of at least one modified nucleotide or nucleobase in the fragments of genomic DNA, wherein a molecular conversion step is performed to convert said modified base(s) into a different modified or unmodified nucleotide which may be detected during the process of determining a nucleic acid sequence. This conversion step may comprise a bisulfite conversion step, an oxidative bisulfite conversion step, or any other molecular conversion step. Optionally, if barcode sequences are appended, this enrichment step may be performed before the step of appending barcode sequences or after the step of appending barcode sequences. Optionally, if two or more sequences of fragments of genomic DNA from a microparticle are appended to each other, this enrichment step may be performed before the step of appending such sequences to each other or after the step of appending such sequences to each other. Any method of measuring at least one modified nucleotide or nucleobase in the fragments of genomic DNA using a molecular conversion step may be performed with commercially available molecular conversion kits, such as the EpiMark Bisulfite Conversion Kit (New England Biolabs), or the TruMethyl Seq Oxidative Bisulfite Sequencing Kit (Cambridge Epigenetix).

In any method of performing a molecular conversion step, one or more adapter oligonucleotide(s) may be appended to one or both ends of a fragment of genomic DNA (and/or a collection of fragments of genomic DNA within a sample) following the molecular conversion process. For example, a single-stranded adapter oligonucleotide (for example, comprising a binding site for a primer used for amplification, such as by PCR amplification) may be ligated with a single-stranded ligase enzyme to one or both ends of the converted fragment of genomic DNA (and/or a collection of fragments of genomic DNA within a sample). Optionally, a barcode sequence and/or adapter sequence (such as within a barcoded oligonucleotide) may be appended to one end of a fragment of genomic DNA (and/or a collection of fragments of genomic DNA within a sample) prior to a molecular conversion step, and then an adapter oligonucleotide may be appended to a second end of the fragment(s) of genomic DNA following a molecular conversion process. Optionally, said second end may comprise an end created during the molecular conversion process (i.e. wherein the fragment(s) of genomic DNA has/have undergone a fragmentation process, thus creating one or more new ends of said fragment(s) relative to their corresponding original fragment(s)). Such methods of appending adapter oligonucleotides may have the benefit of allowing fragments of genomic DNA that have been fragmented and/or degraded during a molecular conversion process to be further amplified and/or analysed and/or sequenced.

In any method of performing a molecular conversion step, any adapter oligonucleotide, and/or barcoded oligonucleotide, and/or barcode sequence, and/or any coupling sequence and/or any coupling oligonucleotide, may comprise one or more synthetic 5-methylcytosine nucleotides. Optionally, any adapter oligonucleotide, and/or barcoded oligonucleotide, and/or barcode sequence, and/or any coupling sequence and/or any coupling oligonucleotide, may be configured such that any or all cytosine nucleotides contained therein are synthetic 5-methylcytosine nucleotides. Optionally, any adapter oligonucleotide, and/or barcoded oligonucleotide, and/or barcode sequence, and/or any coupling sequence and/or any coupling oligonucleotide, comprising one or more synthetic 5-methylcytosine nucleotides, may be appended to fragment(s) of genomic DNA prior to a molecular conversion step; alternatively and/or additionally, they may be appended to fragment(s) of genomic DNA subsequent to a molecular conversion step. Such synthetic 5-methylcytosine nucleotides within said adapter(s) and/or oligonucleotide(s) and/or sequence(s) may have a benefit of reducing or minimising their degradation and/or fragmentation during a molecular conversion process (such as a bisulfite conversion process), due to their resistance to degradation during such a process.

The methods may comprise determining the presence or absence of at least one modified nucleotide or nucleobase in the fragments of genomic DNA, wherein said modified nucleotide or nucleobase (such as 5-methylcytosine or 5-hydroxy-methylcytosine) is determined or detected by a sequencing reaction. Optionally, said sequencing reaction may be performed by a nanopore-based sequencing instrument, such as a Minion, a Gridion X5, a Promethion, and/or a Smidgion sequencing instrument produced by Oxford Nanopore Technologies, wherein the presence of modified nucleotide(s) or nucleobase(s) is determined during the process of translocating a fragment of genomic DNA through a nanopore within the sequencing instrument and by analysing the current signal through the nanopore apparatus during said translocation of the fragment of genomic DNA. Optionally, said sequencing reaction may be performed by a zero-mode-waveguide-based sequencing instrument, such as a Sequel or RSII sequencing instrument produced by Pacific Biosciences, wherein the presence of modified nucleotide(s) or nucleobase(s) is determined during the process of synthesising a copy of at least part of a fragment of genomic DNA within a zero-mode waveguide within the sequencing instrument and by analysing the optical signal derived from said zero-mode waveguide during said process of copying at least a part of the fragment of genomic DNA.

In any method of performing an enrichment step and/or a molecular-conversion step, said enrichment and/or conversion may be incomplete and/or less than 100% efficient. For example, a molecular conversion process may be performed such that less than 100% of a particular class of targeted modified nucleotide (such as 5-methylcytosine, or 5-hydroxy-methylcytosine) are converted with a molecular conversion process (such as bisulfite conversion or oxidative bisulfite conversion). For example, approximately 99%, or approximately 95%, or approximately 90%, or approximately 80%, or approximately 70%, or approximately 60%, or approximately 50%, or approximately 40%, or approximately 25%, or approximately 10% of such targeted modified nucleotide(s) may be converted during such a molecular conversion process. This incomplete molecular conversion process may be performed by limiting the duration of time for which the molecular conversion process is conducted (e.g., by making said duration of time shorter than the standard time employed to achieve full or near-full efficiency of the molecular conversion process), such that, on average, said target conversion efficiencies are achieved. Such incomplete molecular conversion processes may have a benefit of reducing the amount of sample degradation/fragmentation and/or sample loss that, for example, is characteristic of many molecular conversion processes such as bisulfite conversion.

Similarly, in any method of performing an enrichment step, said enrichment may be incomplete and/or less than 100% efficient. For example, an enrichment step for 5-methylcytosine (and/or 5-hydroxy-methylcytosine) may be performed wherein approximately 99%, or approximately 95%, or approximately 90%, or approximately 80%, or approximately 70%, or approximately 60%, or approximately 50%, or approximately 40%, or approximately 25%, or approximately 10% of fragments of genomic DNA containing such targeted modified nucleotide(s) are captured and recovered during an enrichment step (such as an enrichment step using an affinity probe such as an antibody specific for said targeted modified nucleotide(s)). Optionally, said incomplete enrichment may be performed by limiting and/or reducing the amount and/or concentration of the affinity probe used in the enrichment process (for example, by empirically testing the efficiency of such capture by using different amounts and/or concentrations of said affinity probes, and optionally by using DNA sequences comprising known modified nucleotide profiles as evaluation metrics for said empirical testing). Optionally, said incomplete enrichment may be performed by limiting and/or reducing the duration of time wherein the affinity probe is used to bind and/or capture the target fragments of genomic DNA within the enrichment process (i.e. by using different incubation times wherein the affinity probe is able to interact with potential target fragments of genomic DNA within a sample); for example, by empirically testing the efficiency of such capture by using different durations of incubation, and optionally by using DNA sequences comprising known modified nucleotide profiles as evaluation metrics for said empirical testing). Such incomplete enrichment may have a benefit of reducing false-positive molecular signals (e.g., wherein fragments of genomic DNA are captured during an enrichment process but where said fragments do not have the desired target modified nucleotide). Additionally, said incomplete enrichment may have a benefit of reducing the cost and complexity of the enrichment process(es) themselves.

The methods may comprise performing a sequence-enrichment or sequence-capture step, in which one or more specific genomic DNA sequences are enriched from the fragments of genomic DNA. This step may be performed by any method of performing sequence enrichment, such as using DNA oligonucleotides complementary to said sequences, or RNA oligonucleotides complementary to said sequences, or by a step employing a primer-extension target-enrichment step, or by a step employing a molecular inversion probe set or a by a step employing a padlock probe set. Optionally, if barcode sequences are appended, this enrichment step may be performed before the step of appending barcode sequences or after the step of appending barcode sequences. Optionally, if two or more sequences of fragments of genomic DNA from a microparticle are appended to each other, this enrichment step may be performed before the step of appending such sequences to each other or after the step of appending such sequences to each other.

The method may comprise enriching at least 1, at least 5, at least 10, at least 50, at least 100, at least 500, at least 1000, at least 5000, at least 10,000, at least 100,000, at least 1,000,000, or at least 10,000,000 different fragments of genomic DNA.

In the methods, each unique input molecule may be sequenced within the sequencing reaction on average at least 1.0 times, on average at least 1.5 times, on average at least 2.0 times, on average at least 3.0 times, on average at least 5.0 times, on average at least 10.0 times, on average at least 20.0 times, on average at least 50.0 times, or on average at least 100 times. Optionally, unique input molecules that are sequenced at least two times within the sequencing reaction (i.e. redundantly sequenced with at least two sequence reads) are used to detect and/or remove errors or inconsistencies in sequencing between said at least two sequence reads made by the sequencing reaction.

Prior to performing a sequencing reaction, and/or prior to performing an amplification reaction, a nucleotide repair reaction may be performed, in which damaged and/or excised bases or oligonucleotides are removed and/or repaired. Optionally, said repair reaction may performed in the presence of one or more of the following: *Thermus aquaticus* DNA Ligase, *E. coli* Endonuclease IV, *Bacillus stearothermophilus* DNA Polymerase, *E. coli* formamidopyrimidine [fapy]-DNA glycosylase, *E. coli* Uracil-DNA Glycosylase, T4 Endonuclease V, and *E. coli Endonuclease VIII*.

In the methods, a universal adapter sequence (e.g. one or two universal adapter sequences) may be appended prior to a sequencing step, and/or prior to an amplification step such as a PCR amplification step. Optionally, one or more such universal adapter sequences may be added by a random-primed or gene-specific primer extension step, by an in vitro transposition reaction wherein one or more said universal adapter sequences are comprised within a synthetic transposome, by a double-stranded or single-stranded ligation reaction (with or without a preceding fragmentation step, such as a chemical fragmentation step, an acoustic or mechanical fragmentation step, or an enzymatic fragmentation step; and optionally with or without a blunting, and/or 3' A-tailing step).

Barcode Sequences Comprising Enzymatically-Produced Copies or Enzymatically-Produced Complements One or more barcode sequences may be comprised within oligonucleotides (e.g. comprised within barcoded oligonucleotides) comprising enzymatically-produced copies or enzymatically-produced complements of a barcode sequence.

Optionally, one or more barcode sequences may be comprised within a barcoded oligonucleotide, wherein the barcode region of the barcoded oligonucleotide comprises an enzymatically-produced copy or enzymatically-produced complement of a barcode sequence. Optionally, one or more barcode sequences may be comprised within a barcoded oligonucleotide, wherein the barcode region of the barcoded oligonucleotide comprises an enzymatically-produced complement of a barcode sequence comprised within a barcode molecule. Optionally, one or more barcode sequences may be comprised within a barcoded oligonucleotide, wherein the barcode region of the barcoded oligonucleotide comprises an enzymatically-produced copy of a barcode sequence comprised within a barcode molecule.

Optionally, one or more barcode sequences may be comprised within a barcoded oligonucleotide, wherein the barcode region of the barcoded oligonucleotide comprises an enzymatically-produced complement of a barcode sequence comprised within a multimeric barcode molecule. Optionally, one or more barcode sequences may be comprised within a barcoded oligonucleotide, wherein the barcode region of the barcoded oligonucleotide comprises an enzymatically-produced copy of a barcode sequence comprised within a multimeric barcode molecule.

Optionally, one or more barcode sequences may be comprised within a first barcoded oligonucleotide, wherein the barcode region of the barcoded oligonucleotide comprises an enzymatically-produced complement of a barcode sequence comprised within a second barcoded oligonucleotide. Optionally, one or more barcode sequences may be comprised within a first barcoded oligonucleotide, wherein the barcode region of the barcoded oligonucleotide comprises an enzymatically-produced copy of a barcode sequence comprised within a second barcoded oligonucleotide.

Any enzymatic process used for copying, replicating, and/or synthesising nucleic acid sequences may be employed to produce enzymatically-produced copies or enzymatically-produced complements of a barcode sequence. Optionally, a primer-extension process may be employed. Optionally, a primer-extension process may be employed, wherein a barcode sequence comprised within a barcode molecule (and/or comprised within a multimeric barcode molecule, and/or comprised within a barcoded oligonucleotide) is copied within a primer-extension step, and wherein the resulting primer-extension product of the primer-extension step comprises all or part of a barcode sequence (e.g. comprises all or part of a barcoded oligonucleotide) which is then appended to the sequence of a nucleic acid from a circulating microparticle (e.g., appended to the sequence of a fragment of genomic DNA from a circulating microparticle).

Optionally, a polymerase chain reaction (PCR) process may be employed. Optionally, a polymerase chain reaction (PCR) process may be employed, wherein a barcode sequence comprised within a barcode molecule (and/or comprised within a multimeric barcode molecule, and/or comprised within a barcoded oligonucleotide) is copied within a PCR extension step, and wherein the resulting extension product of the PCR extension step comprises all or part of a barcode sequence (e.g. comprises all or part of a barcoded oligonucleotide) which is then appended to the sequence of a nucleic acid from a circulating microparticle (e.g., appended to the sequence of a fragment of genomic DNA from a circulating microparticle). Optionally, a polymerase chain reaction (PCR) process may be employed, wherein a barcode sequence comprised within a barcode molecule (and/or comprised within a multimeric barcode molecule, and/or comprised within a barcoded oligonucleotide) is copied with at least two sequential PCR extension steps (e.g. copied with at least a first PCR cycle and then a second PCR cycle), and wherein at least two resulting PCR extension products each comprise all or part of a barcode sequence (e.g. comprises all or part of a barcoded oligonucleotide) which is then appended to the sequence of a nucleic acid from a circulating microparticle (e.g., appended to the sequence of a fragment of genomic DNA from a circulating microparticle).

Optionally, a rolling-circle amplification (RCA) process may be employed. Optionally, a rolling-circle amplification (RCA) process may be employed, wherein a barcode sequence comprised within a barcode molecule (and/or comprised within a multimeric barcode molecule, and/or comprised within a barcoded oligonucleotide) is copied within a rolling-circle amplification step, and wherein the resulting extension product of the rolling-circle amplification step comprises all or part of a barcode sequence (e.g. comprises all or part of a barcoded oligonucleotide, and/or comprises all or part of a barcode molecule, and/or comprises all or part of a multimeric barcode molecule) which is then appended to the sequence of a nucleic acid from a circulating microparticle (e.g., appended to the sequence of a fragment of genomic DNA from a circulating microparticle).

Optionally, a rolling-circle amplification (RCA) process may be employed, wherein a barcode sequence comprised within a multimeric barcode molecule is copied within a rolling-circle amplification step, and wherein the resulting extension product of the rolling-circle amplification step comprises a secondary multimeric barcode molecule, and wherein said secondary multimeric barcode molecule is employed as a template to synthesise at least one barcoded oligonucleotide (wherein such a barcoded oligonucleotide may be produced by any method described herein; e.g. wherein at least one barcoded oligonucleotide is produced by a primer-extension step using said secondary multimeric barcode molecule as a template, or produced by a primer-extension and ligation step using said secondary multimeric barcode molecule as a template) which is then appended to the sequence of a nucleic acid from a circulating microparticle (e.g., appended to the sequence of a fragment of genomic DNA from a circulating microparticle).

Optionally, any such process of producing enzymatically-produced copies or enzymatically-produced complements of a barcode sequence may be performed in a single reaction volume. Optionally, any such process of producing enzymatically-produced copies or enzymatically-produced complements of a barcode sequence may be performed in two or more different reaction volumes (i.e., performed in two or more different partitions). Optionally, any such process of producing enzymatically-produced copies or enzymatically-produced complements of a barcode sequence may be performed in at least 3, at least 5, at least 10, at least 50, at least 100, at least 500, at least 1000, at least 10,000, at least 100,000, at least 1,000,000, at least 10,000,000, or at least 100,000,000 different reaction volumes (and/or partitions).

Optionally, any such process of producing enzymatically-produced copies or enzymatically-produced complements of a barcode sequence may be performed in a reaction volume comprising sequences of nucleic acids from one or more circulating microparticles (e.g., in a reaction volume comprising one or more circulating microparticles). Optionally, a process of producing enzymatically-produced copies or enzymatically-produced complements of a barcode sequence may be performed in a first reaction volume comprising sequences of nucleic acids of a first circulating microparticle from a sample (e.g., comprising fragments of genomic DNA of a first circulating microparticle from a sample, and/or comprising a first circulating microparticle from a sample) and performed in a second reaction volume comprising sequences of nucleic acids of a second circulating microparticle from the sample (e.g., comprising fragments of genomic DNA of a second circulating microparticle from the sample, and/or comprising a second circulating microparticle from the sample).

Optionally, a process of producing enzymatically-produced copies or enzymatically-produced complements of a barcode sequence may be performed in N different reaction volumes, wherein each such reaction volume comprises at least one barcode sequence and further comprises sequences of nucleic acids of a circulating microparticle from a sample (e.g., further comprises fragments of genomic DNA of a circulating microparticle from a sample, and/or further comprises a circulating microparticle from a sample), wherein N is at least 2, at least 3, at least 5, at least 10, at least 50, at least 100, at least 500, at least 1000, at least 10,000, at least 100,000, at least 1,000,000, at least 10,000,000, or at least 100,000,000. Optionally, the barcode sequences comprised across the N different reaction volumes may together comprise at least 2, at least 3, at least 5, at least 10, at least 50, at least 100, at least 500, at least 1000, at least 10,000, at least 100,000, at least 1,000,000, at least 10,000,000, or at least 100,000,000 different barcode sequences.

Optionally, a process of producing enzymatically-produced copies or enzymatically-produced complements of a barcode sequence may be performed in a first reaction volume comprising a first barcode sequence and further comprising sequences of nucleic acids of a first circulating microparticle of a sample (e.g., further comprising fragments of genomic DNA of a first circulating microparticle from a sample, and/or further comprising a first circulating microparticle from a sample) and performed in a second reaction volume comprising a second barcode sequence and further comprising sequences of nucleic acids of a second circulating microparticle of the sample (e.g., further comprising fragments of genomic DNA of a second circulating microparticle from the sample, and/or further comprising a second circulating microparticle from the sample), wherein the first barcode sequence is different to the second barcode sequence.

Optionally, a process of producing enzymatically-produced copies or enzymatically-produced complements of a barcode sequence may be performed in at first reaction volume comprising sequences of nucleic acids of a first circulating microparticle of a sample (e.g., comprising fragments of genomic DNA of a first circulating microparticle of a sample) wherein at least first and second enzymatically-produced copies or enzymatically-produced complements of a barcode sequence from the first reaction volume are appended to sequences of nucleic acids of the first circulating microparticle of the sample, and performed in at second reaction volume comprising sequences of nucleic acids of a second circulating microparticle of the sample (e.g., comprising fragments of genomic DNA of a second circulating microparticle of the sample) wherein at least first and second enzymatically-produced copies or enzymatically-produced complements of a barcode sequence from the second reaction volume are appended to sequences of nucleic acids of the second circulating microparticle of the sample.

Optionally, any process of producing enzymatically-produced copies or enzymatically-produced complements of a barcode sequence may be performed for (and/or performed on or with) a library comprising two or more barcode sequences. Optionally, any process of producing enzymatically-produced copies or enzymatically-produced complements of a barcode sequence may be performed for (and/or performed on or with) a library comprising two or more barcode molecules. Optionally, any process of producing enzymatically-produced copies or enzymatically-produced complements of a barcode sequence may be performed for (and/or performed on or with) a library comprising two or more multimeric barcode molecules. Optionally, any process of producing enzymatically-produced copies or enzymatically-produced complements of a barcode sequence may be performed for (and/or performed on or with) a library comprising two or more multimeric barcoding reagents. Optionally, any process of producing enzymatically-produced copies or enzymatically-produced complements of a barcode sequence may be performed for (and/or performed on or with) a library comprising two or more barcoded oligonucleotides.

Optionally, any process of producing enzymatically-produced copies or enzymatically-produced complements of a barcode sequence may further comprise appending any one or more enzymatically-produced copies or enzymatically-produced complements of a barcode sequence to each of one or more sequences of nucleic acids of a circulating microparticle (e.g. to fragments of genomic DNA of a circulating microparticle) in an appending step. Optionally, any one or more such appending step may comprise a step of hybridisation (e.g. a step of hybridising a barcoded oligonucleotide to a nucleic acid sequence), a step of hybridisation and extension hybridisation (e.g. a step of hybridising a barcoded oligonucleotide to a nucleic acid sequence and then extending the hybridised barcoded oligonucleotide with a polymerase), and/or a step of ligation (e.g. a step of ligating a barcoded oligonucleotide to a nucleic acid sequence). Following any one or more such appending steps, the nucleic acid sequences comprising barcode sequences and the sequences of nucleic acids from circulating microparticle(s) to which they have been appended, may then be subject to a sequencing step.

Optionally, any process of producing enzymatically-produced copies or enzymatically-produced complements of a barcode sequence may further comprise appending any one or more enzymatically-produced copies or enzymatically-produced complements of a barcode sequence to each of one or more sequences of nucleic acids of a circulating microparticle (e.g. to fragments of genomic DNA of a circulating microparticle), wherein said sequences of nucleic acids of a circulating microparticle further comprise a coupling sequence. Any coupling sequence and/or method(s) of appending coupling sequences, and/or methods of appending barcode sequences to coupling sequences (and/or to oligonucleotides comprising coupling sequences) described herein may be employed.

Optionally, any process of producing enzymatically-produced copies or enzymatically-produced complements of a barcode sequence and further comprising appending any one or more enzymatically-produced copies or enzymatically-produced complements of a barcode sequence to sequences of nucleic acids of a circulating microparticle, may further comprise a step of chemically crosslinking a circulating microparticle (and/or chemically crosslinking a sample comprising two or more circulating microparticles). Optionally, said step of chemical crosslinking may be performed prior to and/or after a step of partitioning circulating microparticles and/or barcode molecules into two or more different partitions. Optionally, said step of chemical crosslinking may be followed by a step of reversing said crosslinks, for example with a high-temperature thermal incubation step. Optionally, any process of producing enzymatically-produced copies or enzymatically-produced complements of a barcode sequence and further comprising appending any one or more enzymatically-produced copies or enzymatically-produced complements of a barcode sequence to sequences of nucleic acids of a circulating microparticle, may further comprise a step of permeabilising said circulating microparticle(s), for example with a high-temperature incubation step and/or with a chemical surfactant.

Optionally, any process of producing enzymatically-produced copies or enzymatically-produced complements of a barcode sequence may be performed with any number and/or type and/or volume of partition described herein. Optionally, any process of producing enzymatically-produced copies or enzymatically-produced complements of a barcode sequence in one or more partitions may comprise one or more partitions comprising any number of circulating microparticles as described herein. Optionally, any process of producing enzymatically-produced copies or enzymatically-produced complements of a barcode sequence in one or more partitions may comprise one or more partitions comprising any number (or average number) of circulating microparticles as described herein. Optionally, any process of producing enzymatically-produced copies or enzymatically-produced complements of a barcode sequence in one or more partitions may comprise one or more partitions comprising any mass (or average mass) of nucleic acids (e.g. any mass of fragments of genomic DNA) from circulating microparticles as described herein.

Processes of producing enzymatically-produced copies and/or enzymatically-produced complements of a barcode sequence may have a variety of desirable features and characteristics for the purposes of analysing linked sequences from circulating microparticles. In the first case, producing enzymatically-produced copies and/or enzymatically-produced complements of a barcode sequence enables the production of a large absolute mass of barcode sequences (e.g. a large absolute mass of barcode molecules or barcoded oligonucleotides), using only a small amount of starting barcode sequence material (e.g., PCR and RCA processing can produce vast exponential amplification of input material for subsequent use and manipulation).

Furthermore, producing enzymatically-produced copies and/or enzymatically-produced complements of barcode sequences wherein such barcode sequences are comprised within libraries (e.g. comprised within libraries of barcode molecules, libraries of multimeric barcode molecules, libraries of multimeric barcoding reagents, and/or libraries of barcoded oligonucleotides) enables the production of a large absolute mass of barcode sequences of defined sequence character (e.g. wherein the large absolute mass of barcode sequences comprise sequences from the previously-established and/or previously-characterised library or libraries).

Furthermore, many enzymatic copying and amplification processes (such as rolling circle amplification by the phi29 polymerase, and primer-extension and/or PCR amplification by thermostable polymerases such as Phusion polymerase) exhibit high molecular accuracy during said copying (in terms of the rate of error production within newly copied sequence), and thus exhibit favourable accuracy profiles of the resulting barcode sequences (e.g. the resulting barcode molecules, multimeric barcode molecules, and/or barcoded oligonucleotides) in comparison with non-enzymatic approaches (e.g. in comparison with standard chemical oligonucleotide synthesis procedures, such a phosphoramidite oligonucleotide synthesis).

Furthermore, enzymatic copying and amplification processes (e.g. primer-extension and PCR processes) are highly amenable to subsequent steps of modification, processing, and functionalisation of said sequences, which also may have the further benefit of themselves being achievable on large absolute masses of substrate in relatively straightforward fashion. For example, primer-extension products are readily configured and/or configurable for subsequent ligation processes (e.g., as in a primer-extension and ligation process, as for example may be performed to produce barcoded oligonucleotides and/or multimeric barcoding reagents). And for further example, the direct products of enzymatic-copying processes themselves (e.g. wherein a complement/copy of a barcode sequence is annealed to the barcode sequence itself) may have desirable functional and/or structural properties. For example, a barcoded oligonucleotide produced through an enzymatic primer-extension process is retained structurally tethered (through the annealed nucleotide sequence) to the barcode molecule (e.g. multimeric barcode molecules) along which it was produced, in a singular macromolecular complex that may then be further processed and/or functionalised as a singular, intact reagent in solution.

11. General Properties of Multimeric Barcoding Reagents

Use of multimeric barcoding reagents exhibits a variety of useful features and functionalities to link sequences from circulating microparticles. In the first case, such reagents (and/or libraries thereof) can comprise very well-defined, well-characterised sets of barcodes, which can inform and enhance subsequent bioinformatic analysis (for example, as relates to use of multimeric barcode molecules and/or multimeric barcoding reagents of known and/or empirically determined sequence). Additionally, such reagents enable extremely easy partitioning and/or other molecular or biophysical processes of multiple barcode sequences at once (i.e., since multiple barcode sequences are comprised within each such reagent, they automatically 'move together' within solution and during liquid handling and/or processing steps). Furthermore, the proximity between multiple barcode sequences of such reagents itself can enable novel functional assay forms, such as crosslinking circulating microparticles and then appending sequences from such multimeric reagents to the fragments of genomic DNA contained therein (including e.g. within solution-phase reactions thereof, i.e. with two or more microparticles within a single partition).

The invention provides multimeric barcoding reagents for labelling one or more target nucleic acids. A multimeric barcoding reagent comprises two or more barcode regions are linked together (directly or indirectly).

Each barcode region comprises a nucleic acid sequence. The nucleic acid sequence may be single-stranded DNA, double-stranded DNA, or single stranded DNA with one or more double-stranded regions.

Each barcode region may comprise a sequence that identifies the multimeric barcoding reagent. For example, this sequence may be a constant region shared by all barcode regions of a single multimeric barcoding reagent. Each barcode region may contain a unique sequence which is not present in other regions, and may thus serve to uniquely identify each barcode region. Each barcode region may comprise at least 5, at least 10, at least 15, at least 20, at least 25, at least 50 or at least 100 nucleotides. Preferably, each barcode region comprises at least 5 nucleotides. Preferably each barcode region comprises deoxyribonucleotides, optionally all of the nucleotides in a barcode region are deoxyribonucleotides. One or more of the deoxyribonucleotides may be a modified deoxyribonucleotide (e.g. a deoxyribonucleotide modified with a biotin moiety or a deoxyuracil nucleotide). The barcode regions may comprise one or more degenerate nucleotides or sequences. The barcode regions may not comprise any degenerate nucleotides or sequences.

The multimeric barcoding reagent may comprise at least 5, at least 10, at least 20, at least 25, at least 50, at least 75, at least 100, at least 200, at least 500, at least 1000, at least 5000, or at least 10,000 barcode regions. Preferably, the multimeric barcoding reagent comprises at least 5 barcode regions.

The multimeric barcoding reagent may comprise at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ unique or different barcode regions. Preferably, the multimeric barcoding reagent comprises at least 5 unique or different barcode regions.

A multimeric barcoding reagent may comprise: first and second barcode molecules linked together (i.e. a multimeric barcode molecule), wherein each of the barcode molecules comprises a nucleic acid sequence comprising a barcode region.

The barcode molecules of a multimeric barcode molecule may be linked on a nucleic acid molecule. The barcode molecules of a multimeric barcode molecule may be comprised within a (single) nucleic acid molecule. A multimeric barcode molecule may comprise a single, contiguous nucleic acid sequence comprising two or more barcode molecules. A multimeric barcode molecule may be a single-stranded nucleic acid molecule (e.g. single-stranded DNA), a double-stranded-stranded nucleic acid molecule or a single stranded molecule comprising one or more double-stranded regions. A multimeric barcode molecule may comprise one or more phosphorylated 5' ends capable of ligating to 3' ends of other nucleic acid molecules. Optionally, in a double-stranded region or between two different double-stranded regions, a multimeric barcode molecule may comprise one or more nicks, or one or more gaps, where the multimeric barcode molecule itself has been divided or separated. Any said gap may be at least one, at least 2, at least 5, at least 10, at least 20, at least 50, or at least 100 nucleotides in length. Said nicks and/or gaps may serve the purpose of increasing the molecular flexibility of the multimeric barcode molecule and/or multimeric barcoding reagent, for example to increase the accessibility of the molecule or reagent to interact with target nucleic acid molecules. Said nicks and/or gaps may also enable more efficient purification or removal of said molecules or reagents. A molecule and/or reagent comprising said nick(s) and/or gap(s) may retain links between different barcode molecules by having a complementary DNA strand which is jointly hybridised to regions of two or more divided parts of a multimeric barcode molecule.

The barcode molecules may be linked by a support e.g. a macromolecule, solid support or semi-solid support. The sequences of the barcode molecules linked to each support may be known. The barcode molecules may be linked to the support directly or indirectly (e.g. via a linker molecule). The barcode molecules may be linked by being bound to the support and/or by being bound or annealed to linker molecules that are bound to the support. The barcode molecules may be bound to the support (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The barcode molecules may be linked by a macromolecule by being bound to the macromolecule and/or by being annealed to the macromolecule.

The barcode molecules may be linked to the macromolecule directly or indirectly (e.g. via a linker molecule). The barcode molecules may be linked by being bound to the macromolecule and/or by being bound or annealed to linker molecules that are bound to the macromolecule. The barcode molecules may be bound to the macromolecule (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The macromolecule may be a synthetic polymer (e.g. a dendrimer) or a biopolymer such as a nucleic acid (e.g. a single-stranded nucleic acid such as single-stranded DNA), a peptide, a polypeptide or a protein (e.g. a multimeric protein).

The dendrimer may comprise at least 2, at least 3, at least 5, or at least 10 generations.

The macromolecule may be a nucleic acid comprising two or more nucleotides each capable of binding to a barcode molecule. Additionally or alternatively, the nucleic acid may comprise two or more regions each capable of hybridizing to a barcode molecule.

The nucleic acid may comprise a first modified nucleotide and a second modified nucleotide, wherein each modified nucleotide comprises a binding moiety (e.g. a biotin moiety, or an alkyne moiety which may be used for a click-chemical reaction) capable of binding to a barcode molecule. Optionally, the first and second modified nucleotides may be separated by an intervening nucleic acid sequence of at least one, at least two, at least 5 or at least 10 nucleotides.

The nucleic acid may comprise a first hybridisation region and a second hybridisation region, wherein each hybridisation region comprises a sequence complementary to and capable of hybridizing to a sequence of at least one nucleotide within a barcode molecule. The complementary sequence may be at least 5, at least 10, at least 15, at least 20, at least 25 or at least 50 contiguous nucleotides. Preferably, the complementary sequence is at least 10 contiguous nucleotides. Optionally, the first and second hybridisation regions may be separated by an intervening nucleic acid sequence of at least one, at least two, at least 5 or at least 10 nucleotides.

The macromolecule may be a protein such as a multimeric protein e.g. a homomeric protein or a heteromeric protein. For example, the protein may comprise streptavidin e.g. tetrameric streptavidin.

The support may be a solid support or a semi-solid support. The support may comprise a planar surface. The support may be a slide e.g. a glass slide. The slide may be a flow cell for sequencing. If the support is a slide, the first and second barcode molecules may be immobilized in a discrete region on the slide. Optionally, the barcode molecules of each multimeric barcoding reagent in a library are immobilized in a different discrete region on the slide to the barcode molecules of the other multimeric barcoding reagents in the library. The support may be a plate comprising wells, optionally wherein the first and second barcode molecules are immobilized in the same well. Optionally, the barcode molecules of each multimeric barcoding reagent in library are immobilized in a different well of the plate to the barcode molecules of the other multimeric barcoding reagents in the library.

Preferably, the support is a bead (e.g. a gel bead). The bead may be an agarose bead, a silica bead, a styrofoam bead, a gel bead (such as those available from 10× Genomics®), an antibody conjugated bead, an oligo-dT conjugated bead, a streptavidin bead or a magnetic bead (e.g. a superparamagnetic bead). The bead may be of any size and/or molecular structure. For example, the bead may be 10 nanometres to 100 microns in diameter, 100 nanometres to 10 microns in diameter, or 1 micron to 5 microns in diameter. Optionally, the bead is approximately 10 nanometres in diameter, approximately 100 nanometres in diameter, approximately 1 micron in diameter, approximately 10 microns in diameter or approximately 100 microns in diameter. The bead may be solid, or alternatively the bead may be hollow or partially hollow or porous. Beads of certain sizes may be most preferable for certain barcoding methods. For example, beads less than 5.0 microns, or less than 1.0 micron, may be most useful for barcoding nucleic acid targets within individual cells. Preferably, the barcode molecules of each multimeric barcoding reagent in a library are linked together on a different bead to the barcode molecules of the other multimeric barcoding reagents in the library.

The support may be functionalised to enable attachment of two or more barcode molecules. This functionalisation may be enabled through the addition of chemical moieties (e.g. carboxylated groups, alkynes, azides, acrylate groups, amino groups, sulphate groups, or succinimide groups), and/or protein-based moieties (e.g. streptavidin, avidin, or protein G) to the support. The barcode molecules may be attached to the moieties directly or indirectly (e.g. via a linker molecule).

Functionalised supports (e.g. beads) may be brought into contact with a solution of barcode molecules under conditions which promote the attachment of two or more barcode molecules to each bead in the solution (generating multimeric barcoding reagents).

In a library of multimeric barcoding reagents, the barcode molecules of each multimeric barcoding reagent in a library may be linked together on a different support to the barcode molecules of the other multimeric barcoding reagents in the library.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 barcode molecules linked together, wherein each barcode molecule is as defined herein; and a barcoded oligonucleotide annealed to each barcode molecule, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ unique or different barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 unique or different barcode molecules linked together, wherein each barcode molecule is as defined herein; and a barcoded oligonucleotide annealed to each barcode molecule, wherein each barcoded oligonucleotide is as defined herein.

A multimeric barcoding reagent may comprise two or more barcoded oligonucleotides as defined herein, wherein the barcoded oligonucleotides each comprise a barcode region. A multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least 10,000, at least 100,000, or at least 1,000,000 unique or different barcoded oligonucleotides. Preferably, the multimeric barcoding reagent comprises at least 5 unique or different barcoded oligonucleotides.

The barcoded oligonucleotides of a multimeric barcoding reagent are linked together (directly or indirectly). The barcoded oligonucleotides of a multimeric barcoding reagent are linked together by a support e.g. a macromolecule, solid support or semi-solid support, as described herein. The multimeric barcoding reagent may comprise one or more polymers to which the barcoded oligonucleotides are annealed or attached. For example, the barcoded oligonucleotides of a multimeric barcoding reagent may be annealed to a multimeric hybridization molecule e.g. a multimeric barcode molecule. Alternatively, the barcoded oligonucleotides of a multimeric barcoding reagent may be linked together by a macromolecule (such as a synthetic polymer e.g. a dendrimer, or a biopolymer e.g. a protein) or a support (such as a solid support or a semi-solid support e.g. a gel bead). Additionally or alternatively, the barcoded oligonucleotides of a (single) multimeric barcoding reagent may linked together by being comprised within a (single) lipid carrier (e.g. a liposome or a micelle).

A multimeric barcoding reagent may comprise: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule.

The hybridization molecules comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The hybridization molecules may comprise one or more degenerate nucleotides or sequences. The hybridization molecules may not comprise any degenerate nucleotides or sequences.

The hybridization molecules of a multimeric hybridization molecule may be linked on a nucleic acid molecule. Such a nucleic acid molecule may provide the backbone to which single-stranded barcoded oligonucleotides may be annealed. The hybridization molecules of a multimeric hybridization molecule may be comprised within a (single) nucleic acid molecule. A multimeric hybridization molecule may comprise a single, contiguous nucleic acid sequence comprising two or more hybridization molecules. A multimeric hybridization molecule may be a single-stranded nucleic acid molecule (e.g. single-stranded DNA) comprising two or more hybridization molecules.

A multimeric hybridization molecule may comprise one or more double-stranded regions. Optionally, in a double-stranded region or between two different double-stranded regions, a multimeric hybridization molecule may comprise one or more nicks, or one or more gaps, where the multimeric hybridization molecule itself has been divided or separated. Any said gap may be at least one, at least 2, at least 5, at least 10, at least 20, at least 50, or at least 100 nucleotides in length. Said nicks and/or gaps may serve the purpose of increasing the molecular flexibility of the multimeric hybridization molecule and/or multimeric barcoding reagent, for example to increase the accessibility of the molecule or reagent to interact with target nucleic acid molecules. Said nicks and/or gaps may also enable more efficient purification or removal of said molecules or reagents. A molecule and/or reagent comprising said nick(s) and/or gap(s) may retain links between different hybridization molecules by having a complementary DNA strand which is jointly hybridised to regions of two or more divided parts of a multimeric hybridization molecule.

The hybridization molecules may be linked by a macromolecule by being bound to the macromolecule and/or by being annealed to the macromolecule.

The hybridization molecules may be linked to the macromolecule directly or indirectly (e.g. via a linker molecule). The hybridization molecules may be linked by being bound to the macromolecule and/or by being bound or annealed to linker molecules that are bound to the macromolecule. The hybridization molecules may be bound to the macromolecule (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The macromolecule may be a synthetic polymer (e.g. a dendrimer) or a biopolymer such as a nucleic acid (e.g. a single-stranded nucleic acid such as single-stranded DNA), a peptide, a polypeptide or a protein (e.g. a multimeric protein).

The dendrimer may comprise at least 2, at least 3, at least 5, or at least 10 generations.

The macromolecule may be a nucleic acid comprising two or more nucleotides each capable of binding to a hybridization molecule. Additionally or alternatively, the nucleic acid may comprise two or more regions each capable of hybridizing to a hybridization molecule.

The nucleic acid may comprise a first modified nucleotide and a second modified nucleotide, wherein each modified nucleotide comprises a binding moiety (e.g. a biotin moiety, or an alkyne moiety which may be used for a click-chemical reaction) capable of binding to a hybridization molecule. Optionally, the first and second modified nucleotides may be separated by an intervening nucleic acid sequence of at least one, at least two, at least 5 or at least 10 nucleotides.

The nucleic acid may comprise a first hybridisation region and a second hybridisation region, wherein each hybridisation region comprises a sequence complementary to and capable of hybridizing to a sequence of at least one nucleotide within a hybridization molecule. The complementary sequence may be at least 5, at least 10, at least 15, at least 20, at least 25 or at least 50 contiguous nucleotides. Optionally, the first and second hybridisation regions may be separated by an intervening nucleic acid sequence of at least one, at least two, at least 5 or at least 10 nucleotides.

The macromolecule may be a protein such as a multimeric protein e.g. a homomeric protein or a heteromeric protein. For example, the protein may comprise streptavidin e.g. tetrameric streptavidin.

The hybridization molecules may be linked by a support. The hybridization molecules may be linked to the support directly or indirectly (e.g. via a linker molecule). The hybridization molecules may be linked by being bound to the support and/or by being bound or annealed to linker molecules that are bound to the support. The hybridization molecules may be bound to the support (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The support may be a solid support or a semi-solid support. The support may comprise a planar surface. The support may be a slide e.g. a glass slide. The slide may be a flow cell for sequencing. If the support is a slide, the first and second hybridization molecules may be immobilized in a discrete region on the slide. Optionally, the hybridization molecules of each multimeric barcoding reagent in a library are immobilized in a different discrete region on the slide to the hybridization molecules of the other multimeric barcoding reagents in the library. The support may be a plate comprising wells, optionally wherein the first and second hybridization molecules are immobilized in the same well. Optionally, the hybridization molecules of each multimeric barcoding reagent in library are immobilized in a different well of the plate to the hybridization molecules of the other multimeric barcoding reagents in the library.

Preferably, the support is a bead (e.g. a gel bead). The bead may be an agarose bead, a silica bead, a styrofoam bead, a gel bead (such as those available from 10× Genomics®), an antibody conjugated bead, an oligo-dT conjugated bead, a streptavidin bead or a magnetic bead (e.g. a superparamagnetic bead). The bead may be of any size and/or molecular structure. For example, the bead may be 10 nanometres to 100 microns in diameter, 100 nanometres to 10 microns in diameter, or 1 micron to 5 microns in diameter. Optionally, the bead is approximately 10 nanometres in diameter, approximately 100 nanometres in diameter, approximately 1 micron in diameter, approximately 10 microns in diameter or approximately 100 microns in diameter. The bead may be solid, or alternatively the bead may be hollow or partially hollow or porous. Beads of certain sizes may be most preferable for certain barcoding methods. For example, beads less than 5.0 microns, or less than 1.0 micron, may be most useful for barcoding nucleic acid targets within individual cells. Preferably, the hybridization molecules of each multimeric barcoding reagent in a library are linked together on a different bead to hybridization molecules of the other multimeric barcoding reagents in the library.

The support may be functionalised to enable attachment of two or more hybridization molecules. This functionalisation may be enabled through the addition of chemical moieties (e.g. carboxylated groups, alkynes, azides, acrylate groups, amino groups, sulphate groups, or succinimide groups), and/or protein-based moieties (e.g. streptavidin, avidin, or protein G) to the support. The hybridization molecules may be attached to the moieties directly or indirectly (e.g. via a linker molecule).

Functionalised supports (e.g. beads) may be brought into contact with a solution of hybridization molecules under conditions which promote the attachment of two or more hybridization molecules to each bead in the solution (generating multimeric barcoding reagents).

In a library of multimeric barcoding reagents, the hybridization molecules of each multimeric barcoding reagent in a library may be linked together on a different support to the hybridization molecules of the other multimeric barcoding reagents in the library.

Optionally, the hybridization molecules are attached to the beads by covalent linkage, non-covalent linkage (e.g. a streptavidin-biotin bond) or nucleic acid hybridization.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, or at least 10,000 hybridization molecules linked together, wherein each hybridization molecule is as defined herein; and a barcoded oligonucleotide annealed to each hybridization molecule, wherein each barcoded oligonucleotide is as defined herein. Preferably, the multimeric barcoding reagent comprises at least 5 hybridization molecules linked together, wherein each hybridization molecule is as defined herein; and a barcoded oligonucleotide annealed to each hybridization molecule, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, or at least 10,000 unique or different hybridization molecules linked together, wherein each hybridization molecule is as defined herein; and a barcoded oligonucleotide annealed to each hybridization molecule, wherein each barcoded oligonucleotide is as defined herein. Preferably, the multimeric barcoding reagent comprises at least 5 unique or different hybridization molecules linked together, wherein each hybridization molecule is as defined herein; and a barcoded oligonucleotide annealed to each hybridization molecule, wherein each barcoded oligonucleotide is as defined herein.

The multimeric hybridization molecule may be a multimeric barcode molecule, wherein the first hybridization molecule is a first barcode molecule and the second hybridization molecule is a second barcode molecule. A multimeric barcoding reagent may comprise: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide is annealed to the barcode region of the first barcode molecule, and wherein the second barcoded oligonucleotide is annealed to the barcode region of the second barcode molecule.

The barcoded oligonucleotides of a multimeric barcoding reagent may comprise: a first barcoded oligonucleotide comprising, optionally in the 5' to 3' direction, a barcode region, and a target region capable of annealing or ligating to a first fragment of the target nucleic acid; and a second barcoded oligonucleotide comprising, optionally in the 5' to 3' direction, a barcode region, and a target region capable of annealing or ligating to a second fragment of the target nucleic acid.

The barcoded oligonucleotides of a multimeric barcoding reagent may comprise: a first barcoded oligonucleotide comprising a barcode region, and a target region capable of ligating to a first fragment of the target nucleic acid; and a second barcoded oligonucleotide comprising a barcode region, and a target region capable of ligating to a second fragment of the target nucleic acid.

The barcoded oligonucleotides of a multimeric barcoding reagent may comprise: a first barcoded oligonucleotide comprising, in the 5' to 3' direction, a barcode region, and a target region capable of annealing to a first fragment of the target nucleic acid; and a second barcoded oligonucleotide comprising, in the 5' to 3' direction, a barcode region, and a target region capable of annealing to a second fragment of the target nucleic acid.

12. General Properties of Barcoded Oligonucleotides

A barcoded oligonucleotide comprises a barcode region. The barcoded oligonucleotides may comprise, optionally in the 5' to 3' direction, a barcode region and a target region. The target region is capable of annealing or ligating to a fragment of the target nucleic acid. Alternatively, a barcoded oligonucleotide may consist essentially of or consist of a barcode region.

The 5' end of a barcoded oligonucleotide may be phosphorylated. This may enable the 5' end of the barcoded oligonucleotide to be ligated to the 3' end of a target nucleic acid. Alternatively, the 5' end of a barcoded oligonucleotide may not be phosphorylated.

A barcoded oligonucleotide may be a single-stranded nucleic acid molecule (e.g. single-stranded DNA). A barcoded oligonucleotide may comprise one or more double-stranded regions. A barcoded oligonucleotide may be a double-stranded nucleic acid molecule (e.g. double-stranded DNA).

The barcoded oligonucleotides may comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The barcoded oligonucleotides may comprise one or more degenerate nucleotides or sequences. The barcoded oligonucleotides may not comprise any degenerate nucleotides or sequences.

The barcode regions of each barcoded oligonucleotide may comprise different sequences. Each barcode region may comprise a sequence that identifies the multimeric barcoding reagent. For example, this sequence may be a constant region shared by all barcode regions of a single multimeric barcoding reagent. The barcode region of each barcoded oligonucleotide may contain a unique sequence which is not present in other barcoded oligonucleotides, and may thus serve to uniquely identify each barcoded oligonucleotide. Each barcode region may comprise at least 5, at least 10, at least 15, at least 20, at least 25, at least 50 or at least 100 nucleotides. Preferably, each barcode region comprises at least 5 nucleotides. Preferably each barcode region comprises deoxyribonucleotides, optionally all of the nucleotides in a barcode region are deoxyribonucleotides. One or more of the deoxyribonucleotides may be a modified deoxyribonucleotide (e.g. a deoxyribonucleotide modified with a biotin moiety or a deoxyuracil nucleotide). The barcode regions may comprise one or more degenerate nucleotides or sequences. The barcode regions may not comprise any degenerate nucleotides or sequences.

The target regions of each barcoded oligonucleotide may comprise different sequences. Each target region may comprise a sequence capable of annealing to only a single fragment of a target nucleic acid within a sample of nucleic acids (i.e. a target specific sequence). Each target region may comprise one or more random, or one or more degenerate, sequences to enable the target region to anneal to more than one fragment of a target nucleic acid. Each target region may comprise at least 5, at least 10, at least 15, at least 20, at least 25, at least 50 or at least 100 nucleotides. Preferably, each target region comprises at least 5 nucleotides. Each target region may comprise 5 to 100 nucleotides, 5 to 10 nucleotides, 10 to 20 nucleotides, 20 to 30 nucleotides, 30 to 50 nucleotides, 50 to 100 nucleotides, 10 to 90 nucleotides, 20 to 80 nucleotides, 30 to 70 nucleotides or 50 to 60 nucleotides. Preferably, each target region comprises 30 to 70 nucleotides. Preferably each target region comprises deoxyribonucleotides, optionally all of the nucleotides in a target region are deoxyribonucleotides. One or more of the deoxyribonucleotides may be a modified deoxyribonucleotide (e.g. a deoxyribonucleotide modified with a biotin moiety or a deoxyuracil nucleotide). Each target region may comprise one or more universal bases (e.g. inosine), one or modified nucleotides and/or one or more nucleotide analogues.

The target regions may be used to anneal the barcoded oligonucleotides to fragments of target nucleic acids, and then may be used as primers for a primer-extension reaction or an amplification reaction e.g. a polymerase chain reaction. Alternatively, the target regions may be used to ligate the barcoded oligonucleotides to fragments of target nucleic acids. The target region may be at the 5' end of a barcoded oligonucleotide. Such a target region may be phosphorylated. This may enable the 5' end of the target region to be ligated to the 3' end of a fragment of a target nucleic acid.

The barcoded oligonucleotides may further comprise one or more adapter region(s). An adapter region may be between the barcode region and the target region. A barcoded oligonucleotide may, for example, comprise an adapter region 5' of a barcode region (a 5' adapter region) and/or an adapter region 3' of the barcode region (a 3' adapter region). Optionally, the barcoded oligonucleotides comprise, in the 5' to 3' direction, a barcode region, an adapter region and a target region.

The adapter region(s) of the barcoded oligonucleotides may comprise a sequence complementary to an adapter region of a multimeric barcode molecule or a sequence complementary to a hybridization region of a multimeric hybridization molecule. The adapter region(s) of the barcoded oligonucleotides may enable the barcoded oligonucleotides to be linked to a macromolecule or support (e.g. a bead). The adapter region(s) may be used for manipulating, purifying, retrieving, amplifying, or detecting barcoded oligonucleotides and/or target nucleic acids to which they may anneal or ligate.

The adapter region of each barcoded oligonucleotide may comprise a constant region. Optionally, all adapter regions of barcoded oligonucleotides of each multimeric barcoding reagent are substantially identical. The adapter region may comprise at least 1, at least 2, at least 3, at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

The barcoded oligonucleotides may be synthesized by a chemical oligonucleotide synthesis process. The barcoded oligonucleotides synthesis process may include one or more step of an enzymatic production process, an enzymatic amplification process, or an enzymatic modification procedure, such as an in vitro transcription process, a reverse transcription process, a primer-extension process, or a polymerase chain reaction process.

These general properties of barcoded oligonucleotides are applicable to any of the multimeric barcoding reagents described herein.

13. General Properties of Libraries of Multimeric Barcoding Reagents

The invention provides a library of multimeric barcoding reagents comprising first and second multimeric barcoding reagents as defined herein, wherein the barcode regions of the first multimeric barcoding reagent are different to the barcode regions of the second multimeric barcoding reagent.

The library of multimeric barcoding reagents may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the library comprises at least 10 multimeric barcoding reagents as defined herein. Preferably, the first and second barcode regions of each multimeric barcoding reagent are different to the barcode regions of at least 9 other multimeric barcoding reagents in the library.

The first and second barcode regions of each multimeric barcoding reagent may be different to the barcode regions of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The first and second barcode regions of each multimeric barcoding reagent may be different to the barcode regions of all of the other multimeric barcoding reagents in the library. Preferably, the first and second barcode regions of each multimeric barcoding reagent are different to the barcode regions of at least 9 other multimeric barcoding reagents in the library.

The barcode regions of each multimeric barcoding reagent may be different to the barcode regions of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The barcode regions of each multimeric barcoding reagent may be different to the barcode regions of all of the other multimeric barcoding reagents in the library. Preferably, the barcode regions of each multimeric barcoding reagent are different to the barcode regions of at least 9 other multimeric barcoding reagents in the library.

The invention provides a library of multimeric barcoding reagents comprising first and second multimeric barcoding reagents as defined herein, wherein the barcode regions of the barcoded oligonucleotides of the first multimeric barcoding reagent are different to the barcode regions of the barcoded oligonucleotides of the second multimeric barcoding reagent.

Different multimeric barcoding reagents within a library of multimeric barcoding reagents may comprise different numbers of barcoded oligonucleotides.

The library of multimeric barcoding reagents may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the library comprises at least 10 multimeric barcoding reagents as defined herein. Preferably, the barcode regions of the first and second barcoded oligonucleotides of each multimeric barcoding reagent are different to the barcode regions of the barcoded oligonucleotides of at least 9 other multimeric barcoding reagents in the library.

The barcode regions of the first and second barcoded oligonucleotides of each multimeric barcoding reagent may be different to the barcode regions of the barcoded oligonucleotides of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The barcode regions of the first and second barcoded oligonucleotides of each multimeric barcoding reagent may be different to the barcode regions of the barcoded oligonucleotides of all of the other multimeric barcoding reagents in the library. Preferably, the barcode regions of the first and second barcoded oligonucleotides of each multimeric barcoding reagent are different to the barcode regions of the barcoded oligonucleotides of at least 9 other multimeric barcoding reagents in the library.

The barcode regions of the barcoded oligonucleotides of each multimeric barcoding reagent may be different to the barcode regions of the barcoded oligonucleotides of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The barcode regions of the barcoded oligonucleotides of each multimeric barcoding reagent may be different to the barcode regions of the barcoded oligonucleotides of all of the other multimeric barcoding reagents in the library. Preferably, the barcode regions of the barcoded oligonucleotides of each multimeric barcoding reagent are different to the barcode regions of the barcoded oligonucleotides of at least 9 other multimeric barcoding reagents in the library.

These general properties of libraries of multimeric barcoding reagents are applicable to any of the multimeric barcoding reagents described herein.

14. Multimeric Barcoding Reagents Comprising Barcoded Oligonucleotides Annealed to a Multimeric Barcode Molecule The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises, optionally in the 5' to 3' direction, a barcode region annealed to the barcode region of the first barcode molecule and a target region capable of annealing or ligating to a first fragment of the target nucleic acid, and wherein the second barcoded oligonucleotide comprises, optionally in the 5' to 3' direction, a barcode region annealed to the barcode region of the second barcode molecule and a target region capable of annealing or ligating to a second fragment of the target nucleic acid.

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises a barcode region annealed to the barcode region of the first barcode molecule and a target region capable of ligating to a first fragment of the target nucleic acid, and wherein the second barcoded oligonucleotide comprises a barcode region annealed to the barcode region of the second barcode molecule and a target region capable of ligating to a second fragment of the target nucleic acid.

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises in the 5' to 3' direction a barcode region annealed to the barcode region of the first barcode molecule and a target region capable of annealing to a first fragment of the target nucleic acid, and wherein the second barcoded oligonucleotide comprises in the 5' to 3' direction a barcode region annealed to the barcode region of the second barcode molecule and a target region capable of annealing to a second fragment of the target nucleic acid.

The invention provides a multimeric barcoding reagent for labelling a target nucleic acid, wherein the reagent comprises: first and second barcode molecules linked together (i.e. a multimeric barcode molecule), wherein each of the barcode molecules comprises a nucleic acid sequence comprising a barcode region; and first and second barcoded oligonucleotides, wherein the first barcoded oligonucleotide comprises a barcode region annealed to the barcode region of the first barcode molecule and capable of ligating to a first fragment of the target nucleic acid, and wherein the second barcoded oligonucleotide comprises a barcode region annealed to the barcode region of the second barcode molecule and capable of ligating to a second fragment of the target nucleic acid.

Each barcoded oligonucleotide may consist essentially of or consist of a barcode region.

Preferably, the barcode molecules comprise or consist of deoxyribonucleotides. One or more of the deoxyribonucleotides may be a modified deoxyribonucleotide (e.g. a deoxyribonucleotide modified with a biotin moiety or a deoxyuracil nucleotide). The barcode molecules may comprise one or more degenerate nucleotides or sequences. The barcode molecules may not comprise any degenerate nucleotides or sequences.

The barcode regions may uniquely identify each of the barcode molecules. Each barcode region may comprise a sequence that identifies the multimeric barcoding reagent. For example, this sequence may be a constant region shared by all barcode regions of a single multimeric barcoding reagent. Each barcode region may comprise at least 5, at least 10, at least 15, at least 20, at least 25, at least 50 or at least 100 nucleotides. Preferably, each barcode region comprises at least 5 nucleotides. Preferably each barcode region comprises deoxyribonucleotides, optionally all of the nucleotides in a barcode region are deoxyribonucleotides. One or more of the deoxyribonucleotides may be a modified deoxyribonucleotide (e.g. a deoxyribonucleotide modified with a biotin moiety or a deoxyuracil nucleotide). The barcode regions may comprise one or more degenerate nucleotides or sequences. The barcode regions may not comprise any degenerate nucleotides or sequences.

Preferably, the barcode region of the first barcoded oligonucleotide comprises a sequence that is complementary and annealed to the barcode region of the first barcode molecule and the barcode region of the second barcoded oligonucleotide comprises a sequence that is complementary and annealed to the barcode region of the second barcode molecule. The complementary sequence of each barcoded oligonucleotide may be at least 5, at least 10, at least 15, at least 20, at least 25, at least 50 or at least 100 contiguous nucleotides.

The target regions of the barcoded oligonucleotides (which are not annealed to the multimeric barcode molecule(s)) may be non-complementary to the multimeric barcode molecule(s).

The barcoded oligonucleotides may comprise a linker region between the barcode region and the target region. The linker region may comprise one or more contiguous nucleotides that are not annealed to the multimeric barcode molecule and are non-complementary to the fragments of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

Barcode molecules may further comprise one or more nucleic acid sequences that are not complementary to barcode regions of barcoded oligonucleotides. For example, barcode molecules may comprise one or more adapter regions. A barcode molecule, may, for example, comprise an adapter region 5' of a barcode region (a 5' adapter region) and/or an adapter region 3' of the barcode region (a 3' adapter region). The adapter region(s) (and/or one or more portions of an adapter region) may be complementary to and anneal to oligonucleotides e.g. the adapter regions of barcoded oligonucleotides. Alternatively, the adapter region(s) (and/or one or more portions of an adapter region) of barcode molecule may not be complementary to sequences of barcoded oligonucleotides. The adapter region(s) may be used for manipulating, purifying, retrieving, amplifying, and/or detecting barcode molecules.

The multimeric barcoding reagent may be configured such that: each of the barcode molecules comprises a nucleic acid sequence comprising in the 5' to 3' direction an adapter region and a barcode region; the first barcoded oligonucleotide comprises, optionally in the 5' to 3' direction, a barcode region annealed to the barcode region of the first barcode molecule, an adapter region annealed to the adapter region of the first barcode molecule and a target region capable of annealing to a first fragment of the target nucleic acid; and the second barcoded oligonucleotide comprises, optionally in the 5' to 3' direction, a barcode region annealed to the barcode region of the second barcode molecule, an adapter region annealed to the adapter region of the second barcode molecule and a target region capable of annealing to a second fragment of the target nucleic acid.

The adapter region of each barcode molecule may comprise a constant region. Optionally, all adapter regions of a multimeric barcoding reagent are substantially identical. The adapter region may comprise at least 1, at least 2, at least 3, at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

The barcoded oligonucleotides may comprise a linker region between the adapter region and the target region. The linker region may comprise one or more contiguous nucleotides that are not annealed to the multimeric barcode molecule and are non-complementary to the fragments of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

The barcode molecules of a multimeric barcode molecule may be linked on a nucleic acid molecule. Such a nucleic acid molecule may provide the backbone to which single-stranded barcoded oligonucleotides may be annealed. Alternatively, the barcode molecules of a multimeric barcode molecule may be linked together by any of the other means described herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, or at least 10,000 barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 barcode molecules linked together, wherein each barcode molecule is as defined herein; and a barcoded oligonucleotide annealed to each barcode molecule, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ unique or different barcode molecules linked together, wherein each barcode molecule is as defined herein; and a barcoded oligonucleotide annealed to each barcode molecule, wherein each barcoded oligonucleotide is as defined herein. Preferably, the multimeric barcoding reagent comprises at least 5 unique or different barcode molecules linked together, wherein each barcode molecule is as defined herein; and a barcoded oligonucleotide annealed to each barcode molecule, wherein each barcoded oligonucleotide is as defined herein.

The multimeric barcoding reagent may comprise: at least 5, at least 10, at least 20, at least 25, at least 50, at least 75, at least 100, at least 200, at least 500, at least 1000, at least 5000, or at least 10,000 barcode regions, wherein each barcode region is as defined herein; and a barcoded oligonucleotide annealed to each barcode region, wherein each barcoded oligonucleotide is as defined herein. Preferably, the multimeric barcoding reagent comprises at least 5 barcode regions, wherein each barcode region is as defined herein; and a barcoded oligonucleotide annealed to each barcode region, wherein each barcoded oligonucleotide is as defined herein.

The multimeric barcoding reagent may comprise: at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ unique or different barcode regions, wherein each barcode region is as defined herein; and a barcoded oligonucleotide annealed to each barcode region, wherein each barcoded oligonucleotide is as defined herein. Preferably, the multimeric barcoding reagent comprises at least 5 unique or different barcode regions, wherein each barcode region is as defined herein; and a barcoded oligonucleotide annealed to each barcode region, wherein each barcoded oligonucleotide is as defined herein.

FIG. 1 shows a multimeric barcoding reagent, including first (D1, E1, and F1) and second (D2, E2, and F2) barcode molecules, which each include a nucleic acid sequence comprising a barcode region (E1 and E2). These first and second barcode molecules are linked together, for example by a connecting nucleic acid sequence (S). The multimeric barcoding reagent also comprises first (A1, B1, C1, and G1) and second (A2, B2, C2, and G2) barcoded oligonucleotides. These barcoded oligonucleotides each comprise a barcode region (B1 and B2) and a target region (G1 and G2).

The barcode regions within the barcoded oligonucleotides may each contain a unique sequence which is not present in other barcoded oligonucleotides, and may thus serve to uniquely identify each such barcode molecule. The target regions may be used to anneal the barcoded oligonucleotides to fragments of target nucleic acids, and then may be used as primers for a primer-extension reaction or an amplification reaction e.g. a polymerase chain reaction.

Each barcode molecule may optionally also include a 5' adapter region (F1 and F2). The barcoded oligonucleotides may then also include a 3' adapter region (C1 and C2) that is complementary to the 5' adapter region of the barcode molecules.

Each barcode molecule may optionally also include a 3' region (D1 and D2), which may be comprised of identical sequences within each barcode molecule. The barcoded oligonucleotides may then also include a 5' region (A1 and A2) which is complementary to the 3' region of the barcode molecules. These 3' regions may be useful for manipulation or amplification of nucleic acid sequences, for example sequences that are generated by labeling a nucleic acid target with a barcoded oligonucleotide. The 3' region may comprise at least 4, at least 5, at least 6, at least 8, at least 10, at least 15, at least 20, at least 25, at least 50, at least 100, or at least 250 nucleotides. Preferably, the 3' region comprises at least 4 nucleotides. Preferably each 3' region comprises deoxyribonucleotides, optionally all of the nucleotides in an 3' region are deoxyribonucleotides. One or more of the deoxyribonucleotides may be a modified deoxyribonucleotide (e.g. a deoxyribonucleotide modified with a biotin moiety or a deoxyuracil nucleotide). Each 3' region may comprise one or more universal bases (e.g. inosine), one or modified nucleotides and/or one or more nucleotide analogues.

The invention provides a library of multimeric barcoding reagents comprising at least 10 multimeric barcoding reagents for labelling a target nucleic acid for sequencing, wherein each multimeric barcoding reagent comprises: first and second barcode molecules comprised within a (single) nucleic acid molecule, wherein each of the barcode molecules comprises a nucleic acid sequence comprising a barcode region; and first and second barcoded oligonucleotides, wherein the first barcoded oligonucleotide comprises, optionally in the 5' to 3' direction, a barcode region complementary and annealed to the barcode region of the first barcode molecule and a target region capable of annealing or ligating to a first fragment of the target nucleic acid, and wherein the second barcoded oligonucleotide comprises, optionally in the 5' to 3' direction, a barcode region complementary and annealed to the barcode region of the second barcode molecule and a target region capable of annealing or ligating to a second fragment of the target nucleic acid. Preferably, the barcode regions of the first and second barcoded oligonucleotides of each multimeric barcoding reagent are different to the barcode regions of the barcoded oligonucleotides of at least 9 other multimeric barcoding reagents in the library.

15. Multimeric Barcoding Reagents Comprising Barcoded Oligonucleotides Annealed to a Multimeric Hybridization Molecule The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide comprises, optionally in the 5' to 3' direction, an adapter region annealed to the hybridization region of the first hybridization molecule, a barcode region, and a target region capable of annealing or ligating to a first fragment of the target nucleic acid, and wherein the second barcoded oligonucleotide comprises, optionally in the 5' to 3' direction, an adapter region annealed to the hybridization region of the second hybridization molecule, a barcode region, and a target region capable of annealing or ligating to a second fragment of the target nucleic acid.

Optionally, the first and second barcoded oligonucleotides each comprise an adapter region and a target region in a single contiguous sequence that is complementary and annealed to a hybridization region of a hybridization molecule, and also capable of annealing or ligating to a fragment of a target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide comprises, optionally in the 5' to 3' direction, a barcode region, an adapter region annealed to the hybridization region of the first hybridization molecule and a target region capable of annealing or ligating to a first fragment of the target nucleic acid, and wherein the second barcoded oligonucleotide comprises, optionally in the 5' to 3' direction, a barcode region, an adapter region annealed to the hybridization region of the second hybridization molecule and a target region capable of annealing or ligating to a second fragment of the target nucleic acid.

Optionally, the first and second barcoded oligonucleotides each comprise an adapter region and a target region in a single contiguous sequence that is complementary and annealed to a hybridization region of a hybridization molecule, and also capable of annealing or ligating to a fragment of a target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide comprises (in the 5'-3' or 3'-5' direction) an adapter region annealed to the hybridization region of the first hybridization molecule, a barcode region and a target region capable of ligating to a first fragment of the target nucleic acid, and wherein the second barcoded oligonucleotide comprises (in the 5'-3' or 3'-5' direction) an adapter region annealed to the hybridization region of the second hybridization molecule, a barcode region and a target region capable of ligating to a second fragment of the target nucleic acid.

Optionally, the first and second barcoded oligonucleotides each comprise an adapter region and a target region in a single contiguous sequence that is complementary and annealed to a hybridization region of a hybridization molecule, and also capable of ligating to a fragment of a target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a hybridization region; and first and second barcoded oligonucleotides, wherein the first barcoded oligonucleotide comprises (in the 5'-3' or 3'-5' direction) a barcode region, an adapter region annealed to the hybridization region of the first hybridization molecule and a target region capable of ligating to a first fragment of the target nucleic acid, and wherein the second barcoded oligonucleotide comprises (in the 5'-3' or 3'-5' direction) a barcode region, an adapter region annealed to the hybridization region of the second hybridization molecule and a target region capable of ligating to a second fragment of the target nucleic acid.

Optionally, the first and second barcoded oligonucleotides each comprise an adapter region and a target region in a single contiguous sequence that is complementary and annealed to a hybridization region of a hybridization molecule, and also capable of ligating to a fragment of a target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a barcode region; and first and second barcoded oligonucleotides, wherein the first barcoded oligonucleotide comprises in the 5' to 3' direction an adapter region annealed to the hybridization region of the first hybridization molecule, a barcode region and a target region capable of annealing to a first fragment of the target nucleic acid, and wherein the second barcoded oligonucleotide comprises in the 5' to 3' direction an adapter region annealed to the hybridization region of the second hybridization molecule, a barcode region and a target region capable of annealing to a second fragment of the target nucleic acid.

The invention provides a multimeric barcoding reagent for labelling a target nucleic acid, wherein the reagent comprises: first and second hybridization molecules linked together (i.e. a multimeric hybridization molecule), wherein each of the hybridization molecules comprises a nucleic acid sequence comprising a barcode region; and first and second barcoded oligonucleotides, wherein the first barcoded oligonucleotide comprises in the 5' to 3' direction a barcode region, an adapter region annealed to the hybridization region of the first hybridization molecule and a target region capable of annealing to a first fragment of the target nucleic acid, and wherein the second barcoded oligonucleotide comprises in the 5' to 3' direction a barcode region, an adapter region annealed to the hybridization region of the second hybridization molecule and a target region capable of annealing to a second fragment of the target nucleic acid.

Optionally, the first and second barcoded oligonucleotides each comprise an adapter region and a target region in a single contiguous sequence that is complementary and annealed to a hybridization region of a hybridization molecule, and also capable of annealing to a fragment of a target nucleic acid.

Preferably, the adapter region of the first barcoded oligonucleotide comprises a sequence that is complementary and annealed to the hybridization region of the first hybridization molecule and the adapter region of the second barcoded oligonucleotide comprises a sequence that is complementary and annealed to the hybridization region of the second hybridization molecule. The complementary sequence of each barcoded oligonucleotide may be at least 5, at least 10, at least 15, at least 20, at least 25, at least 50 or at least 100 contiguous nucleotides.

The hybridization region of each hybridization molecule may comprise a constant region. Preferably, all hybridization regions of a multimeric barcoding reagent are substantially identical. Optionally, all hybridization regions of a library of multimeric barcoding reagents are substantially identical. The hybridization region may comprise at least 1, at least 2, at least 3, at least 4, at least 5, at least 6, at least 8, at least 10, at least 15, at least 20, at least 25, at least 50, at least 100, or at least 250 nucleotides. Preferably, the hybridization region comprises at least 4 nucleotides. Preferably each hybridization region comprises deoxyribonucleotides, optionally all of the nucleotides in a hybridization region are deoxyribonucleotides. One or more of the deoxyribonucleotides may be a modified deoxyribonucleotide (e.g. a deoxyribonucleotide modified with a biotin moiety or a deoxyuracil nucleotide). Each hybridization region may comprise one or more universal bases (e.g. inosine), one or modified nucleotides and/or one or more nucleotide analogues.

The target regions of the barcoded oligonucleotides may not be annealed to the multimeric hybridization molecule(s). The target regions of the barcoded oligonucleotides may be non-complementary to the multimeric hybridization molecule(s).

The barcoded oligonucleotides may comprise a linker region between the adapter region and the target region. The linker region may comprise one or more contiguous nucleotides that are not annealed to the multimeric hybridization molecule and are non-complementary to the fragments of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

Hybridization molecules may further comprise one or more nucleic acid sequences that are not complementary to barcoded oligonucleotides. For example, hybridization molecules may comprise one or more adapter regions. A hybridization molecule, may, for example, comprise an adapter region 5' of a hybridization region (a 5' adapter region) and/or an adapter region 3' of the hybridization region (a 3' adapter region). The adapter region(s) may be used for manipulating, purifying, retrieving, amplifying, and/or detecting hybridization molecules.

The adapter region of each hybridization molecule may comprise a constant region. Optionally, all adapter regions of a multimeric hybridization reagent are substantially identical. The adapter region may comprise at least 1, at least 2, at least 3, at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

The barcoded oligonucleotides may comprise a linker region between the adapter region and the target region. The linker region may comprise one or more contiguous nucleotides that are not annealed to the multimeric hybridization molecule and are non-complementary to the fragments of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the multimeric barcoding reagents.

The invention provides a library of multimeric barcoding reagents comprising at least 10 multimeric barcoding reagents for labelling a target nucleic acid for sequencing, wherein each multimeric barcoding reagent comprises: first and second hybridization molecules comprised within a (single) nucleic acid molecule, wherein each of the hybridization molecules comprises a nucleic acid sequence comprising a hybridization region; and first and second barcoded oligonucleotides, wherein the first barcoded oligonucleotide comprises, optionally in the 5' to 3' direction, an adapter region complementary and annealed to the hybridization region of the first hybridization molecule, a barcode region and a target region capable of annealing or ligating to a first fragment of the target nucleic acid, and wherein the second barcoded oligonucleotide comprises, optionally in the 5' to 3' direction, an adapter region complementary and annealed to the hybridization region of the second hybridization molecule, a barcode region and a target region capable of annealing or ligating to a second fragment of the target nucleic acid.

Preferably, the barcode regions of the first and second barcoded oligonucleotides of each multimeric barcoding reagent are different to the barcode regions of the barcoded oligonucleotides of at least 9 other multimeric barcoding reagents in the library.

The invention provides a library of multimeric barcoding reagents comprising at least 10 multimeric barcoding reagents for labelling a target nucleic acid for sequencing, wherein each multimeric barcoding reagent comprises: first and second hybridization molecules comprised within a (single) nucleic acid molecule, wherein each of the hybridization molecules comprises a nucleic acid sequence comprising a hybridization region; and first and second barcoded oligonucleotides, wherein the first barcoded oligonucleotide comprises, optionally in the 5' to 3' direction, a barcode region, an adapter region complementary and annealed to the hybridization region of the first hybridization molecule and a target region capable of annealing or ligating to a first fragment of the target nucleic acid, and wherein the second barcoded oligonucleotide comprises, optionally in the 5' to 3' direction, a barcode region, an adapter region complementary and annealed to the hybridization region of the second hybridization molecule and a target region capable of annealing or ligating to a second fragment of the target nucleic acid. Preferably, the barcode regions of the first and second barcoded oligonucleotides of each multimeric barcoding reagent are different to the barcode regions of the barcoded oligonucleotides of at least 9 other multimeric barcoding reagents in the library.

16. Multimeric Barcoding Reagents Comprising Barcoded Oligonucleotides Linked by a Macromolecule The invention provides a multimeric barcoding reagent for labelling a target nucleic acid, wherein the reagent comprises first and second barcoded oligonucleotides linked together by a macromolecule, and wherein the barcoded oligonucleotides each comprise a barcode region.

The first barcoded oligonucleotide may further comprise a target region capable of annealing or ligating to a first fragment of the target nucleic acid, and the second barcoded oligonucleotide may further comprise a target region capable of annealing or ligating to a second fragment of the target nucleic acid.

The first barcoded oligonucleotide may comprise in the 5'-3' direction a barcode region and a target region capable of annealing to a first fragment of the target nucleic acid, and the second barcoded oligonucleotide may comprise in the 5'-3' direction a barcode region and a target region capable of annealing to a second fragment of the target nucleic acid.

The barcoded oligonucleotides may further comprise any of the features described herein.

The barcoded oligonucleotides may be linked by a macromolecule by being bound to the macromolecule and/or by being annealed to the macromolecule.

The barcoded oligonucleotides may be linked to the macromolecule directly or indirectly (e.g. via a linker molecule). The barcoded oligonucleotides may be linked by being bound to the macromolecule and/or by being bound or annealed to linker molecules that are bound to the macromolecule. The barcoded oligonucleotides may be bound to the macromolecule (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The macromolecule may be a synthetic polymer (e.g. a dendrimer) or a biopolymer such as a nucleic acid (e.g. a single-stranded nucleic acid such as single-stranded DNA), a peptide, a polypeptide or a protein (e.g. a multimeric protein).

The dendrimer may comprise at least 2, at least 3, at least 5, or at least 10 generations.

The macromolecule may be a nucleic acid comprising two or more nucleotides each capable of binding to a barcoded oligonucleotide. Additionally or alternatively, the nucleic acid may comprise two or more regions each capable of hybridizing to a barcoded oligonucleotide.

The nucleic acid may comprise a first modified nucleotide and a second modified nucleotide, wherein each modified nucleotide comprises a binding moiety (e.g. a biotin moiety, or an alkyne moiety which may be used for a click-chemical reaction) capable of binding to a barcoded oligonucleotide. Optionally, the first and second modified nucleotides may be separated by an intervening nucleic acid sequence of at least one, at least two, at least 5 or at least 10 nucleotides.

The nucleic acid may comprise a first hybridisation region and a second hybridisation region, wherein each hybridisation region comprises a sequence complementary to and capable of hybridizing to a sequence of at least one nucleotide within a barcoded oligonucleotide. The complementary sequence may be at least 5, at least 10, at least 15, at least 20, at least 25 or at least 50 contiguous nucleotides. Optionally, the first and second hybridisation regions may be separated by an intervening nucleic acid sequence of at least one, at least two, at least 5 or at least 10 nucleotides.

The macromolecule may be a protein such as a multimeric protein e.g. a homomeric protein or a heteromeric protein. For example, the protein may comprise streptavidin e.g. tetrameric streptavidin.

Libraries of multimeric barcoding reagents comprising barcoded oligonucleotides linked by a macromolecule are also provided. Such libraries may be based on the general properties of libraries of multimeric barcoding reagents described herein. In the libraries, each multimeric barcoding reagent may comprise a different macromolecule.

17. Multimeric Barcoding Reagents Comprising Barcoded Oligonucleotides Linked by a Solid Support or a Semi-Solid Support The invention provides a multimeric barcoding reagent for labelling a target nucleic acid, wherein the reagent comprises first and second barcoded oligonucleotides linked together by a solid support or a semi-solid support, and wherein the barcoded oligonucleotides each comprise a barcode region.

The first barcoded oligonucleotide may further comprise a target region capable of annealing or ligating to a first fragment of the target nucleic acid, and the second barcoded oligonucleotide may further comprise a target region capable of annealing or ligating to a second fragment of the target nucleic acid.

The first barcoded oligonucleotide may comprise in the 5'-3' direction a barcode region and a target region capable of annealing to a first fragment of the target nucleic acid, and the second barcoded oligonucleotide may comprise in the 5'-3' direction a barcode region and a target region capable of annealing to a second fragment of the target nucleic acid.

The barcoded oligonucleotides may further comprise any of the features described herein.

The barcoded oligonucleotides may be linked by a solid support or a semi-solid support. The barcoded oligonucleotides may be linked to the support directly or indirectly (e.g. via a linker molecule). The barcoded oligonucleotides may be linked by being bound to the support and/or by being bound or annealed to linker molecules that are bound to the support. The barcoded oligonucleotides may be bound to the support (or to the linker molecules) by covalent linkage, non-covalent linkage (e.g. a protein-protein interaction or a streptavidin-biotin bond) or nucleic acid hybridization. The linker molecule may be a biopolymer (e.g. a nucleic acid molecule) or a synthetic polymer. The linker molecule may comprise one or more units of ethylene glycol and/or poly(ethylene) glycol (e.g. hexa-ethylene glycol or penta-ethylene glycol). The linker molecule may comprise one or more ethyl groups, such as a C3 (three-carbon) spacer, C6 spacer, C12 spacer, or C18 spacer.

The support may comprise a planar surface. The support may be a slide e.g. a glass slide. The slide may be a flow cell for sequencing. If the support is a slide, the first and second barcoded oligonucleotides may be immobilized in a discrete region on the slide. Optionally, the barcoded oligonucleotides of each multimeric barcoding reagent in a library are immobilized in a different discrete region on the slide to the barcoded oligonucleotides of the other multimeric barcoding reagents in the library. The support may be a plate comprising wells, optionally wherein the first and second barcoded oligonucleotides are immobilized in the same well. Optionally, the barcoded oligonucleotides of each multimeric barcoding reagent in library are immobilized in a different well of the plate to the barcoded oligonucleotides of the other multimeric barcoding reagents in the library.

Preferably, the support is a bead (e.g. a gel bead). The bead may be an agarose bead, a silica bead, a styrofoam bead, a gel bead (such as those available from 10x Genomics®), an antibody conjugated bead, an oligo-dT conjugated bead, a streptavidin bead or a magnetic bead (e.g. a superparamagnetic bead). The bead may be of any size and/or molecular structure. For example, the bead may be 10 nanometres to 100 microns in diameter, 100 nanometres to 10 microns in diameter, or 1 micron to 5 microns in diameter. Optionally, the bead is approximately 10 nanometres in diameter, approximately 100 nanometres in diameter, approximately 1 micron in diameter, approximately 10 microns in diameter or approximately 100 microns in diameter. The bead may be solid, or alternatively the bead may be hollow or partially hollow or porous. Beads of certain sizes may be most preferable for certain barcoding methods. For example, beads less than 5.0 microns, or less than 1.0 micron, may be most useful for barcoding nucleic acid targets within individual cells. Preferably, the barcoded oligonucleotides of each multimeric barcoding reagent in a library are linked together on a different bead to the barcoded oligonucleotides of the other multimeric barcoding reagents in the library.

The support may be functionalised to enable attachment of two or more barcoded oligonucleotides. This functionalisation may be enabled through the addition of chemical moieties (e.g. carboxylated groups, alkynes, azides, acrylate groups, amino groups, sulphate groups, or succinimide groups), and/or protein-based moieties (e.g. streptavidin, avidin, or protein G) to the support. The barcoded oligonucleotides may be attached to the moieties directly or indirectly (e.g. via a linker molecule).

Functionalised supports (e.g. beads) may be brought into contact with a solution of barcoded oligonucleotides under conditions which promote the attachment of two or more barcoded oligonucleotides to each bead in the solution (generating multimeric barcoding reagents).

Libraries of multimeric barcoding reagents comprising barcoded oligonucleotides linked by a support are also provided. Such libraries may be based on the general properties of libraries of multimeric barcoding reagents described herein. In the libraries, each multimeric barcoding reagent may comprise a different support (e.g. a differently labelled bead). In a library of multimeric barcoding reagents, the barcoded oligonucleotides of each multimeric barcoding reagent in a library may be linked together on a different support to the barcoded oligonucleotides of the other multimeric barcoding reagents in the library.

18. Multimeric Barcoding Reagents Comprising Barcoded Oligonucleotides Linked Together by being Comprised within a Lipid Carrier The invention provides a multimeric barcoding reagent for labelling a target nucleic acid, wherein the reagent comprises first and second barcoded oligonucleotides and a lipid carrier, wherein the first and second barcoded oligonucleotides are linked together by being comprised within the lipid carrier, and wherein the barcoded oligonucleotides each comprise a barcode region.

The first barcoded oligonucleotide may further comprise a target region capable of annealing or ligating to a first fragment of the target nucleic acid, and the second barcoded oligonucleotide may further comprise a target region capable of annealing or ligating to a second fragment of the target nucleic acid.

The first barcoded oligonucleotide may comprise in the 5'-3' direction a barcode region and a target region capable of annealing to a first fragment of the target nucleic acid, and the second barcoded oligonucleotide may comprise in the 5'-3' direction a barcode region and a target region capable of annealing to a second fragment of the target nucleic acid.

The barcoded oligonucleotides may further comprise any of the features described herein.

The invention provides a library of multimeric barcoding reagents comprising first and second multimeric barcoding reagents as defined herein, wherein the barcoded oligonucleotides of the first multimeric barcoding reagent are comprised within a first lipid carrier, and wherein the barcoded oligonucleotides of the second multimeric barcoding reagent are comprised with a second lipid carrier, and wherein the barcode regions of the barcoded oligonucleotides of the first multimeric barcoding reagent are different to the barcode regions of the barcoded oligonucleotides of the second multimeric barcoding reagent.

The library of multimeric barcoding reagents may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the library comprises at least 10 multimeric barcoding reagents as defined herein. Preferably, the barcode regions of the first and second barcoded oligonucleotides of each multimeric barcoding reagent are different to the barcode regions of the barcoded oligonucleotides of at least 9 other multimeric barcoding reagents in the library.

The barcoded oligonucleodides of each multimeric barcoding reagent are comprised within a different lipid carrier.

The lipid carrier may be a liposome or a micelle. The lipid carrier may be a phospholipid carrier. The lipid carrier may comprise one or more amphiphilic molecules. The lipid carrier may comprise one or more phospholipids. The phospholipid may be phosphatidylcholine. The lipid carrier may comprise one or more of the following constituents: phosphatidylethanolamine, phosphatidylserine, cholesterol, cardiolipin, dicetylphosphate, stearylamine, phosphatidylglycerol, dipalmitoylphosphatidylcholine, distearylphosphatidylcholine, and/or any related and/or derivative molecules thereof. Optionally, the lipid carrier may comprise any combination of two or more constituents described above, with or without further constituents.

The lipid carrier (e.g. a liposome or a micelle) may be unilamellar or multilamellar. A library of multimeric barcoding reagents may comprise both unilamellar and multilamellar lipid carriers. The lipid carrier may comprise a copolymer e.g. a block copolymer.

The lipid carrier may comprise at least 2, at least 3, at least 5, at least 10, at least 50, at least 100, at least 500, at least 1000, at least 10,000, or at least 100,000 barcoded oligonucleotides, or any greater number of barcoded oligonucleotides.

Any lipid carrier (e.g. liposome or micelle, and/or liposomal or micellar reagent) may on average be complexed with 1, or less than 1, or greater than 1 multimeric barcoding reagent(s) to form a library of such multimeric barcoding reagent(s).

The invention provides a library of multimeric barcoding reagents comprising at least 10 multimeric barcoding reagents as defined herein, wherein each multimeric barcoding reagent comprises first and second barcoded oligonucleotides comprised within a different lipid carrier, and wherein the barcode regions of the first and second barcoded oligonucleotides of each multimeric barcoding reagent are different to the barcode regions of the barcoded oligonucleotides of at least 9 other multimeric barcoding reagents in the library.

A method for preparing multimeric barcoding reagents comprises loading barcoded oligonucleotides and/or multimeric barcoding reagent(s) into lipid carriers (e.g. liposomes or micelles). The method may comprise a step of passive, active, and/or remote loading. Pre-formed lipid carriers (e.g. liposomes and/or micelles) may be loaded by contacting them with a solution of barcoded oligonucleotides and/or multimeric barcoding reagent(s). Lipid carriers (e.g. liposomes and/or micelles) may be loaded by contacting them with a solution of barcoded oligonucleotides and/or multimeric barcoding reagent(s) prior to and/or during the formation or synthesis of the lipid carriers. The method may comprise passive encapsulation and/or trapping of barcoded oligonucleotides and/or multimeric barcoding reagent(s) in lipid carriers.

Lipid carriers (e.g. liposomes and/or micelles) may be prepared by a method based on sonication, a French press-based method, a reverse phase method, a solvent evaporation method, an extrusion-based method, a mechanical mixing-based method, a freeze/thaw-based method, a dehydrate/rehydrate-based method, and/or any combination hereof.

Lipid carriers (e.g. liposomes and/or micelles) may be stabilized and/or stored prior to use using known methods.

Any of the multimeric barcoding reagents or kits described herein may be comprised with a lipid carrier.

19. Kits Comprising Multimeric Barcoding Reagents and Adapter Oligonucleotides

The invention further provides kits comprising one or more of the components defined herein. The invention also provides kits specifically adapted for performing any of the methods defined herein.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (b) first and second adapter oligonucleotides, wherein the first adapter oligonucleotide comprises, optionally in the 5' to 3' direction, an adapter region capable of annealing to the adapter region of the first barcode molecule and a target region capable of annealing or ligating to a first fragment of the target nucleic acid, and wherein the second adapter oligonucleotide comprises, optionally in the 5' to 3' direction, an adapter region capable of annealing to the adapter region of the second barcode molecule and a target region capable of annealing or ligating to a second fragment of the target nucleic acid.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising an adapter region and a barcode region, and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (b) first and second adapter oligonucleotides, wherein the first adapter oligonucleotide comprises an adapter region capable of annealing to the adapter region of the first barcode molecule and a target region capable of ligating to a first fragment of the target nucleic acid, and wherein the second adapter oligonucleotide comprises an adapter region capable of annealing to the adapter region of the second barcode molecule and a target region capable of ligating to a second fragment of the target nucleic acid.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising in the 5' to 3' direction an adapter region and a barcode region, and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (b) first and second adapter oligonucleotides, wherein the first adapter oligonucleotide comprises in the 5' to 3' direction an adapter region capable of annealing to the adapter region of the first barcode molecule and a target region capable of annealing to a first fragment of the target nucleic acid, and wherein the second adapter oligonucleotide comprises in the 5' to 3' direction an adapter region capable of annealing to the adapter region of the second barcode molecule and a target region capable of annealing to a second fragment of the target nucleic acid.

The invention further provides a kit for labelling a target nucleic acid, wherein the kit comprises: (a) a multimeric barcoding reagent comprising (i) first and second barcode molecules linked together (i.e. a multimeric barcode molecule), wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule; and (b) first and second adapter oligonucleotides, wherein the first adapter oligonucleotide comprises an adapter region capable of annealing to the adapter region of the first barcode molecule and capable of ligating to a first fragment of the target nucleic acid, and wherein the second adapter oligonucleotide comprises an adapter region capable of annealing to the adapter region of the second barcode molecule and capable of ligating to a second fragment of the target nucleic acid.

Each adapter oligonucleotide may consist essentially of or consist of an adapter region. Each adapter oligonucleotide may not comprise a target region.

Preferably, the adapter region of the first adapter oligonucleotide comprises a sequence that is complementary to and capable of annealing to the adapter region of the first barcode molecule and the adapter region of the second adapter oligonucleotide comprises a sequence that is complementary to and capable of annealing to the adapter region of the second barcode molecule. The complementary sequence of each adapter oligonucleotide may be at least 5, at least 10, at least 15, at least 20, at least 25, at least 50 or at least 100 contiguous nucleotides.

The target regions of the adapter oligonucleotides may not be capable of annealing to the multimeric barcode molecule(s)). The target regions of the adapter oligonucleotides may be non-complementary to the multimeric barcode molecule(s).

The target regions of each adapter oligonucleotide may comprise different sequences. Each target region may comprise a sequence capable of annealing to only a single fragment of a target nucleic acid within a sample of nucleic acids. Each target region may comprise one or more random, or one or more degenerate, sequences to enable the target region to anneal to more than one fragment of a target nucleic acid. Each target region may comprise at least 5, at least 10, at least 15, at least 20, at least 25, at least 50 or at least 100 nucleotides. Preferably, each target region comprises at least 5 nucleotides. Each target region may comprise 5 to 100 nucleotides, 5 to 10 nucleotides, 10 to 20 nucleotides, 20 to 30 nucleotides, 30 to 50 nucleotides, 50 to 100 nucleotides, 10 to 90 nucleotides, 20 to 80 nucleotides, 30 to 70 nucleotides or 50 to 60 nucleotides. Preferably, each target region comprises 30 to 70 nucleotides. Preferably each target region comprises deoxyribonucleotides, optionally all of the nucleotides in a target region are deoxyribonucleotides. One or more of the deoxyribonucleotides may be a modified deoxyribonucleotide (e.g. a deoxyribonucleotide modified with a biotin moiety or a deoxyuracil nucleotide). Each target region may comprise one or more universal bases (e.g. inosine), one or modified nucleotides and/or one or more nucleotide analogues.

The target regions may be used to anneal the adapter oligonucleotides to fragments of target nucleic acids, and then may be used as primers for a primer-extension reaction or an amplification reaction e.g. a polymerase chain reaction. Alternatively, the target regions may be used to ligate the adapter oligonucleotides to fragments of target nucleic acids. The target region may be at the 5' end of an adapter oligonucleotide. Such a target region may be phosphorylated. This may enable the 5' end of the target region to be ligated to the 3' end of a fragment of a target nucleic acid.

The adapter oligonucleotides may comprise a linker region between the adapter region and the target region. The linker region may comprise one or more contiguous nucleotides that are not annealed to the first and second barcode molecules (i.e. the multimeric barcode molecule) and are non-complementary to the fragments of the target nucleic acid. The linker may comprise 1 to 100, 5 to 75, 10 to 50, 15 to 30 or 20 to 25 non-complementary nucleotides. Preferably, the linker comprises 15 to 30 non-complementary nucleotides. The use of such a linker region enhances the efficiency of the barcoding reactions performed using the kits described herein.

Each of the components of the kit may take any of the forms defined herein.

The multimeric barcoding reagent(s) and adapter oligonucleotides may be provided in the kit as physically separated components.

The kit may comprise: (a) a multimeric barcoding reagent comprising at least 5, at least 10, at least 20, at least 25, at least 50, at least 75 or at least 100 barcode molecules linked together, wherein each barcode molecule is as defined herein; and (b) an adapter oligonucleotide capable of annealing to each barcode molecule, wherein each adapter oligonucleotide is as defined herein.

FIG. 2 shows a kit comprising a multimeric barcoding reagent and adapter oligonucleotides for labelling a target nucleic acid. In more detail, the kit comprises first (D1, E1, and F1) and second (D2, E2, and F2) barcode molecules, with each incorporating a barcode region (E1 and E2) and also a 5' adapter region (F1 and F2). These first and second barcode molecules are linked together, in this embodiment by a connecting nucleic acid sequence (S).

The kit further comprises first (A1 and B1) and second (A2 and B2) barcoded oligonucleotides, which each comprise a barcode region (B1 and B2), as well as 5' regions (A1 and A2). The 5' region of each barcoded oligonucleotide is complementary to, and thus may be annealed to, the 3' regions of the barcode molecules (D1 and D2). The barcode regions (B1 and B2) are complementary to, and thus may be annealed to, the barcode regions (E1 and E2) of the barcode molecules.

The kit further comprises first (C1 and G1) and second (C2 and G2) adapter oligonucleotides, wherein each adapter oligonucleotide comprises an adapter region (C1 and C2) that is complementary to, and thus able to anneal to, the 5' adapter region of a barcode molecule (F1 and F2). These adapter oligonucleotides may be synthesised to include a 5'-terminal phosphate group. Each adapter oligonucleotide also comprises a target region (G1 and G2), which may be used to anneal the barcoded-adapter oligonucleotides (A1, B1, C1 and G1, and A2, B2, C2 and G2) to target nucleic acids, and then may be used as primers for a primer-extension reaction or a polymerase chain reaction.

The kit may comprise a library of two or more multimeric barcoding reagents, wherein each multimeric barcoding reagent is as defined herein, and adapter oligonucleotides for each of the multimeric barcoding reagents, wherein each adapter oligonucleotide is as defined herein. The barcode regions of the first and second barcoded oligonucleotides of the first multimeric barcoding reagent are different to the barcode regions of the first and second barcoded oligonucleotides of the second multimeric barcoding reagent.

The kit may comprise a library comprising at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcoding reagents as defined herein. Preferably, the kit comprises a library comprising at least 10 multimeric barcoding reagents as defined herein. The kit may further comprise adapter oligonucleotides for each of the multimeric barcoding reagents, wherein each adapter oligonucleotide may take the form of any of the adapter oligonucleotides defined herein. Preferably, the barcode regions of the first and second barcoded oligonucleotides of each multimeric barcoding reagent are different to the barcode regions of the barcoded oligonucleotides of at least 9 other multimeric barcoding reagents in the library.

The barcode regions of the first and second barcoded oligonucleotides of each multimeric barcoding reagent may be different to the barcode regions of the barcoded oligonucleotides of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The barcode regions of the first and second barcoded oligonucleotides of each multimeric barcoding reagent may be different to the barcode regions of the barcoded oligonucleotides of all of the other multimeric barcoding reagents in the library. Preferably, the barcode regions of the first and second barcoded oligonucleotides of each multimeric barcoding reagent are different to the barcode regions of the barcoded oligonucleotides of at least 9 other multimeric barcoding reagents in the library.

The barcode regions of the barcoded oligonucleotides of each multimeric barcoding reagent may be different to the barcode regions of the barcoded oligonucleotides of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcoding reagents in the library. The barcode regions of the barcoded oligonucleotides of each multimeric barcoding reagent may be different to the barcode regions of the barcoded oligonucleotides of all of the other multimeric barcoding reagents in the library. Preferably, the barcode regions of the barcoded oligonucleotides of each multimeric barcoding reagent are different to the barcode regions of the barcoded oligonucleotides of at least 9 other multimeric barcoding reagents in the library The invention provides a kit for labelling a target nucleic acid for sequencing, wherein the kit comprises: (a) a library of multimeric barcoding reagents comprising at least 10 multimeric barcoding reagents, wherein each multimeric barcoding reagent comprises: (i) first and second barcode molecules comprised within a (single) nucleic acid molecule, wherein each of the barcode molecules comprises a nucleic acid sequence comprising, optionally in the 5' to 3' direction, an adapter region and a barcode region, and (ii) first and second barcoded oligonucleotides, wherein the first barcoded oligonucleotide comprises a barcode region complementary and annealed to the barcode region of the first barcode molecule, and wherein the second barcoded oligonucleotide comprises a barcode region complementary and annealed to the barcode region of the second barcode molecule; and (b) first and second adapter oligonucleotides for each of the multimeric barcoding reagents, wherein the first adapter oligonucleotide comprises, optionally in the 5' to 3' direction, an adapter region capable of annealing to the adapter region of the first barcode molecule and a target region capable of annealing or ligating to a first fragment of the target nucleic acid, and wherein the second adapter oligonucleotide comprises, optionally in the 5' to 3' direction, an adapter region capable of annealing to the adapter region of the second barcode molecule and a target region capable of annealing or ligating to a second fragment of the target nucleic acid.

20. Kits Comprising Multimeric Barcoding Reagents, Adapter Oligonucleotides and Extension Primers The invention further provides a kit for labelling a target nucleic acid for sequencing, wherein the kit comprises: (a) a multimeric barcode molecule comprising first and second barcode molecules linked together, wherein each of the barcode molecules comprises a nucleic acid sequence comprising, optionally in the 5' to 3' direction, an adapter region, a barcode region, and a priming region; (b) first and second extension primers for the multimeric barcode molecule, wherein the first extension primer comprises a sequence capable of annealing to the priming region of the first barcode molecule, and wherein the second extension primer comprises a sequence capable of annealing to the priming region of the second barcode molecule; and (c) first and second adapter oligonucleotides for the multimeric barcode molecule, wherein the first adapter oligonucleotide comprises, optionally in the 5' to 3' direction, an adapter region capable of annealing to the adapter region of the first barcode molecule and a target region capable of annealing or ligating to a first fragment of the target nucleic acid, and wherein the second adapter oligonucleotide comprises, optionally in the 5' to 3' direction, an adapter region capable of annealing to the adapter region of the second barcode molecule and a target region capable of annealing or ligating to a second fragment of the target nucleic acid.

The invention further provides a kit for labelling a target nucleic acid for sequencing, wherein the kit comprises: (a) a multimeric barcode molecule comprising first and second barcode molecules linked together, wherein each of the barcode molecules comprises a nucleic acid sequence comprising, optionally in the 5' to 3' direction, an adapter region, a barcode region, and a priming region; (b) first and second extension primers for the multimeric barcode molecule, wherein the first extension primer comprises a sequence capable of annealing to the priming region of the first barcode molecule, and wherein the second extension primer comprises a sequence capable of annealing to the priming region of the second barcode molecule; and (c) first and second adapter oligonucleotides for the multimeric barcode molecule, wherein the first adapter oligonucleotide comprises an adapter region capable of annealing to the adapter region of the first barcode molecule and capable of ligating to a first fragment of the target nucleic acid, and wherein the second adapter oligonucleotide comprises an adapter region capable of annealing to the adapter region of the second barcode molecule and capable of ligating to a second fragment of the target nucleic acid.

Each adapter oligonucleotide may consist essentially of or consist of an adapter region.

The components of the kit may take any of the forms described herein.

Preferably, the first extension primer comprises a sequence that is complementary to and capable of annealing to the priming region of the first barcode molecule and the second extension primer comprises a sequence that is complementary to and capable of annealing to the priming region of the second barcode molecule. The complementary sequence of each extension primer may be at least 5, at least 10, at least 15, at least 20, at least 25, at least 50 or at least 100 contiguous nucleotides.

The first and second extension primers may be capable of being extended using the barcode regions of the first and second barcode molecules as templates to produce first and second barcoded oligonucleotides, wherein the first barcoded oligonucleotide comprises a sequence complementary to the barcode region of the first barcode molecule and the second barcoded oligonucleotide comprises a sequence complementary to the barcode region of the second barcode molecule.

The first and second extension primers may be identical in sequence. Alternatively, the first and second extension primers may be different in sequence.

The first and/or second extension primers may further comprise one or more regions with nucleic acid sequences that are not complementary to the first barcode molecule and second barcode molecule, respectively. Optionally, such a non-complementary region may include a binding site for one or more amplification primers. Optionally, such a non-complementary region may be positioned within the 5' region of the molecule. Optionally, the first and second extension primers may comprise a terminal 5' phosphate group capable of ligating to a 3' end of a nucleic acid molecule.

The first and/or second extension primers may further comprise one or more secondary barcode regions. Optionally, a secondary barcode region may be comprised within a region of the extension primer that is non-complementary to a barcode molecule. Optionally, a secondary barcode region may be comprised within a region of the extension primer that is between a 3' region of the extension primer that is complementary to a barcode molecule and a 5' region of the extension primer that comprises a binding site for an amplification primer.

A secondary barcode region may comprise a sequence of one or more nucleotides, wherein sequences of the secondary barcode regions of the first extension primer and the second extension primer are different. Optionally, said one or more nucleotides may comprise random or degenerate nucleotides. Optionally, said one or more nucleotides may comprise different but non-random nucleotides. Any secondary barcode region may comprise at least 2, at least 3, at least 5, at least 10, at least 15, at least 20, or at least 30 nucleotides. Any secondary barcode region may comprise a contiguous sequence of barcode oligonucleotides, or may comprise two or more different segments separated by at least one non-barcode or invariant nucleotide. Optionally, any secondary barcode region may comprise a unique molecular identifier (UMI).

The kit may comprise a library of two or more multimeric barcode molecules, wherein each multimeric barcode molecule is as defined herein, and first and second extension primers, and first and second adapter oligonucleotides, for each of the multimeric barcode molecule. The extension primers and adapter oligonucleotides may take any of the forms described herein. The barcode regions of the first and second barcode molecules of the first multimeric barcode molecule are different to the barcode regions of the first and second barcode molecules of the second multimeric barcode molecule.

The kit may comprise a library comprising at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ multimeric barcode molecules as defined herein. Preferably, the kit comprises a library comprising at least 10 multimeric barcode molecules as defined herein. The kit may further comprise extension primers and/or adapter oligonucleotides for each of the multimeric barcode molecules. The extension primers and adapter oligonucleotides may take any of the forms described herein. Preferably, the barcode regions of the first and second barcode molecules of each multimeric barcode molecule are different to the barcode regions of the barcode molecules of at least 9 other multimeric barcode molecules in the library.

The barcode regions of the first and second barcode molecules of each multimeric barcode molecule may be different to the barcode regions of the barcoded molecules of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcode molecules in the library. The barcode regions of the first and second barcode molecules of each multimeric barcode molecule may be different to the barcode regions of the barcode molecules of all of the other multimeric barcode molecules in the library. Preferably, the barcode regions of the first and second barcode molecules of each multimeric barcode molecule are different to the barcode regions of the at least 9 other multimeric barcode molecules in the library.

The barcode regions of the barcode molecules of each multimeric barcode molecule may be different to the barcode regions of the barcode molecules of at least 4, at least 9, at least 19, at least 24, at least 49, at least 74, at least 99, at least 249, at least 499, at least 999 (i.e. $10^3$-1), at least $10^4$-1, at least $10^5$-1, at least $10^6$-1, at least $10^7$-1, at least $10^8$-1 or at least $10^9$-1 other multimeric barcode molecules in the library. The barcode regions of the barcode molecules of each multimeric barcode molecules may be different to the barcode regions of the barcode molecules of all of the other multimeric barcode molecules in the library. Preferably, the barcode regions of the barcode molecules of each multimeric barcode molecule are different to the barcode regions of the barcode molecules of at least 9 other multimeric barcode molecules in the library.

The invention further provides a kit for labelling a target nucleic acid for sequencing, wherein the kit comprises: (a) a library of multimeric barcode molecules comprising at least 10 multimeric barcode molecules, each multimeric barcode molecule comprising first and second barcode molecules comprised within a (single) nucleic acid molecule, wherein each of the barcode molecules comprises a nucleic acid sequence comprising, optionally in the 5' to 3' direction, an adapter region, a barcode region, and a priming region, and wherein the barcode regions of the first and second barcode molecules of each multimeric barcode molecule are different to the barcode regions of at least 9 other multimeric barcode molecules in the library; (b) first and second extension primers for each of the multimeric barcode molecules, wherein the first extension primer comprises a sequence capable of annealing to the priming region of the first barcode molecule, and wherein the second extension primer comprises a sequence capable of annealing to the priming region of the second barcode molecule; and (c) first and second adapter oligonucleotides for each of the multimeric barcode molecules, wherein the first adapter oligonucleotide comprises, optionally in the 5' to 3' direction, an adapter region capable of annealing to the adapter region of the first barcode molecule and a target region capable of annealing or ligating to a first fragment of the target nucleic acid, and wherein the second adapter oligonucleotide comprises, optionally in the 5' to 3' direction, an adapter region capable of annealing to the adapter region of the second barcode molecule and a target region capable of annealing or ligating to a second fragment of the target nucleic acid.

21. Methods of Preparing a Nucleic Acid Sample for Sequencing

The methods of preparing a nucleic acid sample for sequencing may comprise (i) contacting the nucleic acid sample with a multimeric barcoding reagent comprising first and second barcode regions linked together, wherein each barcode region comprises a nucleic acid sequence, and (ii) appending barcode sequences to first and second fragments of a target nucleic acid to produce first and second different barcoded target nucleic acid molecules, wherein the first barcoded target nucleic acid molecule comprises the nucleic acid sequence of the first barcode region and the second barcoded target nucleic acid molecule comprises the nucleic acid sequence of the second barcode region.

In methods in which the multimeric barcoding reagent comprises first and second barcoded oligonucleotides linked together, the barcode sequences may be appended to first and second fragments of the target nucleic acid by any of the methods described herein.

The first and second barcoded oligonucleotides may be ligated to the first and second fragments of the target nucleic acid to produce the first and second different barcoded target nucleic acid molecules. Optionally, prior to the ligation step, the method comprises appending first and second coupling sequences to the target nucleic acid, wherein the first and second coupling sequences are the first and second fragments of the target nucleic acid to which the first and second barcoded oligonucleotides are ligated.

The first and second barcoded oligonucleotides may be annealed to the first and second fragments of the target nucleic acid extended to produce the first and second different barcoded target nucleic acid molecules. Optionally, prior to the annealing step, the method comprises appending first and second coupling sequences to the target nucleic acid, wherein the first and second coupling sequences are the first and second fragments of the target nucleic acid to which the first and second barcoded oligonucleotides are annealed.

The first and second barcoded oligonucleotides may be annealed at their 5' ends to the first and second subsequences of the target nucleic acid and first and second target primers may be annealed to third and fourth subsequences of the target nucleic acid, respectively, wherein the third subsequence is 3' of the first subsequence and wherein the fourth sub-sequence is 3' of the second subsequence. The method further comprises extending the first target primer using the target nucleic acid as template until it reaches the first sub-sequence to produce a first extended target primer, and extending the second target primer using the target nucleic acid as template until it reaches the second sub-sequence to produce a second extended target primer, and ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different and each comprises at least one nucleotide synthesised from the target nucleic acid as a template. Optionally, prior to either or both annealing step(s), the method comprises appending first and second, and/or third and fourth, coupling sequences to the target nucleic acid, wherein the first and second coupling sequences are the first and second sub-sequences of the target nucleic acid to which the first and second barcoded oligonucleotides are annealed, and/or wherein the third and fourth coupling sequences are the third and fourth sub-sequences of the target nucleic acid to which the first and second target primers are annealed.

As described herein, prior to annealing or ligating a multimeric hybridization molecule, multimeric barcode molecule, barcoded oligonucleotide, adapter oligonucleotide or target primer to a target nucleic acid, a coupling sequence may be appended to the target nucleic acid. The multimeric hybridization molecule, multimeric barcode molecule, barcoded oligonucleotide, adapter oligonucleotide or target primer may then be annealed or ligated to the coupling sequence.

A coupling sequence may be added to the 5' end or 3' end of two or more target nucleic acids of the nucleic acid sample. In this method, the target regions (of the barcoded oligonucleotides) may comprise a sequence that is complementary to the coupling sequence.

A coupling sequence may be comprised within a double-stranded coupling oligonucleotide or within a single-stranded coupling oligonucleotide. A coupling oligonucleotide may be appended to the target nucleic acid by a double-stranded ligation reaction or a single-stranded ligation reaction. A coupling oligonucleotide may comprise a single-stranded 5' or 3' region capable of ligating to a target nucleic acid and the coupling sequence may be appended to the target nucleic acid by a single-stranded ligation reaction.

A coupling oligonucleotide may comprise a blunt, recessed, or overhanging 5' or 3' region capable of ligating to a target nucleic acid and the coupling sequence may be appended to the target nucleic acid a double-stranded ligation reaction.

The end(s) of a target nucleic acid may be converted into blunt double-stranded end(s) in a blunting reaction, and the coupling oligonucleotide may comprise a blunt double-stranded end, and wherein the coupling oligonucleotide may be ligated to the target nucleic acid in a blunt-end ligation reaction.

The end(s) of a target nucleic acid may be converted into blunt double-stranded end(s) in a blunting reaction, and then converted into a form with (a) single 3' adenosine overhang(s), and wherein the coupling oligonucleotide may comprise a double-stranded end with a single 3' thymine overhang capable of annealing to the single 3' adenosine overhang of the target nucleic acid, and wherein the coupling oligonucleotide is ligated to the target nucleic acid in a double-stranded A/T ligation reaction The target nucleic acid may be contacted with a restriction enzyme, wherein the restriction enzyme digests the target nucleic acid at restriction sites to create (a) ligation junction(s) at the restriction site(s), and wherein the coupling oligonucleotide comprises an end compatible with the ligation junction, and wherein the coupling oligonucleotide is then ligated to the target nucleic acid in a double-stranded ligation reaction.

A coupling oligonucleotide may be appended via a primer-extension or polymerase chain reaction step.

A coupling oligonucleotide may be appended via a primer-extension or polymerase chain reaction step, using one or more oligonucleotide(s) that comprise a priming segment including one or more degenerate bases.

A coupling oligonucleotide may be appended via a primer-extension or polymerase chain reaction step, using one or more oligonucleotide(s) that further comprise a priming or hybridisation segment specific for a particular target nucleic acid sequence.

A coupling sequence may be added by a polynucleotide tailing reaction. A coupling sequence may be added by a terminal transferase enzyme (e.g. a terminal deoxynucleotidyl transferase enzyme). A coupling sequence may be appended via a polynucleotide tailing reaction performed with a terminal deoxynucleotidyl transferase enzyme, and wherein the coupling sequence comprises at least two contiguous nucleotides of a homopolymeric sequence.

A coupling sequence may comprise a homopolymeric 3' tail (e.g. a poly(A) tail). Optionally, in such methods, the target regions (of the barcoded oligonucleotides) comprise a complementary homopolymeric 3' tail (e.g. a poly(T) tail).

A coupling sequence may be comprised within a synthetic transposome, and may be appended via an in vitro transposition reaction.

A coupling sequence may be appended to a target nucleic acid, and wherein a barcode oligonucleotide is appended to the target nucleic acid by at least one primer-extension step or polymerase chain reaction step, and wherein said barcode oligonucleotide comprises a region of at least one nucleotide in length that is complementary to said coupling sequence. Optionally, this region of complementarity is at the 3' end of the barcode oligonucleotide. Optionally, this region of complementarity is at least 2 nucleotides in length, at least 5 nucleotides in length, at least 10 nucleotides in length, at least 20 nucleotides in length, or at least 50 nucleotides in length.

In methods in which an adapter oligonucleotide is appended (e.g. ligated or annealed) to a target nucleic acid, the adapter region of the adapter oligonucleotide provides a coupling sequence capable of hybridizing to the adapter region of a multimeric hybridization molecule or a multimeric barcode molecule.

The invention provides a method of preparing a nucleic acid sample for sequencing comprising the steps of: (a) appending a coupling sequence to first and second fragments of a target nucleic acid; (b) contacting the nucleic acid sample with a multimeric barcoding reagent comprising first and second barcode molecules linked together, wherein each of the barcode molecules comprises a nucleic acid sequence comprising (in the 5' to 3' or 3' to 5' direction), a barcode region and an adapter region; (c) annealing the coupling sequence of the first fragment to the adapter region of the first barcode molecule, and annealing the coupling sequence of the second fragment to the adapter region of the second barcode molecule; and (d) appending barcode sequences to each of the at least two fragments of the target nucleic acid to produce first and second different barcoded target nucleic acid molecules, wherein the first barcoded target nucleic acid molecule comprises the nucleic acid sequence of the barcode region of the first barcode molecule and the second barcoded target nucleic acid molecule comprises the nucleic acid sequence of the barcode region of the second barcode molecule.

In the method, each of the barcode molecules may comprise a nucleic acid sequence comprising, in the 5' to 3' direction, a barcode region and an adapter region, and step (d) may comprise extending the coupling sequence of the first fragment of the target nucleic acid using the barcode region of the first barcode molecule as a template to produce a first barcoded target nucleic acid molecule, and extending the coupling sequence of the second fragment of the target nucleic acid using the barcode region of the second barcode molecule as a template to produce a second barcoded target nucleic acid molecule, wherein the first barcoded target nucleic acid molecule comprises a sequence complementary to the barcode region of the first barcode molecule and the second barcoded target nucleic acid molecule comprises a sequence complementary to the barcode region of the second barcode molecule.

In the method, each of the barcode molecules may comprise a nucleic acid sequence comprising, in the 5' to 3' direction, an adapter region and a barcode region, and step (d) may comprise (i) annealing and extending a first extension primer using the barcode region of the first barcode molecule as a template to produce a first barcoded oligonucleotide, and annealing and extending a second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule, (ii) ligating the 3' end of the first barcoded oligonucleotide to the 5' end of the coupling sequence of the first fragment of the target nucleic acid to produce a first barcoded target nucleic acid molecule and ligating the 3' end of the second barcoded oligonucleotide to the 5' end of the coupling sequence of the second fragment of the target nucleic acid to produce a second barcoded target nucleic acid molecule.

In the method, each of the barcode molecules may comprise a nucleic acid sequence comprising, in the 5' to 3' direction, an adapter region, a barcode region and a priming region wherein step (d) comprises (i) annealing a first extension primer to the priming region of the first barcode molecule and extending the first extension primer using the barcode region of the first barcode molecule as a template to produce a first barcoded oligonucleotide, and annealing a second extension primer to the priming region of the second barcode molecule and extending the second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule, (ii) ligating the 3' end of the first barcoded oligonucleotide to the 5' end of the coupling sequence of the first fragment of the target nucleic acid to produce a first barcoded target nucleic acid molecule and ligating the 3' end of the second barcoded oligonucleotide to the 5' end of the coupling sequence of the second fragment of the target nucleic acid to produce a second barcoded target nucleic acid molecule.

The methods for preparing a nucleic acid sample for sequencing may be used to prepare a range of different nucleic acid samples for sequencing. The target nucleic acids may be DNA molecules (e.g. genomic DNA molecules) or RNA molecules (e.g. mRNA molecules). The target nucleic acids may be from any sample. For example, an individual cell (or cells), a tissue, a bodily fluid (e.g. blood, plasma and/or serum), a biopsy or a formalin-fixed paraffin-embedded (FFPE) sample.

The sample may comprise at least 10, at least 100, or at least $10^3$, at least $10^4$, at least $10^5$, at least $10^6$, at least $10^7$, at least $10^8$ or at least $10^9$ target nucleic acids The method may comprise producing at least 2, at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$ or at least $10^9$ different barcoded target nucleic acid molecules. Preferably, the method comprises producing at least 5 different barcoded target nucleic acid molecules.

Each barcoded target nucleic acid molecule may comprise at least 1, at least 5, at least 10, at least 25, at least 50, at least 100, at least 250, at least 500, at least 1000, at least 2000, at least 5000, or at least 10,000 nucleotides synthesised from the target nucleic acid as template. Preferably, each barcoded target nucleic acid molecule comprises at least 20 nucleotides synthesised from the target nucleic acid as template.

Alternatively, each barcoded target nucleic acid molecule may comprise at least 5, at least 10, at least 25, at least 50, at least 100, at least 250, at least 500, at least 1000, at least 2000, at least 5000, or at least 10,000 nucleotides of the target nucleic acid. Preferably, each barcoded target nucleic acid molecule comprises at least 5 nucleotides of the target nucleic acid.

A universal priming sequence may be added to the barcoded target nucleic acid molecules. This sequence may enable the subsequent amplification of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different barcoded target nucleic acid molecules using one forward primer and one reverse primer.

The method may comprise preparing two or more independent nucleic acid samples for sequencing, wherein each nucleic acid sample is prepared using a different library of multimeric barcoding reagents (or a different library of multimeric barcode molecules), and wherein the barcode regions of each library of multimeric barcoding reagents (or multimeric barcode molecules) comprise a sequence that is different to the barcode regions of the other libraries of multimeric barcoding reagents (or multimeric barcode molecules). Following the separate preparation of each of the samples for sequencing, the barcoded target nucleic acid molecules prepared from the different samples may be pooled and sequenced together. The sequence read generated for each barcoded target nucleic acid molecule may be used to identify the library of multimeric barcoding reagents (or multimeric barcode molecules) that was used in its preparation and thereby to identify the nucleic acid sample from which it was prepared.

In any method of preparing a nucleic acid sample for sequencing, the target nucleic acid molecules may be present at particular concentrations within the nucleic acid sample, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, 10 picomolar to 10 nanomolar, or 100 picomolar to 1 nanomolar. Preferably, the concentrations are 10 picomolar to 1 nanomolar.

In any method of preparing a nucleic acid sample for sequencing, the multimeric barcoding reagents may be present at particular concentrations within the nucleic acid sample, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, 10 picomolar to 10 nanomolar, or 100 picomolar to 1 nanomolar. Preferably, the concentrations are 1 picomolar to 100 picomolar.

In any method of preparing a nucleic acid sample for sequencing, the multimeric barcode molecules may be present at particular concentrations within the nucleic acid sample, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, 10 picomolar to 10 nanomolar, or 100 picomolar to 1 nanomolar. Preferably, the concentrations are 1 picomolar to 100 picomolar.

In any method of preparing a nucleic acid sample for sequencing, the barcoded oligonucleotides may be present at particular concentrations within the nucleic acid sample, for example at concentrations of at least 100 nanomolar, at least 10 nanomolar, at least 1 nanomolar, at least 100 picomolar, at least 10 picomolar, at least 1 picomolar, at least 100 femtomolar, at least 10 femtomolar, or at least 1 femtomolar. The concentrations may be 1 picomolar to 100 nanomolar, 10 picomolar to 10 nanomolar, or 100 picomolar to 1 nanomolar. Preferably, the concentrations are 100 picomolar to 100 nanomolar.

22. Methods of Preparing a Nucleic Acid Sample for Sequencing Using Multimeric Barcoding Reagents The invention provides a method of preparing a nucleic acid sample for sequencing, wherein the method comprises the steps of: contacting the nucleic acid sample with a multimeric barcoding reagent as defined herein; annealing the target region of the first barcoded oligonucleotide to a first fragment of a target nucleic acid, and annealing the target region of the second barcoded oligonucleotide to a second fragment of the target nucleic acid; and extending the first and second barcoded oligonucleotides to produce first and second different barcoded target nucleic acid molecules, wherein each of the barcoded target nucleic acid molecules comprises at least one nucleotide synthesised from the target nucleic acid as a template.

In any method of preparing a nucleic acid sample for sequencing, either the nucleic acid molecules within the nucleic acid sample, and/or the multimeric barcoding reagents, may be present at particular concentrations within the solution volume, for example at concentrations of at least 100 nanomolar, at least 10 nanomolar, at least 1 nanomolar, at least 100 picomolar, at least 10 picomolar, or at least 1 picomolar. The concentrations may be 1 picomolar to 100 nanomolar, 10 picomolar to 10 nanomolar, or 100 picomolar to 1 nanomolar. Alternative higher or lower concentrations may also be used.

The method of preparing a nucleic acid sample for sequencing may comprise contacting the nucleic acid sample with a library of multimeric barcoding reagents as defined herein, and wherein: the barcoded oligonucleotides of the first multimeric barcoding reagent anneal to fragments of a first target nucleic acid and first and second different barcoded target nucleic acid molecules are produced, wherein each barcoded target nucleic acid molecule comprises at least one nucleotide synthesised from the first target nucleic acid as a template; and the barcoded oligonucleotides of the second multimeric barcoding reagent anneal to fragments of a second target nucleic acid and first and second different barcoded target nucleic acid molecules are produced, wherein each barcoded target nucleic acid molecule comprises at least one nucleotide synthesised from the second target nucleic acid as a template.

In the method the barcoded oligonucleotides may be isolated from the nucleic acid sample after annealing to the fragments of the target nucleic acid and before the barcoded target nucleic acid molecules are produced. Optionally, the barcoded oligonucleotides are isolated by capture on a solid support through a streptavidin-biotin interaction.

Additionally or alternatively, the barcoded target nucleic acid molecules may be isolated from the nucleic acid sample. Optionally, the barcoded target nucleic acid molecules are isolated by capture on a solid support through a streptavidin-biotin interaction.

The step of extending the barcoded oligonucleotides may be performed while the barcoded oligonucleotides are annealed to the barcode molecules.

FIG. 3 shows a method of preparing a nucleic acid sample for sequencing, in which a multimeric barcoding reagent defined herein (for example, as illustrated in FIG. 1) is used to label and extend two or more nucleic acid sub-sequences in a nucleic acid sample. In this method, a multimeric barcoding reagent is synthesised which incorporates at least a first (A1, B1, C1, and G1) and a second (A2, B2, C2, and G2) barcoded oligonucleotide, which each comprise both a barcode region (B1 and B2) and a target region (G1 and G2 respectively).

A nucleic acid sample comprising a target nucleic acid is contacted or mixed with the multimeric barcoding reagent, and the target regions (G1 and G2) of two or more barcoded oligonucleotides are allowed to anneal to two or more corresponding sub-sequences within the target nucleic acid (H1 and H2). Following the annealing step, the first and second barcoded oligonucleotides are extended (e.g. with the target regions serving as primers for a polymerase) into the sequence of the target nucleic acid, such that at least one nucleotide of a sub-sequence is incorporated into the extended 3' end of each of the barcoded oligonucleotides. This method creates barcoded target nucleic acid molecules, wherein two or more sub-sequences from the target nucleic acid are labeled by a barcoded oligonucleotide.

Alternatively, the method may further comprise the step of dissociating the barcoded oligonucleotides from the barcode molecules before annealing the target regions of the barcoded oligonucleotides to sub-sequences of the target nucleic acid.

FIG. 4 shows a method of preparing a nucleic acid sample for sequencing, in which a multimeric barcoding reagent described herein (for example, as illustrated in FIG. 1) is used to label and extend two or more nucleic acid sub-sequences in a nucleic acid sample, but wherein the barcoded oligonucleotides from the multimeric barcoding reagent are dissociated from the barcode molecules prior to annealing to (and extension of) target nucleic acid sequences. In this method, a multimeric barcoding reagent is synthesised which incorporates at least a first (A1, B1, C1, and G1) and a second (A2, B2, C2, and G2) barcoded oligonucleotide, which each comprise a barcode region (B1 and B2) and a target region (G1 and G2).

A nucleic acid sample comprising a target nucleic acid is contacted with the multimeric barcoding reagent, and then the barcoded oligonucleotides are dissociated from the barcode molecules. This step may be achieved, for example, through exposing the reagent to an elevated temperature (e.g. a temperature of at least 35° C., at least 40° C., at least 45° C., at least 50° C., at least 55° C., at least 60° C., at least 65° C., at least 70° C., at least 75° C., at least 80° C., at least 85° C., or at least 90° C.) or through a chemical denaturant, or a combination thereof. This step may also denature double-stranded nucleic acids within the sample itself. The barcoded oligonucleotides may then be allowed to for diffuse for a certain amount of time (e.g. at least 5 seconds, at least 15 seconds, at least 30 seconds, at least 60 seconds, at least 2 minutes, at least 5 minutes, at least 15 minutes, at least 30 minutes, or at least 60 minutes) (and correspondingly, to diffuse a certain physical distance within the sample).

The conditions of the reagent-sample mixture may then be changed to allow the target regions (G1 and G2) of two or more barcoded oligonucleotides to anneal to two or more corresponding sub-sequences within the target nucleic acid (H1 and H2). This could comprise, for example, lowering the temperature of the solution to allow annealing (for example, lowering the temperature to less than 90° C., less than 85° C., less than 70° C., less than 65° C., less than 60° C., less than 55° C., less than 50° C., less than 45° C., less than 40° C., less than 35° C., less than 30° C., less than 25° C., or less than 20° C.). Following this annealing step (or for example, following a purification/preparation step), the first and second barcoded oligonucleotides are extended (e.g. with the target regions serving as primers for a polymerase) into the sequence of the target nucleic acid, such that at least one nucleotide of a sub-sequence is incorporated into the extended 3' end of each of the barcoded oligonucleotides.

This method creates barcoded target nucleic acid molecules wherein two or more sub-sequences from the nucleic acid sample are labeled by a barcoded oligonucleotide. In addition, the step of dissociating the barcoded oligonucleotides and allowing them to diffuse through the sample holds advantages for particular types of samples. For example, cross-linked nucleic acid samples (e.g. formalin-fixed, paraffin-embedded (FFPE) samples) may be amenable to the diffusion of relatively small, individual barcoded oligonucleotides. This method may allow labeling of nucleic acid samples with poor accessibility (e.g. FFPE samples) or other biophysical properties e.g. where target nucleic acid sub-sequences are physically far away from each other.

A universal priming sequence may be added to the barcoded target nucleic acid molecules. This sequence may enable the subsequent amplification of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different barcoded target nucleic acid molecules using one forward primer and one reverse primer.

Prior to contacting the nucleic acid sample with a multimeric barcoding reagent, or library of multimeric barcoding reagents, as defined herein, a coupling sequence may be added to the 5' end or 3' end of two or more target nucleic acids of the nucleic acid sample. In this method, the target regions may comprise a sequence that is complementary to the coupling sequence. The coupling sequence may comprise a homopolymeric 3' tail (e.g. a poly(A) tail). The coupling sequence may be added by a terminal transferase enzyme. In the method in which the coupling sequence comprises a poly(A) tail, the target regions may comprise a poly(T) sequence. Such coupling sequences may be added following a high-temperature incubation of the nucleic acid sample, to denature the nucleic acids contained therein prior to adding a coupling sequence.

Alternatively, a coupling sequence could be added by digestion of a target nucleic acid sample with a restriction enzyme, in which case a coupling sequence may be comprised of one or more nucleotides of a restriction enzyme recognition sequence. In this case, a coupling sequence may be at least partially double-stranded, and may comprise a blunt-ended double-stranded DNA sequence, or a sequence with a 5' overhang region of 1 or more nucleotides, or a sequence with a 3' overhang region of 1 or more nucleotides. In these cases, target regions in multimeric barcoding reagents may then comprise sequences that are either double-stranded and blunt-ended (and thus able to ligate to blunt-ended restriction digestion products), or the target regions may contain 5' or 3' overhang sequences of 1 or more nucleotides, which make them cohesive (and thus able to anneal with and ligate to) against said restriction digestion products.

The method may comprise preparing two or more independent nucleic acid samples for sequencing, wherein each nucleic acid sample is prepared using a different library of multimeric barcoding reagents (or a different library of multimeric barcode molecules), and wherein the barcode regions of each library of multimeric barcoding reagents (or multimeric barcode molecules) comprise a sequence that is different to the barcode regions of the other libraries of multimeric barcoding reagents (or multimeric barcode molecules). Following the separate preparation of each of the samples for sequencing, the barcoded target nucleic acid molecules prepared from the different samples may be pooled and sequenced together. The sequence read generated for each barcoded target nucleic acid molecule may be used to identify the library of multimeric barcoding reagents (or multimeric barcode molecules) that was used in its preparation and thereby to identify the nucleic acid sample from which it was prepared.

The invention provides a method of preparing a nucleic acid sample for sequencing, wherein the method comprises the steps of: (a) contacting the nucleic acid sample with a multimeric barcoding reagent, wherein each barcoded oligonucleotide comprises in the 5' to 3' direction a target region and a barcode region, and first and second target primers; (b) annealing the target region of the first barcoded oligonucleotide to a first sub-sequence of a target nucleic acid and annealing the target region of the second barcoded oligonucleotide to a second sub-sequence of the target nucleic acid; (c) annealing the first target primer to a third sub-sequence of the target nucleic acid, wherein the third sub-sequence is 3' of the first sub-sequence, and annealing the second target primer to a fourth sub-sequence of the target nucleic acid, wherein the fourth sub-sequence is 3' of the second sub-sequence; (d) extending the first target primer using the target nucleic acid as template until it reaches the first sub-sequence to produce a first extended target primer, and extending the second target primer using the target nucleic acid as template until it reaches the second sub-sequence to produce a second extended target primer; and (e) ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different, and wherein each of the barcoded target nucleic acid molecules comprises at least one nucleotide synthesised from the target nucleic acid as a template.

In the method, steps (b) and (c) may be performed at the same time.

23. Methods of Preparing a Nucleic Acid Sample for Sequencing Using Multimeric Barcoding Reagents and Adapter Oligonucleotides The methods provided below may be performed with any of the kits defined herein.

The invention further provides a method of preparing a nucleic acid sample for sequencing, wherein the method comprises the steps of: (a) contacting the nucleic acid sample with a first and second adapter oligonucleotide as defined herein; (b) annealing or ligating the first adapter oligonucleotide to a first fragment of a target nucleic acid, and annealing or ligating the second adapter oligonucleotide to a second fragment of the target nucleic acid; (c) contacting the nucleic acid sample with a multimeric barcoding reagent as defined herein; (d) annealing the adapter region of the first adapter oligonucleotide to the adapter region of the first barcode molecule, and annealing the adapter region of the second adapter oligonucleotide to the adapter region of the second barcode molecule; and (e) ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide.

The invention further provides a method of preparing a nucleic acid sample for sequencing, wherein the method comprises the steps of: (a) contacting the nucleic acid sample with a first and second adapter oligonucleotide as defined herein; (b) the first adapter oligonucleotide to a first fragment of a target nucleic acid, and ligating the second adapter oligonucleotide to a second fragment of the target nucleic acid; (c) contacting the nucleic acid sample with a multimeric barcoding reagent as defined herein; (d) annealing the adapter region of the first adapter oligonucleotide to the adapter region of the first barcode molecule, and annealing the adapter region of the second adapter oligonucleotide to the adapter region of the second barcode molecule; and (e) extending the first adapter oligonucleotide using the barcode region of the first barcode molecule as a template to produce a first barcoded target nucleic acid molecule, and extending the second adapter oligonucleotide using the barcode region of the second barcode molecule as a template to produce a second barcoded target nucleic acid molecule, wherein the first barcoded target nucleic acid molecule comprises a sequence complementary to the barcode region of the first barcode molecule and the second barcoded target nucleic acid molecule comprises a sequence complementary to the barcode region of the second barcode molecule.

The invention further provides a method of preparing a nucleic acid sample for sequencing, wherein the method comprises the steps of: (a) contacting the nucleic acid sample with a first and second adapter oligonucleotide as defined herein; (b) annealing the target region of the first adapter oligonucleotide to a first fragment of a target nucleic acid, and annealing the target region of the second adapter oligonucleotide to a second fragment of the target nucleic acid; (c) contacting the nucleic acid sample with a multimeric barcoding reagent as defined herein; (d) annealing the adapter region of the first adapter oligonucleotide to the adapter region of the first barcode molecule, and annealing the adapter region of the second adapter oligonucleotide to the adapter region of the second barcode molecule; and (e) ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide.

In the method the first and second barcoded-adapter oligonucleotides may be extended to produce first and second different barcoded target nucleic acid molecules each of which comprises at least one nucleotide synthesised from the target nucleic acid as a template.

Alternatively, the first and second adapter oligonucleotides may be extended to produce first and second different target nucleic acid molecules each of which comprises at least one nucleotide synthesised from the target nucleic acid as a template. In this method, step (f) produces a first barcoded target nucleic acid molecule (i.e. the first barcoded oligonucleotide ligated to the extended first adapter oligonucleotide) and a second barcoded target nucleic acid molecule (i.e. the second barcoded oligonucleotide ligated to the extended second adapter oligonucleotide).

The step of extending the adapter oligonucleotides may be performed before step (c), before step (d) and/or before step (e), and the first and second adapter oligonucleotides may remain annealed to the first and second barcode molecules until after step (e).

The method may be performed using a library of multimeric barcoding reagents as defined herein and an adapter oligonucleotide as defined herein for each of the multimeric barcoding reagents. Preferably, the barcoded-adapter oligonucleotides of the first multimeric barcoding reagent anneal to fragments of a first target nucleic acid and first and second different barcoded target nucleic acid molecules are produced, wherein each barcoded target nucleic acid molecule comprises at least one nucleotide synthesised from the first target nucleic acid as a template; and the barcoded-adapter oligonucleotides of the second multimeric barcoding reagent anneal to fragments of a second target nucleic acid and first and second different barcoded target nucleic acid molecules are produced, wherein each barcoded target nucleic acid molecule comprises at least one nucleotide synthesised from the second target nucleic acid as a template.

The method may be performed using a library of multimeric barcoding reagents as defined herein and an adapter oligonucleotide as defined herein for each of the multimeric barcoding reagents. Preferably, the adapter oligonucleotides of the first multimeric barcoding reagent anneal to fragments of a first target nucleic acid and first and second different target nucleic acid molecules are produced, wherein each target nucleic acid molecule comprises at least one nucleotide synthesised from the first target nucleic acid as a template; and the adapter oligonucleotides of the second multimeric barcoding reagent anneal to fragments of a second target nucleic acid and first and second different target nucleic acid molecules are produced, wherein each target nucleic acid molecule comprises at least one nucleotide synthesised from the second target nucleic acid as a template.

The barcoded-adapter oligonucleotides may be isolated from the nucleic acid sample after annealing to the fragments of the target nucleic acid and before the barcoded target nucleic acid molecules are produced. Optionally, the barcoded-adapter oligonucleotides are isolated by capture on a solid support through a streptavidin-biotin interaction.

The barcoded target nucleic acid molecules may be isolated from the nucleic acid sample. Optionally, the barcoded target nucleic acid molecules are isolated by capture on a solid support through a streptavidin-biotin interaction.

FIG. 5 shows a method of preparing a nucleic acid sample for sequencing using a multimeric barcoding reagent. In the method first (C1 and G1) and second (C2 and G2) adapter oligonucleotides are annealed to a target nucleic acid in the nucleic acid sample, and then used in a primer extension reaction. Each adapter oligonucleotide is comprised of an adapter region (C1 and C2) that is complementary to, and thus able to anneal to, the 5' adapter region of a barcode molecule (F1 and F2). Each adapter oligonucleotide is also comprised of a target region (G1 and G2), which may be used to anneal the barcoded oligonucleotides to target nucleic acids, and then may be used as primers for a primer-extension reaction or a polymerase chain reaction. These adapter oligonucleotides may be synthesised to include a 5'-terminal phosphate group.

The adapter oligonucleotides, each of which has been extended to include sequence from the target nucleic acid, are then contacted with a multimeric barcoding reagent which comprises a first (D1, E1, and F1) and second (D2, E2, and F2) barcode molecule, as well as first (A1 and B1) and second (A2 and B2) barcoded oligonucleotides, which each comprise a barcode region (B1 and B2), as well as 5' regions (A1 and A2). The first and second barcode molecules each comprise a barcode region (E1 and E2), an adapter region (F1 and F2), and a 3' region (D1 and D2), and are linked together, in this embodiment by a connecting nucleic acid sequence (S).

After contacting the primer-extended nucleic acid sample with a multimeric barcoding reagent, the 5' adapter regions (C1 and C2) of each adapter oligonucleotides are able to anneal to a 'ligation junction' adjacent to the 3' end of each barcoded oligonucleotide (J1 and J2). The 5' end of the extended adapter oligonucleotides are then ligated to the 3' end of the barcoded oligonucleotides within the multimeric barcoding reagent, creating a ligated base pair (K1 and K2) where the ligation junction was formerly located. The solution may subsequently be processed further or amplified, and used in a sequencing reaction.

This method, like the methods illustrated in FIGS. 3 and 4, creates barcoded target nucleic acid molecules, wherein two or more fragments from the nucleic acid sample are labeled by a barcoded oligonucleotide. In this method a multimeric barcoding reagent does not need to be present for the step of annealing target regions to fragments of the target nucleic acid, or the step of extending the annealed target regions using a polymerase. This feature may hold advantages in certain applications, for example wherein a large number of target sequences are of interest, and the target regions are able to hybridise more rapidly to target nucleic acids when they are not constrained molecularly by a multimeric barcoding reagent.

24. Methods of Preparing a Nucleic Acid Sample for Sequencing Using Multimeric Barcoding Reagents, Adapter Oligonucleotides and Extension Primers The invention further provides a method of preparing a nucleic acid sample for sequencing, wherein the method comprises the steps of: (a) contacting the nucleic acid sample with first and second adapter oligonucleotides as defined herein; (b) annealing the target region of the first adapter oligonucleotide to a first fragment of a target nucleic acid, and annealing the target region of the second adapter oligonucleotide to a second fragment of the target oligonucleotide; (c) contacting the nucleic acid sample with a library of multimeric barcode molecules as defined herein and first and second extension primers as defined herein; (d) annealing the adapter region of the first adapter oligonucleotide to the adapter region of the first barcode molecule, and annealing the adapter region of the second adapter oligonucleotide to the adapter region of the second barcode molecule; (e) extending the first extension primer using the barcode region of the first barcode molecule as a template to produce a first barcoded oligonucleotide, and extending the second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule; and (f) ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide.

In the method the first and second barcoded-adapter oligonucleotides may be extended to produce first and second different barcoded target nucleic acid molecules each of which comprises at least one nucleotide synthesised from the target nucleic acid as a template.

Alternatively, the first and second adapter oligonucleotides may be extended to produce first and second different target nucleic acid molecules each of which comprises at least one nucleotide synthesised from the target nucleic acid as a template. In this method, step (f) produces a first barcoded target nucleic acid molecule (i.e. the first barcoded oligonucleotide ligated to the extended first adapter oligonucleotide) and a second barcoded target nucleic acid molecule (i.e. the second barcoded oligonucleotide ligated to the extended second adapter oligonucleotide).

The step of extending the adapter oligonucleotides may be performed before step (c), before step (d), before step (e) and/or before step (f), and the first and second adapter oligonucleotides may remain annealed to the first and second barcode molecules until after step (f).

The extension primers may be annealed to the multimeric barcode molecules prior to step (c). Alternatively, the nucleic acid sample may be contacted with a library of multimeric barcode molecules as defined herein and separate extension primers as defined herein. The extension primers may then be annealed to the multimeric barcode molecules in the nucleic acid sample. The extension primers may be annealed to the multimeric barcode molecules during step (d).

The methods may use a library of first and second extension primers e.g. the library may comprise first and second extension primers for each multimeric barcode molecule. Optionally, each extension primer in the library of extension primers may comprise a secondary barcode region, wherein said secondary barcode region is different to the secondary barcode regions within the other extension primers within the library. Optionally, such a library may comprise at least 2, at least 3, at least 4, at least 5, at least 10, at least 20, at least 50, at least 100, at least 500, at least 1000, at least 5,000, or at least 10,000 different extension primers.

25. Methods of Preparing a Nucleic Acid Sample for Sequencing Using Multimeric Barcoding Reagents, Adapter Oligonucleotides and Target Primers The invention further provides a method of preparing a nucleic acid sample for sequencing, wherein the method comprises the steps of: (a) contacting the nucleic acid sample with first and second adapter oligonucleotides, wherein each adapter oligonucleotide comprises in the 5' to 3' direction a target region and an adapter region, and first and second target primers; (b) annealing the target region of the first adapter oligonucleotide to a first sub-sequence of a target nucleic acid, and annealing the target region of the second adapter oligonucleotide to a second sub-sequence of the target nucleic acid; (c) annealing the first target primer to a third sub-sequence of the target nucleic acid, wherein the third sub-sequence is 3' of the first sub-sequence, and annealing the second target primer to a fourth sub-sequence of the target nucleic acid, wherein the fourth sub-sequence is 3' of the second sub-sequence; (d) extending the first target primer using the target nucleic acid as template until it reaches the first sub-sequence to produce a first extended target primer, and extending the second target primer using the target nucleic acid as template until it reaches the second sub-sequence to produce a second extended target primer; (e) ligating the 3' end of the first extended target primer to the 5' end of the first adapter oligonucleotide, and ligating the 3' end of the second extended target primer to the 5' end of the second adapter oligonucleotide; (f) contacting the nucleic acid sample with a library of multimeric barcode molecules as defined herein; (g) annealing the adapter region of the first adapter oligonucleotide to the adapter region of the first barcode molecule, and annealing the adapter region of the second adapter oligonucleotide to the adapter region of the second barcode molecule; and (h) extending the first adapter oligonucleotide using the barcode region of the first barcode molecule as a template to produce a first barcoded oligonucleotide, and extending the second adapter oligonucleotide using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule.

In the method, steps (b) and (c) may be performed at the same time.

In the method, steps (f)-(h) may be performed before steps (d) and (e). In this method, first and second different barcoded target nucleic acid molecules, each of which comprises at least one nucleotide synthesised from the target nucleic acid as a template, are produced by the completion of step (e).

In the method, steps (f)-(h) may be performed after steps (d) and (e). In this method, first and second different barcoded target nucleic acid molecules, each of which comprises at least one nucleotide synthesised from the target nucleic acid as a template, are produced by the completion of step (h).

FIG. 6 illustrates one way in which this method may be performed. In this method, the target nucleic acid is genomic DNA. It will be appreciated that the target nucleic acid may be another type of nucleic acid e.g. an RNA molecule such as an mRNA molecule.

26. Methods of Preparing a Nucleic Acid Sample for Sequencing Using Multimeric Barcoding Reagents and Target Primers The invention further provides a method of preparing a nucleic acid sample for sequencing, wherein the method comprises the steps of: (a) contacting the nucleic acid sample with first and second barcoded oligonucleotides linked together, wherein each barcoded oligonucleotide comprises in the 5' to 3' direction a target region and a barcode region, and first and second target primers; (b) annealing the target region of the first barcoded oligonucleotide to a first sub-sequence of a target nucleic acid, and annealing the target region of the second barcoded oligonucleotide to a second sub-sequence of the target nucleic acid; (c) annealing the first target primer to a third sub-sequence of the target nucleic acid, wherein the third sub-sequence is 3' of the first sub-sequence, and annealing the second target primer to a fourth sub-sequence of the target nucleic acid, wherein the fourth sub-sequence is 3' of the second sub-sequence; (d) extending the first target primer using the target nucleic acid as template until it reaches the first sub-sequence to produce a first extended target primer, and extending the second target primer using the target nucleic acid as template until it reaches the second sub-sequence to produce a second extended target primer; (e) ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different and each comprises at least one nucleotide synthesised from the target nucleic acid as a template.

27. Methods of Assembling Multimeric Barcode Molecules by Rolling Circle Amplification The invention further provides a method of assembling a library of multimeric barcode molecules from a library of nucleic acid barcode molecules, wherein said nucleic acid barcode molecules are amplified by one or more rolling circle amplification (RCA) processes. In this method, nucleic acid barcode molecules may each comprise, optionally in the 5' to 3' direction, a barcode region and an adapter region. Optionally, the nucleic acid barcode molecules may comprise a phosphorylated 5' end capable of ligating to a 3' end of a nucleic acid molecule.

In this method, nucleic acid barcode molecules within the library are converted into a circular form, such that the barcode region and the adapter region from a barcode molecule are comprised within a contiguous circular nucleic acid molecule. Optionally, such a step of converting nucleic acid barcode molecules into circular form may be performed by an intramolecular single-stranded ligation reaction. For example, nucleic acid barcode molecules comprising a phosphorylated 5' end may be circularised by incubation with a single-stranded nucleic acid ligase, such as T4 RNA Ligase 1, or by incubation with a thermostable single-stranded nucleic acid ligase, such as the CircLigase thermostable single-stranded nucleic acid ligase (from Epicentre Bio). Optionally, an exonuclease step may be performed to deplete or degrade uncircularised and/or unligated molecules; optionally wherein the exonuclease step is performed by *E. coli* exonuclease I, or by *E. coli* lambda exonuclease.

Optionally, a step of converting nucleic acid barcode molecules into circular form may be performed using a circularisation primer. In this embodiment, nucleic acid barcode molecules comprise a phosphorylated 5' end. Furthermore, in this embodiment, a circularisation primer comprising a 5' region complementary to the 3' region of a barcode molecule, and a 3' region complementary to the 5' region of a barcode molecule, is annealed to a barcode molecule, such that the 5' end and the 3' end of the barcode molecule are immediately adjacent to each other whilst annealed along the circularisation primer. Following the annealing step, the annealed barcode molecules are ligated with a ligase enzyme, such as T4 DNA ligase, which ligates the 3' end of the barcode molecule to the 5' end of the barcode molecule. Optionally, an exonuclease step may be performed to deplete or degrade uncircularised and/or unligated molecules; optionally wherein the exonuclease step is performed by E. coli exonuclease I, or by E. coli lambda exonuclease.

Following a circularisation step, circularised barcode molecules may be amplified with a rolling circle amplification step. In this process, a primer is annealed to a circularised nucleic acid strand comprising a barcode molecule, and the 3' end of said primer is extended with a polymerase exhibiting strand displacement behaviour. For each original circularised barcode molecule, this process may form a linear (non-circular) multimeric barcode molecule comprising copies of the original circularised barcode molecule, as illustrated in FIG. 7. In one embodiment, a circularisation primer that has been annealed to a barcode molecule may serve as the primer for a rolling circle amplification step. Optionally, following circularisation, a separate amplification primer which is at least partially complementary to the circularised barcode molecule, may be annealed to the circularised barcode molecule to prime a rolling circle amplification step.

During said rolling circle amplification step, the primer may be extended by the polymerase, wherein the polymerase extends along the circularised template until it encounters the 5' end of the amplification primer and/or circularisation primer, whereupon it continues amplification along the circularised template whilst displacing the 5' end of the primer, and then displacing the previously amplified strand, in a process of rolling circle amplification. Following any such amplification step, a purification and/or cleanup step may be performed to isolate products of such rolling circle amplification. Optionally, a purification and/or cleanup step may comprise a size-selection process, such as a gel-based size selection process, or a solid-phase reversible immobilisation size-selection process, such as a magnetic bead-based solid-phase reversible immobilisation size-selection process. Optionally, amplification products at least 100 nucleotides in length, at least 500 nucleotides in length, at least 1000 nucleotides in length, at least 2000 nucleotides in length, at least 5000 nucleotides in length, at least 10,000 nucleotides in length, at least 20,000 nucleotides in length, at least 50,000 nucleotides in length, or at least 100,000 nucleotides in length may be purified. Optionally, before and/or during any rolling circle amplification step, a single-stranded DNA binding protein (such as T4 Gene 32 Protein) may be included in a reaction mixture, such as to prevent the formation of secondary structures by circularised templates and/or amplification products. During or after any such rolling circle amplification step, said single-stranded DNA binding protein may be removed and/or inactivated, such as by a heat-inactivation step.

Optionally, such a process of rolling circle amplification may be performed by phi29 DNA polymerase. Optionally, such a process of rolling circle amplification may be performed by a Bst or Bsm DNA polymerase. Optionally, such a process of rolling circle amplification may be performed such that at least one full copy of the circularised template is produced by the polymerase. Optionally, such a process of rolling circle amplification may be performed such that at least 2, at least 3, at least 5, at least 10, at least 50, at least 100, at least 200, at least 500, at least 1000, at least 2000, at least 5000, or at least 10,000 full copies of the circularised template are produced by the polymerase.

An example of this method is provided in FIG. 7. In the figure, a barcode molecule comprising an adapter region and a barcode region is circularised (e.g. using a single-stranded ligation reaction). A primer is then annealed to the resulting circularised product, and said primer is then extended using a strand-displacing polymerase (such as phi29 DNA polymerase). Whilst synthesising the extension product, the polymerase then processes one circumference around the circularised product, and then displaces the original primer in a strand-displacement reaction. The rolling-circle amplification process may then proceed to create a long contiguous nucleic acid molecule comprising many tandem copies of the circularised sequence—i.e. many tandem copies of a barcode and adapter sequence (and/or sequences complementary to a barcode and adapter sequence) of a barcode molecule.

Multimeric barcode molecules may also be amplified by rolling circle amplification.

28. Methods of Amplifying Multimeric Barcode Molecules by Rolling Circle Amplification A) Properties of Multimeric Barcode Molecules The invention further provides a method of amplifying multimeric barcode molecules from a library of nucleic acid barcode molecules, wherein said multimeric barcode molecules are amplified by one or more rolling circle amplification (RCA) processes. In this method, a multimeric barcode molecule comprises at least two barcode molecules linked together within a (single) nucleic acid molecule. Optionally, each barcode region of a barcode molecule may be adjacent to one or more adapter regions; optionally, such an adapter region may be at the 5' end of the associated barcode region, or may be at the 3' end of the associated barcode region. Optionally, each barcode region is associated with both a 3' adapter region and a 5' adapter region; optionally the 3' adapter region and a 5' adapter region may comprise different adapter sequences. Optionally, one or more adapter regions may comprise a sequence complementary to or identical to an adapter region of an adapter oligonucleotide. Optionally, one or more adapter regions may comprise a sequence complementary to or identical to all or part of an extension primer. A multimeric barcode molecule may take any of the forms described herein.

Each multimeric barcode molecule may further comprise, optionally within the 5' end of the multimeric barcode molecule, a forward reagent amplification sequence, which may comprise a sequence complementary to or identical to a forward reagent amplification primer. Each multimeric barcode molecule may further comprise, optionally within the 3' end of the multimeric barcode molecule, a reverse reagent amplification sequence, which may comprise a sequence complementary to or identical to a reverse reagent amplification primer.

A multimeric barcoding molecule may comprise at least 2, at least 3, at least 4, at least 5, at least 10, at least 20, at least 25, at least 50, at least 75, at least 100, at least 200, at least 500, at least 1000, at least 5000, at least $10^4$, at least $10^5$, or at least $10^6$ different barcode molecules. Any library of multimeric barcode molecules may comprise at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, or at least $10^9$ different multimeric barcode molecules.

B) Methods of Circularising Multimeric Barcode Molecules and/or Libraries Thereof In a method of amplifying multimeric barcode molecules, multimeric barcode molecules (and/or a library thereof) are converted into a circular form, such that the 2 or more barcode regions (and, optionally, 2 or more adapter regions) from a multimeric barcode molecule are comprised within a contiguous circular nucleic acid molecule. Optionally, such a step of converting multimeric barcode molecules into circular form may be performed by an intramolecular single-stranded ligation reaction. For example, multimeric barcode molecules comprising a phosphorylated 5' end may be circularised by incubation with a single-stranded nucleic acid ligase, such as T4 RNA Ligase 1, or by incubation with a thermostable single-stranded nucleic acid ligase, such as the CircLigase thermostable single-stranded nucleic acid ligase (from Epicentre Bio), wherein such a said ligase enzyme ligates the 5' phosphorylated end of a multimeric barcode molecule to the 3' end of the same molecule. Optionally, an exonuclease step may be performed to deplete or degrade uncircularised and/or unligated molecules; optionally wherein the exonuclease step is performed by *E. coli* exonuclease I, or by *E. coli* lambda exonuclease.

Optionally, a step of converting multimeric barcode molecules into circular form may be performed by an intramolecular double-stranded ligation reaction. For example, multimeric barcode molecules comprising double-stranded sequences and phosphorylated 5' ends may comprise blunt ends, or optionally may have their ends converted into a blunt form with a blunting reaction. Such multimeric barcode molecules may then be converted into circular form by an intramolecular double-stranded ligation reaction with a T4 DNA Ligase enzyme, such that one end of a multimeric barcode molecule is ligated on one or both stranded to the other end of the same multimeric barcode molecule.

In an alternative embodiment, a step of converting multimeric barcode molecules into circular form may be performed by an intramolecular double-stranded ligation reaction wherein the ends of multimeric barcode molecules comprise ends generated by a restriction digestion step. In one such embodiment, multimeric barcode molecules comprising double-stranded sequences comprise recognition sites for one or more restriction endonuclease enzymes within their 5' and 3' regions. In a digestion reaction, said multimeric barcode molecules are digested with such one or more restriction endonuclease enzymes to create digested multimeric barcode molecules comprising ends with the restriction digestion products. These digested multimeric barcode molecules may optionally then be purified, for example with a gel-based or bead-based size selection step. The digested multimeric barcode molecules may then be converted into circular form by an intramolecular double-stranded ligation reaction with a T4 DNA Ligase enzyme, such that the restriction-digested site on one end of a multimeric barcode molecule is ligated to the restriction-digested site on the other end of the same multimeric barcode molecule. Optionally, the ends produced by the restriction enzyme(s) may be blunt, or may comprise a 3' overhang of 1 or more nucleotides, or may comprise a 5' overhang of 1 or more nucleotides.

Optionally, a step of converting multimeric barcode molecules into circular form may be performed using a circularisation primer. In this embodiment, multimeric barcode molecules comprise a phosphorylated 5' end. Furthermore, in this embodiment, a circularisation primer comprising a 5' region complementary to the 3' region of a multimeric barcode molecule, and a 3' region complementary to the 5' region of a multimeric barcode molecule, is annealed to a multimeric barcode molecule, such that the 5' end and the 3' end of the multimeric barcode molecule are immediately adjacent to each other whilst annealed along the circularisation primer. Optionally, the multimeric barcode molecules may comprise forward reagent amplification sequences and reverse reagent amplification sequences within their 5' and 3' ends respectively, and the circularisation primer may comprise sequences at least partially complementary to said reagent amplification sequences. Optionally, following a step of annealing circularisation primers to a multimeric barcode molecule or library thereof, excess circularisation primers, which are not annealed to multimeric barcode molecules, may be depleted from the solution by a cleanup reaction, such as a gel-based size-selection step or bead-based size selection step, such as a solid-phase reversible immobilisation step.

Following a circularisation-primer annealing step, the annealed multimeric barcode molecules are ligated with a ligase enzyme, such as T4 DNA ligase, which ligates the 3' end of the multimeric barcode molecule to the 5' end of the multimeric barcode molecule that is annealed immediately adjacent to it along the circularisation primer. Optionally, an exonuclease step may be performed to deplete or degrade uncircularised and/or unligated molecules; optionally wherein the exonuclease step is performed by *E. coli* exonuclease I, or by *E. coli* lambda exonuclease.

During any step of assembling, amplifying, ligating, and/or circularising barcode molecules and/or multimeric barcode molecules, and/or libraries or constituents thereof, the concentration of such molecules within solution may be retained within certain ranges. For example, the concentration of barcode molecules and/or multimeric barcode molecules may be less than 100 nanomolar, less than 10 nanomolar, less than 1 nanomolar, less than 100 picomolar, less than 10 picomolar, less than 1 picomolar, less than 100 femtomolar, less than 10 femtomolar, or less than 1 femtomolar. Optionally, during any step of assembling, amplifying, ligating, and/or circularising barcode molecules and/or multimeric barcode molecules, and/or libraries or constituents thereof, the concentration of such molecules within solution may allow two or more different barcode molecules and/or multimeric barcode molecules to become appended, concatenated, or ligated to each other within solution, optionally wherein such appended, concatenated, or ligated products are then further amplified during an amplification step.

C) Methods of Amplifying Circularised Multimeric Barcode Molecules with Rolling Circle Amplification Following a circularisation step, circularised multimeric barcode molecules are amplified with a rolling circle amplification step. In this process, a primer is annealed to a circularised nucleic acid strand comprising a multimeric barcode molecule, and the 3' end of said primer is extended with a polymerase exhibiting strand displacement behaviour. In one embodiment, a circularisation primer that has been annealed to a multimeric barcode molecule may serve as the primer for a rolling circle amplification step. Optionally, following circularisation, one or more separate amplification primer(s) which are at least partially complementary to a circularised multimeric barcode molecule, may be annealed to the circularised barcode molecule to prime a rolling circle amplification step. Optionally, oligonucleotides at least partially complementary to one or more adapter regions comprised within a multimeric barcode molecule may be employed as amplification primers. Optionally, following any step of annealing one or more amplification primers to circularised multimeric barcode molecules, a cleanup step may be performed to deplete non-annealed primers from the solution and/or to isolate primer-annealed multimeric barcode molecules. Optionally, such a cleanup step may comprise a size-selection step, such as a gel-based size-selection step or bead-based size selection step, such as a solid-phase reversible immobilisation step.

During said rolling circle amplification step, each primer may be extended by the polymerase, wherein the polymerase extends along the circularised template until it encounters the 5' end of an amplification primer and/or a circularisation primer, whereupon it continues amplification along the circularised template whilst displacing the 5' end of the primer, and then displacing the previously amplified strand, in a process of rolling circle amplification. Following any such amplification step, a purification and/or cleanup step may be performed to isolate products of such rolling circle amplification. Optionally, a purification step and/or cleanup step may comprise a size-selection process, such as a gel-based size selection process, or a solid-phase reversible immobilisation size-selection process, such as a magnetic bead-based solid-phase reversible immobilisation size-selection process. Optionally, amplification products at least 100 nucleotides in length, at least 500 nucleotides in length, at least 1000 nucleotides in length, at least 2000 nucleotides in length, at least 5000 nucleotides in length, at least 10,000 nucleotides in length, at least 20,000 nucleotides in length, at least 50,000 nucleotides in length, or at least 100,000 nucleotides in length may be purified.

Optionally, such a process of rolling circle amplification may be performed by phi29 DNA polymerase. Optionally, such a process of rolling circle amplification may be performed by a Bst or Bsm DNA polymerase. Optionally, such a process of rolling circle amplification may be performed such that at least one full copy of the circularised template is produced by the polymerase. Optionally, such a process of rolling circle amplification may be performed such that at least 2, at least 3, at least 5, at least 10, at least 50, at least 100, at least 200, at least 500, at least 1000, at least 2000, at least 5000, or at least 10,000 full copies of the circularised template are produced by the polymerase.

D) Methods of Amplifying Multimeric Barcode Molecules with Secondary Rolling Circle Amplification Processes Following any step of amplifying multimeric barcode molecules by rolling circle amplification, a process of secondary rolling circle amplification may be performed. In this process, products from the first rolling circle amplification step (or constituent parts thereof) are themselves circularised, and then used as template molecules for a second (or further) rolling circle amplification step.

For example, in one such embodiment, a library of multimeric barcode molecules are amplified in a first rolling circle amplification step. The resulting products are then converted into a double-stranded or partially double-stranded form. For example, a primer may be annealed to the said products; optionally, said primer may be complementary to or identical to all or part of one or more 'reagent amplification sequence(s)' comprised within the original multimeric barcode reagents. Optionally, following such an annealing step, a primer-extension step may be performed, wherein the 3' end of the primer is extended by at least one nucleotide by a polymerase. Optionally, such a primer extension may proceed until a full copy of the associated multimeric barcode molecule is produced, i.e. until a full double-stranded molecule is produced. Optionally, such a primer extension may be performed by a polymerase which lacks strand displacement, or 5'-3' exonuclease or flap endonuclease behaviour (such as Phusion polymerase, or T4 DNA polymerase).

The double-stranded region comprising said primer and the reagent amplification sequence to which it is annealed (along with, optionally, any primer-extension product produced by a primer extension step) may contain a recognition site for a restriction endonuclease. The resulting double-stranded or partially double-stranded products may then be digested with said restriction endonuclease, such that the ends of each molecule comprise ligation-capable restriction junctions. Optionally, the ends produced by the restriction enzyme(s) may be blunt, or may comprise a 3' overhang of 1 or more nucleotides, or may comprise a 5' overhang of 1 or more nucleotides.

The resulting digested molecules may then be converted into circular form by an intramolecular double-stranded ligation reaction with a T4 DNA Ligase enzyme, such that the restriction-digested site on one end of a molecule is ligated to the restriction-digested site on the other end of the same molecule. Optionally, before such a ligation reaction, the restriction-digested multimeric barcode molecules may be diluted in solution. Optionally, the resulting concentration of multimeric barcode molecules may be less than 100 nanomolar, less than 10 nanomolar, less than 1 nanomolar, less than 100 picomolar, less than 10 picomolar, less than 1 picomolar, less than 100 femtomolar, less than 10 femtomolar, or less than 1 femtomolar.

The resulting circularised molecules may be used for any rolling circle amplification process as described in any of the methods herein. Optionally, this overall process of performing a first rolling circle amplification process, circularising the resulting products and then performing a second rolling circle amplification process may be repeated two times, three times, four times, five times, or any larger number of times to increase the amount of products ultimately produced by the overall process.

E) Methods of Processing Rolling-Circle-Amplified Multimeric Barcode Molecules With A Primer Extension Process Following any process of rolling circle amplification of a multimeric barcode molecule and/or library thereof, one or more primer extension steps may be performed on the resulting products. The resulting primer-extension products may comprise single stranded nucleic acid molecules comprising all or part of multimeric barcode molecules, and or parts of two or more multimeric barcode molecules. In some embodiments, such primer-extension products may comprise a library of single stranded nucleic acid molecules, wherein each single nucleic acid strand comprises a multimeric barcode molecule. In other embodiments, such primer-extension products may be annealed or partially annealed to the template molecules from which they are synthesised. Optionally, any multimeric barcode molecules resulting from any such primer-extension process may be used to create a multimeric barcoding reagent and/or library thereof. Optionally, any multimeric barcode molecules resulting from any such primer-extension process may be used to barcode nucleic acid molecules within a nucleic acid sample; optionally the barcode sequences comprising said multimeric barcode molecules may be appended to nucleic acid molecules within a nucleic acid sample.

In one such embodiment of a primer-extension process, a primer complementary to, or identical in sequence to, all or part of a forward reagent amplification sequence and/or all or part of a reverse reagent amplification sequence may be used. In one such embodiment, a primer at least partially complementary to a reagent amplification sequence(s) comprised within the polymerase-extension products of the rolling circle amplification reaction may be used to perform one or more primer-extension reactions and/or cycles. In one embodiment of a primer-extension process, a library of random primers are used for said primer-extension process, for example random hexamer primers, random octamer primers, or random decamer primers. Optionally, any primer used in a primer-extension process may comprise one or more modifications, such as phosphorothioate bonds, and specifically such as phosphorothioate bonds within the 3' most one or two nucleotide bonds within the primer. Such 3' phosphorothioate bonds may prevent degradation of said primers by polymerases which exhibit exonuclease behaviour.

Optionally, such a primer-extension step may be performed by a polymerase that exhibits 5'-3' exonuclease behaviour (such as DNA Polymerase I from *E. coli*) and/or flap endonuclease behaviour (such as Taq polymerase from *Thermus aquaticus*), such that nucleic acid sequences annealed immediately downstream of a processing polymerase are degraded or partially degraded during the process of primer-extension by said polymerase.

Optionally, such a primer-extension step may be performed by a polymerase that exhibits strand displacement behaviour, such as phi29 DNA polymerase, Vent polymerase, Deep Vent polymerase, or exonuclease-deficient derivatives thereof (e.g. from New England Bioloabs), or Bst or Bsm DNA polymerase, such that nucleic acid sequences annealed immediately downstream of a processing polymerase are displaced during the process of primer-extension by said polymerase. Optionally, said displaced nucleic acid sequences may comprise other primer-extension products produced during the primer-extension process. Optionally, such a primer-extension step may be performed by phi29 DNA polymerase, wherein the primers used for said primer-extension step comprise random primers.

Any such primer-extension step performed by a polymerase that exhibits strand displacement behaviour may have the effect of displacing regions of multimeric barcode molecules (and/or nucleic acid strands comprising sequences from multimeric barcode molecules, e.g. those that are produced by such a primer extension process) comprising one or more adapter regions and/or adapter sequences, such that said adapter regions and/or adapter sequences are converted into a single-stranded form, such that the resulting single-stranded adapter regions are able to hybridise to complementary sequences, for example complementary sequences comprised within coupling oligonucleotides, adapter oligonucleotides, and/or extension primers. Parts of such strand-displaced molecules may remain annealed to the template molecules from which they were synthesised. Part of any given strand-displaced nucleic acid molecule synthesised by such a primer-extension process may be used to synthesise a multimeric barcoding reagent. Part of any given strand-displaced nucleic acid molecule synthesised by such a primer-extension process may be used to barcode nucleic acid molecules within a nucleic acid sample.

Optionally, such a primer-extension step may be performed by a polymerase that does not exhibit 5'-3' exonuclease, or flap endonuclease behaviour, or strand-displacement behaviour (such as Pfu and/or Phusion polymerases or derivatives thereof (New England Biolabs), or T4 DNA Polymerase), such that nucleic acid sequences annealed immediately downstream of a processing polymerase halt the extension of the polymerase when it encounters them thereat. Optionally, any such primer-extension step may comprise at least 1, at least 5, at least 10, at least 15, at least 20, at least 30, at least 50, or at least 100 cycles of primer-extension. Optionally, such primer-extension cycles may be performed within repeating cycles of primer extension, template denaturating, and primer annealing. Optionally, any such primer-extension step may be performed in a buffer comprising one or more macromolecular crowding agents, such as poly ethylene glycol (PEG) reagents, for example PEG 8000.

Optionally, primer-extension products at least 100 nucleotides in length, at least 500 nucleotides in length, at least 1000 nucleotides in length, at least 2000 nucleotides in length, at least 5000 nucleotides in length, at least 10,000 nucleotides in length, at least 20,000 nucleotides in length, at least 50,000 nucleotides in length, or at least 100,000 nucleotides in length may be produced by any above primer extension process. Optionally, such a process of primer-extension may be performed such that at least one full copy of the circularised template is produced by the polymerase. Optionally, such a process of rolling circle amplification may be performed such that at least 2, at least 3, at least 5, at least 10, at least 50, at least 100, at least 200, at least 500, at least 1000, at least 2000, at least 5000, or at least 10,000 copies of the multimeric barcode molecule template are produced by the polymerase during each primer extension step. Optionally, the length in time (eg seconds, or minutes) of a primer-extension reaction may be configured such that each primer-extension product is approximately the same length as a single multimeric barcode reagent within the library. For example, if a polymerase used for primer extension processes at a rate of 1000 nucleotides per minute, and the mean length of a multimeric barcode reagent within a library of multimeric barcode reagents is 1000 nucleotides, then the primer-extension cycle may be configured to be 1 minute in length.

Optionally, following one or more primer-extension steps, the resulting primer-extension products may be isolated or purified by a cleanup reaction. Optionally, such a cleanup reaction may comprise a size-selection step, such as a gel-based size-selection step or bead-based size selection step, such as a solid-phase reversible immobilisation step. Optionally, primer-extension products at least 100 nucleotides in length, at least 500 nucleotides in length, at least 1000 nucleotides in length, at least 2000 nucleotides in length, at least 5000 nucleotides in length, at least 10,000 nucleotides in length, at least 20,000 nucleotides in length, at least 50,000 nucleotides in length, or at least 100,000 nucleotides in length may be purified.

F) Methods of Processing Rolling-Circle-Amplified and/or Primer-Extended Multimeric Barcode Molecules With A Denaturation Process Prior to or following any purification step and/or size selection step, and/or prior to use for synthesising multimeric barcoding reagents, and/or prior to use for barcoding nucleic acids within a sample of nucleic acids, any rolling circle amplification products or primer-extension products produced as above may be denatured with a denaturing step. Such a denaturing step may be a thermal denaturing step, wherein the products are incubated at a high temperature to melt annealed sequences and/or secondary structure. Such a denaturing step may be performed at a temperature of at least 60 degrees Celsius, at least 70 degrees Celsius, at least 80 degrees Celsius, at least 90 degrees Celsius, or at least 95 degrees Celsius. Such a denaturing step may have the effect of denaturing regions of multimeric barcode molecules comprising one or more adapter regions and/or adapter sequences into single-stranded form, such that the resulting single-stranded adapter regions are able to hybridise to complementary sequences, for example complementary sequences comprised within coupling oligonucleotides, adapter oligonucleotides, and/or extension primers.

In alternative embodiments, no such denaturing step may be performed prior to or following any purification step and/or size selection step, and/or prior to use for synthesising multimeric barcoding reagents, and/or prior to use for barcoding nucleic acids within a sample of nucleic acids. For example, nucleic acid strands comprising primer-extension products produced during a primer-extension step may remain annealed or partially annealed to the template molecules from which they were synthesised. The resulting nucleic acid macromolecules may comprise a total of at least 2 individual nucleic acid strands, at least 3 individual nucleic acid strands, at least 5 individual nucleic acid strands, at least 10 individual nucleic acid strands, at least 50 individual nucleic acid strands, at least 100 individual nucleic acid strands, at least 500 individual nucleic acid strands, at least 1000 individual nucleic acid strands, at least 5000 individual nucleic acid strands, or at least 10,000 individual nucleic acid strands. Optionally, individual nucleic acid strands may comprise all or parts of one or more multimeric barcoding molecules. Such nucleic acid macromolecules and/or libraries thereof may be used for synthesising multimeric barcoding reagents, and/or for barcoding nucleic acids within a sample of nucleic acids.

29. Methods of Synthesising a Multimeric Barcoding Reagent

The invention further provides a method of synthesising a multimeric barcoding reagent for labelling a target nucleic acid comprising: (a) contacting first and second barcode molecules with first and second extension primers, wherein each of the barcode molecules comprises a single-stranded nucleic acid comprising in the 5' to 3' direction an adapter region, a barcode region and a priming region; (b) annealing the first extension primer to the priming region of the first barcode molecule and annealing the second extension primer to the priming region of the second barcode molecule; and (c) synthesising a first barcoded extension product by extending the first extension primer and synthesising a second barcoded extension product by extending the second extension primer, wherein the first barcoded extension product comprises a sequence complementary to the barcode region of the first barcode molecule and the second barcoded extension product comprises a sequence complementary to the barcode region of the second barcode molecule, and wherein the first barcoded extension product does not comprise a sequence complementary to the adapter region of the first barcode molecule and the second barcoded extension product does not comprise a sequence complementary to the adapter region of the second barcode molecule; and wherein the first and second barcode molecules are linked together.

The method may further comprise the following steps before the step of synthesising the first and second barcoded extension products: (a) contacting first and second barcode molecules with first and second blocking primers; and (b) annealing the first blocking primer to the adapter region of the first barcode molecule and annealing the second blocking primer to the adapter region of the second barcode molecule; and wherein the method further comprises the step of dissociating the blocking primers from the barcode molecules after the step of synthesising the barcoded extension products.

In the method, the extension step, or a second extension step performed after the synthesis of an extension product, may be performed, in which one or more of the four canonical deoxyribonucleotides is excluded from the extension reaction, such that the second extension step terminates at a position before the adapter region sequence, wherein the position comprises a nucleotide complementary to the excluded deoxyribonucleotide. This extension step may be performed with a polymerase lacking 3' to 5' exonuclease activity.

The barcode molecules may be provided by a single-stranded multimeric barcode molecule as defined herein.

The barcode molecules may be synthesised by any of the methods defined herein. The barcode regions may uniquely identify each of the barcode molecules. The barcode molecules may be linked on a nucleic acid molecule. The barcode molecules may be linked together in a ligation reaction. The barcode molecules may be linked together by a further step comprising attaching the barcode molecules to a solid support.

The first and second barcode molecules may be assembled as a double-stranded multimeric barcode molecule by any of the methods defined herein prior to step (a) defined above (i.e. contacting first and second barcode molecules with first and second extension primers). The double-stranded multimeric barcode molecule may be dissociated to produce single-stranded multimeric barcode molecules for use in step (a) defined above (i.e. contacting first and second barcode molecules with first and second extension primers).

The method may further comprise the steps of: (a) annealing an adapter region of a first adapter oligonucleotide to the adapter region of the first barcode molecule and annealing an adapter region of a second adapter oligonucleotide to the adapter region of the second barcode molecule, wherein the first adapter oligonucleotide further comprises a target region capable of annealing to a first sub-sequence of the target nucleic acid and the second adapter oligonucleotide further comprises a target region capable of annealing to a second sub-sequence of the target nucleic acid; and (b) ligating the 3' end of the first barcoded extension product to the 5' end of the first adapter oligonucleotide to produce a first barcoded oligonucleotide and ligating the 3' end of the second barcoded extension product to the 5' end of the second adapter oligonucleotide to produce a second barcoded oligonucleotide. Optionally, the annealing step (a) may be performed before the step of synthesising the first and second barcoded extension products and wherein the step of synthesising the first and second barcoded extension products is conducted in the presence of a ligase enzyme that performs the ligation step (b). The ligase may be a thermostable ligase. The extension and ligation reaction may proceed at over 37 degrees Celsius, over 45 degrees Celsius, or over 50 degrees Celsius.

The target regions may comprise different sequences. Each target region may comprise a sequence capable of annealing to only a single sub-sequence of a target nucleic acid within a sample of nucleic acids. Each target region may comprise one or more random, or one or more degenerate, sequences to enable the target region to anneal to more than one sub-sequence of a target nucleic acid. Each target region may comprise at least 5, at least 10, at least 15, at least 20, at least 25, at least 50 or at least 100 nucleotides. Preferably, each target region comprises at least 5 nucleotides. Each target region may comprise 5 to 100 nucleotides, 5 to 10 nucleotides, 10 to 20 nucleotides, 20 to 30 nucleotides, 30 to 50 nucleotides, 50 to 100 nucleotides, 10 to 90 nucleotides, 20 to 80 nucleotides, 30 to 70 nucleotides or 50 to 60 nucleotides. Preferably, each target region comprises 30 to 70 nucleotides. Preferably each target region comprises deoxyribonucleotides, optionally all of the nucleotides in a target region are deoxyribonucleotides. One or more of the deoxyribonucleotides may be a modified deoxyribonucleotide (e.g. a deoxyribonucleotide modified with a biotin moiety or a deoxyuracil nucleotide). Each target region may comprise one or more universal bases (e.g. inosine), one or modified nucleotides and/or one or more nucleotide analogues.

The adapter region of each adapter oligonucleotide may comprise a constant region. Optionally, all adapter regions of adapter oligonucleotides that anneal to a single multimeric barcoding reagent are substantially identical. The adapter region may comprise at least 4, at least 5, at least 6, at least 8, at least 10, at least 15, at least 20, at least 25, at least 50, at least 100, or at least 250 nucleotides. Preferably, the adapter region comprises at least 4 nucleotides. Preferably each adapter region comprises deoxyribonucleotides, optionally all of the nucleotides in an adapter region are deoxyribonucleotides. One or more of the deoxyribonucleotides may be a modified deoxyribonucleotide (e.g. a deoxyribonucleotide modified with a biotin moiety or a deoxyuracil nucleotide). Each adapter region may comprise one or more universal bases (e.g. inosine), one or modified nucleotides and/or one or more nucleotide analogues.

For any of the methods involving adapter oligonucleotides, the 3' end of the adapter oligonucleotide may include a reversible terminator moiety or a reversible terminator nucleotide (for example, a 3'-O-blocked nucleotide), for example at the 3' terminal nucleotide of the target region. When used in an extension and/or extension and ligation reaction, the 3' ends of these adapter oligonucleotides may be prevented from priming any extension events. This may minimize mis-priming or other spurious extension events during the production of barcoded oligonucleotides. Prior to using the assembled multimeric barcoding reagents, the terminator moiety of the reversible terminator may be removed by chemical or other means, thus allowing the target region to be extended along a target nucleic acid template to which it is annealed.

Similarly, for any of the methods involving adapter oligonucleotides, one or more blocking oligonucleotides complementary to one or more sequences within the target region(s) may be employed during extension and/or extension and ligation reactions. The blocking oligonucleotides may comprise a terminator and/or other moiety on their 3' and/or 5' ends such that they are not able to be extended by polymerases. The blocking oligonucleotides may be designed such that they anneal to sequences fully or partially complementary to one or more target regions, and are annealed to said target regions prior to an extension and/or extension and ligation reaction. The use of blocking primers may prevent target regions from annealing to, and potentially mis-priming along, sequences within the solution for which such annealing is not desired (for example, sequence features within barcode molecules themselves). The blocking oligonucleotides may be designed to achieve particular annealing and/or melting temperatures. Prior to using the assembled multimeric barcoding reagents, the blocking oligonucleotide(s) may then be removed by, for example, heat-denaturation and then size-selective cleanup, or other means. The removal of the blocking oligonucleotide(s) may allow the target region to be extended along a target nucleic acid template to which it is annealed.

The method may comprise synthesising a multimeric barcoding reagent comprising at least 5, at least 10, at least 20, at least 25, at least 50, at least 75 or at least 100 barcode molecules, and wherein: (a) each barcode molecule is as defined herein; and (b) a barcoded extension product is synthesised from each barcode molecule according to any method defined herein; and, optionally, (c) an adapter oligonucleotide is ligated to each of the barcoded extension products to produce barcoded oligonucleotides according to any of the methods defined herein.

The invention further provides a method of synthesising a library of multimeric barcoding reagents, wherein the method comprises repeating the steps of any of the methods defined herein to synthesise two or more multimeric barcoding reagents. Optionally, the method comprises synthesising a library of at least 5, at least 10, at least 20, at least 25, at least 50, at least 75, at least 100, at least 250, at least 500, at least $10^3$, at least $10^4$, at least $10^5$, at least $10^6$, at least $10^7$, at least $10^8$, at least $10^9$ or at least $10^{10}$ multimeric barcoding reagents as defined herein. Preferably, the library comprises at least 5 multimeric barcoding reagents as defined herein. Preferably, the barcode regions of each of the multimeric barcoding reagents may be different to the barcode regions of the other multimeric barcoding reagents.

FIG. 8 illustrates a method of synthesizing a multimeric barcoding reagent for labeling a target nucleic acid. In this method, first (D1, E1, and F1) and second (D2, E2, and F2) barcode molecules, which each include a nucleic acid sequence comprising a barcode region (E1 and E2), and which are linked by a connecting nucleic acid sequence (S), are denatured into single-stranded form. To these single-stranded barcode molecules, a first and second extension primer (A1 and A2) is annealed to the 3' region of the first and second barcode molecules (D1 and D2), and a first and second blocking primer (R1 and R2) is annealed to the 5' adapter region (F1 and F2) of the first and second barcode molecules. These blocking primers (R1 and R2) may be modified on the 3' end such that they cannot serve as a priming site for a polymerase.

A polymerase is then used to perform a primer extension reaction, in which the extension primers are extended to make a copy (B1 and B2) of the barcode region of the barcode molecules (E1 and E2). This primer extension reaction is performed such that the extension product terminates immediately adjacent to the blocking primer sequence, for example through use of a polymerase which lacks strand displacement or 5'-3' exonuclease activity. The blocking primers (R1 and R2) are then removed, for example through high-temperature denaturation.

This method thus creates a multimeric barcoding reagent containing a first and second ligation junction (J1 and J2) adjacent to a single-stranded adapter region (F1 and F2). This multimeric barcoding reagent may be used in the method illustrated in FIG. 5.

The method may further comprise the step of ligating the 3' end of the first and second barcoded oligonucleotides created by the primer-extension step (the 3' end of B1 and B2) to first (C1 and G1) and second (C2 and G2) adapter oligonucleotides, wherein each adapter oligonucleotide comprises an adapter region (C1 and C2) which is complementary to, and thus able to anneal to, the adapter region of a barcode molecule (F1 and F2). The adapter oligonucleotides may be synthesised to include a 5'-terminal phosphate group.

Each adapter oligonucleotide may also comprise a target region (G1 and G2), which may be used to anneal the barcoded oligonucleotides to target nucleic acids, and may separately or subsequently be used as primers for a primer-extension reaction or a polymerase chain reaction. The step of ligating the first and second barcoded oligonucleotides to the adapter oligonucleotides produces a multimeric barcoding reagent as illustrated in FIG. 1 that may be used in the methods illustrated in FIG. 3 and/or FIG. 4.

FIG. 9 shows a method of synthesizing multimeric barcoding reagents (as illustrated in FIG. 1) for labeling a target nucleic acid. In this method, first (D1, E1, and F1) and second (D2, E2, and F2) barcode molecules, which each include a nucleic acid sequence comprising a barcode region (E1 and E2), and which are linked by a connecting nucleic acid sequence (S), are denatured into single-stranded form. To these single-stranded barcode molecules, a first and second extension primer (A1 and A2) is annealed to the 3' region of the first and second barcode molecules (D1 and D2), and the adapter regions (C1 and C2) of first (C1 and G1) and second (C2 and G2) adapter oligonucleotides are annealed to the 5' adapter regions (F1 and F2) of the first and second barcode molecules. These adapter oligonucleotides may be synthesised to include a 5'-terminal phosphate group.

A polymerase is then used to perform a primer extension reaction, in which the extension primers are extended to make a copy (B1 and B2) of the barcode region of the barcode molecules (E1 and E2). This primer extension reaction is performed such that the extension product terminates immediately adjacent to the adapter region (C1 and C2) sequence, for example through use of a polymerase which lacks strand displacement or 5'-3' exonuclease activity.

A ligase enzyme is then used to ligate the 5' end of the adapter oligonucleotides to the adjacent 3' end of the corresponding extension product. In an alternative embodiment, a ligase enzyme may be included with the polymerase enzyme in one reaction which simultaneously effects both primer-extension and ligation of the resulting product to the adapter oligonucleotide. Through this method, the resulting barcoded oligonucleotides may subsequently be used as primers for a primer-extension reaction or a polymerase chain reaction, for example as in the method shown in FIG. 3 and/or FIG. 4.

30. Methods of Sequencing and/or Processing Sequencing Data

The invention provides a method of sequencing a target nucleic acid of a circulating microparticle, wherein the circulating microparticle contains at least two fragments of a target nucleic acid, and wherein the method comprises: (a) preparing a sample for sequencing comprising linking at least two of the at least two fragments of the target nucleic acid to produce a set of at least two linked fragments of the target nucleic acid; and (b) sequencing each of the linked fragments in the set to produce at least two (informatically) linked sequence reads.

The invention provides a method of sequencing genomic DNA of a circulating microparticle, wherein the circulating microparticle contains at least two fragments of genomic DNA, and wherein the method comprises: (a) preparing a sample for sequencing comprising linking at least two of the at least two fragments of genomic DNA to produce a set of at least two linked fragments of genomic DNA; and (b) sequencing each of the linked fragments in the set to produce at least two (informatically) linked sequence reads.

The invention provides a method of sequencing a target nucleic acid of a circulating microparticle comprising: (a) linking at least two fragments of the target nucleic acid from a (single) circulating microparticle to produce a set of at least two linked fragments of the target nucleic acid; and (b) sequencing each of the linked fragments in the set to produce at least two (informatically) linked sequence reads.

The invention provides a method of sequencing circulating microparticle genomic DNA comprising: (a) linking at least two fragments of genomic DNA from a (single) circulating microparticle to produce a set of at least two linked fragments of circulating microparticle genomic DNA; and (b) sequencing each of the linked fragments in the set to produce at least two (informatically) linked sequence reads.

The invention further provides a method of sequencing a sample, wherein the sample has been prepared by any one of the methods of preparing a nucleic acid sample for sequencing as defined herein. The method of sequencing the sample comprises the steps of: isolating the barcoded target nucleic acid molecules, and producing a sequence read from each barcoded target nucleic acid molecule that comprises the barcode region, the target region and at least one additional nucleotide from the target nucleic acid. Each sequence read may comprise at least 5, at least 10, at least 25, at least 50, at least 100, at least 250, at least 500, at least 1000, at least 2000, at least 5000, or at least 10,000 nucleotides from the target nucleic acid. Preferably, each sequence read comprises at least 5 nucleotides from the target nucleic acid.

The methods may produce a sequence read from one or more barcoded target nucleic acid molecule produced from at least 10, at least 100, or at least $10^3$, at least $10^4$, at least $10^5$, at least $10^6$, at least $10^7$, at least $10^8$ or at least $10^9$ different target nucleic acids.

Sequencing may be performed by any method known in the art. For example, by chain-termination or Sanger sequencing. Preferably, sequencing is performed by a next-generation sequencing method such as sequencing by synthesis, sequencing by synthesis using reversible terminators (e.g. Illumina sequencing), pyrosequencing (e.g. 454 sequencing), sequencing by ligation (e.g. SOLiD sequencing), single-molecule sequencing (e.g. Single Molecule, Real-Time (SMRT) sequencing, Pacific Biosciences), or by nanopore sequencing (e.g. on the Minion or Promethion platforms, Oxford Nanopore Technologies).

The invention further provides a method for processing sequencing data obtained by any of the methods defined herein. The method for processing sequence data comprises the steps of: (a) identifying for each sequence read the sequence of the barcode region and the sequence from the target nucleic acid; and (b) using the information from step (a) to determine a group of sequences from the target nucleic acid that were labelled with barcode regions from the same multimeric barcoding reagent.

The method may further comprise the step of determining a sequence of a target nucleic acid by analysing the group of sequences to identify contiguous sequences, wherein the sequence of the target nucleic acid comprises nucleotides from at least two sequence reads.

The invention further provides an algorithm for processing (or analysing) sequencing data obtained by any of the methods defined herein. The algorithm may be configured to perform any of the methods for processing sequencing data defined herein. The algorithm may be used to detect the sequence of a barcode region within each sequence read, and also to detect the sequence within a sequence read that is derived from a target nucleic acid, and to separate these into two associated data sets.

The invention further provides a method of generating a synthetic long read from a target nucleic acid comprising the steps of: (a) preparing a nucleic acid sample for sequencing according to any of the methods defined herein; (b) sequencing the sample, optionally wherein the sample is sequenced by any of the methods defined herein; and (c) processing the sequence data obtained by step (b), optionally wherein the sequence data is processed according to any of the methods defined herein; wherein step (c) generates a synthetic long read comprising at least one nucleotide from each of the at least two sequence reads.

The method may enable the phasing of a target sequence of a target nucleic acid molecule i.e. it may enable the determination of which copy of a chromosome (i.e. paternal or maternal) the sequence is located. The target sequence may comprise a specific target mutation, translocation, deletion or amplification and the method may be used to assign the mutation, translocation, deletion or amplification to a specific chromosome. The phasing two or more target sequences may also enable the detection of aneuploidy.

The synthetic long read may comprise at least 50, at least 100, at least 250, at least 500, at least 750, at least 1000, at least 2000, at least $10^4$, at least $10^5$, at least $10^6$, at least $10^7$ or at least $10^8$ nucleotides. Preferably, the synthetic long read comprises at least 50 nucleotides.

The invention further provides a method of sequencing two or more co-localised target nucleic acids comprising the steps of: (a) preparing a nucleic acid sample for sequencing according to any of the methods defined herein; (b) sequencing the sample, optionally wherein the sample is sequenced by any of the methods defined herein; and (c) processing the sequence data obtained by step (b), optionally wherein the sequence data is processed according to any of the methods defined herein; wherein step (c) identifies at least two sequence reads comprising nucleotides from at least two target nucleic acids co-localised in the sample.

Any method of analysing barcoded or linked nucleic acid molecules by sequencing may comprise a redundant sequencing reaction, wherein target nucleic acid molecules (e.g. that have been barcoded in a barcoding reaction) are sequenced two or more times within a sequencing reaction. Optionally, each such molecule prepared from a sample may be sequenced, on average, at least twice, at least 3 times, at least 5 times, at least 10 times, at least 20 times, at least 50 times, or at least 100 times.

In any method of analysing barcoded nucleic acid molecules by sequencing, an error correction process may be employed. This process may comprise the steps of: (i) determining two or more sequence reads from a sequencing dataset comprising the same barcode sequence, and (ii) aligning the sequences from said two or more sequence reads to each other. Optionally, this error correction process may further comprise a step of (iii) determining a majority and/or most common and/or most likely nucleotide at each position within the sequence read and/or at each position within the sequence of the target nucleic acid molecule. This step may optionally comprise establishing a consensus sequence of each target nucleic acid sequence by any process of error correction, error removal, error detection, error counting, or statistical error removal. This step may further comprise the step of collapsing multiple sequence reads comprising the same barcode sequence into a representation comprising a single, error-corrected read. Optionally, any step of determining two or more sequence reads from a sequencing dataset comprising the same barcode sequence, may comprise determining sequence reads comprising barcode sequences with at least a certain extent of identical nucleotides and/or sequence similarity, for example at least 70%, at least 80%, at least 90%, or at least 95% sequence similarity (for example, allowing for mismatches and/or insertions or deletions at any point between to barcode sequences).

In any method of using analysing barcoded nucleic acid molecules by sequencing, an alternative error correction process may be employed, comprising the steps of: (i) determining two or more sequence reads from a sequencing dataset that comprise the same target nucleic acid sequence, wherein said two or more sequence reads further comprise two or more different barcode sequences, wherein the barcode sequences are from the same multimeric barcode molecule and/or multimeric barcoding reagent, and (ii) aligning the sequences from said two or more sequence reads to each other. Optionally, this error correction process may further comprise a step of (iii) determining a majority and/or most common and/or most likely nucleotide at each position within the sequence of the target nucleic acid molecule. This step may optionally comprise establishing a consensus sequence of the target nucleic acid molecule by any process of error correction, error removal, error detection, error counting, or statistical error removal. This step may further comprise the step of collapsing multiple sequence reads comprising the same target nucleic acid molecule into a representation comprising a single, error-corrected read. The target nucleic acid molecule may comprise, for example, a genomic DNA sequence. Optionally, any step of comparing two barcode sequences, and/or comparing a sequenced barcode sequence and a reference barcode sequence, may comprise determining sequences comprising at least a certain extent of identical nucleotides and/or sequence similarity, for example at least 70%, at least 80%, at least 90%, or at least 95% sequence similarity (for example, allowing for mismatches and/or insertions or deletions at any point between to barcode sequences).

31. Methods for Determining and Analysing Sets of Linked Sequence Reads from Microparticles The invention provides a method of determining a set of linked sequence reads of fragments of a target nucleic acid (e.g. genomic DNA) from a single microparticle, wherein the method comprises: (a) analyzing a sample according to any of the methods described herein; and (b) determining a set of two or more linked sequence reads.

The set of two or more linked sequence reads may be determined by identifying sequence reads comprising the same barcode sequence.

The set of two or more linked sequence reads may be determined by identifying sequence reads comprising different barcode sequences from the same set of barcode sequences.

The set of two or more linked sequence reads may be determined by identifying sequence reads comprising barcode sequences of barcode regions from the same multimeric barcoding reagent.

Two or more linked sequence reads may be determining by identifying sequence reads comprised within two or more non-overlapping segments of the same sequenced molecule The set of two or more linked sequence reads may be determined by identifying their spatial proximity within the sequencing instrument used for their sequencing. Optionally this spatial proximity is determined through the use of a cutoff or threshold value, or determined through a non-random or above-average proximity. Optionally, this spatial proximity is represented as a quantitative, semi-quantitative, or categorical value corresponding to different degrees of spatial proximity within the sequencing instrument.

The method may comprise determining at least 3, at least 5, at least 10, at least 50, at least 100, at least 1000, at least 10,000, at least 100,000, at least 1,000,000 sets of linked sequence reads.

The invention provides a method of determining the total number of sets of linked sequence reads within a sequence dataset comprising: (a) analyzing a sample according to any of the methods described herein; and (b) determining the number of sets of linked sequence reads.

The number of sets of linked sequence reads may determined by counting the number of sequence reads comprising different barcode sequences.

The number of sets of linked sequence reads may be determined by counting the sets of barcode sequences that have a barcode sequence in a sequence read.

The number of sets of linked sequence reads may be determined by counting the number of multimeric barcoding reagents that have a barcode region that barcode sequence of which is in a sequence read.

Optionally, only barcode sequences represented at least 2 times, at least 3 times, at least 5 times, at least 10 times, at least 20 times, at least 50 times, or at least 100 times within the sequence dataset are included in these counting processes. Optionally, sequence reads and/or barcode sequences are processed through an error-correction process prior to said counting processes. Optionally, technical duplicate reads represented more than once in the overall sequence dataset are collapsed into single de-duplicated reads in a de-duplication process prior to said counting processes.

The method may comprise counting or estimating a total number of sets of linked sequence reads, wherein two or more nucleic acid sequences comprising fragments of a target nucleic acid (e.g. genomic DNA) from a microparticle are appended to each other within sequences comprising said sequence dataset, and the number of sequence reads from said sequence dataset comprising at least two different segments of the target nucleic acid are counted, thus determining the number of sets of linked sequence reads within the sequence dataset. Optionally, the total number of sequenced molecules within said sequence dataset are counted, thus determining the number of sets of linked sequence reads within the sequence dataset. Optionally, only sequenced molecules comprising at least 3 different segments of the target nucleic acid, comprising at least 5 different segments of the target nucleic acid, comprising at least 10 different segments of the target nucleic acid, or comprising at least 50 different segments of the target nucleic acid are counted.

The method may comprise counting or estimating a total number of sets of linked sequence reads, wherein sets of sequences are linked informatically by spatial proximity within the sequencing instrument, and wherein the total number of sequenced molecules within said sequence dataset are counted, thus determining the number of sets of linked sequence reads within the sequence dataset. Optionally, the total number of sequenced molecules within said sequence dataset are counted and then divided by an invariant normalization factor, thus determining the number of sets of linked sequence reads within the sequence dataset.

The invention provides a method of determining a parameter value from a set of linked sequence reads, wherein the method comprises: (a) determining a set of linked sequence reads according to any of the methods described herein; and (b) mapping (at least a portion of) each sequence of the set of linked sequence reads to one or more reference nucleotide sequences; and (c) determining the parameter value by counting or identifying the presence of one or more reference nucleotide sequences within the set of linked sequence reads.

Optionally, this reference sequence may comprise an entire genome, an entire chromosome, a part of a chromosome, a gene, a part of a gene, any other part or parts of a genome, or any other synthetic or actual sequence. The reference sequence may comprise a transcript, a part of a transcript, a transcript isoform, or a part of a transcript isoform; the reference sequence may comprise a splice junction of a transcript. The reference sequence may be from the human genome. The reference sequence may be from one or more different reference human genome sequences, such as different reference sequences from a library of two or more different reference human genome sequences, or from a library of two or more different haplotype-phased reference human genome sequences (for example, different genome sequences from the International HapMap Project, and/or the 100 Genomes Project).

Optionally, one or more reference sequence(s) may comprise a pseudo-reference sequence, wherein said reference sequences comprise one or more nucleotides that are different to a normal or standard reference sequence, such as a human genome reference sequence. For example, said pseudo-reference sequence(s) may comprise one or more sequences produced from a molecular-conversion process, such as a bisulfite conversion process, or an oxidative bisulfite conversion process. A pseudo-reference sequence may comprise one or more nucleotides corresponding to sites of cytosine nucleotides within a standard reference genome sequence, wherein said pseudo-reference sequence comprises one or more modified and/or variant nucleotide(s) at said sites. Optionally, said pseudo-reference sequences may comprise nucleotides at said sites of cytosine nucleotides that correspond to different molecular-conversion profiles (i.e. corresponding to different sequences produced during a process of molecular conversion, such as bisulfite conversion or oxidative bisulfite conversion, e.g. wherein said different sequences are produced as a function of whether said sites of cytosine nucleotides comprise unmethylated, methylated, and/or hydroxymethylated cytosine nucleotides), optionally wherein sequences obtained following a molecular conversion process will be differentially mapped to said reference sequence as a function of their methylation and/or hydroxymethylation status.

Optionally, one or more reference sequence(s) may comprise a sequence that is present exclusively within, or found preferentially within, or found at high and/or above-average levels within particular tissues (i.e. particular cell types) and/or within particular specific diseased tissue. Optionally, one or more reference sequence(s) may be present exclusively within, or found preferentially within, or found at high and/or above-average levels within, non-maternal and/or paternal tissues. Optionally, one or more reference sequence(s) may be present exclusively within, or found preferentially within, or found at high and/or above-average levels within, maternal tissues. Optionally, one or more reference sequence(s) may be present exclusively within, or found preferentially within, or found at high and/or above-average levels within, one or more particular tissue types (for example, a lung tissue, or a pancreas tissue, or a lymphocyte). Optionally, one or more reference sequence(s) may be present exclusively within, or found preferentially within, or found at high and/or above-average levels within, a particular type of diseased tissue (such as a cancer tissue, such as a lung cancer tissue or a colorectal cancer tissue, or from a non-cancer diseased tissue such as an infarcted myocardial tissue, or a diseased cerebrovascular tissue, or a placental tissue undergoing eclampsia or pre-eclampsia). Optionally, one or more reference sequence(s) may be present exclusively within, or found preferentially within, or found at high and/or above-average levels within, a particular type of tissue (such as a lung tissue, or a pancreas tissue, or a lymphocyte). Optionally, one or more reference sequence(s) may be present exclusively within, or found preferentially within, or found at high and/or above-average levels within, a particular type of healthy tissue (such as a healthy lung tissue, or a healthy pancreas tissue, or a healthy lymphocyte).

Optionally, any one or more reference sequence(s) that comprise a sequence that is present exclusively within, or found preferentially within, or found at high and/or above-average levels within particular tissues (i.e. particular cell types) and/or within particular specific diseased tissue, may be established by an empirical measurement and/or evaluation process. Optionally, the expression (e.g. RNA levels) of one or more transcripts in two or more different tissue types (for example, a diseased tissue and a healthy tissue) may be measured, to establish one or more transcripts present exclusively within, or found preferentially within, or found at high and/or above-average levels within one of the said different tissue types. Optionally, the 5-methylcytosine (or, similarly, 5-hydroxy-methylcytosine) level(s) of one or more genes (or, e.g., gene promoters) in two or more different tissue types (for example, a diseased tissue and a healthy tissue) may be measured, to establish one or more methylated (or hydroxymethylated) genes or gene promoters present exclusively within, or found preferentially within, or found at high and/or above-average levels within one of the said different tissue types. Optionally, the DNAse accessibility and/or openness of chromatin (for example, by an ATAC-seq assay) of one or more genes (or, e.g., gene promoters) in two or more different tissue types (for example, a diseased tissue and a healthy tissue) may be measured, to establish one or more DNAse accessible (and/or open chromatin) genes or gene promoters present exclusively within, or found preferentially within, or found at high and/or above-average levels within one of the said different tissue types.

The reference nucleotide sequence may comprise a sequence corresponding to a chromosome or a portion of a chromosome. Optionally this sequence is at least 1 nucleotide in length, at least 10 nucleotides in length, at least 100 nucleotides in length, at least 1000 nucleotides in length, at least 10,000 nucleotides in length, at least 100,000 nucleotides in length, at least 1,000,000 nucleotides in length, at least 10,000,000 nucleotides in length, or at least 100,000,000 nucleotides in length.

The reference nucleotide sequence may comprise two or more sequences corresponding to two or more chromosomes, or to sequences corresponding to two or more portions of one or more chromosomes. Optionally these sequences are each at least 1 nucleotide in length, at least 10 nucleotides in length, at least 100 nucleotides in length, at least 1000 nucleotides in length, at least 10,000 nucleotides in length, at least 100,000 nucleotides in length, at least 1,000,000 nucleotides in length, at least 10,000,000 nucleotides in length, or at least 100,000,000 nucleotides in length. Optionally, this reference sequence may comprise an entire genome sequence.

The reference nucleotide sequence may comprise one or more sliding windows, wherein each window comprises a span of a genomic region of a finite length, and wherein two or more windows are offset a certain finite number of nucleotides along said genomic region. Optionally, these sliding windows may be partially overlapping, immediately adjacent to each other, or separated by a span of a certain number of nucleotides.

The reference nucleotide sequence may comprise a repeat sequence. Optionally this repeat sequence comprises a dinucleotide repeat, a trinucleotide repeat, a tetranucleotide repeat, or a pentanucleotide repeat. Optionally, the reference nucleotide sequence comprises a series of two or more immediately adjacent copies of the same repeat unit, such as 2 immediately adjacent copies, 5 immediately adjacent copies, 8 immediately adjacent copies, 10 immediately adjacent copies, 15 immediately adjacent copies, 20 immediately adjacent copies, 30 immediately adjacent copies, 40 immediately adjacent copies, 50 immediately adjacent copies, or 100 immediately adjacent copies.

Optionally, any one or more reference sequences may be employed to analyse sequences determined by any method described herein. Any one or more reference sequences may be employed to analyse sequences of fragments of genomic DNA. Any one or more reference sequences may be employed to analyse sequences of RNA. Any one or more reference sequences may be employed to analyse sequences of fragments of genomic DNA wherein a measurement of a modified nucleotide or nucleobase is performed upon one or more said fragment(s) of genomic DNA (as one such example, any one or more reference sequences may be employed to analyse sequences of fragments of genomic DNA that have been enriched by an enrichment process for a modified nucleotide such as 5-methylcytosine, or 5-hydroxy-methylcytosine; as another such example, any one or more reference sequences may be employed to analyse sequences of fragments of genomic DNA that have had at least one nucleotide contained therein converted by a molecular-conversion process, such as a bisulfite conversion process, or an oxidative bisulfite conversion process, wherein said conversion process is employed to detect one or more modified nucleotides such as 5-methylcytosine, or 5-hydroxy-methylcytosine).

Optionally, any one or more reference sequences may be employed to analyse sequences of fragments of genomic DNA, wherein the 5'-most and/or 3'-most nucleotides of any such fragments of genomic DNA (and/or nucleotides near to the 5'-most and/or 3'-most nucleotides, such as nucleotides within the nearest 2, 3, 4, or 5 nucleotides of the 5'-most and/or 3'-most nucleotides) are mapped to said reference sequences. Optionally, sequences of fragments of genomic DNA may be mapped to determine their position(s) and/or span(s) within a reference human genomic DNA sequence, and then it may be determined whether their 5'-most and/or 3'-most nucleotides (and/or, for example, nucleotides within the nearest 2, 3, 4, or 5 nucleotides of the 5'-most and/or 3'-most nucleotides) fall within one or more reference sequences. Optionally, such an approach of analysing the 5' and or 3' ends of sequences of fragments of genomic DNA may be employed to analyse the fragmentation pattern(s) of said fragments—for example, to analyse the spacing and/or placement and/or positioning of nucleosomes and/or other proteins along genomic DNA molecules. Optionally, two or more different reference sequences and/or reference maps may be employed to analyse such fragmentation patterns, wherein said different reference maps may correspond to and/or be associated with specific tissue types and/or diseased tissue types (for example, a first reference map may correspond to and/or be able to measure the fragmentation patterns present in a first tissue type, such as a lung tissue, and a second reference map may correspond to and/or be able to measure the fragmentation patterns present in a second tissue type, such as a liver tissue; by way of additional example, a first reference map may correspond to and/or be able to measure the fragmentation patterns present in a specific healthy tissue type, such as a healthy lung tissue, and a second reference map may correspond to and/or be able to measure the fragmentation patterns present in a specific diseased tissue type, such as a diseased and/or cancerous lung tissue).

The parameter value may be a quantitative or semi-quantitative value and is determined by counting the number of sequence reads within the set of sequences that are determined to comprise a sequence originating from the said reference nucleotide sequence or sequences. Optionally, the step of determining whether determined sequences originate from reference nucleotide sequence(s) may include only perfect matches between the two sequences, and optionally the step may allow for imperfect matches between the two sequences. Optionally, imperfect matches may include variant nucleotides as well as insertions or deletions of nucleotides when comparing the two sequences. Optionally, matches may be determined by determining the fraction of nucleotides within one of the sequences which match perfectly with the other sequence. Optionally, matches may be determined by detecting a perfect match for a portion of the sequence that is of a certain specific length or of a certain minimum length. Optionally, matches may be determined by specifically evaluating the presence of an allele or of multiple alleles within the reference nucleotide sequence, wherein said allele(s) comprise a single nucleotide, or a region of two or more nucleotides, or insertions or deletions thereof, that may be variant in different chromosomes or in different haplotypes. Optionally, the allele(s) is/are variant across two or more reference nucleotide sequences. Optionally, the allele(s) may comprise non-maternal and/or paternal alleles, wherein the sample of microparticles is derived from a maternal blood, serum, or plasma sample.

The parameter value may be a binary value and may be determined by detecting whether at least one sequence read within the set of sequence reads comprises a sequence originating from the said reference nucleotide sequence or sequences. Optionally, the step of determining whether determined sequences originate from reference nucleotide sequence(s) may include only perfect matches between the two sequences, and optionally the step may allow for imperfect matches between the two sequences. Optionally, imperfect matches may include variant nucleotides as well as insertions or deletions of nucleotides when comparing the two sequences. Optionally, matches may be determined by determining the fraction of nucleotides within one of the sequences which match perfectly with the other sequence. Optionally, matches may be determined by detecting a perfect match for a portion of the sequence that is of a certain specific length or of a certain minimum length. Optionally, matches may be determined by specifically evaluating the presence of an allele or of multiple alleles within the reference nucleotide sequence, wherein said allele(s) comprise a single nucleotide, or a region of two or more nucleotides, or insertions or deletions thereof, that may be variant in different chromosomes or in different haplotypes. Optionally, the allele is variant across two or more reference nucleotide sequences. Optionally, the allele(s) may comprise non-maternal and/or paternal alleles, wherein the sample of microparticles is derived from a maternal blood, serum, or plasma sample.

Optionally, each reference sequence within a list and/or group of two or more reference sequences may be associated with a weighting and/or association value. Optionally, this weighting and/or association value may correspond to a likelihood or probability that a given sequence is non-maternal or paternal, or correspond to a likelihood or probability that a given sequence is maternal. Optionally, this weighting and/or association value may correspond to a likelihood or probability that a given sequence is from a particular tissue type (for example, a lung tissue, or a pancreas tissue, or a lymphocyte). Optionally, this weighting and/or association value may correspond to a likelihood or probability that a given sequence is from a particular type of diseased tissue (such as a cancer tissue such as a lung cancer tissue or a colorectal cancer tissue, or from a non-cancer diseased tissue such as an infarcted myocardial tissue, or a diseased cerebrovascular tissue, or a placental tissue undergoing eclampsia or pre-eclampsia).

Optionally, any such weighting and/or association value for any one or more reference sequences may be established by an empirical measurement and/or evaluation process. Optionally, a weighting and/or association value for any one or more reference sequences may be established by measuring the expression (e.g. RNA levels) of two or more transcripts in two or more different tissue types (for example, a diseased tissue and a healthy tissue), and then the absolute and/or relative expression level(s) of said two or more transcripts within the first and second tissue types may be established empirically as said weighting and/or association value(s) for said first and second tissue types respectively. Optionally, any weighting and/or association value for any one or more reference sequences may be established by measuring the level of 5-methylcytosine (or, similarly, 5-hydroxy-methylcytosine) of two or more genomic regions (for example, two or more genes, or two or more gene promoter regions) in two or more different tissue types (for example, a diseased tissue and a healthy tissue), and then the absolute and/or relative 5-methylcytosine level(s) of said two or more genes (or promoters) within the first and second tissue types may be established empirically as said weighting and/or association value(s) for said first and second tissue types respectively. Optionally, any weighting and/or association value for any one or more reference sequences may be established by measuring the DNAse accessibility and/or openness of chromatin (for example, by an ATAC-seq assay) of two or more genomic regions (for example, two or more genes, or two or more gene promoter regions) in two or more different tissue types (for example, a diseased tissue and a healthy tissue), and then the absolute and/or relative DNAse accessibility (or chromatin-openness) level(s) of said two or more genes (or promoters) within the first and second tissue types may be established empirically as said weighting and/or association value(s) for said first and second tissue types respectively.

Optionally, any such weighting and/or association value for any one or more reference sequences may be established by an empirical measurement and/or evaluation process, wherein said empirical measurement and/or evaluation process employs one or more samples comprising one or more circulating microparticles as input samples for said empirical measurement and/or evaluation process (for example, wherein first and second sequences of fragments of genomic DNA from a circulating microparticle are linked, such as by any method(s) described herein). Optionally, any said one or more circulating microparticles each comprise at least first and second fragments of genomic DNA. Optionally, any said one or more samples comprising one or more circulating microparticles may be obtained from patients with one or more particular diseases, such as cancer (such as lung cancer, or pancreatic cancer), or such as cancer at a particular stage (such as stage I, stage II, stage III, stage IV) or such as cancer with particular clinical characteristics (such as benign cancer, such as malignant cancer, such as local cancer, such as metastatic cancer, or such as treatment-resistant cancer). Optionally, said one or more samples comprising one or more circulating microparticles may be from patients who do not have any such one or more particular diseases. Optionally, said one or more samples comprising one or more circulating microparticles may be from patients who are considered to be healthy. Optionally, any said one or more samples comprising one or more circulating microparticles may comprise at least first and second samples from the same individual, wherein the first sample is made from the individual at an earlier time, and the second sample is made from the individual at a later time, separated by a duration of time between the first and second samples (such as an hour, or a day, or a week, or a month, or 3 months, or 6 months, or 12 months, or 2 years, or 3 years, or 5 years, or 10 years). Optionally, any such weighting and/or association value for any one or more reference sequences may be established by an empirical measurement and/or evaluation process, wherein said empirical measurement and/or evaluation process employs at least one sample (comprising one or more circulating microparticles) from a patient with a disease, and at least one sample (comprising one or more circulating microparticles) from a person without said disease (for example, wherein the amount and/or signal corresponding to said reference sequence within the sample(s) from the person(s) with the disease is compared to the amount and/or signal corresponding to said reference sequence within the sample(s) from the person(s) without the disease, for example wherein the ratio of said two measures is employed as said weighting and/or association value). Optionally, any such weighting and/or association value for any one or more reference sequences may be established by an empirical measurement and/or evaluation process, wherein said empirical measurement and/or evaluation process employs samples (comprising one or more circulating microparticles) from a group of at least two patients with a disease, and samples (comprising one or more circulating microparticles) from a group of at least two people without said disease. Optionally, any said groups of patients with a disease (or groups of persons without said disease) may each comprise at least 3, at least 5, at least 10, at least 20, at least 50, at least 100, at least 200, at least 500, at least 1000, at least 2000, at least 10,000, at least 20,000, at least 50,000, at least 100,000, at least 500,000, at least 1,000,000, or at least 10,000,000 individuals. Optionally, any patients within said groups of patients with a disease (or any persons within said groups of persons without said disease) may each provide two or more samples comprising circulating microparticles, wherein each sample is obtained at a different time point (such as time points separated by at least a day, by at least a week, by at least a month, by at least 2 months, by at least 6 months, by at least a year, by at least 2 years, or by at least 5 years).

Optionally, in any method wherein one or more samples comprising one or more circulating microparticles are employed as input samples to establish any weighting and/or association value for any one or more reference sequences by an empirical measurement and/or evaluation process, said weighting and/or association value(s) may relate to a 5-methylcytosine level (for example they may relate to a 5-methylcytosine level within a particular healthy or particular diseased tissue), or optionally may relate to a 5-hydroxy-methylcytosine level (for example they may relate to a 5-hydroxy-methylcytosine level within a particular healthy or particular diseased tissue), or optionally may relate to a DNAse-accessibility and/or chromatin-openness level (for example they may relate to a DNAse-accessibility and/or chromatin-openness level within a particular healthy or particular diseased tissue), or optionally may relate to a frequency and/or probability that the 5'-most and/or 3'-most nucleotides (and/or nucleotides near to the 5'-most and/or 3'-most nucleotides, such as nucleotides within the nearest 2, 3, 4, or 5 nucleotides of the 5'-most and/or 3'-most nucleotides) of fragments of genomic DNA from a particular tissue type and/or diseased tissue type and/or healthy tissue type, are found within said reference sequences.

Optionally, the method may comprise counting the number of reference sequences from one or more list(s) of reference sequences in a set of linked sequence reads. Optionally, this counting process may be performed for all sets of linked sequence reads in a sample, or any one or more subsets thereof. Optionally, each reference sequence may be associated with a weighting and/or association value, such that the counting process comprises a weighted counting process, wherein a weighted sum of reference sequences within a set of linked sequence reads is determined. Optionally, this weighting value may correspond to a likelihood or probability that a given sequence is non-maternal or paternal, or correspond to a likelihood or probability that a given sequence is maternal, or correspond to a likelihood or probability that a given sequence is from a particular tissue of origin (such as a lung tissue, or a pancreas tissue, or a lymphocyte), or correspond to a likelihood or probability that a given sequence is from a particular healthy tissue of origin (such as a healthy lung tissue, or a healthy pancreas tissue, or a healthy lymphocyte), or correspond to a likelihood or probability that a given sequence is from a particular diseased tissue of origin (such as a diseased lung tissue, or a diseased pancreas tissue, or a diseased lymphocyte), or correspond to a likelihood or probability that a given sequence is from a particular cancerous tissue of origin (such as a cancerous lung tissue, or a cancerous pancreas tissue, or a cancerous lymphocyte), Optionally, any sum or weighted sum of reference sequences from a set of linked sequence reads may be compared to one or more threshold values, and wherein sets of linked sequence reads comprising a number of reference sequences greater than said threshold value(s) are determined and/or suspected to be from a particular tissue of origin. Optionally, any process of determining any such said sum and comparing with one or more threshold may be performed for all sets of linked sequence reads in the sample, and/or any one or more subsets thereof. Optionally, the process of determining any such said sum may comprise determining a weighted sum as described above. Optionally, a set of linked sequence reads with a sum or weighted sum equal to a threshold value, within one or more ranges of threshold values, less than a threshold value, or within a set of specific values may be determined to be from a particular tissue of origin. Optionally, any method as described in this application may used to determine sets of linked sequence reads of a particular tissue of origin. Optionally, the total number of sets of linked sequence reads found or suspected by any method to be of particular tissue of origin may be counted, to determine a total number of sets of linked sequence reads of said particular tissue of origin.

Optionally, any one or more sets of linked sequences (or, for example, all sets of linked sequence reads in a sample) may be analysed by and/or compared with two or more different lists of reference sequences. Optionally, sets of linked sequence reads in a sample may be analysed with a first list of reference sequences that correspond to a first particular tissue type, and also analysed with a second list of reference sequences that correspond to a second particular tissue type. Optionally, sets of linked sequence reads in a sample may be analysed with a first list of reference sequences that correspond to a particular healthy tissue type, and also analysed with a second list of reference sequences that correspond to a particular diseased tissue type. Optionally, sets of linked sequence reads in a sample may be analysed with a first list of reference sequences that correspond to a particular healthy tissue type, and also analysed with a second list of reference sequences that correspond to a cancerous tissue of the same tissue type. Optionally, sets of linked sequence reads in a sample may be analysed with at least 3, at least 4, at least 5, at least 10, at least 20, or at least 30 lists of reference sequences, wherein each list of reference sequences corresponds to a different tissue type and/or healthy tissue type and/or diseased tissue type and/or cancerous tissue type. Optionally, sets of linked sequence reads in a sample may be analysed with at least 50, at least 100, at least 500, at least 1000, at least 10,000, at least 100,000, at least 1,000,000, at least 10,000,000, or at least 100,000,000 lists of reference sequences, optionally wherein each list of reference sequences corresponds to a different tissue type and/or healthy tissue type and/or diseased tissue type. Optionally, any process of analysing sets of linked sequence reads in a sample with two or more lists of reference sequences may comprise comparing fragments of genomic DNA from said samples containing 5-methylcytosine to said two or more lists of reference sequences. Optionally, any process of analysing sets of linked sequence reads in a sample with two or more lists of reference sequences may comprise comparing fragments of genomic DNA from said samples containing 5-hydroxy-methylcytosine to said two or more lists of reference sequences. Optionally, any process of analysing sets of linked sequence reads in a sample with two or more lists of reference sequences may comprise comparing sequences of RNA from said samples to said two or more lists of reference sequences. Optionally, any process of analysing sets of linked sequence reads in a sample with two or more lists of reference sequences may comprise comparing the 5'-most and/or 3'-most nucleotides (and/or nucleotides near to the 5'-most and/or 3'-most nucleotides, such as nucleotides within the nearest 2, 3, 4, or 5 nucleotides of the 5'-most and/or 3'-most nucleotides) of fragments of genomic DNA from said sample to said two or more lists of reference sequences.

The sequence reads from the set of linked sequence reads may be mapped to two or more reference nucleotide sequences corresponding to the same genomic region or genomic regions, wherein each reference nucleotide sequence comprises a different mutated allele or different set of mutated alleles within said genomic region or genomic regions, and said parameter value may be determined by the presence of one or more reference nucleotide sequences within said set of linked sequence reads.

The lengths of said fragments of a target nucleic acid (e.g. genomic DNA) may be determined or estimated, and the parameter may comprise a mean, media, mode, maximum, minimum, or any other single representative value of said determined or estimated lengths. Optionally, the lengths of genomic DNA sequence within each sequenced fragment is determined by sequencing substantially an entire sequence of a fragment of genomic DNA (i.e. from its approximate 5' end to its approximate 3' end) and counting the number of nucleotides sequenced therein. Optionally, this is performed by sequencing a sufficient number of nucleotides at the 5' end of the sequence of fragmented genomic DNA to map said 5' end to a locus within a reference human genome sequence, and likewise sequencing a sufficient number of nucleotides at the 3' end of the sequence of fragmented genomic DNA to map said 3' end to a locus within a reference human genome sequence, and by then calculating the total span in nucleotides comprising said 5' segment within the reference human genome sequence, said 3' segment within the reference human genome sequence, as well as any un-sequenced human genome sequence contained between the two sequenced portions.

The parameter value may be determined for at least 2, at least 10, at least 100, at least 1000, at least 10,000, at least 100,000, at least 1,000,000, at least 10,000,000, at least 100,000,000, or at least 1,000,000,000 sets of linked sequence reads.

The parameter value may be determined for at least 2 sets of linked sequence reads, and the parameter value may be evaluated by determining the number of sets of linked sequence reads where the parameter value is equal to a specific parameter value, equal to one of a set of two or more parameter values, less than a specific parameter value, greater than a specific parameter value, or within at least one range of values for the said parameter, or within one of two or more ranges of values for the said parameter. Optionally, the fraction or proportion of sets of linked sequence reads determined to meet one or more of the above conditions out of all evaluated sets of linked sequence reads is determined. Optionally, a parameter value is determined for at least 2 sets of linked sequence reads, and the mean, average, mode, or median parameter value across the group of parameter values is determined.

The parameter value is determined for a group of at least 2 sets of linked sequence reads, and the parameter values may be evaluated by comparing the group of parameter values with a second group of parameter values. Optionally, said second group of parameter values may correspond to an expected normal distribution of parameter values, or to an expected abnormal distribution of parameter values. Optionally, these parameter values may be derived from synthetic data, from randomized data, or from experimental data generated from one or more separate samples of circulating microparticles representing one or more normal or abnormal conditions. Optionally, at least 1, at least 10, at least 100, at least 1000, at least 10,000, at least 100,000, or at least 1,000,000 further groups of parameter values may be determined and further compared with the first group of parameter values. Optionally, a statistical test may be performed to compare the first and second or more groups of parameter values, such as a T test, a binomial test, a chi-squared test, or an analysis-of-variance (ANOVA) test. Optionally, a false-discovery-rate evaluation is performed, wherein the first group of parameter values is compared with a catalogue of two or more groups of parameter values, and wherein the fraction of groups within the catalogue of two or more groups with parameter values, mean parameter values, median parameter values, or other quantities derived from said parameter values, above or below that of the first group of parameter values is determined.

At least two different parameter values may determined for the set of linked sequence reads. Optionally, at least 3, at least 10, at least 100, at least 1000, at least 10,000, at least 100,000, at least 1,000,000, at least 10,000,000, or at least 100,000,000 different parameter values are determined.

The invention provides a method of determining a group of sets of linked sequence reads comprising: (a) determining a parameter value for each of two or more sets of linked sequence reads, wherein the parameter value for each set of linked sequence reads is determined according to any method described herein; and (b) comparing the parameter values for the sets of linked sequence reads to identify a group of two or more sets of linked sequence reads.

The group of sets of linked sequence reads may be determined by identifying sets of linked sequence reads having a parameter value equal to a specific parameter value, equal to one of a set of two or more parameter values, less than a specific parameter value, greater than a specific parameter value, or within at least one range of values for the said parameter value, or within one of two or more ranges of values for the said parameter value. Optionally, the number of sets of linked sequence reads within the group is determined, thus determining the size of the group.

The method may comprise further evaluating a group of sets of linked sequence reads, wherein the group of sets of linked sequence reads is further analysed by a second analysis step. Optionally, this second analysis step comprises determining and/or evaluating a second parameter value for the group of sets of linked sequence reads. Optionally, this second analysis step comprises determining the presence or absence of specific alleles within the sequences comprised within the group of sets of linked sequence reads. Optionally, this second analysis step comprises determining the presence or absence of chromosomal abnormalities such as one or more aneuploidies, or microdeletions, or copy number variations, or a loss-of-heterozygosity, or a rearrangement or translocation event, a single-nucleotide variant, a de novo mutation, or any other genomic feature or mutation.

The method may comprise further evaluating the group of sets of linked sequence reads by a second analysis step, wherein the second analysis step comprises determining the number of sequence reads within each set of linked sequence reads within the group of sets of linked sequence reads that map to one or more reference nucleotide sequences. Optionally, this reference sequence or reference sequences may comprise an entire genome, an entire chromosome, a part of a chromosome, a gene, a part of a gene, any other part or parts of a genome, or any other synthetic or actual sequence. Optionally, this second analysis step comprises counting the total number of sequence reads within the group that map within a reference sequence, and then dividing this number of sequence reads by the total number of sets within the group, to estimate a relative number of sequence reads within the reference sequence per set. This may thus form an estimate of the relative number of sequence reads within the reference sequence per microparticle within the original sample of microparticles corresponding to the group of sets of linked sequence reads. Optionally, this second analysis step may further comprise a step of comparing this estimated relative number to a threshold value, wherein an estimated relative number greater than said threshold value, or alternatively an estimated relative number lesser than said threshold value may indicate the presence or absence of a specific medical or genetic condition, such as a chromosomal aneuploidy or microdeletion.

32. Methods for Transforming Linked Sequence Read Data for Analysis by Algorithms The invention provides methods for transforming linked sequence data into forms representative thereof that may be more readily or more comprehensively analysed by analytic or statistical tools. Of particular importance, the methods may be used to analyse particular samples of circulating microparticles for the presence of structural abnormalities (for exampling, translocations, or large-scale copy number variations), but wherein the specific nature, genomic location, or size of said structural abnormalities is not known previously, and furthermore, where such factors may not be of direct importance to the particular biological measurement.

Sequences from microparticles may be used to detect the presence of structural abnormalities that may indicate the presence of cancer within the body of the person from whom the sample was derived. The presence and/or burden of a certain number of structural abnormalities itself may be indicative of cancer (or indicative of a risk thereof), but the genomic locations of such potential abnormalities may be neither known prospectively nor relevant to the cancer risk assessment; thus transforming linked microparticle sequence data into a form more readily analysable with informatic or statistical tools may enhance the sensitivity and specificity of this method. Of particular importance, the transformation methods may enable analysis of such microparticle linked-sequence data with a particular family of numeric tools that typically require some transformation of the data for effective analysis, such as deep learning and/or machine learning approaches, as well as neural network/recurrent neural network approaches.

The invention provides a method of transforming linked sequence data generated from a sample of microparticles, wherein a first set of linked sequence reads is generated from fragments of a target nucleic acid of a first circulating microparticle, and wherein a second set of linked sequence reads is generated from fragments of a target nucleic acid of a second circulating microparticle.

The first and second sets of linked sequence reads may be mapped to a reference genome sequence, and wherein each sequence read is transformed into a representation comprising the chromosome to which it was mapped, and an index function, wherein said index function comprises its linkage to another at least 1 sequence from the same set of linked sequence reads. Optionally, said index function may be a unique identifier that identifies the corresponding set of linked sequence reads.

The first and second sets of linked sequence reads may be mapped to a reference genome sequence, and wherein each sequence is transformed into a representation comprising its genomic coordinates (including chromosome number and position on said chromosome) and an index function, wherein said index function comprises or represents its linkage to another at least 1 sequence from the same set of linked sequence reads. Optionally, said index function may be a unique identifier that identifies the corresponding set of linked sequence reads. Optionally, the genome coordinates may be represented as approximate or windowed values, for example by representation to within the nearest 2 bases on the chromosome, or to within the nearest 10 bases on the chromosome, or to within the nearest 100 bases on the chromosome, or to within the nearest 1000 bases on the chromosome, or to within the nearest 10 kilobases on the chromosome, or to within the nearest 100 kilobases on the chromosome, or to within the nearest 1 megabase on the chromosome, or to within the nearest 10 megabases on the chromosome; or, for example, the genome coordinates may be represented within windows corresponding to positions within each chromosome, wherein such windows may be at least 2 nucleotides in length, or at least 10 nucleotides in length, or at least 100, nucleotides in length, or at least 1000, nucleotides in length, or at least 10,000 nucleotides in length, or at least 100,000 nucleotides in length, or at least 1,000,000 nucleotides in length, or at least 10,000,000 nucleotides in length. Optionally, the genome coordinates (or windowed or approximate representations thereof) of a sequence representation may be shifted by a factor along the chromosome, for example by a certain number of nucleotides upstream or downstream.

The first and second sets of linked sequence reads may be mapped to a reference genome sequence, and wherein a first sequence read and a second sequence read within a set of linked sequence reads each comprise sequences from the same chromosome, wherein the second sequence read is transformed into a representation comprising the genomic distance between said first and second sequence reads along the chromosome. Optionally, said representative of genomic distance is an approximate or windowed value, for example to the nearest 2 base pairs, the nearest 10 base pairs, the nearest 100 base pairs, the nearest 1000 base pairs, the nearest 10,000 base pairs, the nearest 100,000 base pairs, the nearest 1,00,000 base pairs, or the nearest 10,000,000 base pairs. Optionally, any such method may be performed on a set of 3 or more sequences within the same set of linked sequence reads. Optionally, the mean or median chromosomal position of sequences within the set of linked sequence reads is calculated, and each sequence is represented by a distance in nucleotides relative to said mean or median position. Optionally, wherein such a method is performed on a set of 3 or more sequences within the same set of linked sequence reads, one sequence of the 3 or more sequences may serve as a reference sequence, and its chromosomal position may serve as a reference chromosomal position, and each sequence is represented by a distance in nucleotides relative to said reference chromosomal position.

The first and second sets of linked sequence reads may be mapped to a group of two or more reference nucleotide sequences, and wherein each sequence is transformed into a representation comprising the reference nucleotide sequence to which it was mapped (if any), and an index function, wherein said index function comprises its linkage to another at least 1 sequence from the same set of linked sequence reads. Optionally, said index function may be a unique identifier that identifies the corresponding set of linked sequence reads. Optionally, said reference nucleotide sequences may each be identified by a unique reference sequence identifier, and each sequence may be represented by a corresponding unique reference sequence identifier. Optionally, at least 3, at least 10, at least 100, at least 1000, at least 10,000, at least 100,000, at least 1,000,000, at least 10,000,000, at least 100,000,000, at least 1,000,000,000, at least 10,000,000,000, or at least 100,000,000,000 different reference nucleotide sequences may be used. Optionally, each reference nucleotide sequence may comprise a single contiguous sequence of any length, or may comprise a group of two or more contiguous sequences of any length.

The first and second sets of linked sequence reads may be mapped to a group of two or more variant alleles or variants, and wherein each sequence is transformed into a representation comprising the variant allele(s) or variant(s) to which it was mapped (if any), and an index function, wherein said index function comprises its linkage to another at least 1 sequence from the same set of linked sequence reads. Optionally, said variant allele(s) or variant(s) may each be identified by a unique variant allele(s) or variant(s) identifier, and each sequence may be represented by any corresponding unique variant allele(s) or variant(s) identifier respectively. Optionally, two or more different groups of variant alleles or variants may be employed, wherein each sequence is transformed into a representation comprising the variant allele(s) or variant(s) from the first group thereof to which it was mapped (if any), as well as the variant allele(s) or variant(s) from the second group and any further groups thereof to which it was mapped (if any), and an index function comprising its linkage to another at least 1 sequence from the same set of linked sequence reads. Optionally, said variant allele(s) or variant(s) within each group thereof may each be identified by a unique variant allele(s) or variant(s) identifier, Optionally, each group of variant allele(s) or variant(s) may further be identified by a unique variant or variant allele group identifier.

The method may comprise determining the lengths of sequence reads of the first and second sets of linked sequence reads, and wherein each sequence is transformed into a representation comprising its determined length, and an index function, wherein said index function comprises its linkage to another at least 1 sequence from the same set of linked sequence reads. Optionally, each length of a sequence of genomic DNA is compared with one or more ranges of potential lengths, and each sequence is transformed into a representation comprising a parameter representing whether said length falls within each such range, and an index function, wherein said index function comprises its linkage to another at least 1 sequence from the same set of linked sequence reads. Optionally, an average length of any two or more lengths within a set of linked sequence reads may be determined.

The method may be performed for at least 2 sets of linked sequence reads, at least 10 sets of linked sequence reads, at least 100 sets of linked sequence reads, at least 1000 sets of linked sequence reads, at least 10,000 sets of linked sequence reads, at least 100,000 sets of linked sequence reads, at least 1,000,000 sets of linked sequence reads, at least 10,000,000 sets of linked sequence reads, at least 100,000,000 sets of linked sequence reads, or at least 1,000,000,000 sets of linked sequence reads. Optionally, the method may be performed for a subset of sets of linked sequence reads from a sample of microparticles. Optionally, within a particular set of linked sequence reads, only an incomplete proportion or fraction of all sequences within the said set of linked sequence reads may be employed for any analysis as above.

In the method, linked sequence data generated from a sample of two or more microparticles may transformed as described herein, and wherein said transformed data is used to train an algorithm, such as a neural network, or an artificial neural network, or a recurrent neural network, or a deep neural network, or a decision tree, or a support vector machine, or a Bayesian network, or a genetic algorithm, or a sparse dictionary, or a machine-learning algorithm, or a deep learning algorithm, or a supervised, unsupervised or semi-supervised machine learning algorithm or feature learning or feature extraction algorithm, or a reinforcement learning algorithm, or a representation learning algorithm, or any combination, component or constituent thereof. Optionally, said algorithms may be trained based on transformed data generated from two or more different microparticle samples. Optionally, said algorithms may be trained to detect the presence of cancer within the body of the person providing said sample. Optionally, said algorithms may be trained to detect the presence of structural or chromosomal abnormalities in genomic DNA from circulating microparticles.

In the method, linked sequence data generated from a sample of two or more microparticles may transformed as described herein, and wherein said transformed data is evaluated using an algorithm, such as a neural network, or an artificial neural network, or a recurrent neural network, or a deep neural network, or a decision tree, or a support vector machine, or a Bayesian network, or a genetic algorithm, or a sparse dictionary, or a machine-learning algorithm, or a deep learning algorithm, or a supervised, unsupervised or semi-supervised machine learning algorithm or feature learning or feature extraction algorithm, or a reinforcement learning algorithm, or a representation learning algorithm, or any combination, component or constituent thereof.

In the method, linked sequence data generated from a sample of two or more microparticles may transformed as described herein, and wherein said transformed data is used to train an algorithm such as any above, wherein said algorithm takes as input a first transformed dataset from a first biological microparticle sample, and a second transformed dataset from a second biological microparticle sample, wherein the second sample is taken from an the same individual as the first biological sample, but taken at a second and later time period compared with the first sample. The second sample may be taken at a time point at least 1 day, at least 1 week, at least 1 month, at least 2 months, at least 6 months, as least 12 months, at least 24 months, at least 36 months, at least 5 years or at least 10 years after the first sample. Optionally, the algorithm may also take as input data a third, or fourth, or fifth, or greater number of samples also separated in sequence by one or more days or greater period of time. Optionally, the algorithm may be trained to detect the presence of structural abnormalities that increase in individual frequency, cumulative burden, or statistical significance across samples from two or more time points. Optionally, the algorithm may be trained to detect the presence or burden of cancer, and/or to detect the growth of a malignancy between two or more time points, and/or to stratify the risk of a malignant process. Optionally, the algorithm may be trained using linked sequence data generated from a first population of individuals and a second population of individuals, wherein each population provides a first sample and a second sample taken at least 1 day (or any greater length of time) apart, and wherein the first population is found to have been diagnosed with a malignant process, and wherein the second population is found to have not been diagnosed with a malignant process, thus training the algorithm to detect the presence of a malignant process. Optionally, this algorithm training process may be performed using three or more samples per individual separated in sequence by at least 1 day each, and/or the process may be performed using three or more populations of individuals with different features, such as different age ranges, different smoking status, different ethnicities, different genetic cancer susceptibility levels and/or different family histories of cancer burden.

In the method, linked sequence data generated from a sample of two or more microparticles may transformed as described herein, and wherein said transformed data is evaluated using an algorithm such as any above, wherein said algorithm takes as input a first transformed dataset from a first microparticle sample, and a second transformed dataset from a second microparticle sample, wherein the second sample is taken from an the same individual as the first biological sample, but taken at a second and later time period compared with the first sample. The second sample may be taken at a time point at least 1 day, at least 1 week, at least 1 month, at least 2 months, at least 6 months, as least 12 months, at least 24 months, at least 36 months, at least 5 years or at least 10 years after the first sample. Optionally, the algorithm may also take as input data a third, or fourth, or fifth, or greater number of samples also separated in sequence by one or more days or greater period of time. Optionally, the algorithm may be used to detect the presence of structural abnormalities that increase in individual frequency, cumulative burden, or statistical significance across samples from two or more time points. Optionally, the algorithm may be used to detect the presence or burden of cancer, and/or to detect the growth of a malignancy between two or more time points, and/or to stratify the risk of a malignant process.

In any of the methods, the algorithm is configured to detect sets of linked sequence reads from microparticles of foetal origin, from a sample comprising a mixture of microparticles of maternal origin and foetal origin.

33. Methods for Determining Genomic Rearrangements, Translocations, Structural Variants, or Genomic Linkages The invention provides a method of determining the presence of a genomic rearrangement or structural variant within a set of linked sequence reads of fragments of a target nucleic acid (e.g. genomic DNA) from a single microparticle, wherein the method comprises: (a) determining a set of linked sequence reads according to any of the methods described herein; and (b) mapping (at least a portion of) each sequence of the set of linked sequence reads to a first reference nucleotide sequence comprising a first genomic region, and mapping (at least a portion of) each sequence of the set of linked sequence reads to a second reference nucleotide sequence comprising a second genomic region; and (c) counting the number of sequence reads from the set of linked sequence reads that are found to map within the first genomic region, and counting the number of sequence reads from the set of linked sequence reads that are found to map within the second genomic region.

The genomic rearrangement or structural variant may be any type of genomic-structural phenomenon e.g. a genomic copy number variation (including a copy number gain or a copy number loss), a microdeletion, or any sort of rearrangement (e.g. an inversion), a translocation such a chromosomal translocation (e.g. an intra-chromosomal translocation or an inter-chromosomal translocation).

In the methods, the numbers of counted number of sequence reads may then be used in a further evaluation step or statistical analysis to determine whether a genomic linkage (i.e, a connection along the same stretch of a chromosome) may exist between the first genomic region and the second genomic region. The method may be conducted for a single set of linked sequence reads, and it may also be conducted for a group of two or more sets of linked sequence reads, as well as conducted for all sets of linked sequence reads within a sample of microparticles, or a subgroup thereof.

Optionally, the total number of sequence reads within the set of linked sequence reads is also determined. The first and the second genomic regions may be located within the same chromosome, and if so then may be immediately adjacent to each other or may be separated by any number of nucleotides. Alternatively, the first and the second genomic regions may be located within two different chromosomes. The first and second genomic regions may each be any number of nucleotides in length, from 1 nucleotide to the length of a chromosome arm or an entire chromosome.

Optionally, an evaluation is performed wherein the number of sequence reads within the first genomic region are compared with a first threshold value, and the number of sequence reads within the second genomic region compared with a second threshold value, wherein the first number being equal to or above the first threshold value and the second number being equal to or above the second threshold value determines or indicates the presence of a genomic linkage between the first genomic region and the second genomic region and/or the presence of a rearrangement or translocation event involving the first and the second genomic regions. Optionally, this evaluation may further incorporate the total number of sequence reads in a linked set of sequence reads from a microparticle. For example, this evaluation may include calculation of the fraction of sequence reads out of the entire linked set that map within any given genomic region; optionally these fraction values may be compared with one or more threshold values to determine or indicate the presence of a genomic linkage.

Optionally, a statistical test may be performed wherein the number of sequence reads within the first genomic region and/or the number of sequence reads within the second genomic region are evaluated by a statistical test or by an algorithm to estimate a probability or likelihood that a genomic linkage or rearrangement event exists between the first and the second region. Optionally, this evaluation may further incorporate the total number of sequence reads in a linked set of sequence reads from a microparticle.

Optionally, the method may be performed on a single set of linked sequence reads from a microparticle, or it may be performed on a group of two or more sets of linked sequence reads. It may also be performed on all sets of linked sequence reads from a particular sample, and it may also be performed on a group of sets of linked sequence reads. Optionally, wherein the method is performed on a group of two or more sets of linked sequence reads, one or more further evaluation steps may be performed to evaluate the statistical significance of, or probability or likelihood of, there being a genomic linkage between the first and second region, wherein the numbers of sequences from two or more sets of linked sequence reads that are found to map within the first and second region are evaluated together.

34. Methods for Phasing Variants or Variant Alleles

The invention provides methods for phasing alleles that are distributed across a chromosomal region. These analyses may be geared towards any application or task where the presence of two nucleic acid variants on the same chromosome or on two different chromosomes may have biological or medical significance. For example, wherein two different variant sites may be found within a single gene (the case of compound heterozygosity), it can be highly relevant whether a mutation in the first site is located within the same copy of the gene within an individual's genome as a mutation in the second site, or if, by contrast, they are each located on one of the two different copies of the gene within the individual's genome—for example, if two mutations are inactivating mutations, then their being located on the same copy of the gene will still allow for one active, functioning copy of the gene, whereas if the two inactivating mutations are each located on one of the two copies of the gene, then neither copy of the gene will be active.

The invention provides a method of phasing two variant alleles, wherein a first variant allele is comprised within a first genomic region, and wherein a second variant allele is comprised within a second genomic region, and wherein each variant allele has at least two variants or potential variants, wherein the method comprises: (a) determining a set of linked sequence reads according to any of the methods described herein; and (b) determining whether a sequence comprising each potential variant from the first variant allele is present within the set of linked sequence reads, and determining whether a sequence comprising each potential variant from the second variant allele is present within the same set of linked sequence reads.

The variant allele may comprise a single nucleotide, or a region of two or more nucleotides, or insertions and/or deletions of one or more nucleotides. Optionally, a further evaluation step is performed in which the presence of a first variant of a first allele is detected, and wherein the presence of a first variant of a second allele is detected, and wherein these two alleles being found within the same set of linked sequence reads indicates or estimates a probability that the two alleles are in the same chromosomal phase as each other, and/or linked along the same chromosome or haplotype or haplotype block.

The method may be repeated for two or more pairs of variant alleles, comprising any potential variant allele, and any potential variant within an allele or a variant allele site, and any combination thereof of any two or more different such variant alleles.

The method may be performed on a single set of linked sequence reads from a microparticle, or it may be performed on a group of two or more sets of linked sequence reads. It may also be performed on all sets of linked sequence reads from a particular sample, and it may also be performed on one or more particular groups of sets of linked sequence reads. Optionally, the method is performed on a group of two or more sets of linked sequence reads, one or more further evaluation steps may be performed to evaluate the statistical significance of, or probability or likelihood of, the two alleles being in the same chromosomal phase as each other, and/or found within the same chromosome or the same haplotype. Optionally, sequences from two or more sets of linked sequence reads comprising one or more variants from the first and/or second variant alleles may be evaluated together. Optionally, wherein the method is performed on a group of two or more sets of linked sequence reads, the number of times that a particular pair of (or a greater number of) variants within variant alleles are found phased within an individual set of linked sequence reads may be counted; optionally, the resulting number may be compared with one or more threshold values, or evaluated with one or more statistical tests or algorithms, to evaluate the likelihood or probability that the said variants are in phase with each within the sample.

Optionally, the method may be used to phase three or more variant alleles. Optionally, this may be performed by phasing all said three or more variant alleles simultaneously within a single step, or may be performed by a sequence of two or more sequential steps.

Optionally, the method may be used to phase variant alleles (e.g. at least 2, at least 5, at least 10, at least 25, at least 50, at least 100, at least 500, at least 1000, at least 10,000, or at least 100,000 variant alleles) across a genomic span. The genomic span may be at least 100 kilobases, at least 1 megabase, at least 10 megabases, or an entire chromosome arm or an entire chromosome. Optionally, the method may be used to phase entire sequences including any type of variant or invariant sequence, including genomic spans thereof at least 1 kilobase in size, at least 10 kilobases in size, at least 100 kilobases in size, at least 1 megabase in size, at least 10 megabases in size, at least 100 megabases in size, at least a chromosome arm in length, and an entire chromosome in length.

The variant allele may be any sort of genetic variant, including single-nucleotide variant or single-nucleotide polymorphism, a variant that is two or more nucleotides in length, an insertion or deletion of one or more nucleotides, a de novo mutation, a loss-of-heterozygosity, a rearrangement or translocation event, a copy number variation, or any other genomic feature or mutation.

The method may comprise or be extended to comprise a genetic imputation process. Optionally, a list of one or more alleles or variant alleles from a set of linked sequence reads from a microparticle is determined to perform a genetic imputation process; optionally this list may be determined from a group of two or more sets of linked sequence reads, or from a particular subgroup of sets of linked sequence reads. A genetic imputation process may be performed in which one or more such lists are compared with one or more previously known haplotypes or haplotype blocks from a human population, to phase or to estimate the phase of the alleles or variant alleles within said lists, or to determine or estimate a haplotype or haplotype block for a portion of the genome from which said sequences were derived. Optionally, two or more alleles or variant alleles may be phased prior to performing a genetic imputation process. Optionally, the phasing of such two or more alleles or variant alleles may be performed through any process as above. Optionally, a combined and/or iterative process of phasing and/or genetic imputation and/or haplotype estimation may be performed, wherein any such step or component may be repeated one, two or a greater number of times.

Any tools and/or methods and/or informatic approaches to performing genetic imputation and/or haplotype estimation and/or phasing and/or variant estimation may be employed. Optionally, SHAPEIT2, MaCH, Minimac, IMPUTE2, and/or Beagle may be employed.

Optionally, a genetic imputation process may be employed to generate one or more reference sequences (e.g. to generate one or more lists of reference sequences). Optionally, a genetic imputation process may be employed concurrently to and/or along with a haplotype-estimation process. Optionally, a genetic imputation process may be employed to generate one or more reference sequences comprising sequences contained within, and/or likely to be contained within, and/or enriched within, a foetal genome (e.g. to generate one or more lists of reference sequences sequences comprising sequences contained within, and/or likely to be contained within, and/or enriched within, a foetal genome). Optionally, a genetic imputation process may be employed to generate one or more reference sequences comprising sequences contained within, and/or likely to be contained within, and/or enriched within, a maternal genome (e.g. to generate one or more lists of reference sequences sequences comprising sequences contained within, and/or likely to be contained within, and/or enriched within, a maternal genome). Optionally, a genetic imputation process may be employed to generate one or more reference sequences comprising sequences contained within, and/or likely to be contained within, and/or enriched within, a paternal genome (e.g. to generate one or more lists of reference sequences sequences comprising sequences contained within, and/or likely to be contained within, and/or enriched within, a paternal genome). Optionally, a genetic imputation process may be employed to generate one or more reference sequences comprising sequences contained within, and/or likely to be contained within, and/or enriched within, a cancer genome (e.g. to generate one or more lists of reference sequences sequences comprising sequences contained within, and/or likely to be contained within, and/or enriched within, a cancer genome).

Optionally, a genetic imputation process may employ an input list of sequences and/or alleles (e.g. a list of single-nucleotide polymorphisms), wherein said input list is derived from sequences of fragments of genomic DNA from circulating microparticles. Optionally, said input list may be derived from linked sequences of fragments of genomic DNA from circulating microparticles. Optionally, said input list may be derived from unlinked sequences of fragments of genomic DNA from circulating microparticles. Optionally, said input list may be derived from a subset of (linked or unlinked) sequences of fragments of genomic DNA from circulating microparticles. Optionally, said input list may be derived from a subset of (linked or unlinked) sequences of fragments of genomic DNA from circulating microparticles, wherein said subset of sequences comprises sequences contained within, and/or likely to be contained within, and/or enriched within, and/or suspected to be enriched within, a maternal genome. Optionally, said input list may be derived from a subset of (linked or unlinked) sequences of fragments of genomic DNA from circulating microparticles, wherein said subset of sequences comprises sequences contained within, and/or likely to be contained within, and/or enriched within, and/or suspected to be enriched within, a paternal genome. Optionally, said input list may be derived from a subset of (linked or unlinked) sequences of fragments of genomic DNA from circulating microparticles, wherein said subset of sequences comprises sequences contained within, and/or likely to be contained within, and/or enriched within, and/or suspected to be enriched within, a foetal genome. Optionally, said input list may be derived from a subset of (linked or unlinked) sequences of fragments of genomic DNA from circulating microparticles, wherein said subset of sequences comprises sequences contained within, and/or likely to be contained within, and/or enriched within, and/or suspected to be enriched within, a cancer genome.

Any an input list of sequences and/or alleles (e.g. a list of single-nucleotide polymorphisms), and/or any one or more reference sequences (e.g. one or more lists of reference sequences) and/or any subset thereof may be generated by any method described herein.

Optionally, a genetic imputation process may be employed to generate, determine, or estimate a haplotype or haplotype block for a portion of a genome. Optionally, a genetic imputation process may be employed to generate, determine, or estimate a haplotype or haplotype block for a portion of a maternal genome. Optionally, a genetic imputation process may be employed to generate, determine, or estimate a haplotype or haplotype block for a portion of a paternal genome. Optionally, a genetic imputation process may be employed to generate, determine, or estimate a haplotype or haplotype block for a portion of a foetal genome. Optionally, a genetic imputation process may be employed to generate, determine, or estimate a haplotype or haplotype block for a portion of a cancer genome. Optionally, such a said haplotype or haplotype block may relate to a genomic region at least 2 nucleotides, at least 10, at least 100, at least 1000, at least 10,000, at least 100,000, at least 1,000,000, at least 10,000,000, or at least 100,000,000 nucleotides in length; optionally, such a said a haplotype or haplotype block may relate to a chromosome arm, a full chromosome, and/or a full genome.

Optionally, a genetic imputation process may employ a catalogue of two or more previously known (and/or previously predicted or created) haplotypes or haplotype blocks from a human population. Optionally, a haplotype or haplotype block may relate to a genomic region at least 2 nucleotides, at least 10, at least 100, at least 1000, at least 10,000, at least 100,000, at least 1,000,000, at least 10,000, 000, or at least 100,000,000 nucleotides in length; optionally, a haplotype or haplotype block may relate to a chromosome arm, a full chromosome, and/or a full genome.

Optionally, a genetic imputation process may employ a catalogue of at least 2, at least 3, at least 5, at least 10, at least 50, at least 100, at least 500, at least 1000, at least 5000, at least 10,000, at least 50,000, at least 100,000, at least 500,000, or at least 1,000,000 more previously known (and/or previously predicted or created) haplotypes or haplotype blocks.

The method may be conducted for a single set of linked sequence reads, and it may also be conducted for a group of two or more sets of linked sequence reads, as well as conducted for all sets of linked sequence reads within a sample of microparticles, or a subgroup thereof.

35. Methods for Determining and Analysing Linked Sequence Reads of Foetal Origin The invention provides methods for analyzing linked sequence data wherein said data is generated from a sample from a pregnant female (thus the sample may comprise a mixture of microparticles of maternal origin, i.e. from normal somatic maternal tissues, and microparticles of foetal (and/or placental) origin). The methods may be used to detect the presence of a foetal chromosomal abnormality, such as a foetal trisomy, or a foetal chromosomal microdeletion. Several such methods may be performed on the same set of foetal sequences, thus enabling multiplexed and sensitive detection of foetal genetic conditions.

The invention provides a method of determining a set of linked sequence reads of foetal origin, wherein the method comprises: (a) determining a set of linked sequence reads according to any of the methods described herein, wherein the sample comprises microparticles originating from maternal blood; and (b) comparing (at least a portion of) each sequence read of the set of linked sequence reads to a reference list of sequences present in the foetal genome; and (c) identifying a set of linked sequence reads of foetal origin by the presence of one or more sequences from the reference list within one or more sequence reads of the set of linked sequence reads.

A set of linked sequence reads of foetal origin may comprise, consist of or consist essentially of sequence reads of fragments of a target nucleic acid originating from a foetus. Optionally, a set of linked sequence reads of foetal origin may comprise or consist of sequence reads of fragments of a target nucleic acid originating from a foetus, and also comprise or consist of sequence reads of fragments of a target nucleic acid originating from one or more maternal tissues and/or maternal cells.

The reference list of sequences (or sequence variants) present in the foetal genome may comprise, consist of, or consist essentially of, sequences enriched in the foetal genome. The reference list of sequences present in the foetal genome may comprise, consist of, or consist essentially of, sequences enriched in the foetal genome (compared to the maternal genome). The reference list of sequences present in the foetal genome may comprise, consist of, or consist essentially of, sequences depleted in the maternal genome (compared to the foetal genome). The reference list of sequences present in the foetal genome may comprise, consist of, or consist essentially of, sequences not present in the maternal genome. The reference list of sequences present in the foetal genome may comprise, consist of, or consist essentially of, sequences paternal sequences or paternal sequence variants.

The microparticles may originate from the maternal blood of a pregnant individual. Optionally, the microparticles may originate from the maternal blood of a pregnant individual wherein the individual is pregnant with at least two developing foetuses (e.g. the individual is pregnant with twins, or triplets, or any larger number of developing foetuses). Optionally, the microparticles may originate from the maternal blood of a pregnant individual wherein the pregnancy has been generated through an in vitro fertilisation. Optionally, any in vitro fertilisation process may further comprise any step of pre-implantation genetic screening, pre-implantation genetic diagnosis, pre-implantation embryo evaluation, and/or pre-implantation embryo selection.

The microparticles may originate from the maternal blood of a pregnant individual, wherein the embryo (or embryos) from which the corresponding developing foetus (or foetuses) is produced has been subject to (or produced by) one or more synthetic genetic modification processes. Optionally, any one or more synthetic genetic modification processes may comprise a CRISPR modification procedure. Optionally, any one or more synthetic genetic modification processes may comprise a mitochondrial replacement procedure. Optionally, any one or more synthetic genetic modification processes may involve the modification and/or correction of a disease-associated or disease-caustative mutation and/or sequence and/or allele. Optionally, any one or more synthetic genetic modification processes may involve the modification of a sequence comprised within a single gene. Optionally, any one or more synthetic genetic modification processes may involve the modification of a sequence comprised within a non-genic (e.g. an intergenic) region. Optionally, any one or more synthetic genetic modification processes may involve the insertion of a sequence, the deletion of a sequence, and/or the modification and/or inactivation of a sequence. Optionally, any one or more synthetic genetic modification processes may involve the insertion, deletion, replacement, or modification of a genomic region; optionally, such a genomic region may be at least 2 nucleotides, at least 3 nucleotides, at least 5 nucleotides, at least 100 nucleotides, at least 1000 nucleotides, at least 10,000 nucleotides, at least 100,000 nucleotides, at least 1,000,000 nucleotides, at least 10,000,000 nucleotides, at least a chromosome arm, or at least a chromosome in length.

Any synthetic genetic modification process may comprise a set of at least 2, at least 3, at least 5, at least 10, at least 50, at least 100, at least 1000, or at least 10,000 different synthetic genetic modification processes. Any such set of synthetic genetic modification processes may be performed sequentially (e.g. wherein a first synthetic genetic modification process is performed, followed by a second synthetic genetic modification process), or in parallel (e.g. wherein two or more synthetic genetic modification processes are performed simultaneously upon a single sample).

The microparticles may originate from the maternal blood of a pregnant individual, wherein the embryo (or embryos) from which the corresponding developing foetus (or foetuses) is produced has been generated by one or more in vitro gametogenesis processes. Optionally, one such in vitro gametogenesis process may comprise in vitro oogenesis. Optionally, one such in vitro gametogenesis process may comprise in vitro spermatogenesis. Optionally, any one or more such in vitro gametogenesis processes may comprise the in vitro synthesis of gametes from somatic tissue (e.g. skin and/or fibroblast tissue or cells) obtained from one or more individuals. Optionally, any one or more such in vitro gametogenesis processes may further comprise an in vitro fertilisation process. Optionally, any one or more such in vitro gametogenesis processes may further comprise one or more synthetic genetic modification processes (of one or more gametes, and/or of one or more embryos following an in vitro fertilisation process).

The method may comprise: performing step (a) to determine at least 2, at least 10, at least 100, at least 1000, at least 10,000, at least 100,000, at least 1,000,000, at least 10,000,000, at least 100,000,000, or at least 1,000,000,000 sets of linked sequence reads; performing step (b) for each of the sets of linked sequence reads; and performing step (c) to identify set(s) of linked sequence reads of foetal origin by the presence of one or more sequences from the reference list within one or more sequence reads of the sets of linked sequence reads.

The method may comprise identifying at least 2, at least 10, at least 100, at least 1000, at least 10,000, at least 100,000, at least 1,000,000 sets of linked sequence reads of foetal origin.

The method may comprise identifying a set of linked sequence reads of maternal origin and/or non-foetal origin.

The sequence reads from each set of linked sequence reads may be compared to a reference list of sequences or sequence variants, wherein said reference list of sequences or sequence variants are present or enriched in the foetal genome. Optionally wherein the sequences or sequence variants are not present or are depleted in the maternal genome. A set(s) of linked of sequence reads of foetal origin may be determined or predicted via detection of one or more sequences or sequence variants from said reference list within the sequence reads of the set(s) of linked of sequence reads.

Paternal sequences or sequence variants or a set thereof may be determined by evaluating their allele fraction within the or all set(s) of linked sequence reads and wherein said allele fraction is found to be less than a particular fraction, such as less than 50%, less than 40%, less than 30%, less than 25%, less than 20%, less than 15%, less than 10%, less than 8%, less than 5%, less than 4%, less than 3%, less than 2%, less than 1%, or less than any other threshold value, within said sequence reads. Optionally, said paternal sequences or sequence variants are determined from a finite list of one or more sequences or sequence variants, optionally wherein said finite list comprises a list of single nucleotide variants and/or single nucleotide insertions or deletions that are common within human populations. Any said sequences or sequence variants may be in the form of single nucleotide variants, in the form of insertions or deletions of at least 1 nucleotide, at least 2 nucleotides, or a greater number of nucleotides, or any other category or size of sequence or sequence variant. Any one or more paternal sequences or sequence variants determined by a method as above may then be used as a reference list to evaluate sets of linked sequence reads from a microparticle sample, such as to evaluate whether a given set of linked sequence reads is foetal in origin. Optionally, any method as above may instead be used to determine sets of linked sequence reads of maternal origin.

Paternal sequences or sequence variants or a set thereof may be determined by genetic imputation. Optionally, a first set of paternal sequences comprising single nucleotide variants, or comprising any other class of sequence or sequence variant or combination thereof, is used to estimate a haplotype or haplotype block, and a second set of paternal sequences or sequence variants is determined from said haplotype or haplotype block, wherein both sequences from the first set of sequences and sequences from the second set of sequences are comprised within the haplotype or haplotype block, but wherein the second set of paternal sequences or sequence variants is not comprised within the first set of paternal sequences or sequence variants. Optionally, said first set of paternal sequences may be determined as by determining sequences below a specific threshold allele fraction within all set(s) of linked sequence reads. One or both sets of paternal sequences or sequence variants may then be used as a reference list to evaluate sets of linked sequence reads from a microparticle sample, such as to evaluate whether a given set of linked sequence reads is foetal in origin. Optionally, any method as above may instead used to determine or predict sets of linked sequence reads of maternal origin.

Paternal sequences or sequence variants or a set thereof may be determined by sequencing a sample comprising genomic DNA from the father (e.g. by performing targeted and/or whole-genome sequencing of paternal genomic DNA). Maternal sequences or sequence variants or a set thereof may be determined by sequencing a sample comprising genomic DNA from the mother (e.g. by performing targeted and/or whole-genome sequencing of maternal genomic DNA).

Sequences from each set of linked sequence reads may be compared to two or more different reference lists of sequences or sequence variants.

The method may comprise determining the number of sequence reads from each set of linked sequence reads comprised within said reference list or reference lists.

The method may comprise counting the number of non-maternal or paternal sequences from a list of non-maternal or paternal sequences in a set of linked sequence reads. Optionally, this counting process may be performed for all sets of linked sequence reads in the sample. Optionally, each non-maternal or paternal sequence may be associated with a weighting value, such that the counting process comprises a weighted counting process, wherein a weighted sum of non-maternal or paternal sequences within a set of linked sequence reads is determined. Optionally, this weighting value may correspond to a likelihood or probability that a given sequence is non-maternal or paternal, or correspond to a likelihood or probability that a given sequence is maternal.

The sum or weighted sum of non-maternal or paternal sequences from a set of linked sequence reads may be compared to one or more threshold values, and wherein sets of linked sequence reads comprising a number of non-maternal or paternal sequences greater than said threshold value(s) are determined to be foetal in origin. Optionally, the process of determining any such said sum and comparing with one or more threshold may be performed for all sets of linked sequence reads in the sample. Optionally, the process of determining any such said sum may comprise determining a weighted sum as described above. Optionally, a set of linked sequence reads with a sum or weighted sum equal to a threshold value, within one or more ranges of threshold values, less than a threshold value, or within a set of specific values may be determined to be foetal in origin. Optionally, any method as above may used to determine sets of linked sequence reads of maternal origin. Optionally, the total number of sets of linked sequence reads found by any above method to be foetal in origin, or found to be maternal in origin, may be counted, to determine a total number of sets of linked sequence reads of foetal origin or maternal origin respectively.

Optionally, the total number of sets of linked sequence reads of foetal origin may be compared to or divided by a total number of sets of linked sequence reads of maternal origin, to estimate or determine a fraction or ratio of foetal microparticles to maternal microparticles and/or to all microparticles.

The method may comprise determining the length of two or more genomic sequences from said one or more sets of linked sequence reads, and wherein said lengths determine whether said sets of linked sequence reads correspond to microparticles of foetal or maternal origin. Optionally, the process of determining such said lengths may be performed for all sets of linked sequence reads in the sample. Optionally, a mean, median, or mode of genomic sequence lengths from a set of linked sequence reads are determined, and then compared with a threshold value, wherein sets of linked sequence reads comprising such a value less than, greater than, or equal to said threshold value are determined to be foetal in origin. Optionally, said mean, median, or mode of genomic sequence lengths from a set of linked sequence reads are compared with one or more ranges of values, or one or more finite sets of values, and values within said ranges or within said sets are determined to be foetal in origin. Optionally, any method as above may used to determine sets of linked sequence reads maternal origin. Optionally, the total number of sets of linked sequence reads found by any above method to be foetal in origin or found to be maternal in origin may be counted, to determine a total number of sets of linked sequence reads of foetal origin or maternal origin respectively.

Optionally, the a total number of sets of linked sequence reads of foetal origin may be compared to or divided by a total number of sets of linked sequence reads of maternal origin, to estimate or determine a fraction or ratio of foetal microparticles to maternal microparticles and/or to all microparticles.

The method may comprise determining the lengths of two or more genomic sequences from one or more sets of linked sequence reads, and comparing the lengths to a reference genomic length distribution, wherein a statistical test is performed to compare the lengths from said set of linked sequence reads and said reference distribution, and sets of linked sequence reads within lengths determined to be statistically similar to, statistically different to, statistically greater than, and/or statistically lesser than lengths of said reference distribution are determined to be foetal or maternal in origin. Optionally, a t-test, a Mann-Whitney test, an Analysis of Variance (ANOVA) test, or any other statistical test, may be used as said statistical test. Optionally, genomic lengths of molecules within sets of linked sequence reads may be determined by mapping the first end and the second end of each linked sequence to a reference genome sequence, and then determining the total span of said genomic sequence from the 5' end of the first end to the 3' end of the second end, thus calculating the total length in base pairs. Optionally, genomic lengths of molecules within sets of linked sequence reads may be determined by sequencing each linked sequence in entirety, from the 5' end of the first end to the 3' end of the second end, thereby directly determining the length in base pairs of the molecule comprising genomic sequence. Optionally, the process of determining and statistically evaluating said lengths may be performed for all sets of linked sequence reads in the sample. Optionally, any method as above may instead used to determine sets of linked sequence reads of maternal origin. Optionally, the total number of sets of linked sequence reads found by any above method to be foetal in origin or found to be maternal in origin may be counted, to determine a total number of sets of linked sequence reads of foetal origin or maternal origin respectively. Optionally, the a total number of sets of linked sequence reads of foetal origin may be compared to or divided by a total number of sets of linked sequence reads of maternal origin, to estimate or determine a fraction or ratio of foetal microparticles to maternal microparticles and/or to all microparticles.

The method may comprise determining the genomic length for each sequence read in a set of linked sequence reads, and wherein the presence and/or number of non-maternal or paternal sequences in sequence reads of the same set of linked sequence reads is determined, and wherein both parameters are used to determine whether the set of linked sequence reads is foetal in origin. Optionally, this process of determining lengths and sequences may be performed for all sets of linked sequence reads in the sample. Optionally, an algorithm is used to evaluate both parameters to determine whether the set of linked sequence reads is foetal in origin. Optionally, sets of linked sequence reads are determined to be foetal in origin, wherein each such set of linked sequence reads is determined to have a mean sequence length within a specific range of lengths, and wherein the same set of linked sequence reads is also found to comprise a number of non-maternal or paternal sequences above a specific threshold number of non-maternal or paternal sequences. Optionally, two or more such pairs of length ranges and sequence counts may each be employed to determine whether a set of linked sequence reads is foetal in origin, wherein a set of linked sequence reads is determined to be foetal in origin if it falls within the parameters of any one or more such pairs of length ranges and sequence counts.

The method may comprise counting the total number of sequence reads within one or more sets of linked sequence reads that map within a particular reference sequence are counted, wherein said reference sequence is at least 1 nucleotide in length, at least 2 nucleotides in length, or at least 10 nucleotides in length, or at least 100, nucleotides in length, or at least 1000, nucleotides in length, or at least 10,000 nucleotides in length, or at least 100,000 nucleotides in length, or at least 1,000,000 nucleotides in length, or at least 10,000,000 nucleotides in length, or a chromosome arm in length, or an entire chromosome in length. Optionally, the reference sequence may be comprised of two or more separate segments and thus discontinuous in nature. Optionally, this counting process may be performed for two or more different reference sequences, or at least 10 reference sequences, at least 100 reference sequences, at least 1000 reference sequences, at least 10,000 reference sequences, at least 100,000 reference sequences, at least 1,000,000 reference sequences, at least 10,000,000 reference sequences, at least 100,000,000 reference sequences, or at least 1,000,000,000 reference sequences. Optionally, this counting process may be performed for a sliding window, wherein two or more windows are tiled across a part of a chromosome, or across an entire chromosome arm, or across an entire chromosome, or across all chromosomes of the genome. Optionally, the absolute number of all sequences determined to be foetal in origin that map to a given such reference sequence may be determined. Optionally, the fraction or proportion of all sequences determined to be foetal in origin that map to a given such reference sequence may be determined. Optionally, the number of all sequences determined to be foetal in origin that map to a given such reference sequence may be determined and then divided by the total number of sets of linked sequence reads determined to be of foetal origin, to determine an average number of sequence reads that map to said reference sequence per set of linked sequence reads of foetal origin. Optionally, any such analysis may be performed independently for each of one or more individual sets of linked sequence reads of foetal origin. Optionally, any such analysis may be performed jointly across all sequences from two or more sets of linked sequence reads of foetal origin. Optionally, any such analysis as above may be performed for sequences from one or more sets of linked sequence reads of maternal origin. Optionally, any such number or fraction corresponding to sequences from microparticles of foetal origin that map within a specific reference sequence may be compared to any such number or fraction corresponding to sequences from microparticles of maternal origin that map within the same reference sequence. Optionally, any such analysis as above may be performed to determine such a number or fraction for sets of linked sequence reads from microparticles of foetal origin, and the same analysis may be performed to determine such a number or fraction for sets of linked sequence reads from microparticles of maternal origin, and the number for sequences of foetal origin may be compared with the corresponding number for sequences of maternal origin to create a ratio, fraction, or comparative value thereof.

In the methods, at least one reference sequence (of the reference list of sequences) may comprise a repeat sequence. Optionally this repeat sequence comprises a dinucleotide repeat, a trinucleotide repeat, a tetranucleotide repeat, or a pentanucleotide repeat. Optionally, the reference nucleotide sequence comprises a series of two or more immediately adjacent copies of the same repeat unit, such as 2 immediately adjacent copies, 5 immediately adjacent copies, 8 immediately adjacent copies, 10 immediately adjacent copies, 15 immediately adjacent copies, 20 immediately adjacent copies, 30 immediately adjacent copies, 40 immediately adjacent copies, 50 immediately adjacent copies, or 100 immediately adjacent copies.

The method may comprise a further evaluation step, wherein any such absolute number of sequence reads per set of linked sequence reads or group of sets of linked sequence reads, average number of sequence reads per set of linked sequence reads or group of sets of linked sequence reads, or relative or fractional number of sequence reads mapping within a reference sequence may be compared to a threshold value, or one or more ranges of values. Optionally, said number being above or below said threshold value, or within one or more ranges of values, indicates or determines the presence of a genetic or chromosomal condition or abnormality. Optionally, any such analysis may indicate or determine a copy number gain of any length in nucleotides, a copy number loss of any length in nucleotides, a chromosomal microdeletion of any length, or a chromosomal aneuploidy, or any other structural or chromosomal condition or abnormality. Optionally, the total number of sets of linked sequence reads or groups of sets of linked sequence reads above such a said threshold, below such a said threshold, or within one or more such ranges of values may be counted.

The method may comprise a further evaluation step, wherein any such absolute number of sequence reads per set of linked sequence reads, average number of sequence reads per set of linked sequence reads, or relative or fractional number of sequence reads mapping within a reference sequence may be compared between two or more different reference sequences. Optionally, such a number from a first reference sequence may be compared with such a number from a second reference sequence. Optionally, two or more second reference sequences of the same length may be used. Optionally, two or more reference sequences of different lengths may be used, wherein the number for each reference sequence is normalized to the length of said reference sequence prior to comparison. Optionally, the absolute difference between a first such number and a second such number may be compared with a threshold value or one or more ranges of values, wherein said difference being above said threshold, below said threshold, or within one or more such ranges indicates or determines the presence of a genetic or chromosomal condition or abnormality. Optionally, the relative difference between a first such number and a second such number, such as expressed in the form of a ratio, fraction, or percentage, may be compared with a threshold value or one or more ranges of values, wherein said difference being above said threshold, below said threshold, or within one or more such ranges indicates or determines the presence of a genetic or chromosomal condition or abnormality. Optionally, any such analysis may indicate or determine a copy number gain of any length in nucleotides, a copy number loss of any length in nucleotides, a chromosomal microdeletion of any length, or a chromosomal aneuploidy, or any other structural or chromosomal condition or abnormality. Optionally, any such analysis as above may be performed to determine such a number, fraction, ratio, or relative difference between two or more different reference sequences for sets of linked sequence reads from microparticles of foetal origin, and the same analysis may be performed to determine such a number, fraction, ratio, or relative difference between two or more different reference sequences for sets of linked sequence reads from microparticles of maternal origin, and the number, fraction, ratio, or relative difference for sequences of foetal origin may be compared with the corresponding number, fraction, ratio, or relative difference for sequences of maternal origin to create a ratio, fraction, or comparative value thereof.

The method may comprise determining the average number of sequence reads per set of linked sequence reads of foetal origin that map within a reference sequence, and wherein this average number is compared with a threshold value, and wherein said number being above or below said threshold value indicates or determines the presence of a foetal genetic or chromosomal condition or abnormality. Optionally, said reference sequence comprises substantially all of a chromosome, and said number being above said threshold value indicates or determines the presence of a foetal chromosomal trisomy. Optionally, said reference sequence comprises substantially all of a genomic microdeletion region, and said number being below said threshold value indicates or determines the presence of a foetal microdeletion.

The method may comprise determining the average number of sequence reads per set of linked sequence reads of foetal origin that map within a first reference sequence is determined, and wherein the average number of sequence reads per set of linked sequence reads of foetal origin that map within a second reference sequence is determined, and wherein the relative difference between the first such number and the second such number is determined, such as expressed in the form of a ratio, fraction, or percentage, and wherein said relative difference is compared with a threshold value, wherein said difference being above or below said threshold indicates or determines the presence of a foetal genetic or chromosomal condition or abnormality. Optionally, said first reference sequence comprises substantially all of a chromosome, and said relative difference being above said threshold value indicates or determines the presence of a foetal chromosomal trisomy. Optionally, said first reference sequence comprises substantially all of a genomic microdeletion region, and said relative difference being below said threshold value indicates or determines the presence of a foetal microdeletion.

The invention provides a method of determining a foetal genotype comprising: (a) determining a set of linked sequence reads of foetal origin by any of the methods described herein; and (b) determining the foetal genotype from the set of linked sequence reads of foetal origin.

The foetal genotype may be a foetal chromosomal abnormality e.g. aneuploidy.

The invention provides a of determining a foetal genotype, foetal genome sequence, phased foetal genome sequence, or component or fraction thereof, wherein sequences comprising said foetal genotype or sequence are determined from sequences within sets of linked sequence reads from microparticles of foetal origin. Optionally, said genotype or genome may comprise sequences or sequence variants from two haplotypes of a foetal genome, such as a paternally inherited haplotype and a maternally inherited haplotype. Optionally, the foetal genotype or genome may also comprise one or more structural or chromosomal abnormalities that may be inherited paternally or maternally, or may have been generated as de novo structural or chromosomal abnormalities. Optionally, the foetal genotype or genome may also comprise one or more de novo single nucleotide variants not inherited maternally or paternally.

The method may comprise determining sequences of foetal genomic DNA from sequences within sets of linked sequence reads from microparticles of foetal origin, and wherein one haplotype or two haplotypes thereof are determined. Optionally, said genomic DNA may comprise sequences or sequence variants from two haplotypes of a foetal genome, and said one or two haplotypes are estimated or phased therefrom using a haplotype phasing algorithm or a haplotype estimation algorithm. Optionally, a processing or filtering process may be performed upon a list of sequences or sequence variants prior to use of a haplotype phasing algorithm, wherein only sequences or sequence variants of at least a certain confidence level, of at least a certain accuracy level, or at least a threshold value of any other one or more parameters is used within the subsequent phasing or haplotype-estimation step. Optionally, an error-correction and/or redundant sequencing process is used to increase the accuracy of said sequences or sequence variants prior to a phasing or haplotype-estimation step. Optionally, said haplotype phasing or estimation algorithm may also comprise a set of one or more haplotypes or haplotype blocks from a human population. Optionally, a haplotype corresponding to a specific chromosome or portion of a chromosome may be determined using any above method, and optionally both a maternally-inherited haplotype and a paternally-inherited haplotype corresponding to said chromosome or chromosome portion may be determined.

The method may comprise any step of counting sequence reads and/or counting weighted, averaged, absolute, relative, or normalized sequence reads, as described herein. This step or steps may follow a de-duplication step, wherein sequenced molecules from the sequencing reaction that are sequenced two or more times are collapsed into a single representation prior to further analysis, counting, evaluation, processing, or manipulation steps. Optionally, this de-duplication process may further comprise an error-correction process, wherein errors and/or mis-matched sequences duplicated molecules within duplicated molecules are detected, and/or quantitated, and/or corrected, prior to any step of counting or further analysis.

The invention provides a method of performing a combined or joint evaluation of sets of linked sequence reads from microparticles of foetal origin and/or maternal origin, wherein the method comprises performing a first evaluation comprising any analysis as described herein to determine a first sequence or chromosomal condition, event, or abnormality, and performing a second evaluation comprising any analysis as described herein to determine a second sequence or chromosomal condition, event, or abnormality. Optionally, at least 3, at least 10, at least 100, at least 1000, at least 10,000, or at least 1 million such evaluations or analyses are performed for different sequence or chromosomal conditions, events, or abnormalities. Optionally, any such analysis or evaluation may be performed in conjunction with a sequence analysis performed on unlinked sequence data.

36. Methods for Diagnosis and Monitoring

The invention provides methods of diagnosis and monitoring based on any of the methods described herein.

The invention provides a method of diagnosing a disease or condition in a test subject, wherein the method comprises: (a) determining a parameter value for a first set of linked sequence reads determined from a test sample from the subject, wherein the parameter value is determined according to any of the methods described herein; and (b) comparing the parameter value for the set of linked sequence reads determined from the test sample to a control parameter value.

The control parameter value may be determined from a second set of linked sequence reads determined from the test sample from the subject, wherein the control parameter value is determined according to any of the methods described herein.

The control parameter value may be determined from a set of linked sequence reads determined from a control sample, wherein the control parameter value is determined according to any of the methods described herein.

The disease or condition may be cancer, a chromosomal aneuploidy, or a chromosomal microdeletion, a genomic copy number variation (e.g. a copy number gain or a copy number loss), a loss-of-heterozygosity, a rearrangement or translocation event, a single-nucleotide variant, or a de novo mutation.

The invention provides a method of monitoring a disease or condition in a test subject, wherein the method comprises: (a) determining a parameter value for a first set (of sets) of linked sequence reads determined from a test sample from the subject, wherein the parameter value is determined according to any of the methods described herein; and (b) comparing the parameter value for the set of linked sequence reads to a control parameter value.

The control parameter value may be determined from a second set of linked sequence reads determined from a control sample obtained from the same subject at an earlier time point than the test sample. The time interval between the control and test samples being obtained may be at least 1 day, at least 1 week, at least 1 month or at least 1 year.

Any method of determining a parameter value and/or performing a second analysis step described herein may be performed independently on linked sets of sequences from two or more different samples from a subject separated by a time interval, where the two or more different samples are from the same subject, wherein the time interval is at least 1 day, at least 1 week, at least 1 month at least 1 year, at least 2 years, or at least 3 years. Any such parameter value and/or result of a second analysis step may be compared between any two or more such different samples. The absolute or relative difference between such parameter value and/or result of a second analysis step may be determined by such a comparison step. Optionally, such absolute or relative differences may be normalised to and/or divided by the length of the time interval between the two samples. Optionally, such absolute or relative differences and/or associated normalised values may be compared with one or more threshold values, wherein a value above such a threshold value may indicate a disease or a condition, such as cancer or a heightened risk of cancer development.

The disease or condition may be cancer.

The invention provides a method of diagnosing a disease or condition in a subject, wherein the method comprises: (a) determining a set of linked sequence reads according to any of the methods described herein, wherein the sample comprises a microparticle originating from blood;

and (b) comparing (at least a portion of) each sequence read of the set of linked sequence reads to a reference list of sequences present in cells of the disease, wherein the presence of one or more sequences from the reference list within one or more sequence reads of the set of linked sequence reads indicates the presence of the disease.

The disease or condition may be cancer.

The invention provides a method of determining a set of linked sequence reads of diseased cell (e.g. tumour cell) origin, wherein the method comprises: (a) determining a set of linked sequence reads according to any of the methods described herein, wherein the sample comprises a microparticle originating from blood; and (b) comparing (at least a portion of) each sequence read of the set of linked sequence reads to a reference list of sequences present in cells of the disease (e.g. cells of a tumour); and (c) identifying a set of linked sequence reads of diseased cell (e.g. tumour cell) origin by the presence of one or more sequences from the reference list within one or more sequence reads of the set of linked sequence reads.

The invention provides a method of determining a tumour genotype comprising: (a) determining a set of linked sequence reads of tumour origin according to any of the methods described herein; and (b) determining the tumour genotype from the set of linked sequence reads of tumour origin.

The sample may comprise a microparticle (or microparticles) originating from blood from a patient diagnosed with the disease (e.g. cancer).

The invention is further defined in the following set of numbered clauses:

1. A method of analysing a sample comprising a microparticle originating from blood, wherein the microparticle contains at least two fragments of genomic DNA, and wherein the method comprises:
    (a) preparing the sample for sequencing comprising linking at least two of the at least two fragments of genomic DNA to produce a set of at least two linked fragments of genomic DNA; and
    (b) sequencing each of the linked fragments in the set to produce at least two linked sequence reads.
2. The method of clause 1, wherein at least 3, at least 4, at least 5, at least 10, at least 50, at least 100, at least 500, at least 1000, at least 5000, at least 10,000, at least 100,000, or at least 1,000,000 fragments of genomic DNA of the microparticle are linked and then sequenced to produce at least 3, at least 4, at least 5, at least 10, at least 50, at least 100, at least 500, at least 1000, at least 5000, at least 10,000, at least 100,000, or at least 1,000,000 linked sequence reads.
3. The method of clause 1 or clause 2, wherein the diameter of the microparticle is 100-5000 nm.
4. The method of any one of clauses 1-3, wherein the linked fragments of genomic DNA originate from a single genomic DNA molecule.
5. The method of any one of clauses 1-4, wherein the method further comprises estimating or determining the genomic sequence length of the linked fragments of genomic DNA.
6. The method of any one of clauses 1-5, wherein the method further comprises the step of isolating the microparticle(s) from blood, plasma or serum.
7. The method of clause 6, wherein the step of isolating comprises centrifugation.
8. The method of clause 6 or clause 7, wherein the step of isolating comprises size exclusion chromatography.
9. The method of any one of clauses 6-8, wherein the step of isolating comprises filtering.
10. The method of any one of clauses 1-9, wherein the sample comprises first and second microparticles originating from blood, wherein each microparticle contains at least two fragments of genomic DNA, and wherein the method comprises performing step (a) to produce a first set of linked fragments of genomic DNA for the first microparticle and a second set of linked fragments of genomic DNA for the second microparticle, and performing step (b) to produce a first set of linked sequence reads for the first microparticle and a second set of linked sequence reads for the second microparticle.
11. The method of any one of clauses 1-9, wherein the sample comprises n microparticles originating from blood, wherein each microparticle contains at least two fragments of genomic DNA, and wherein the method comprises performing step (a) to produce n sets of linked fragments of genomic DNA, one set for each of the n microparticles, and performing step (b) to produce n sets of linked sequence reads, one for each of the n microparticles.
12. The method of clause 11, wherein n is at least 3, at least 5, at least 10, at least 50, at least 100, at least 1000, at least 10,000, at least 100,000, at least 1,000,000, at least 10,000,000, or at least 100,000,000 microparticles.
13. The method of any one of clauses 10-12, wherein prior to step (a), the method further comprises the step of partitioning the sample into at least two different reaction volumes.
14. A method of preparing a sample for sequencing, wherein the sample comprise a microparticle originating from blood, wherein the microparticle contains at least two fragments of genomic DNA, and wherein the method comprises appending the at least two fragments of genomic DNA of the microparticle to a barcode sequence, or to different barcode sequences of a set of barcode sequences, to produce a set of linked fragments of genomic DNA.
15. The method of clause 14, wherein prior to the step of appending the at least two fragments of genomic DNA of the microparticle to a barcode sequence, or to different barcode sequences of a set of barcode sequences, the method comprises appending a coupling sequence to each of the fragments of genomic DNA of the microparticle, wherein the coupling sequences are then appended to the barcode sequence, or to the different barcode sequences of a set of barcode sequences, to produce the set of linked fragments of genomic DNA.
16. The method of clause 14 or clause 15, wherein the sample comprises first and second microparticles originating from blood, wherein each microparticle contains at least two fragments of genomic DNA, and wherein the method comprises appending the at least two fragments of genomic DNA of the first microparticle to a first barcode sequence, or to different barcode sequences of a first set of barcode sequences, to produce a first set of linked fragments of genomic DNA and appending the at least two fragments of genomic DNA of the second microparticle to a second barcode sequence, or to different barcode sequences of a second set of barcode sequences, to produce a second set of linked fragments of genomic DNA.

17. The method of any one of clauses 1-13, wherein the method comprises:
   (a) preparing the sample for sequencing comprising appending the at least two fragments of genomic DNA of the microparticle to a barcode sequence to produce a set of linked fragments of genomic DNA; and
   (b) sequencing each of the linked fragments in the set to produce at least two linked sequence reads, wherein the at least two linked sequence reads are linked by the barcode sequence.

18. The method of clause 17, wherein prior to the step of appending the at least two fragments of genomic DNA of the microparticle to a barcode sequence, the method comprises appending a coupling sequence to each of the fragments of genomic DNA of the microparticle, wherein the coupling sequences are then appended to the barcode sequence to produce the set of linked fragments of genomic DNA.

19. The method of clause 17 or clause 18, wherein the sample comprises first and second microparticles originating from blood, wherein each microparticle contains at least two fragments of genomic DNA, and wherein the method comprises performing step (a) to produce a first set of linked fragments of genomic DNA for the first microparticle and a second set of linked fragments of genomic DNA for the second microparticle, and performing step (b) to produce a first set of linked sequence reads for the first microparticle and a second set of linked sequence reads for the second microparticle, wherein the at least two linked sequence reads for the first microparticle are linked by a different barcode sequence to the at least two linked sequence reads of the second microparticle.

20. The method of any one of clauses 1-13, wherein the method comprises:
   (a) preparing the sample for sequencing comprising appending each of the at least two fragments of genomic DNA of the microparticle to a different barcode sequence of a set of barcode sequences to produce a set of linked fragments of genomic DNA; and
   (b) sequencing each of the linked fragments in the set to produce at least two linked sequence reads, wherein the at least two linked sequence reads are linked by the set of barcode sequences.

21. The method of clause 20, wherein prior to the step of appending each of the at least two fragments of genomic DNA of the microparticle to a different barcode sequence, the method comprises appending a coupling sequence to each of the fragments of genomic DNA of the microparticle, wherein each of the at least two fragments of genomic DNA of the microparticle is appended to a different barcode sequence of the set of barcode sequences by its coupling sequence.

22. The method of clause 20 or clause 21, wherein the sample comprises first and second microparticles originating from blood, wherein each microparticle contains at least two fragments of genomic DNA, and wherein the method comprises performing step (a) to produce a first set of linked fragments of genomic DNA for the first microparticle and a second set of linked fragments of genomic DNA for the second microparticle, and performing step (b) to produce a first set of linked sequence reads for the first microparticle and a second set of linked sequence reads for the second microparticle, wherein the first set of linked sequence reads are linked by a different set of barcode sequences to the second set of linked sequence reads.

23. The method of any one of clauses 14-22, wherein the method comprises preparing first and second samples for sequencing, wherein each sample comprises at least one microparticle originating from blood, wherein each microparticle contains at least two fragments of genomic DNA, and wherein the barcode sequences each comprise a sample identifier region, and wherein the method comprises:
   (i) performing step (a) for each sample, wherein the barcode sequence(s) appended to the fragments of genomic DNA from the first sample have a different sample identifier region to the barcode sequence(s) appended to the fragments of genomic DNA from the second sample;
   (ii) performing step (b) for each sample, wherein each linked sequence read comprises the sequence of the sample identifier region; and
   (iii) determining the sample from which each linked sequence read is derived by its sample identifier region.

24. The method of any one of clauses 14-23, wherein before, during, and/or after the step(s) of appending barcode sequences and/or coupling sequences, the method comprises the step of cross-linking the fragments of genomic DNA in the microparticle(s).

25. The method of any one of clauses 14-24, wherein before, during, and/or after the step(s) of appending barcode sequences and/or coupling sequences, and/or optionally after the step of cross-linking the fragments of genomic DNA in the microparticle(s), the method comprises the step of permeabilising the microparticle(s).

26. The method of any one of clauses 14-25, wherein prior to the step of appending, the method further comprises the step of partitioning the sample into at least two different reaction volumes.

27. A method of preparing a sample for sequencing, wherein the sample comprises first and second microparticles originating from blood, and wherein each microparticle contains at least two fragments of a target nucleic acid, and wherein the method comprises the steps of:
   (a) contacting the sample with a library comprising at least two multimeric barcoding reagents, wherein each multimeric barcoding reagent comprises first and second barcode regions linked together, wherein each barcode region comprises a nucleic acid sequence and wherein the first and second barcode regions of a first multimeric barcoding reagent are different to the first and second barcode regions of a second multimeric barcoding reagent of the library; and
   (b) appending barcode sequences to each of first and second fragments of the target nucleic acid of the first microparticle to produce first and second barcoded target nucleic acid molecules for the first microparticle, wherein the first barcoded target nucleic acid molecule comprises the nucleic acid sequence of the first barcode region of the first multimeric barcoding reagent and the second barcoded target nucleic acid molecule comprises the nucleic acid sequence of the second barcode region of the first multimeric barcoding reagent, and appending barcode sequences to each of first and second fragments of the target nucleic acid of the second microparticle to produce first and second barcoded target nucleic acid molecules for the second microparticle, wherein the first barcoded target nucleic acid molecule comprises the nucleic acid sequence of the first barcode region of the second multimeric barcoding reagent and the second barcoded target nucleic acid molecule comprises the nucleic acid sequence of the second barcode region of the second multimeric barcoding reagent.
28. The method of clause 27, wherein the method comprises the steps of:
  (a) contacting the sample with a library comprising at least two multimeric barcoding reagents, wherein each multimeric barcoding reagent comprises first and second barcoded oligonucleotides linked together, wherein the barcoded oligonucleotides each comprise a barcode region and wherein the barcode regions of the first and second barcoded oligonucleotides of a first multimeric barcoding reagent of the library are different to the barcode regions of the first and second barcoded oligonucleotides of a second multimeric barcoding reagent of the library; and
  (b) annealing or ligating the first and second barcoded oligonucleotides of the first multimeric barcoding reagent to first and second fragments of the target nucleic acid of the first microparticle to produce first and second barcoded target nucleic acid molecules, and annealing or ligating the first and second barcoded oligonucleotides of the second multimeric barcoding reagent to first and second fragments of the target nucleic acid of the second microparticle to produce first and second barcoded target nucleic acid molecules.
29. The method of clause 28, wherein prior to the step of annealing or ligating the first and second barcoded oligonucleotides to first and second fragments of genomic DNA, the method comprises appending a coupling sequence to each of the fragments of genomic DNA, wherein the first and second barcoded oligonucleotides are then annealed or ligated to the coupling sequences of the first and second fragments of genomic DNA.
30. The method of clause 28 or clause 29, wherein step (b) comprises:
  (i) annealing the first and second barcoded oligonucleotides of the first multimeric barcoding reagent to first and second fragments of genomic DNA of the first microparticle, and annealing the first and second barcoded oligonucleotides of the second multimeric barcoding reagent to first and second fragments of genomic DNA of the second microparticle; and
  (ii) extending the first and second barcoded oligonucleotides of the first multimeric barcoding reagent to produce first and second different barcoded target nucleic acid molecules and extending the first and second barcoded oligonucleotides of the second multimeric barcoding reagent to produce first and second different barcoded target nucleic acid molecules, wherein each of the barcoded target nucleic acid molecules comprises at least one nucleotide synthesised from the fragments of genomic DNA as a template.
31. The method of clause 28 or clause 29, wherein the method comprises:
  (a) contacting the sample with a library comprising at least two multimeric barcoding reagents, wherein each multimeric barcoding reagent comprises first and second barcoded oligonucleotides linked together, wherein the barcoded oligonucleotides each comprise in the 5' to 3' direction a target region and a barcode region, wherein the barcode regions of the first and second barcoded oligonucleotides of a first multimeric barcoding reagent of the library are different to the barcode regions of the first and second barcoded oligonucleotides of a second multimeric barcoding reagent of the library, and wherein the sample is further contacted with first and second target primers for each multimeric barcoding reagent; and
  (b) performing the following steps for each microparticle
    (i) annealing the target region of the first barcoded oligonucleotide to a first sub-sequence of a first fragment of the target nucleic acid of the microparticle, and annealing the target region of the second barcoded oligonucleotide to a first sub-sequence of a second fragment of the target nucleic acid of the microparticle,
    (ii) annealing the first target primer to a second sub-sequence of the first fragment of the target nucleic acid of the microparticle, wherein the second sub-sequence is 3' of the first sub-sequence, and annealing the second target primer to a second sub-sequence of the second fragment of the target nucleic acid of the microparticle, wherein the second sub-sequence is 3' of the first sub-sequence,
    (iii) extending the first target primer using the first fragment of the target nucleic acid of the microparticle as template until it reaches the first sub-sequence to produce a first extended target primer, and extending the second target primer using the second fragment of the target nucleic acid of the microparticle until it reaches the first sub-sequence to produce a second extended target primer, and
    (iv) ligating the 3' end of the first extended target primer to the 5' end of the first barcoded oligonucleotide to produce a first barcoded target nucleic acid molecule, and ligating the 3' end of the second extended target primer to the 5' end of the second barcoded oligonucleotide to produce a second barcoded target nucleic acid molecule, wherein the first and second barcoded target nucleic acid molecules are different and each comprises at least one nucleotide synthesised from the target nucleic acid as a template.
32. The method of any one of clauses 27-31, wherein the multimeric barcoding reagents each comprise:
  (i) first and second hybridization molecules linked together, wherein each of the hybridization molecules comprises a nucleic acid sequence comprising a hybridization region; and
  (ii) first and second barcoded oligonucleotides, wherein the first barcoded oligonucleotide is annealed to the hybridization region of the first hybridization molecule and wherein the second barcoded oligonucleotide is annealed to the hybridization region of the second hybridization molecule.
33. The method of clause 32, wherein the multimeric barcoding reagents each comprise:
  (i) first and second barcode molecules linked together, wherein each of the barcode molecules comprises a nucleic acid sequence comprising a barcode region; and
  (ii) first and second barcoded oligonucleotides, wherein the first barcoded oligonucleotide comprises a barcode region annealed to the barcode region of the first barcode molecule, and wherein the second barcoded oligonucleotide comprises a barcode region annealed to the barcode region of the second barcode molecule.
34. A method of preparing a sample for sequencing, wherein the sample comprises at least two microparticles originating from blood, wherein each microparticle comprises at least two fragments of a target nucleic acid, and wherein the method comprises the steps of:
  (a) contacting the sample with a library comprising first and second multimeric barcoding reagents, wherein each multimeric barcoding reagent comprises first and second barcode molecules linked together, wherein each of the barcode molecules comprises a nucleic acid sequence comprising, optionally in the 5' to 3' direction, a barcode region and an adapter region;
  (b) appending a coupling sequence to first and second fragments of the target nucleic acid of first and second microparticles;
  (c) for each of the multimeric barcoding reagents, annealing the coupling sequence of the first fragment to the adapter region of the first barcode molecule, and annealing the coupling sequence of the second fragment to the adapter region of the second barcode molecule; and
  (d) for each of the multimeric barcoding reagents, appending barcode sequences to each of the at least two fragments of the target nucleic acid of the microparticle to produce first and second different barcoded target nucleic acid molecules, wherein the first barcoded target nucleic acid molecule comprises the nucleic acid sequence of the barcode region of the first barcode molecule and the second barcoded target nucleic acid molecule comprises the nucleic acid sequence of the barcode region of the second barcode molecule.

35. The method of clause 34, wherein each of the barcode molecules comprises a nucleic acid sequence comprising, in the 5' to 3' direction, a barcode region and an adapter region, and wherein step (d) comprises, for each of the multimeric barcoding reagents, extending the coupling sequence of the first fragment using the barcode region of the first barcode molecule as a template to produce a first barcoded target nucleic acid molecule, and extending the coupling sequence of the second fragment using the barcode region of the second barcode molecule as a template to produce a second barcoded target nucleic acid molecule, wherein the first barcoded target nucleic acid molecule comprises a sequence complementary to the barcode region of the first barcode molecule and the second barcoded target nucleic acid molecule comprises a sequence complementary to the barcode region of the second barcode molecule.

36. The method of clause 34, wherein each of the barcode molecules comprises a nucleic acid sequence comprising, in the 5' to 3' direction, an adapter region and a barcode region, wherein step (d) comprises, for each of the multimeric barcoding reagents,
  (i) annealing and extending a first extension primer using the barcode region of the first barcode molecule as a template to produce a first barcoded oligonucleotide, and annealing and extending a second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule,
  (ii) ligating the 3' end of the first barcoded oligonucleotide to the 5' end of the coupling sequence of the first fragment to produce a first barcoded target nucleic acid molecule and ligating the 3' end of the second barcoded oligonucleotide to the 5' end of the coupling sequence of the second fragment to produce a second barcoded target nucleic acid molecule.

37. The method of clause 34, wherein each of the barcode molecules comprises a nucleic acid sequence comprising, in the 5' to 3' direction, an adapter region, a barcode region and a priming region wherein step (d) comprises, for each of the multimeric barcoding reagents,
  (i) annealing a first extension primer to the priming region of the first barcode molecule and extending the first extension primer using the barcode region of the first barcode molecule as a template to produce a first barcoded oligonucleotide, and annealing a second extension primer to the priming region of the second barcode molecule and extending the second extension primer using the barcode region of the second barcode molecule as a template to produce a second barcoded oligonucleotide, wherein the first barcoded oligonucleotide comprises a sequence complementary to the barcode region of the first barcode molecule and the second barcoded oligonucleotide comprises a sequence complementary to the barcode region of the second barcode molecule, and
  (ii) ligating the 3' end of the first barcoded oligonucleotide to the 5' end of the coupling sequence of the first fragment to produce a first barcoded target nucleic acid molecule and ligating the 3' end of the second barcoded oligonucleotide to the 5' end of the coupling sequence of the second fragment to produce a second barcoded target nucleic acid molecule.

38. The method of clause 34, wherein the method comprises the steps of:
  (a) contacting the sample with a library comprising first and second multimeric barcoding reagents, wherein each multimeric barcoding reagent comprises first and second barcode molecules linked together, wherein each of the barcode molecules comprises a nucleic acid sequence comprising, in the 5' to 3' direction, a barcode region and an adapter region, and wherein the sample is further contacted with first and second adapter oligonucleotides for each of the multimeric barcoding reagents, wherein the first and second adapter oligonucleotides each comprise an adapter region, and;
  (b) ligating the first and second adapter oligonucleotides for the first multimeric barcoding reagent to first and second fragments of the target nucleic acid of the first microparticle, and ligating the first and second adapter oligonucleotides for the second multimeric barcoding reagent to first and second fragments of the target nucleic acid of the second microparticle;
  (c) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and
  (d) for each of the multimeric barcoding reagents, extending the first adapter oligonucleotide using the barcode region of the first barcode molecule as a template to produce a first barcoded target nucleic acid molecule, and extending the second adapter oligonucleotide using the barcode region of the second barcode molecule as a template to produce a second barcoded target nucleic acid molecule, wherein the first barcoded target nucleic acid molecule comprises a sequence complementary to the barcode region of the first barcode molecule and the second barcoded target nucleic acid molecule comprises a sequence complementary to the barcode region of the second barcode molecule.
39. The method of clause 34, wherein the method comprises the steps of:
(a) contacting the sample with a library comprising first and second multimeric barcoding reagents, wherein each multimeric barcoding reagent comprises:
(i) first and second barcode molecules linked together, wherein each of the barcode molecules comprises a nucleic acid sequence comprising, optionally in the 5' to 3' direction, an adapter region and a barcode region, and
(ii) first and second barcoded oligonucleotides, wherein the first barcoded oligonucleotide comprises a barcode region annealed to the barcode region of the first barcode molecule, wherein the second barcoded oligonucleotide comprises a barcode region annealed to the barcode region of the second barcode molecule, and wherein the barcode regions of the first and second barcoded oligonucleotides of the first multimeric barcoding reagent of the library are different to the barcode regions of the first and second barcoded oligonucleotides of the second multimeric barcoding reagent of the library;
wherein the sample is further contacted with first and second adapter oligonucleotides for each of the multimeric barcoding reagents, wherein the first and second adapter oligonucleotides each comprise an adapter region;
(b) annealing or ligating the first and second adapter oligonucleotides for the first multimeric barcoding reagent to first and second fragments of the target nucleic acid of the first microparticle, and annealing or ligating the first and second adapter oligonucleotides for the second multimeric barcoding reagent to first and second fragments of the target nucleic acid of the second microparticle;
(c) for each of the multimeric barcoding reagents, annealing the adapter region of the first adapter oligonucleotide to the adapter region of the first barcode molecule, and annealing the adapter region of the second adapter oligonucleotide to the adapter region of the second barcode molecule; and
(d) for each of the multimeric barcoding reagents, ligating the 3' end of the first barcoded oligonucleotide to the 5' end of the first adapter oligonucleotide to produce a first barcoded target nucleic acid molecule and ligating the 3' end of the second barcoded oligonucleotide to the 5' end of the second adapter oligonucleotide to produce a second barcoded target nucleic acid molecule.
40. The method of clause 39, wherein step (b) comprises annealing the first and second adapter oligonucleotides for the first multimeric barcoding reagent to first and second fragments of the target nucleic acid of the first microparticle, and annealing the first and second adapter oligonucleotides for the second multimeric barcoding reagent to first and second fragments of the target nucleic acid of the second microparticle, and wherein either:
(i) for each of the multimeric barcoding reagents, step (d) comprises ligating the 3' end of the first barcoded oligonucleotide to the 5' end of the first adapter oligonucleotide to produce a first barcoded-adapter oligonucleotide and ligating the 3' end of the second barcoded oligonucleotide to the 5' end of the second adapter oligonucleotide to produce a second barcoded-adapter oligonucleotide, and extending the first and second barcoded-adapter oligonucleotides to produce first and second different barcoded target nucleic acid molecules each of which comprises at least one nucleotide synthesised from the fragments of the target nucleic acid as a template, or
(ii) for each of the multimeric barcoding reagents, before step (d), the method comprises extending the first and second adapter oligonucleotides to produce first and second different target nucleic acid molecules each of which comprises at least one nucleotide synthesised from the fragments of the target nucleic acid as a template.
41. The method of any one of clauses 38-40, wherein prior to the step of annealing or ligating the first and second adapter oligonucleotides to first and second fragments of the target nucleic acid, the method comprises appending a coupling sequence to each of the fragments of the target nucleic acid, wherein the first and second adapter oligonucleotides are then annealed or ligated to the coupling sequences of the first and second fragments of the target nucleic acid.
42. The method of any one of clauses 27-41, wherein steps (a) and (b), and optionally (c) and (d), are performed on the at least two microparticles in a single reaction volume.
43. The method of any one of clauses 27-41, wherein prior to step (b), the method further comprises the step of partitioning the sample into at least two different reaction volumes.
44. The method of any one of clauses 1-26, wherein the method comprises:
(a) preparing the sample for sequencing comprising:
(i) contacting the sample with a multimeric barcoding reagent comprising first and second barcode regions linked together, wherein each barcode region comprises a nucleic acid sequence, and
(ii) appending barcode sequences to each of the at least two fragments of genomic DNA of the microparticle to produce first and second different barcoded target nucleic acid molecules, wherein the first barcoded target nucleic acid molecule comprises the nucleic acid sequence of the first barcode region and the second barcoded target nucleic acid molecule comprises the nucleic acid sequence of the second barcode region; and
(b) sequencing each of the barcoded target nucleic acid molecules to produce at least two linked sequence reads.
45. The method of clause 44, wherein prior to the step of appending barcode sequences to each of the at least two fragments of genomic DNA of the microparticle, the method comprises appending a coupling sequence to each of the fragments of genomic DNA of the microparticle, wherein a barcode sequence is then appended to the coupling sequence of each of the at least two fragments of genomic DNA of the microparticle to produce the first and second different barcoded target nucleic acid molecules.
46. The method of clause 44 or clause 45, wherein step (a) is performed by the method of any one of clauses 27-43.
47. The method of any one of clauses 44-46, wherein the method comprises preparing first and second samples for sequencing, wherein each sample comprises at least one microparticle originating from blood, wherein the microparticle contains at least two fragments of genomic DNA, and wherein the barcode sequences each comprise a sample identifier region, and wherein the method comprises:
(i) performing step (a) for each sample, wherein the barcode sequence(s) appended to the fragments of genomic DNA from the first sample have a different sample identifier region to the barcode sequence(s) appended to the fragments of genomic DNA from the second sample;
(ii) performing step (b) for each sample, wherein each sequence read comprises the sequence of the sample identifier region; and
(iii) determining the sample from which each sequence read is derived by its sample identifier region.
48. The method of any one of clauses 44-47, wherein the method comprises analysing a sample comprising at least two microparticles originating from blood, wherein each microparticle contains at least two fragments of genomic DNA, and wherein the method comprises the steps of:
 (a) preparing the sample for sequencing comprising:
  (i) contacting the sample with a library of multimeric barcoding reagents comprising a multimeric barcoding reagent for each of the two or more microparticles, wherein each multimeric barcoding reagent is as defined in any one of clauses 44-46; and
  (ii) appending barcode sequences to each of the at least two fragments of genomic DNA of each microparticle, wherein at least two barcoded target nucleic acid molecules are produced from each of the at least two microparticles, and wherein the at least two barcoded target nucleic acid molecules produced from a single microparticle each comprise the nucleic acid sequence of a barcode region from the same multimeric barcoding reagent; and
 (b) sequencing each of the barcoded target nucleic acid molecules to produce at least two linked sequence reads for each microparticle.
49. The method of clause 48, wherein barcode sequences are appended to the fragments of genomic DNA of the microparticles in a single reaction volume.
50. The method of clause 48, wherein prior to the step of appending, the method further comprises the step of partitioning the sample into at least two different reaction volumes.
51. The method of any one of clauses 1-13, wherein the method comprises:
 (a) preparing the sample for sequencing comprising linking together at least two fragments of genomic DNA of the microparticle to produce a single nucleic acid molecule comprising the sequences of the at least two fragments of genomic DNA; and
 (b) sequencing each of the fragments in the single nucleic acid molecule to produce at least two linked sequence reads.
52. The method of clause 51, wherein the at least two fragments of genomic DNA are contiguous in the single nucleic acid molecule.
53. The method of clause 51, wherein prior to the step of linking, the method comprises appending a coupling sequence to at least one of the fragments of genomic DNA and then linking together the at least two fragments of genomic DNA by the coupling sequence.
54. The method of clause 51-53, wherein the fragments of genomic DNA are linked together by a ligation reaction.
55. The method of any one of clauses 51-54, wherein the sample comprises at least two microparticles originating from blood, wherein each microparticle contains at least two fragments of genomic DNA, and wherein the method comprises performing step (a) to produce a single nucleic acid molecule comprising the sequences of the at least two fragments of genomic DNA for each microparticle, and performing step (b) to produce linked sequence reads for each microparticle.
56. The method of any clauses 51-55, wherein before, during, and/or after the step of linking together at least two fragments of genomic DNA, the method comprises the step of cross-linking the fragments of genomic DNA in the microparticle(s).
57. The method of any clauses 51-56, wherein before, during, and/or after the step of linking together at least two fragments of genomic DNA, and/or optionally after the step of cross-linking the fragments of genomic DNA in the microparticle(s), the method comprises the step of permeabilising the microparticle(s).
58. The method of any one of clauses 55-57, wherein prior to step (a), the method further comprises the step of partitioning the sample into at least two different reaction volumes.
59. The method of any one of clauses 13, 26, 43, 50 and 58, wherein a sample comprising at least two microparticles is partitioned into at least two different reaction volumes.
60. The method of clause 59, wherein the different reaction volumes are provided by different reaction vessels.
61. The method of clause 59, wherein the different reaction volumes are provided by different aqueous droplets.
62. The method of clause 61, wherein the different aqueous droplets are different aqueous droplets within an emulsion.
63. The method of clause 61, wherein the different aqueous droplets are different aqueous droplets on a solid support.
64. The method of any one of clauses 1-13, wherein the method comprises:
 (a) preparing the sample for sequencing, wherein the at least two fragments of genomic DNA of the microparticle are linked by their proximity to each other on a sequencing apparatus to produce a set of at least two linked fragments of genomic DNA; and
 (b) sequencing each of the linked fragments of genomic DNA using the sequencing apparatus to produce at least two linked sequence reads.
65. The method of clause 64, wherein the sample comprises at least two microparticles originating from blood, wherein each microparticle contains at least two fragments of genomic DNA, and wherein the method comprises performing step (a) to produce a set of linked fragments of genomic DNA for each microparticle and wherein the fragments of genomic DNA of each microparticle are spatially distinct on the sequencing apparatus, and performing step (b) to produce linked sequence reads for each microparticle.
66. The method of any one of clauses 1-13, wherein the sample comprises:
 (a) preparing the sample for sequencing, wherein the at least two fragments of genomic DNA of each microparticle are linked by being loaded into a separate sequencing process to produce a set of at least two linked fragments of genomic DNA; and
 (b) sequencing each of the linked fragments of genomic DNA using the sequencing apparatus to produce at least two linked sequence reads.
67. The method of clause 66, wherein the sample comprises at least two microparticles originating blood, wherein each microparticle contains at least two fragments of genomic DNA, and wherein the method comprises performing step (a) to produce linked fragments of genomic DNA for each microparticle wherein the at least two fragments of genomic DNA of each microparticle are linked by being loaded into a separate sequencing process, and performing step (b) for each sequencing process to produce linked sequence reads for each microparticle.

68. A method of determining a set of linked sequence reads of fragments of genomic DNA from a single microparticle, wherein the method comprises:
    (a) analyzing a sample according to the method of any one of clauses 1-26 and 44-67; and
    (b) determining two or more linked sequence reads.

69. The method of clause 68, wherein the two or more linked sequence reads are determined by identifying sequence reads comprising the same barcode sequence.

70. The method of clause 68, wherein the two or more linked sequence reads are determined by identifying sequence reads comprising different barcode sequences from the same set of barcode sequences.

71. The method of clause 68, wherein the two or more linked sequence reads are determined by identifying sequence reads comprising barcode sequences of barcode regions from the same multimeric barcoding reagent.

72. A method of determining the total number of sets of linked sequence reads within a sequence dataset comprising:
    (a) analyzing a sample according to the method of any one of clauses 1-26 and 44-67; and
    (b) determining the number of sets of linked sequence reads.

73. The method of clause 72, wherein the number of sets of linked sequence reads is determined by counting the number of sequence reads comprising different barcode sequences.

74. The method of clause 72, wherein the number of sets of linked sequence reads is determined by counting the sets of barcode sequences that have a barcode sequence in a sequence read.

75. The method of clause 72, wherein the number of sets of linked sequence reads is determined by counting the number of multimeric barcoding reagents that have a barcode region the barcode sequence of which is in a sequence read.

76. A method of determining a parameter value from a set of linked sequence reads, wherein the method comprises:
    (a) determining a set of linked sequence reads according to the method of any one or clauses 68-71; and
    (b) mapping at least a portion of each sequence read of the set of linked sequence reads to one or more reference nucleotide sequences; and
    (c) determining the parameter value by counting or identifying the presence of one or more reference nucleotide sequences within the set of linked sequence reads.

77. A method of determining a group of sets of linked sequence reads comprising:
    (a) determining a parameter value for each of two or more sets of linked sequence reads, wherein the parameter value for each set of linked sequence reads is determined according to the method of clause 76; and
    (b) comparing the parameter values for the sets of linked sequence reads to each other or to one or more threshold values to identify a group of two or more sets of linked sequence reads.

78. A method of determining the presence of a genomic rearrangement or structural variant within a set of linked sequence reads of fragments of genomic DNA from a single microparticle, wherein the method comprises:
    (a) determining a set of linked sequence reads according to the method of any one or clauses 68-71; and
    (b) mapping at least a portion of each sequence of the set of linked sequence reads to a first reference nucleotide sequence comprising a first genomic region, and mapping at least a portion of each sequence of the set of linked sequence reads to a second reference nucleotide sequence comprising a second genomic region; and
    (c) counting the number of sequence reads from the set of linked sequence reads that are found to map within the first genomic region, and counting the number of sequence reads from the set of linked sequence reads that are found to map within the second genomic region.

79. A method of phasing two variant alleles, wherein a first variant allele is comprised within a first genomic region, and wherein a second variant allele is comprised within a second genomic region, and wherein each variant allele has at least two variants or potential variants, wherein the method comprises:
    (a) determining a set of linked sequence reads according to the method of any one or clauses 68-71; and
    (b) determining whether a sequence comprising each potential variant from the first variant allele is present within the set of linked sequence reads, and determining whether a sequence comprising each potential variant from the second variant allele is present within the same set of linked sequence reads.

80. A method of determining a set of linked sequence reads of foetal origin, wherein the method comprises:
    (a) determining a set of linked sequence reads according to the method of any one or clauses 68-71, wherein the sample comprises microparticles originating from maternal blood; and
    (b) comparing at least a portion of each sequence read of the set of linked sequence reads to a reference list of sequences present in the foetal genome; and
    (c) identifying a set of linked sequence reads of foetal origin by the presence of one or more sequences from the reference list within one or more sequence reads of the set of linked sequence reads.

81. A method of determining a foetal genotype comprising:
    (a) determining a set of linked sequence reads of foetal origin according to the method of clause 80; and
    (b) determining the foetal genotype from the set of linked sequence reads of foetal origin.

82. A method of diagnosing a disease or condition in a test subject, wherein the method comprises:
    (a) determining a parameter value for a first set of linked sequence reads determined from a test sample from the subject, wherein the parameter value is determined according to the method of clause 76; and
    (b) comparing the parameter value for the set of linked sequence reads determined from the test sample to a control parameter value.

83. The method of clause 82, wherein the control parameter value is determined from a second set of linked sequence reads determined from the test sample from the subject, wherein the control parameter value is determined according to the method of clause 76.

84. The method of clause 82, wherein the control parameter value is determined from a set of linked sequence reads determined from a control sample, wherein the control parameter value is determined according to the method of clause 76.

85. A method of monitoring a disease or condition in a test subject, wherein the method comprises:
    (a) determining a parameter value for a first set of linked sequence reads determined from a test sample from the subject, wherein the parameter value is determined according to the method of clause 76; and
(b) comparing the parameter value for the set of linked sequence reads to a control parameter value.
86. The method of clause 85, wherein the control parameter value is be determined from a second set of linked sequence reads determined from a control sample obtained from the same subject at an earlier time point than the test sample, optionally wherein the control parameter value is determined according to the method of clause 76.
87. A method of diagnosing a disease in a subject, wherein the method comprises:
(a) determining a set of linked sequence reads according to the method of any one or clauses 68-71, wherein the sample comprises a microparticle originating from blood; and
(b) comparing at least a portion of each sequence read of the set of linked sequence reads to a reference list of sequences present in cells of the disease, wherein the presence of one or more sequences from the reference list within one or more sequence reads of the set of linked sequence reads indicates the presence of the disease.
88. A method of determining a set of linked sequence reads of diseased cell origin, wherein the method comprises:
(a) determining a set of linked sequence reads according to any one or clauses 68-71, wherein the sample comprises a microparticle originating from blood; and
(b) comparing at least a portion of each sequence read of the set of linked sequence reads to a reference list of sequences present in cells of the disease; and
(c) identifying a set of linked sequence reads of diseased cell origin by the presence of one or more sequences from the reference list within one or more sequence reads of the set of linked sequence reads.
89. The method of clause 88, wherein the method comprises determining a set of linked sequence reads of tumour cell origin, and wherein the method comprises:
(a) determining a set of linked sequence reads according to any of one or clauses 68-71, wherein the sample comprises a microparticle originating from blood; and
(b) comparing at least a portion of each sequence read of the set of linked sequence reads to a reference list of sequences present in cells of a tumour; and
(c) identifying a set of linked sequence reads of tumour cell origin by the presence of one or more sequences from the reference list within one or more sequence reads of the set of linked sequence reads.
90. A method of determining a tumour genotype comprising:
(a) determining a set of linked sequence reads of tumour origin according to the method of clause 89; and
(b) determining the tumour genotype from the set of linked sequence reads of tumour origin.

BRIEF DESCRIPTION OF THE DRAWINGS

The invention, together with further objects and advantages thereof, may best be understood by making reference to the description taken together with the accompanying drawings, in which:
FIG. 15 is a table showing the results of barcoding genomic DNA loci of three human genes (BRCA1, HLA-A and DQB1) with multimeric barcoding reagents containing barcoded oligonucleotides.

FIG. 29 illustrates a negative-control experiment, wherein fragments of genomic DNA are purified (i.e. therefore being unlinked) before being appended to barcoded oligonucleotides. No clustering of reads is observed at all, validating that circulating microparticles comprise fragments of genomic DNA from focal, contiguous genomic regions.

A detailed description of each of FIGS. 18-29 is provided below.

Figure 18:
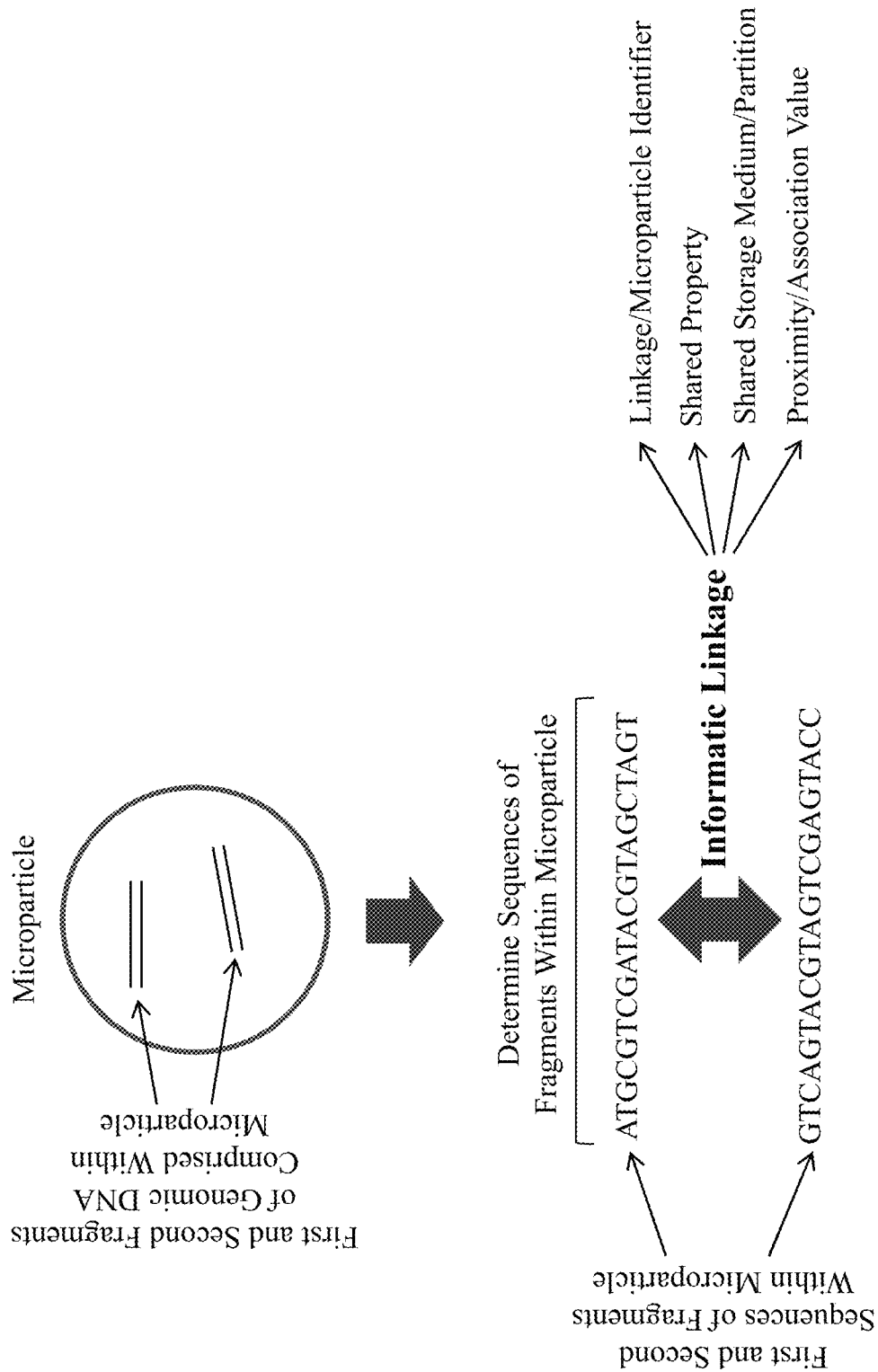
FIG. 18 illustrates a method in which two or more sequences from a microparticle are determined and linked informatically.

FIG. 18 illustrates a method in which two or more sequences from a microparticle are determined and linked informatically. In the method, a microparticle, comprised within or derived from a blood, plasma, or serum sample, comprises two or more fragments of genomic DNA. The sequences of at least parts of these fragments of genomic DNA is determined; and furthermore, through one or more methods, an informatic linkage is established such that the first and second sequences from a microparticle are linked.

This linkage may take any form, such as a shared identifier (which could, for example, derive from a shared barcode that may be appended to said first and second genomic DNA sequences during a molecular barcoding process); any other shared property may also be used to link the two sequences; the data comprising the sequences themselves may be comprised within a shared electronic storage medium or partition thereof. Furthermore, the linkage may comprise a non-binary or relative value, for example representing the physical proximity of the two fragments within a spatially-metered sequencing reaction, or representing an estimated likelihood or probability that the two sequences may derive from fragments of genomic DNA comprised within the same microparticle.

Figure 19:
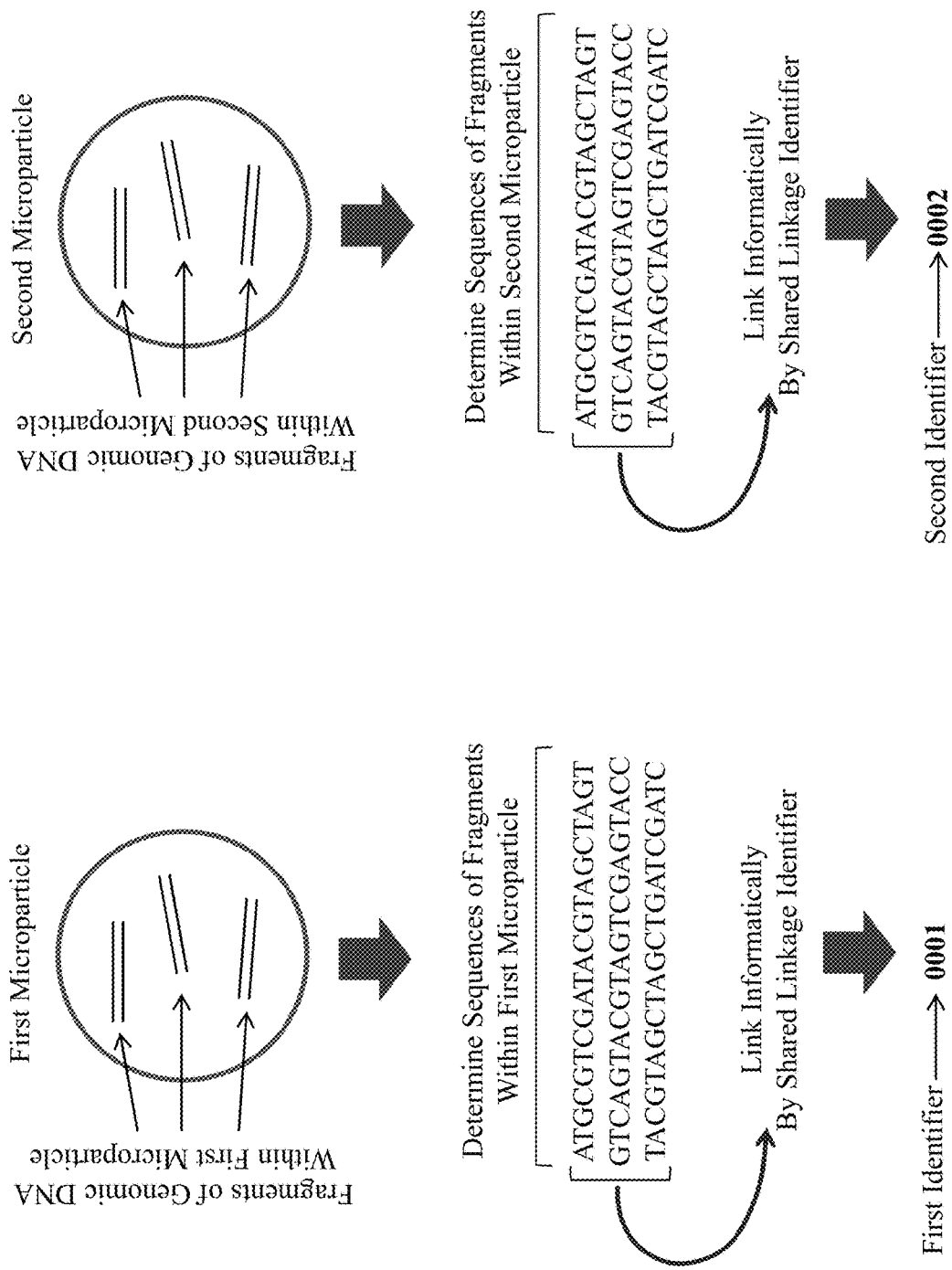
FIG. 19 illustrates a method in which sequences from a particular microparticle are linked by a shared identifier.

FIG. 19 illustrates a method in which sequences from a particular microparticle are linked by a shared identifier. In the method, a number of sequences from fragments of genomic DNA comprised within two different microparticles (e.g. two different microparticles derived from a single blood, plasma, or serum sample) are determined, e.g. by a nucleic acid sequencing reaction. Sequences corresponding to fragments of genomic DNA from the first microparticle are each assigned to the same informatic identifier (here, the identifier '0001'), and sequences corresponding to fragments of genomic DNA from the second microparticle are each assigned to the same, different informatic identifier (here, the identifier '0002'). This information of sequences and corresponding identifiers thus comprises informatic linkages between sequences derived from the same microparticle, with the set of different identifiers serving the function of informatic linkage.

Figure 20:
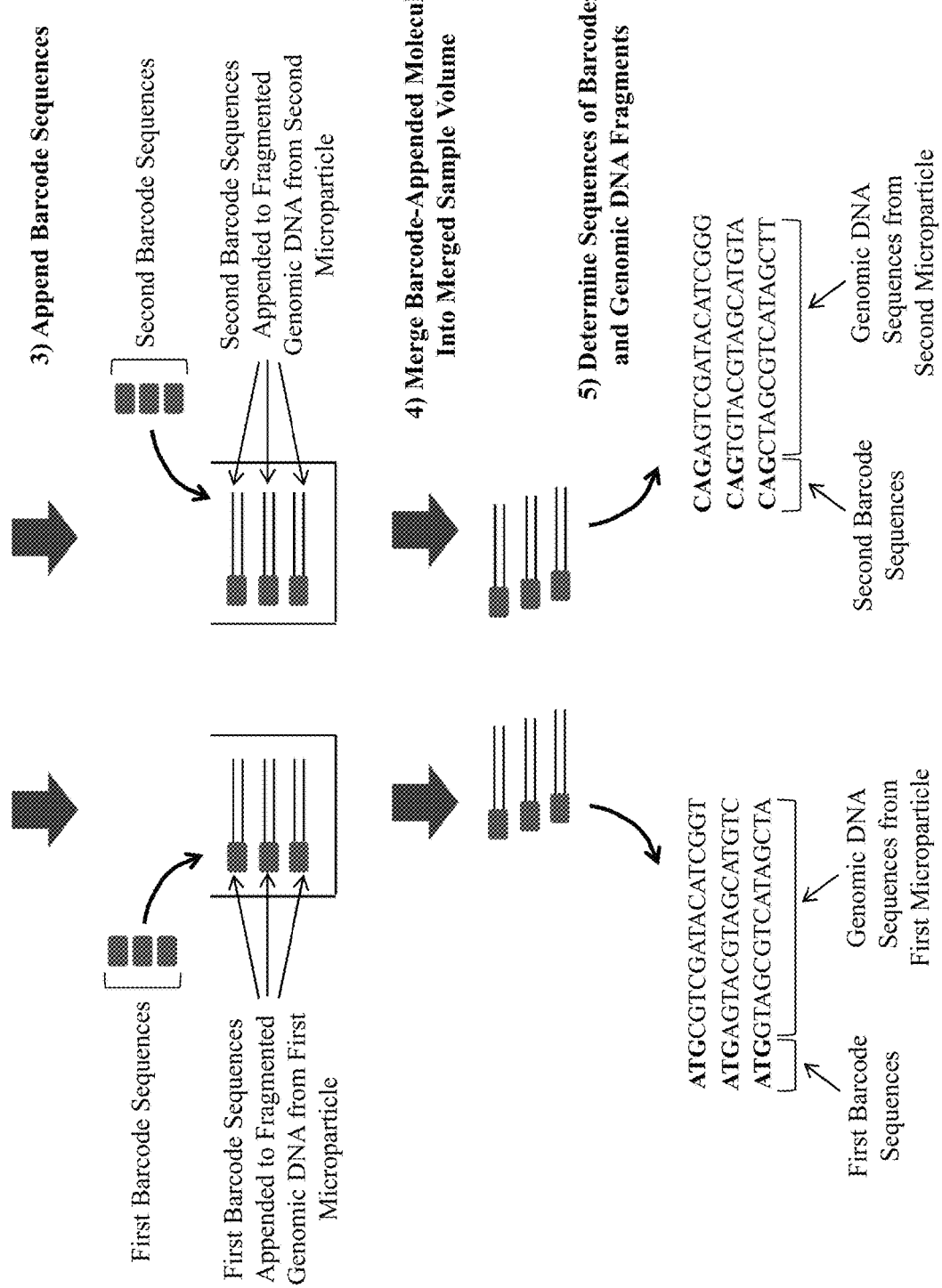
FIG. 20 illustrates a method in which molecular barcodes are appended to fragments of genomic DNA within microparticles that have been partitioned, and wherein said barcodes provide a linkage between sequences derived from the same microparticle.

FIG. 20 illustrates a method in which molecular barcodes are appended to fragments of genomic DNA within microparticles that have been partitioned, and wherein said barcodes provide a linkage between sequences derived from the same microparticle. In the method, microparticles from a sample of microparticles are partitioned into two or more partitions, and then the fragments of genomic DNA within the microparticles are barcoded within the partitions, and then sequences are determined in such a way that the barcodes identify from which partition the sequence was derived, and thereby link the different sequences from individual microparticles.

In the first step, microparticles are partitioned into two or more partitions (which could comprise, for example, different physical reaction vessels, or different droplets within an emulsion). The fragments of genomic DNA are then released from the microparticles within each partition (i.e., the fragments are made physically accessible such that they can then be barcoded). This release step may be performed with a high-temperature incubation step, and/or via incubation with a molecular solvent or chemical surfactant. Optionally (but not shown here), an amplification step may be performed at this point, prior to appending barcode sequences, such that all or part of a fragment of genomic DNA is replicated at least once (e.g. in a PCR reaction), and then barcode sequences may be subsequently appended to the resulting replication products.

Barcode sequences are then appended to the fragments of genomic DNA. The barcode sequences may take any form, such as primers which comprise a barcode region, or barcoded oligonucleotides within multimeric barcoding reagents, or barcode molecules within multimeric barcode molecules. The barcode sequences may also be appended by any means, for example by a primer-extension and/or PCR reaction, or a single-stranded or double-stranded ligation reaction, or by in vitro transposition. In any case, the process of appending barcode sequences produces a solution of molecules within each partition wherein each such molecule comprises a barcode sequence, and then all or part of a sequence corresponding to a fragment of genomic DNA from a microparticle that was partitioned into said partition.

The barcode-containing molecules from different partitions are then merged together into a single reaction, and then a sequencing reaction is performed on the resulting molecules to determine sequences of genomic DNA and the barcode sequences to which they have been appended. The associated barcode sequences are then used to identify the partitions from which each sequence was derived, and thereby link sequences determined in the sequencing reaction that were derived from fragments of genomic DNA comprised within the same microparticle or group of microparticles.

Figure 21:
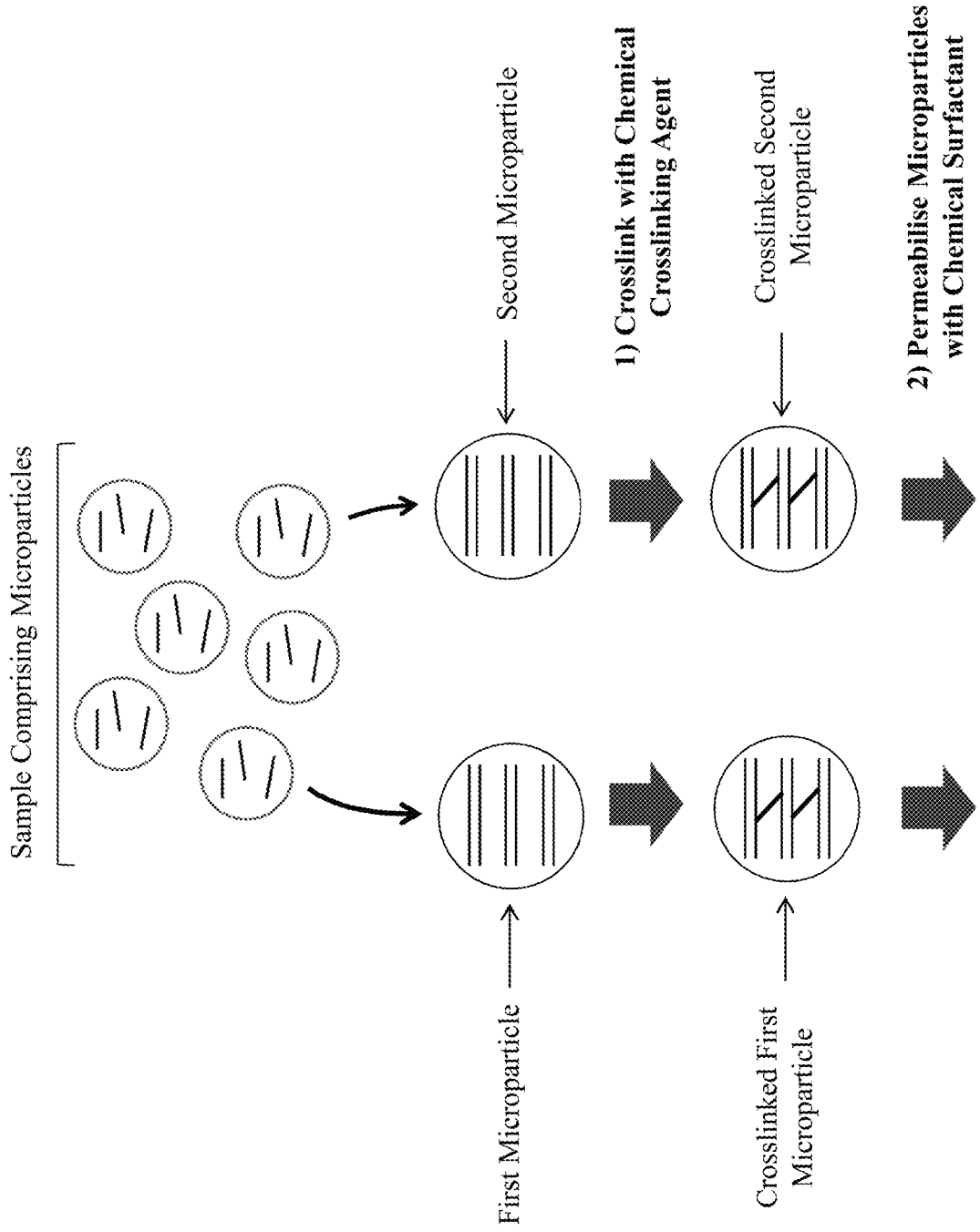
FIG. 21 illustrates a specific method in which molecular barcodes are appended to fragments of genomic DNA within microparticles by multimeric barcoding reagents, and wherein said barcodes provide a linkage between sequences derived from the same microparticle.
Figure 21:
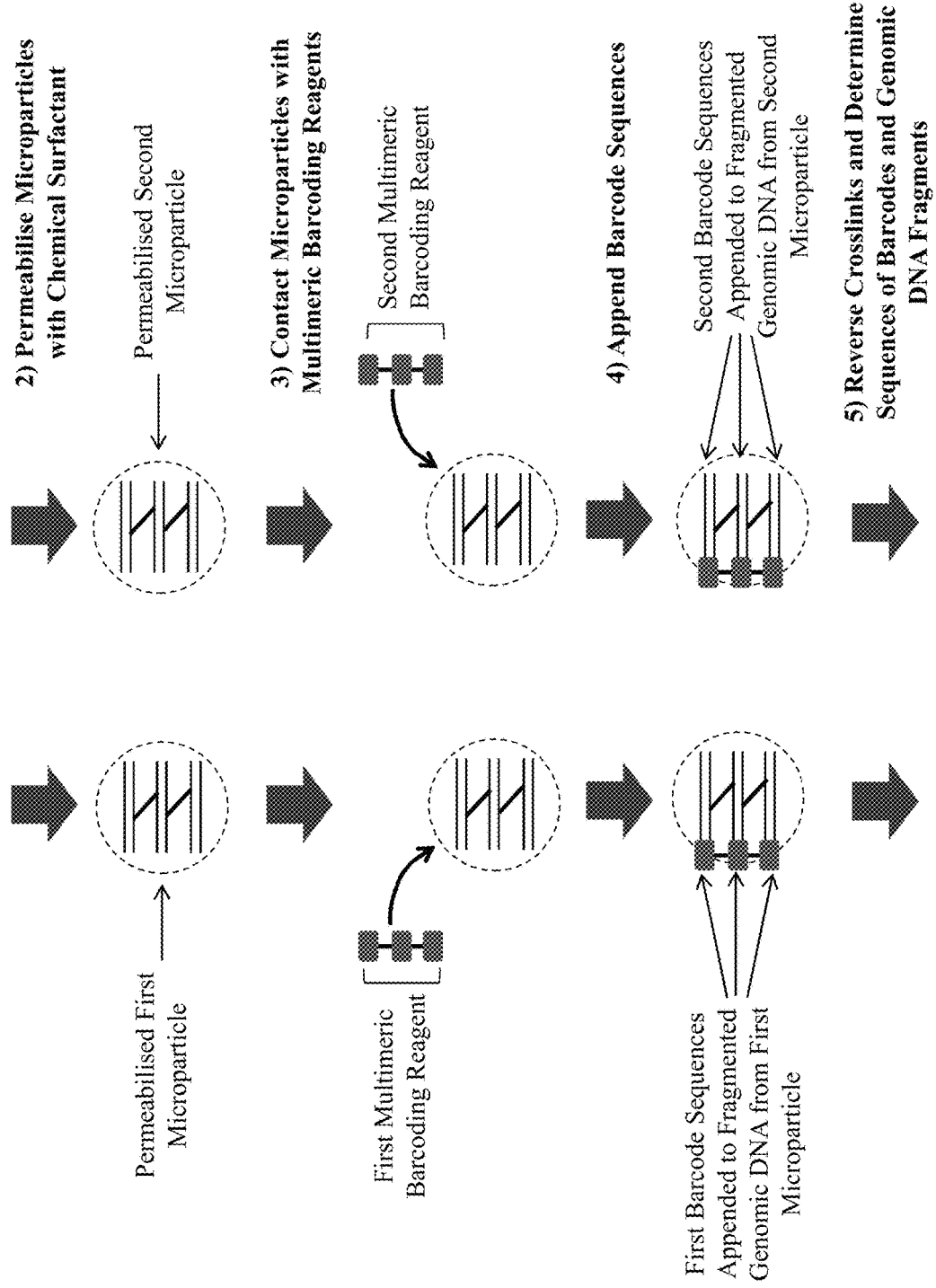

FIG. 21 illustrates a specific method in which molecular barcodes are appended to fragments of genomic DNA within microparticles by multimeric barcoding reagents, and wherein said barcodes provide a linkage between sequences derived from the same microparticle. In the method, microparticles from a sample of microparticles are crosslinked and then permeabilised, and then the fragments of genomic DNA comprised within the microparticles are barcoded by multimeric barcoding reagents, and then sequences are determined in such a way that the barcodes identify by which multimeric barcoding reagent each sequence was barcoded, and thereby link the different sequences from individual microparticles.

In the first step, microparticles from a sample of microparticles are crosslinked by a chemical crosslinking agent. This step serves the purpose of holding fragments of genomic DNA within each microparticle in physical proximity to each other, such that the sample may be manipulated and processed whilst retaining the basic structural nature of the microparticles (i.e., whilst retaining physical proximity of genomic DNA fragments derived from the same microparticle). In a second step, the crosslinked microparticles are permeabilised (i.e., the fragments of genomic DNA are made physically accessible such that they can then be barcoded in a barcoding step); this permeabilisation may for example be performed by incubation with a chemical surfactant such as a non-ionic detergent.

Barcode sequences are then appended to fragments of genomic DNA, wherein barcode sequences comprised within a multimeric barcoding reagent (and/or multimeric barcode molecule) are appended to fragments within the same crosslinked microparticle. The barcode sequences may be appended by any means, for example by a primer-extension reaction, or by a single-stranded or double-stranded ligation reaction. The process of appending barcode sequences is conducted such that a library of many multimeric barcoding reagents (and/or multimeric barcode molecules) is used to append sequences to a sample comprising many crosslinked microparticles, under dilution conditions such that each multimeric barcoding reagent (and/or multimeric barcode molecule) typically will only barcode sequences comprised within a single microparticle.

A sequencing reaction is then performed on the resulting molecules to determine sequences of genomic DNA and the barcode sequences to which they have been appended. The associated barcode sequences are then used to identify by which multimeric barcoding reagent (and/or multimeric barcode molecule) each sequence was barcoded, and thereby link sequences determined in the sequencing reaction that were derived from fragments of genomic DNA comprised within the same microparticle.

Figure 22:
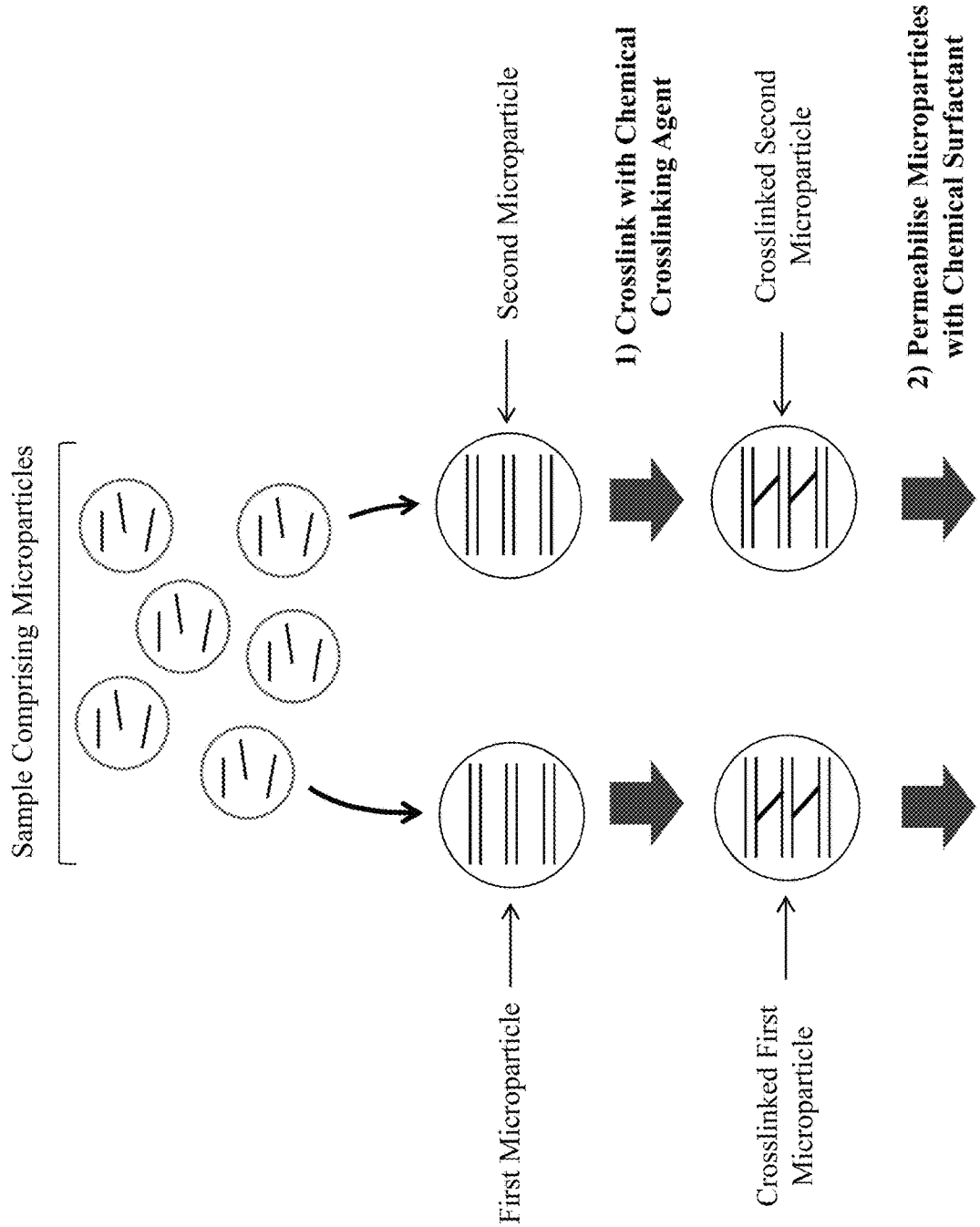
FIG. 22 illustrates a method in which fragments of genomic DNA within individual microparticles are appended to each other, and wherein the resulting molecules are sequenced, such that sequences from two or more fragments of genomic DNA from the same microparticle are determined from the same sequenced molecule, thereby establishing a linkage between fragments within the same microparticle.
Figure 22:
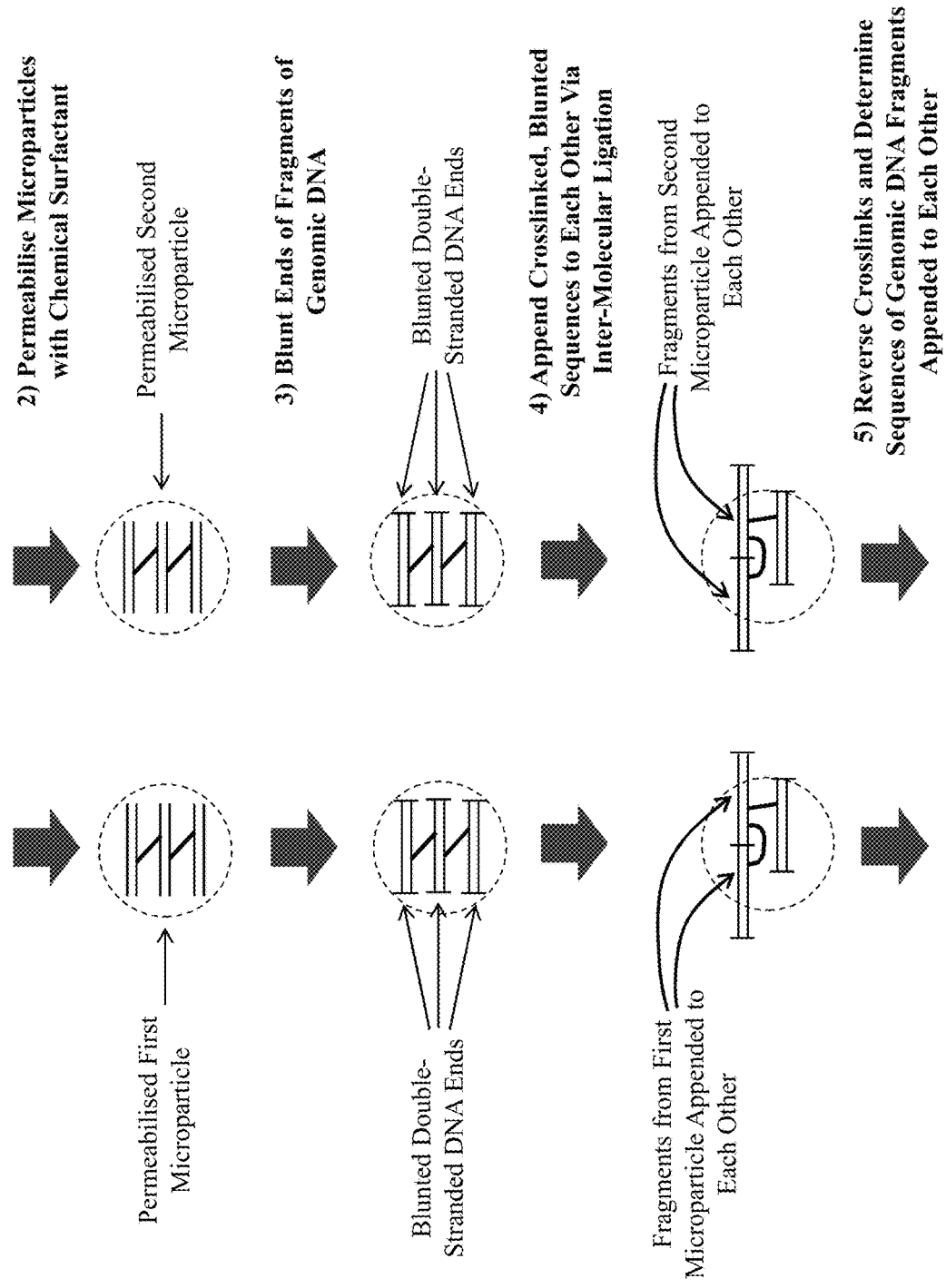

FIG. 22 illustrates a method in which fragments of genomic DNA within individual microparticles are appended to each other, and wherein the resulting molecules are sequenced, such that sequences from two or more fragments of genomic DNA from the same microparticle are determined from the same sequenced molecule, thereby establishing a linkage between fragments within the same microparticle. In the method, fragments of genomic DNA within individual microparticle are crosslinked to each other, and then blunted, and then the resulting blunted fragments of genomic DNA are ligated to each other into contiguous, multi-part sequences. The resulting molecules are then sequenced, such that sequences from two or more fragments of genomic DNA comprised within the same sequenced molecule are thus determined to be linked as deriving from the same microparticle.

In the first step, microparticles from a sample of microparticles are crosslinked by a chemical crosslinking agent. This step serves the purpose of holding fragments of genomic DNA within each microparticle in physical proximity to each other, such that the sample may be manipulated and processed whilst retaining the basic structural nature of the microparticles (i.e., whilst retaining physical proximity of genomic DNA fragments derived from the same microparticle). In a second step, the crosslinked microparticles are permeabilised (i.e., the fragments of genomic DNA are made physically accessible such that they can then be barcoded in a barcoding step); this permeabilisation may for example be performed by incubation with a chemical surfactant such as a non-ionic detergent.

In a next step, the ends of fragments of genomic DNA within each microparticle are blunted (i.e. any overhangs are removed and/or ends are filled-in) such that the ends are able to be appended to each other in a double-stranded ligation reaction. A double-stranded ligation reaction is then performed (e.g. with T4 DNA Ligase), wherein the blunted ends of molecules comprised within the same microparticles are ligated to each other into contiguous, multi-part double-stranded sequences. This ligation reaction (or any other step) may be performed under dilution conditions such that spurious ligation products between sequences comprised within two or more different microparticles are minimised.

A sequencing reaction is then performed on the resulting molecules to determine sequences of genomic DNA within each multi-part molecule. The resulting molecules are then evaluated, such that sequences from two or more fragments of genomic DNA comprised within the same sequenced molecule are thus determined to be linked as deriving from the same microparticle.

Figure 23:
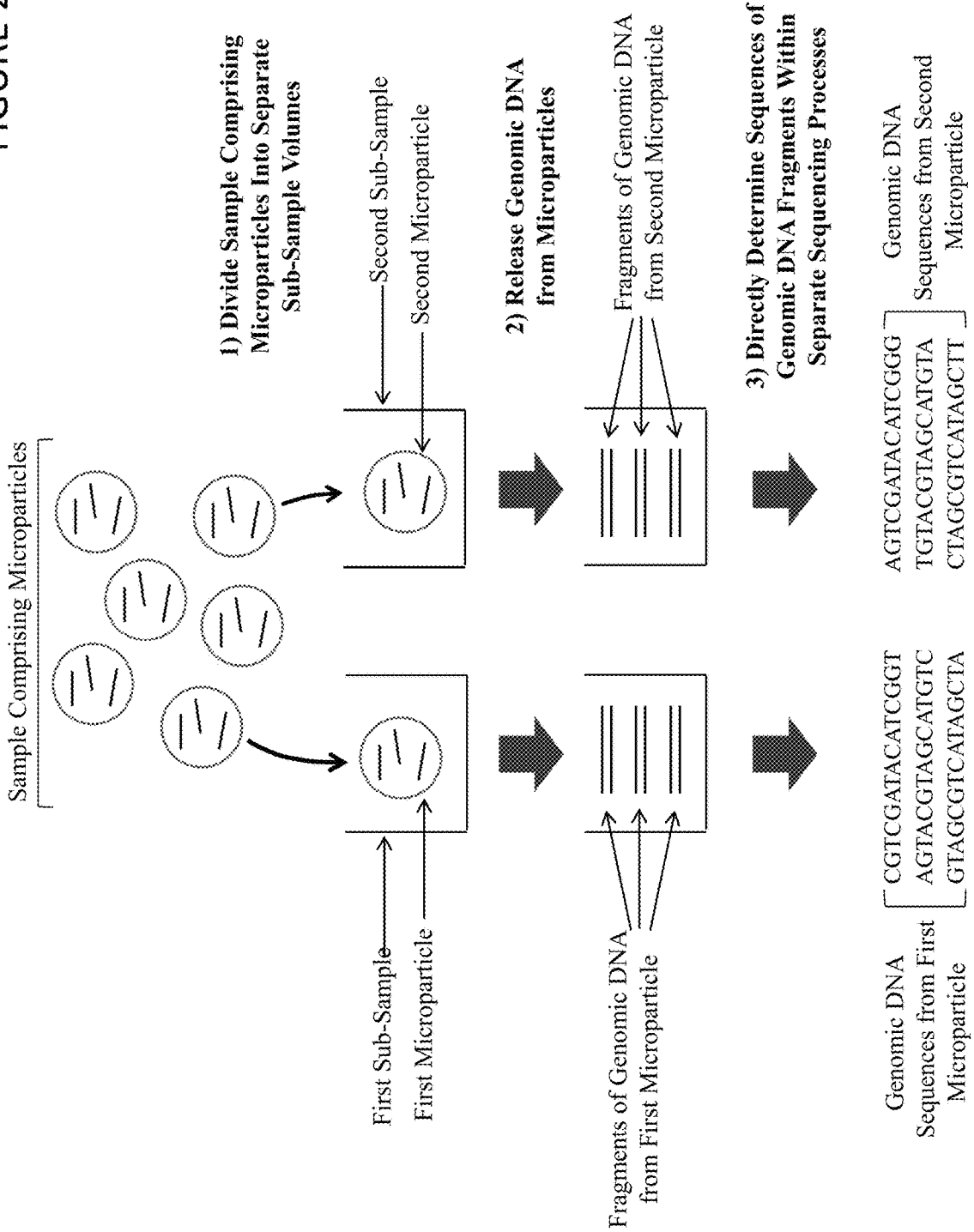
FIG. 23 illustrates a method in which individual microparticles (and/or small groups of microparticles) from a large sample of microparticles are sequenced in two or more separate, individual sequencing reactions, and the sequences determined from each such sequencing reaction are thus determined to be linked informatically and thus predicted to derive from the same individual microparticle (and/or small group of microparticles).

FIG. 23 illustrates a method in which individual microparticles (and/or small groups of microparticles) from a large sample of microparticles are sequenced in two or more separate, individual sequencing reactions, and the sequences determined from each such sequencing reaction are thus determined to be linked informatically and thus predicted to derive from the same individual microparticle (and/or small group of microparticles). In the method, microparticles from a sample of microparticles are divided into two or more separate sub-samples of microparticles. Each sub-sample may comprise one or more individual microparticles, but in any case will comprise only a fraction of the original sample of microparticles.

The fragments of genomic DNA within each sub-sample are then released and processed into a form such that they may be sequenced (e.g., they may be appended to sequencing adapters such as Illumina sequencing adapters, and optionally amplified and purified for sequencing). This method may or may not include a step of appending barcode sequences; optionally the sequenced molecules do not comprise any barcode sequences.

Fragments of genomic DNA (and/or replicated copies thereof) from each individual sub-sample are then sequenced in separate, independent sequencing reactions. For example, molecules from each sub-sample may be sequenced on a separate sequencing flowcell, or may be sequenced within a different lane of a flowcell, or may be sequenced within a different port or flowcell of a nanopore sequencer.

The resulting sequenced molecules are then evaluated, such that sequences from the same individual sequencing reaction are thus determined to be linked as deriving from the same microparticle (and/or from the same small group of microparticles).

Figure 24:
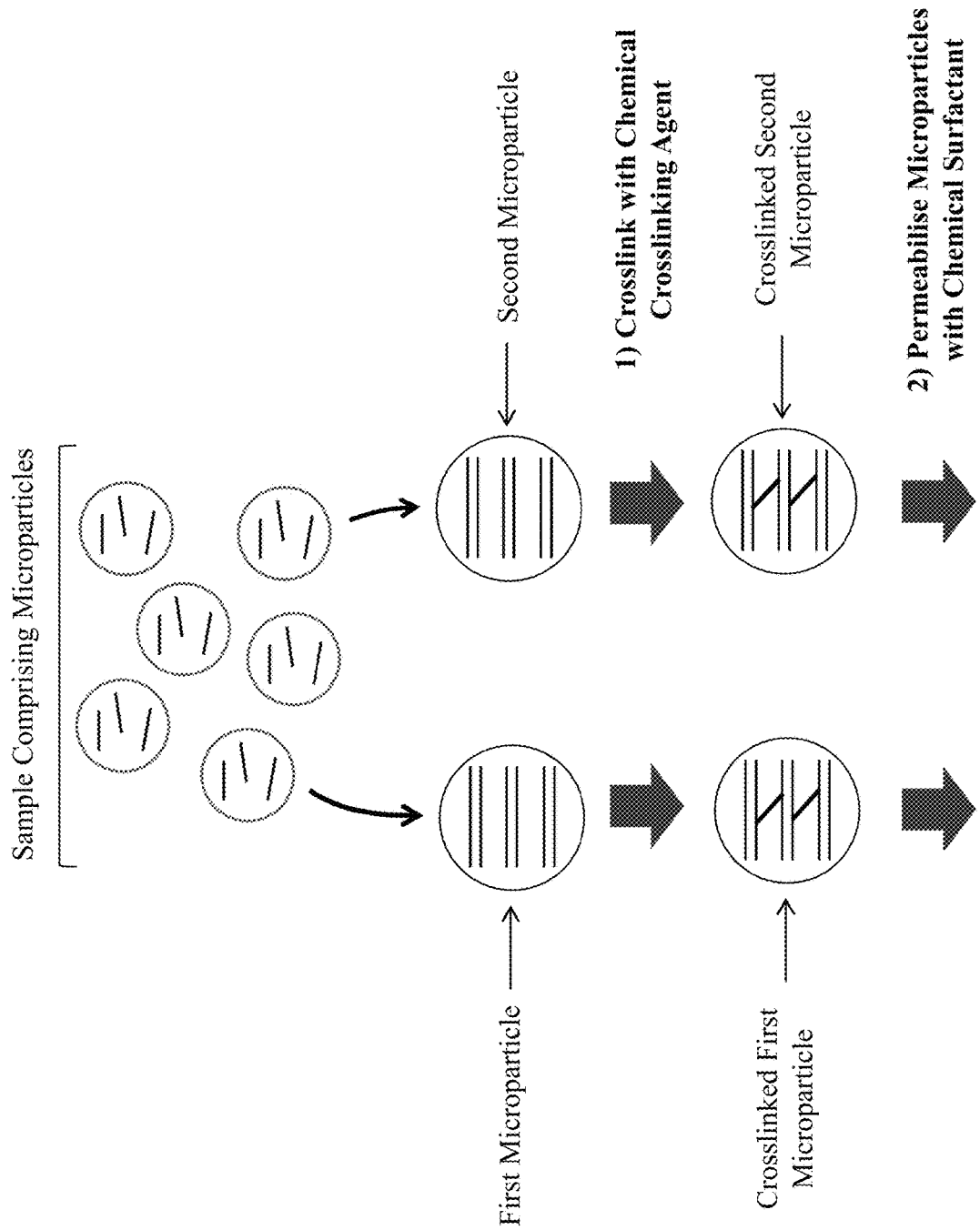
FIG. 24 illustrates a specific method in which fragments of genomic DNA within individual microparticles are appended to a discrete region of a sequencing flow cell prior to sequencing, and wherein the proximity of fragments sequenced on said flow cell provides a linkage between sequences derived from the same microparticle.
Figure 24:
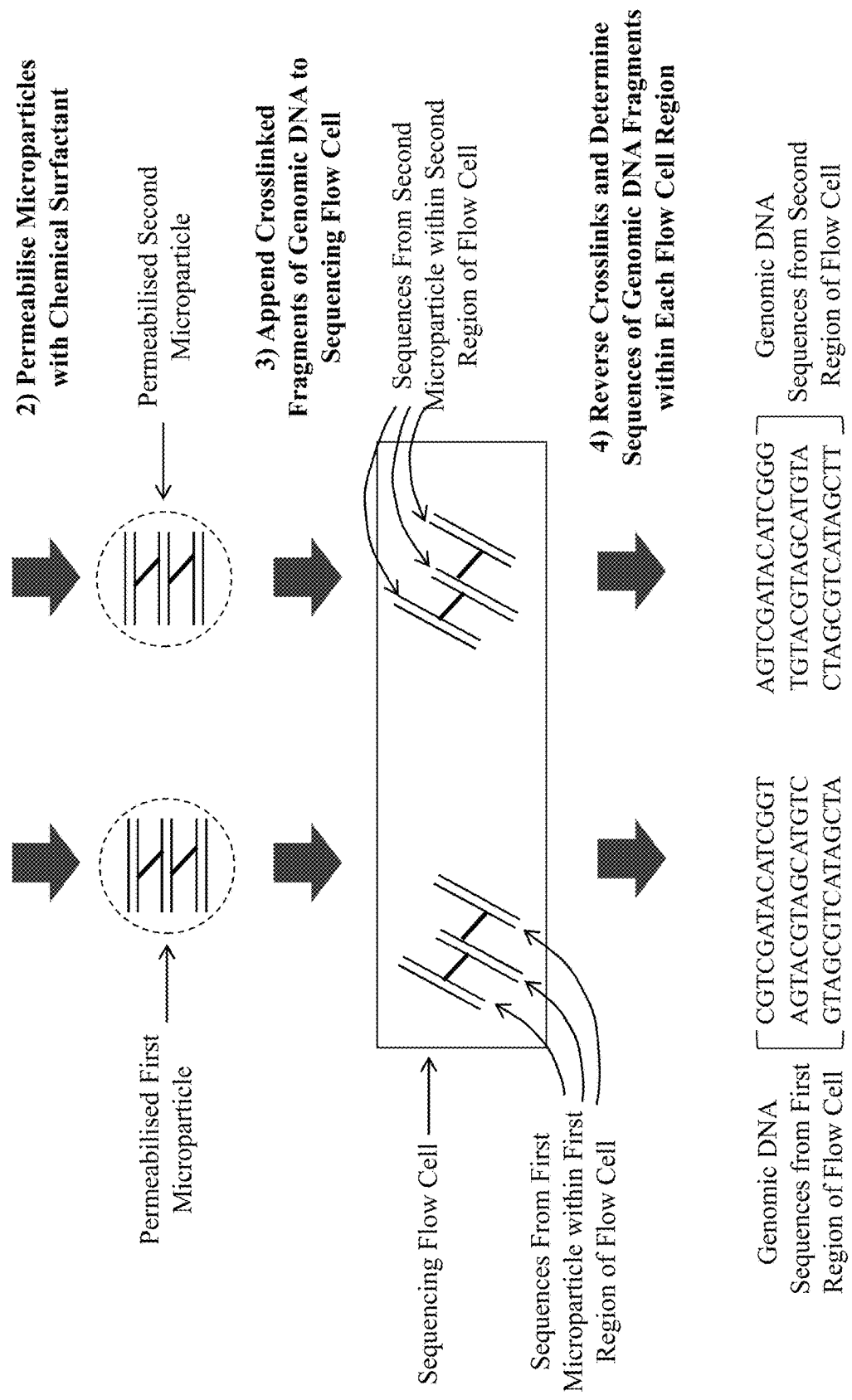

FIG. 24 illustrates a specific method in which fragments of genomic DNA within individual microparticles are appended to a discrete region of a sequencing flowcell prior to sequencing, and wherein the proximity of fragments sequenced on said flowcell comprises a linkage between sequences derived from the same microparticle. In the method, microparticles from a sample of microparticles are crosslinked and then permeabilised, and then fragments of genomic DNA comprised within individual microparticles are appended to a sequencing flowcell, such that two or more fragments from the same individual microparticle are appended to the same region of the flowcell. The appended molecules are then sequenced, and the proximity of the resulting sequences on the flowcell comprises a linking value, wherein sequences within close proximity on the flowcell may be predicted to derive from the same individual microparticle within the original sample.

In the first step, microparticles from a sample of microparticles are crosslinked by a chemical crosslinking agent. This step serves the purpose of holding fragments of genomic DNA within each microparticle in physical proximity to each other, such that the sample may be manipulated and processed whilst retaining the basic structural nature of the microparticles (i.e., whilst retaining physical proximity of genomic DNA fragments derived from the same microparticle). In a second step, the crosslinked microparticles are permeabilised (i.e., the fragments of genomic DNA are made physically accessible such that they can then be appended to a flowcell); this permeabilisation may for example be performed by incubation with a chemical surfactant such as a non-ionic detergent.

In a next step, fragments of genomic DNA from microparticles are then appended to the flowcell of a sequencing apparatus, such that two or more fragments crosslinked within the same microparticle are appended to the same discrete region of the flowcell. This may be performed in a multi-part reaction involving adapter molecules; for example, an adapter molecule may be appended to fragments of genomic DNA within microparticles, and said adapter molecule may comprise a single-stranded portion that is complementary to single-stranded primers on the flowcell. Sequences from a crosslinked microparticle may then be allowed to diffuse and anneal to different primers within the same region of the flowcell.

The resulting sequenced molecules are then sequenced, such that the proximity of the resulting sequences on the flowcell provides a linking value, wherein sequences within close proximity on the flowcell (e.g. within a certain discrete region and/or proximity value) may be predicted to derive from the same individual microparticle within the original sample.

The advantages of the invention may be illustrated, by way of example only, by reference to possible applications in NIPT and cancer detection:

By way of example, in the field of oncology, the invention may enable a powerful new framework to screen for the early detection of cancer. Several groups are seeking to develop cfDNA assays which can detect low levels of circulating DNA from early tumours (so-called 'circulating tumour DNA' or ctDNA) prior to metastatic conversion. One of the chief approaches taken to delineate cancerous from non-cancerous specimens is by detecting 'structural variants' (genetic amplifications, deletions, or translocations) that are a near-universal hallmark of malignancies; however, detection of such large-scale genetic events through the current 'molecular counting' framework requires ultra-deep sequencing of cfDNA to achieve statistically meaningful detection, and even then requires that a sufficient amount of ctDNA be present in the plasma to generate a sufficient absolute molecular signal even with hypothetically unlimited sequencing depth.

By contrast, the current invention may enable direct molecular assessment of structural variation, with potential single-molecule sensitivity: any structural variation that includes a 'rearrangement site' (for example, a point on one chromosome that has been translocated with and thus attached to another chromosome, or a point where a gene or other chromosomal segment has been amplified or deleted within a single chromosome) may be detectable directly by this method, since circulating microparticles containing DNA of the rearrangement may include a population of DNA fragments flanking both sides of the rearrangement site itself, which by this method can then be linked with each other to informatically deduce both the location of the rearrangement itself, and the bound of the two participating genomic loci on each end thereof.

To conceptualise how this may improve both the cost-effectiveness and the absolute analytic sensitivity of a universal cancer screen, the example can be given of a hypothetical single circulating microparticle, which contains a chromosomal translocation from an early cancer cell, and which contains a total of 1 megabase of DNA spanning the left and right halves of this translocation, with this DNA being fragmented as 10,000 different, 100-nucleotide-long individual fragments that cumulatively span the entire 1 megabase segment. To detect the presence of this translocation event using the current, unlinked-fragment-only approach, the single, 100-base-pair fragment that itself contains the exact site of translocation would need to be sequenced, and sequenced across its entire length to detect the actual translocation site itself. This test method would thus need to both: 1) efficiently convert all of the 10,000 fragments into a format that can be read on a sequencer (i.e., the majority of the 10,000 fragments must be successfully processed and retained throughout the entire DNA purification and sequencing sample-preparation process), and then 2) all of the 10,000 fragments must be sequenced at least once by a DNA sequencing process to reliably sequence the one that includes the translocation site (i.e., at least 1 megabase of sequencing must be performed, even assuming a theoretical uniform sampling of all input molecules into the sequencing step). Thus, 1 megabase of sequencing would need to be performed to detect the translocation event.

By contrast, to detect the presence of the translocation with a high degree of statistical confidence but using the linked-fragment approach, only a small number of input fragments from each side of the translocation site itself would need to be sequenced (to distinguish a 'confident' translocation event from e.g. statistical noise or mis-mapping errors). To provide a high degree of statistical confidence, on the order of 10 fragments from each side of the translocation could be sequenced; and since they need only be mapped to a location in the genome and not sequenced across their entire length to observe the actual translocation itself, on the order of only 50 base pairs from each fragment need be sequenced. Taken together, this generates a total sequencing requirement of 1000 base pairs to detect the presence of the translocation—a 1000-fold reduction from the 1,000,000 base pairs required by current state-of-the-art.

In addition to this considerable benefit in terms of relative sequencing throughput and cost, a linked-read approach may also increase the absolute achievable sensitivity of these cancer-screening tests. Since, for early-stage (and thus potentially curable) cancers, the absolute amount of tumour DNA in the circulation is low, the loss of sample DNA during the sample processing and preparation process for sequencing could significantly impede test efficacy, even with theoretically limitless sequencing depth. In keeping with the above example, using current approaches, the single DNA fragment containing the translocation site itself would need to be retained and successfully processed throughout the entire sample collection, processing, and sequencing-preparation protocol and then be successfully sequenced. However, all of these steps result in a certain fraction of 'input' molecules thereto being either physically lost from the processed sample (e.g. during a centrifugation or cleanup step), or otherwise simply not successfully processed/modified for subsequent steps (e.g., not successfully amplified prior to placement on a DNA sequencer). In contrast, since the linked-read approach of the invention need only involve sequencing of a small proportion of actual 'input' molecules, this type of sample loss may have a considerably reduced impact upon the ultimate sensitivity of the final assay.

In addition to its applications in oncology and cancer screening, this invention may also enable considerable new tools in the domain of noninvasive prenatal testing (NIPT). A developing foetus (and the placenta in which it is contained) shed fragmented DNA into the maternal circulation, a proportion of which is contained within circulating microparticles. Analogous to the problem of cancer screening from ctDNA, circulating foetal DNA only represents a minor fraction of the overall circulating DNA in pregnant individuals (the majority of circulating DNA being normal maternal DNA). A considerable technical challenge for NIPT revolves around differentiating actual foetal DNA from maternal DNA fragments (which will share the same nucleotide sequence since they are the source of inheritance for half of the foetal genome). An additional technical challenge for NIPT involves the detection of long-range genomic sequences (or mutations) from the short fragments of foetal DNA present in the circulation.

Analysis of linked fragments originating from the same individual circulating microparticle presents a powerful framework for substantially addressing both of these technical challenges for NIPT. Since (approximately) half of the foetal genome will be identical in sequence to the (approximately) half of the maternal genome which the developing foetus has inherited, it is difficult to distinguish whether a given sequenced fragment with a maternal sequence may have been generated by normal maternal tissues, or rather by developing foetal tissues. By contrast, for the (approximately) half of the foetal genome which has been paternally inherited (inherited from the father), the presence of sequence variants (e.g. single nucleotide variants or other variants) present in the paternal genome but not in the maternal genome serves as a molecular marker to identify these paternally-inherited foetal fragments (since the only paternal DNA sequences in circulation will be those from the pregnancy itself).

The ability to sequence multiple fragments from single circulating foetal microparticles that happen to contain both maternal and paternal sequences (e.g. sequences from one particular maternally-inherited foetal chromosome, together with sequences from a second foetal chromosome that has been paternally inherited) thus presents a method for direct recognition of which maternal sequences have been inherited by the developing foetus: maternal sequences that are found co-localised within microparticles that also contain paternal sequences can be predicted to be foetally-inherited maternal sequences, and, in contrast, maternal sequences that are not found co-localised with paternal sequences can be predicted to represent the maternal sequences which were not inherited by the foetus. By this technique, the large majority of circulating DNA that is comprised of normal maternal DNA may be specifically filtered out of the processed sequence dataset, and only sequences evidenced as being true foetal sequences may be isolated informatically for further analysis.

Since 'foetal fractions' (the fraction of all circulating DNA which has been generated by the foetus itself) for NIPT assays are frequently below 10%, and for some clinical specimens between 1% and 5%, and since this paternal-sequence-derived 'informatic-gating' step produces an 'effective foetal fraction' of 100% (assuming minimal mis-mapping errors), this linked-fragment approach has the potential to improve the signal-to-noise ratio for NIPT tests by one to two orders of magnitude. Therefore, the invention has the potential to improve the overall analytic sensitivity and specificity of NIPT tests, as well as considerably reduce the amount of sequencing required for the process, and also enable NIPT tests to be performed earlier in pregnancy (time points at which foetal fractions are sufficiently low that current tests have unacceptable false-positive and false-negative rates).

Importantly, the present invention provides a novel, orthogonal dimensionality within sequence data from circulating DNA in the form of informatically linked sequences, upon which analysis algorithms, computations, and/or statistical tests may be performed directly to generate considerably more sensitive and specific genetic measurements. For example, rather than evaluating overall amounts of sequence between two chromosomes across an entire sample to measure a foetal chromosomal aneuploidy, linked sequences (and/or sets or subsets thereof) can be assessed directly to examine, for example, the number of sequences per informatically-linked set that map to a particular chromosome or chromosome portion. Comparisons and/or statistical tests may be performed to compare linked sets of sequences of different presumed cellular origin (for example, comparison between foetal sequences and maternal sequences, or between presumed healthy tissues and presumed cancerous or malignant tissues), or to evaluate sequence features or numeric features which only exist at the level of linked sets of sequences (and which do not exist at the level of individual, unlinked sequences), such as specific chromosomal distribution patterns, or cumulative enrichments of particular sequences or sequence sets.

In addition to its application for detection of foetal microparticle sequences, this method has the potential to detect long-range genetic sequences or sequence mutations present in the foetal genome. Much in the same manner as described for cancer genome rearrangements, if several DNA fragments from a foetal microparticle are sequenced that span and/or flank a genomic rearrangement site (e.g. a translocation or amplification or deletion), then these classes of rearrangements may be informatically detected even without directly sequencing rearrangement sites themselves. In addition, outside of genomic rearrangement events, this method has the potential to detect 'phasing' information within individual genomic regions. For example, if two single-nucleotide variants are found at different points within a specific gene but separated by several kilobases of genomic distance, this method may enable assessment of whether these two single nucleotide variants are located on the same, single copy of the gene in the foetal genome, or whether they are each located on a different one of the two copies of the gene present in the foetal genome (i.e. whether they are located within the same haplotype). This function may have particular clinical utility for the genetic assessment and prognosis of de novo single nucleotide mutations in foetal genomes, which comprise a large fraction of major developmental disorders with genetic etiology.

EXAMPLES

Example 1

Materials and Methods

Method 1—Synthesis of a Library of Nucleic Acid Barcode Molecules

Synthesis of Double-Stranded Sub-Barcode Molecule Library

In a PCR tube, 10 microliters of 10 micromolar BC_MX3 (an equimolar mixture of all sequences in SEQ ID NO: 18 to 269) were added to 10 microliters of 10 micromolar BC_ADD_TP1 (SEQ ID NO: 1), plus 10 microliters of 10× CutSmart Buffer (New England Biolabs) plus 1.0 microliter of 10 millimolar deoxynucleotide triphosphate nucleotide mix (Invitrogen) plus 68 microliters $H_2O$, to final volume of 99 microliters. The PCR tube was placed on a thermal cycler and incubated at 75° C. for 5 minutes, then slowly annealed to 4° C., then held 4° C., then placed on ice. 1.0 microliter of Klenow polymerase fragment (New England Biolabs; at 5 U/uL) was added to the solution and mixed. The PCR tube was again placed on a thermal cycler and incubated at 25° C. for 15 minutes, then held at 4° C. The solution was then purified with a purification column (Nucleotide Removal Kit; Qiagen), eluted in 50 microliters $H_2O$, and quantitated spectrophotometrically.

Synthesis of Double-Stranded Downstream Adapter Molecule

In a PCR tube, 0.5 microliters of 100 micromolar BC_ANC_TP1 (SEQ ID NO: 2) were added to 0.5 microliters of 100 micromolar BC_ANC_BT1 (SEQ ID NO: 3), plus 20 microliters of 10× CutSmart Buffer (New England Biolabs) plus 178 microliters $H_2O$, to final volume of 200 microliters. The PCR tube was placed on a thermal cycler and incubated at 95° C. for 5 minutes, then slowly annealed to 4° C., then held 4° C., then placed on ice, then stored at −20° C.

Ligation of Double-Stranded Sub-Barcode Molecule Library to Double-Stranded Downstream Adapter Molecule In a 1.5 milliliter Eppendorf tube, 1.0 microliter of Double-Stranded Downstream Adapter Molecule solution was added to 2.5 microliters of Double-Stranded Sub-Barcode Molecule Library, plus 2.0 microliters of 10× T4 DNA Ligase buffer, and 13.5 microliters $H_2O$ to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters $H_2O$.

PCR Amplification of Ligated Library

In a PCR tube, 2.0 microliters of Ligated Library were added to 2.0 microliters of 50 micromolar BC_FWD_PR1 (SEQ ID NO: 4), plus 2.0 microliters of 50 micromolar BC_REV_PR1 (SEQ ID NO: 5), plus 10 microliters of 10× Taq PCR Buffer (Qiagen) plus 2.0 microliter of 10 millimolar deoxynucleotide triphosphate nucleotide mix (Invitrogen) plus 81.5 microliters $H_2O$, plus 0.5 microliters Qiagen Taq Polymerase (at 5 U/uL) to final volume of 100 microliters. The PCR tube was placed on a thermal cycler and amplified for 15 cycles of: 95° C. for 30 seconds, then 59° C. for 30 seconds, then 72° C. for 30 seconds; then held at 4° C. The solution was then purified with 1.8× volume (180 microliters) Ampure XP Beads (Agencourt; as per manufacturer's instructions), and eluted in 50 microliters $H_2O$.

Uracil Glycosylase Enzyme Digestion

To an eppendorf tube 15 microliters of the eluted PCR amplification, 1.0 microliters H2O, plus 2.0 microliters 10× CutSmart Buffer (New England Biolabs), plus 2.0 microliter of USER enzyme solution (New England Biolabs) was added and mixed. The tube was incubated at 37° C. for 60 minutes, then the solution was purified with 1.8× volume (34 microliters) Ampure XP Beads (Agencourt; as per manufacturer's instructions), and eluted in 34 microliters $H_2O$.

MlyI Restriction Enzyme Cleavage

To the eluate from the previous (glycosylase digestion) step, 4.0 microliters 10× CutSmart Buffer (New England Biolabs), plus 2.0 microliter of MlyI enzyme (New England Biolabs, at 5 U/uL) was added and mixed. The tube was incubated at 37° C. for 60 minutes, then the solution was purified with 1.8× volume (72 microliters) Ampure XP Beads (Agencourt; as per manufacturer's instructions), and eluted in 40 microliters $H_2O$.

Ligation of Sub-Barcode Library to MlyI-Cleaved Solution

In a 1.5 milliliter Eppendorf tube, 10 microliter of MlyI-Cleaved Solution solution was added to 2.5 microliters of Double-Stranded Sub-Barcode Molecule Library, plus 2.0 microliters of 10× T4 DNA Ligase buffer, and 4.5 microliters $H_2O$ to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters $H_2O$.

Repeating Cycles of Sub-Barcode Addition

The experimental steps of: 1) Ligation of Sub-Barcode Library to MlyI-Cleaved Solution, 2) PCR Amplification of Ligated Library, 3) Uracil Glycosylase Enzyme Digestion, and 4) MlyI Restriction Enzyme Cleavage were repeated, in sequence, for a total of five cycles.

Synthesis of Double-Stranded Upstream Adapter Molecule

In a PCR tube, 1.0 microliters of 100 micromolar BC_USO_TP1 (SEQ ID NO: 6) were added to 1.0 microliters of 100 micromolar BC_USO_BT1 (SEQ ID NO: 7), plus 20 microliters of 10× CutSmart Buffer (New England Biolabs) plus 178 microliters H$_2$O, to final volume of 200 microliters. The PCR tube was placed on a thermal cycler and incubated at 95° C. for 60 seconds, then slowly annealed to 4° C., then held 4° C., then placed on ice, then stored at −20° C.

Ligation of Double-Stranded Upstream Adapter Molecule

In a 1.5 milliliter Eppendorf tube, 3.0 microliters of Upstream Adapter solution were added to 10.0 microliters of final (after the fifth cycle) MlyI-Cleaved solution, plus 2.0 microliters of 10× T4 DNA Ligase buffer, and 5.0 microliters H$_2$O to final volume of 19 microliters. 1.0 microliter of T4 DNA Ligase (New England Biolabs; high concentration) was added to the solution and mixed. The tube was incubated at room temperature for 60 minutes, then purified with 1.8× volume (34 microliters) Ampure XP Beads (Agencourt; as per manufacturer's instructions), and eluted in 40 microliters H$_2$O.

PCR Amplification of Upstream Adapter-Ligated Library

In a PCR tube, 6.0 microliters of Upstream Adapter-Ligated Library were added to 1.0 microliters of 100 micromolar BC_CS_PCR_FWD1 (SEQ ID NO: 8), plus 1.0 microliters of 100 micromolar BC_CS_PCR_REV1 (SEQ ID NO: 9), plus 10 microliters of 10× Taq PCR Buffer (Qiagen) plus 2.0 microliter of 10 millimolar deoxynucleotide triphosphate nucleotide mix (Invitrogen) plus 73.5 microliters H$_2$O, plus 0.5 microliters Qiagen Taq Polymerase (at 5 U/uL) to final volume of 100 microliters. The PCR tube was placed on a thermal cycler and amplified for 15 cycles of: 95° C. for 30 seconds, then 61° C. for 30 seconds, then 72° C. for 30 seconds; then held at 4° C. The solution, containing a library of amplified nucleic acid barcode molecules, was then purified with 1.8× volume (180 microliters) Ampure XP Beads (Agencourt; as per manufacturer's instructions). The library of amplified nucleic acid barcode molecules was then eluted in 40 microliters H$_2$O.

The library of amplified nucleic acid barcode molecules synthesized by the method described above was then used to assemble a library of multimeric barcode molecules as described below.

Method 2—Assembly of a Library of Multimeric Barcode Molecules

A library of multimeric barcode molecules was assembled using the library of nucleic acid barcode molecules synthesised according to the methods of Method 1.

Primer-Extension with Forward Termination Primer and Forward Splinting Primer

In a PCR tube, 5.0 microliters of the library of amplified nucleic acid barcode molecules were added to 1.0 microliters of 100 micromolar CS_SPLT_FWD1 (SEQ ID NO: 10), plus 1.0 microliters of 5 micromolar CS_TERM_FWD1 (SEQ ID NO: 11), plus 10 microliters of 10× Thermopol Buffer (NEB) plus 2.0 microliter of 10 millimolar deoxynucleotide triphosphate nucleotide mix (Invitrogen) plus 80.0 microliters H$_2$O, plus 1.0 microliters Vent Exo-Minus Polymerase (New England Biolabs, at 2 U/uL) to final volume of 100 microliters. The PCR tube was placed on a thermal cycler and amplified for 1 cycle of: 95° C. for 30 seconds, then 53° C. for 30 seconds, then 72° C. for 60 seconds, then 1 cycle of: 95° C. for 30 seconds, then 50° C. for 30 seconds, then 72° C. for 60 seconds, then held at 4° C. The solution was then purified a PCR purification column (Qiagen), and eluted in 85.0 microliters H$_2$O.

Primer-Extension with Reverse Termination Primer and Reverse Splinting Primer

In a PCR tube, the 85.0 microliters of forward-extension primer-extension products were added to 1.0 microliters of 100 micromolar CS_SPLT_REV1 (SEQ ID NO: 12), plus 1.0 microliters of 5 micromolar CS_TERM_REV1 (SEQ ID NO: 13), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 100 microliters. The PCR tube was placed on a thermal cycler and amplified for 1 cycle of: 95° C. for 30 seconds, then 53° C. for 30 seconds, then 72° C. for 60 seconds, then 1 cycle of: 95° C. for 30 seconds, then 50° C. for 30 seconds, then 72° C. for 60 seconds, then held at 4° C. The solution was then purified a PCR purification column (Qiagen), and eluted in 43.0 microliters H$_2$O.

Linking Primer-Extension Products with Overlap-Extension PCR

In a PCR tube were added the 43.0 microliters of reverse-extension primer-extension products, plus 5.0 microliters of 10× Thermopol Buffer (NEB) plus 1.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 50 microliters. The PCR tube was placed on a thermal cycler and amplified for 5 cycles of: 95° C. for 30 seconds, then 60° C. for 60 seconds, then 72° C. for 2 minutes; then 5 cycles of: 95° C. for 30 seconds, then 60° C. for 60 seconds, then 72° C. for 5 minutes; then 5 cycles of: 95° C. for 30 seconds, then 60° C. for 60 seconds, then 72° C. for 10 minutes; then held at 4° C. The solution was then purified with 0.8× volume (80 microliters) Ampure XP Beads (Agencourt; as per manufacturer's instructions), and eluted in 40 microliters H$_2$O.

Amplification of Overlap-Extension Products

In a PCR tube were added 2.0 microliters of Overlap-Extension PCR solution, plus 1.0 microliters of 100 micromolar CS_PCR_FWD1 (SEQ ID NO: 14), plus 1.0 microliters of 100 micromolar CS_PCR_REV1 (SEQ ID NO: 15), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL), plus 83.0 microliters H$_2$O to final volume of 100 microliters. The PCR tube was placed on a thermal cycler and amplified for 15 cycles of: 95° C. for 30 seconds, then 58° C. for 30 seconds, then 72° C. for 10 minutes; then held at 4° C. The solution was then purified with 0.8× volume (80 microliters) Ampure XP Beads (Agencourt; as per manufacturer's instructions), and eluted in 50 microliters H$_2$O, and quantitated spectrophotometrically.

Gel-Based Size Selection of Amplified Overlap-Extension Products

Approximately 250 nanograms of Amplified Overlap-Extension Products were loaded and run on a 0.9% agarose gel, and then stained and visualised with ethidium bromide. A band corresponding to 1000 nucleotide size (plus and minus 100 nucleotides) was excised and purified with a gel extraction column (Gel Extraction Kit, Qiagen) and eluted in 50 microliters H$_2$O.

Amplification of Overlap-Extension Products

In a PCR tube were added 10.0 microliters of Gel-Size-Selected solution, plus 1.0 microliters of 100 micromolar CS_PCR_FWD1 (SEQ ID NO: 14), plus 1.0 microliters of 100 micromolar CS_PCR_REV1 (SEQ ID NO: 15), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 75.0 microliters H$_2$O to final volume of 100 microliters. The PCR tube was placed on a thermal cycler and amplified for 15 cycles of: 95° C. for 30 seconds, then 58° C. for 30 seconds, then 72° C. for 4 minutes; then held at 4° C. The solution was then purified with 0.8× volume (80 microliters) Ampure XP Beads (Agencourt; as per manufacturer's instructions), and eluted in 50 microliters H$_2$O, and quantitated spectrophotometrically.

Selection and Amplification of Quantitatively Known Number of Multimeric Barcode Molecules Amplified gel-extracted solution was diluted to a concentration of 1 picogram per microliter, and then to a PCR tube was added 2.0 microliters of this diluted solution (approximately 2 million individual molecules), plus 0.1 microliters of 100 micromolar CS_PCR_FWD1 (SEQ ID NO: 14), plus 0.1 microliters of 100 micromolar CS_PCR_REV1 (SEQ ID NO: 15), plus 1.0 microliter 10× Thermopol Buffer (NEB) plus 0.2 microliter of 10 millimolar deoxynucleotide triphosphate nucleotide mix (Invitrogen), plus 0.1 microliters Vent Exo-Minus Polymerase (New England Biolabs, at 2 U/uL) plus 6.5 microliters H$_2$O to final volume of 10 microliters. The PCR tube was placed on a thermal cycler and amplified for 11 cycles of: 95° C. for 30 seconds, then 57° C. for 30 seconds, then 72° C. for 4 minutes; then held at 4° C.

To the PCR tube was added 1.0 microliters of 100 micromolar CS_PCR_FWD1 (SEQ ID NO: 14), plus 1.0 microliters of 100 micromolar CS_PCR_REV1 (SEQ ID NO: 15), plus 9.0 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 76.0 microliters H$_2$O to final volume of 100 microliters. The PCR tube was placed on a thermal cycler and amplified for 10 cycles of: 95° C. for 30 seconds, then 57° C. for 30 seconds, then 72° C. for 4 minutes; then held at 4° C. The solution was then purified with 0.8× volume (80 microliters) Ampure XP Beads (Agencourt; as per manufacturer's instructions), and eluted in 50 microliters H$_2$O, and quantitated spectrophotometrically.

Method 3: Production of Single-Stranded Multimeric Barcode Molecules by In Vitro Transcription and cDNA Synthesis This method describes a series of steps to produce single-stranded DNA strands, to which oligonucleotides may be annealed and then barcoded along. This method begins with four identical reactions performed in parallel, in which a promoter site for the T7 RNA Polymerase is appended to the 5' end of a library of multimeric barcode molecules using an overlap-extension PCR amplification reaction. Four identical reactions are performed in parallel and then merged to increase the quantitative amount and concentration of this product available. In each of four identical PCR tubes, approximately 500 picograms of size-selected and PCR-amplified multimeric barcode molecules (as produced in the 'Selection and Amplification of Quantitatively Known Number of Multimeric Barcode Molecules' step of Method 2) were mixed with 2.0 microliters of 100 micromolar CS_PCR_FWD1_T7 (SEQ ID NO: 270) and 2.0 microliters of 100 micromolar CS_PCR_REV4 (SEQ ID NO: 271), plus 20.0 microliters of 10× Thermopol PCR buffer, plus 4.0 microliters of 10 millimolar deoxynucleotide triphosphate nucleotide mix, and 2.0 microliters Vent Exo Minus polymerse (at 5 units per microliter) plus water to a total volume of 200 microliters. The PCR tube was placed on a thermal cycler and amplified for 22 cycles of: 95° C. for 60 seconds, then 60° C. for 30 seconds, then 72° C. for 3 minutes; then held at 4° C. The solution from all four reactions was then purified with a gel extraction column (Gel Extraction Kit, Qiagen) and eluted in 52 microliters H$_2$O.

Fifty (50) microliters of the eluate was mixed with 10 microliters 10× NEBuffer 2 (NEB), plus 0.5 microliters of 10 millimolar deoxynucleotide triphosphate nucleotide mix, and 1.0 microliters Vent Exo Minus polymerse (at 5 units per microliter) plus water to a total volume of 100 microliters. The reaction was incubated for 15 minutes at room temperature, then purified with 0.8× volume (80 microliters) Ampure XP Beads (Agencourt; as per manufacturer's instructions), and eluted in 40 microliters H$_2$O, and quantitated spectrophotometrically.

A transcription step is then performed, in which the library of PCR-amplified templates containing T7 RNA Polymerase promoter site (as produced in the preceding step) is used as a template for T7 RNA polymerase. This comprises an amplification step to produce a large amount of RNA-based nucleic acid corresponding to the library of multimeric barcode molecules (since each input PCR molecule can serve as a template to produce a large number of cognate RNA molecules). In the subsequent step, these RNA molecules are then reverse transcribed to create the desired, single-stranded multimeric barcode molecules. Ten (10) microliters of the eluate was mixed with 20 microliters 5× Transcription Buffer (Promega), plus 2.0 microliters of 10 millimolar deoxynucleotide triphosphate nucleotide mix, plus 10 microliters of 0.1 millimolar DTT, plus 4.0 microliters SuperAseIn (Ambion), and 4.0 microliters Promega T7 RNA Polymerase (at 20 units per microliter) plus water to a total volume of 100 microliters. The reaction was incubated 4 hours at 37° C., then purified with an RNEasy Mini Kit (Qiagen), and eluted in 50 microliters H$_2$O, and added to 6.0 microliters SuperAseIn (Ambion).

The RNA solution produced in the preceding in vitro transcription step is then reverse transcribed (using a primer specific to the 3' ends of the RNA molecules) and then digested with RNAse H to create single-stranded DNA molecules corresponding to multimeric barcode molecules, to which oligonucleotides maybe be annealed and then barcoded along. In two identical replicate tubes, 23.5 microliters of the eluate was mixed with 5.0 microliters of 10 millimolar deoxynucleotide triphosphate nucleotide mix, plus 3.0 microliters SuperAseIn (Ambion), and 10.0 microliters of 2.0 micromolar CS_PCR_REV1 (SEQ ID NO. 272) plus water to final volume of 73.5 microliters. The reaction was incubated on a thermal cycler at 65° C. for 5 minutes, then 50° C. for 60 seconds; then held at 4° C. To the tube was added 20 microliters 5× Reverse Transcription buffer (Invitrogen), plus 5.0 microliters of 0.1 millimolar DTT, and 1.75 microliters Superscript III Reverse Transcriptase (Invitrogen). The reaction was incubated at 55° C. for 45 minutes, then 60° C. for 5 minutes; then 70° C. for 15 minutes, then held at 4° C., then purified with a PCR Cleanup column (Qiagen) and eluted in 40 microliters H$_2$O.

Sixty (60) microliters of the eluate was mixed with 7.0 microliters 10× RNAse H Buffer (Promega), plus 4.0 microliters RNAse H (Promega. The reaction was incubated 12 hours at 37° C., then 95° C. for 10 minutes, then held at 4° C., then purified with 0.7× volume (49 microliters) Ampure XP Beads (Agencourt; as per manufacturer's instructions), and eluted in 30 microliters H$_2$O, and quantitated spectrophotometrically.

Method 4: Production of Multimeric Barcoding Reagents Containing Barcoded Oligonucleotides This method describes steps to produce multimeric barcoding reagents from single-stranded multimeric barcode molecules (as produced in Method 3) and appropriate extension primers and adapter oligonucleotides.

In a PCR tube, approximately 45 nanograms of single-stranded RNAse H-digested multimeric barcode molecules (as produced in the last step of Method 3) were mixed with 0.25 microliters of 10 micromolar DS_ST_05 (SEQ ID NO. 273, an adapter oligonucleotide) and 0.25 microliters of 10 micromolar US_PCR_Prm_Only_03 (SEQ ID NO. 274, an extension primer), plus 5.0 microliters of 5× Isothermal extension/ligation buffer, plus water to final volume of 19.7 microliters. In order to anneal the adapter oligonucleotides and extension primers to the multimeric barcode molecules, in a thermal cycler, the tube was incubated at 98° C. for 60 seconds, then slowly annealed to 55° C., then held at 55° C. for 60 seconds, then slowly annealed to 50° C. then held at 50° C. for 60 seconds, then slowly annealed to 20° C. at 0.1° C./sec, then held at 4° C. To the tube was added 0.3 microliters (0.625 U) Phusion Polymerase (NEB; 2 U/uL) 2.5 microliters (100 U) Taq DNA Ligase (NEB; 40 U/uL); and 2.5 microliters 100 millimolar DTT. In order to extend the extension primer(s) across the adjacent barcode region(s) of each multimeric barcode molecule, and then to ligate this extension product to the phosphorylated 5' end of the adapter oligonucleotide annealed to the downstream thereof, the tube was then incubated at 50° C. for 3 minutes, then held at 4° C. The reaction was then purified with a PCR Cleanup column (Qiagen) and eluted in 30 microliters $H_2O$, and quantitated spectrophotometrically.

Method 5: Production of Synthetic DNA Templates of Known Sequence

This method describes a technique to produce synthetic DNA templates with a large number of tandemly-repeated, co-linear molecular sequence identifiers, by circularizing and then tandemly amplifying (with a processive, strand-displacing polymerase) oligonucleotides containing said molecular sequence identifiers. This reagent may then be used to evaluate and measure the multimeric barcoding reagents described herein.

In a PCR was added 0.4 microliters of 1.0 micromolar Syn_Temp_01 (SEQ ID NO. 275) and 0.4 microliters of 1.0 micromolar ST_Splint_02 (SEQ ID NO. 276) and 10.0 microliters of 10× NEB CutSmart buffer. On a thermal cycler, the tube was incubated at 95° C. for 60 seconds, then held at 75° C. for 5 minutes, then slowly annealed to 20° C. then held at 20° C. for 60 seconds, then held at 4° C. To circularize the molecules through an intramolecular ligation reaction, the tube was then added 10.0 microliters ribo-ATP and 5.0 microliters T4 DNA Ligase (NEB; High Concentration). The tube was then incubated at room temperature for 30 minutes, then at 65° C. for 10 minutes, then slowly annealed to 20° C. then held at 20° C. for 60 seconds, then held at 4° C. To each tube was then added 10× NEB CutSmart buffer, 4.0 microliters of 10 millimolar deoxynucleotide triphosphate nucleotide mix, and 1.5 microliters of diluted phi29 DNA Polymerase (NEB; Diluted 1:20 in 1× CutSmart buffer) plus water to a total volume of 200 microliters. The reaction was incubated at 30° C. for 5 minutes, then held at 4° C., then purified with 0.7× volume (140 microliters) Ampure XP Beads (Agencourt; as per manufacturer's instructions), and eluted in 30 microliters $H_2O$, and quantitated spectrophotometrically.

Method 6: Barcoding Synthetic DNA Templates of Known Sequence with Multimeric Barcoding Reagents Containing Barcoded Oligonucleotides In a PCR tube were added 10.0 microliters 5× Phusion HF buffer (NEB), plus 1.0 microliters 10 millimolar deoxynucleotide triphosphate nucleotide mix, plus 2.0 microliters (10 nanograms) 5.0 nanogram/microliters Synthetic DNA Templates of Known Sequence (as produced by Method 5), plus water to final volume of 42.5 microliters. The tube was then incubated at 98° C. for 60 seconds, then held at 20° C. To the tube was added 5.0 microliters of 5.0 picogram/microliter Multimeric Barcoding Reagents Containing Barcoded Oligonucleotides (as produced by Method 4). The reaction was then incubated at 70° C. for 60 seconds, then slowly annealed to 60° C., then 60° C. for five minutes, then slowly annealed to 55° C., then 55° C. for five minutes, then slowly annealed to 50° C., then 50° C. for five minutes, then held at 4° C. To the reaction was added 0.5 microliters of Phusion Polymerase (NEB), plus 2.0 microliters 10 uM SynTemp_PE2_B1_Short1 (SEQ ID NO. 277, a primer that is complementary to part of the extension products produced by annealing and extending the multimeric barcoding reagents created by Method 4 along the synthetic DNA templates created by Method 5, serves as a primer for the primer-extension and then PCR reactions described in this method). Of this reaction, a volume of 5.0 microliters was added to a new PCR tube, which was then incubated for 30 seconds at 55° C., 30 seconds 60° C., and 30 seconds 72° C., then followed by 10 cycles of: 98° C. then 65° C. then 72° C. for 30 seconds each, then held at 4° C. To each tube was then added 9.0 microliters 5× Phusion buffer, plus 1.0 microliters 10 millimolar deoxynucleotide triphosphate nucleotide mix, plus 1.75 microliters 10 uM SynTemp_PE2_B1_Short1 (SEQ ID NO. 277), plus 1.75 microliters 10 uM US_PCR_Prm_Only_02 (SEQ ID NO. 278, a primer partially complementary to the extension primer employed to generate the multimeric barcoding reagents as per Method 4, and serving as the 'forward' primer in this PCR amplification reaction), plus 0.5 microliters Phusion Polymerase (NEB), plus water to final volume of 50 microliters. The PCR tube was placed on a thermal cycler and amplified for 24 cycles of: 98° C. for 30 seconds, then 72° C. for 30 seconds; then held at 4° C., then purified with 1.2× volume (60 microliters) Ampure XP Beads (Agencourt; as per manufacturer's instructions), and eluted in 30 microliters $H_2O$, and quantitated spectrophotometrically.

The resulting library was then barcoded for sample identification by a PCR-based method, amplified, and sequenced by standard methods using a 150-cycle, mid-output NextSeq flowcell (Illumina), and demultiplexed informatically for further analysis.

Method 7: Barcoding Synthetic DNA Templates of Known Sequence with Multimeric Barcoding Reagents and Separate Adapter Oligonucleotides To anneal and extend adapter oligonucleotides along the synthetic DNA templates, in a PCR tube were added 10.0 microliters 5× Phusion HF buffer (NEB), plus 1.0 microliters 10 millimolar deoxynucleotide triphosphate nucleotide mix, plus 5.0 microliters (25 nanograms) 5.0 nanogram/microliters Synthetic DNA Templates of Known Sequence (as produced by Method 5), plus 0.25 microliters of 10 micromolar DS_ST_05 (SEQ ID NO. 273, an adapter oligonucleotide), plus water to final volume of 49.7 microliters. On a thermal cycler, the tube was incubated at 98° C. for 2 minutes, then 63° C. for 1 minute, then slowly annealed to 60° C. then held at 60° C. for 1 minute, then slowly annealed to 57° C. then held at 57° C. for 1 minute, then slowly annealed to 54° C. then held at 54° C. for 1 minute, then slowly annealed to 50° C. then held at 50° C. for 1 minute, then slowly annealed to 45° C. then held at 45° C. for 1 minute, then slowly annealed to 40° C. then held at 40° C. for 1 minute, then held at 4° C. To the tube was added 0.3 microliters Phusion Polymerase (NEB), and the reaction was incubated at 45° C. for 20 seconds, then 50° C. for 20 seconds, then 55° C. for 20 seconds, 60° C. for 20 seconds, then 72° C. for 20 seconds, then held at 4° C.; the reaction was then purified with 0.8× volume (40 microliters) Ampure XP Beads (Agencourt; as per manufacturer's instructions), and eluted in 30 microliters H$_2$O, and quantitated spectrophotometrically.

In order to anneal adapter oligonucleotides (annealed and extended along the synthetic DNA templates as in the previous step) to multimeric barcode molecules, and then to anneal and then extend extension primer(s) across the adjacent barcode region(s) of each multimeric barcode molecule, and then to ligate this extension product to the phosphorylated 5' end of the adapter oligonucleotide annealed to the downstream thereof, to a PCR tube was added 10 microliters of the eluate from the previous step (containing the synthetic DNA templates along which the adapter oligonucleotides have been annealed and extended), plus 3.0 microliters of a 50.0 nanomolar solution of RNAse H-digested multimeric barcode molecules (as produced in the last step of Method 3), plus 6.0 microliters of 5× Isothermal extension/ligation buffer, plus water to final volume of 26.6 microliters. On a thermal cycler, the tube was incubated at 70° C. for 60 seconds, then slowly annealed to 60° C., then held at 60° C. for 5 minutes, then slowly annealed to 55° C. then held at 55° C. for 5 minutes, then slowly annealed to 50° C. at 0.1° C./sec then held at 50° C. for 30 minutes, then held at 4° C. To the tube was added 0.6 microliters 10 uM US_PCR_Prm_Only_02 (SEQ ID NO: 278, an extension primer), and the reaction was incubated at 50° C. for 10 minutes, then held at 4° C. To the tube was added 0.3 microliters (0.625 U) Phusion Polymerase (NEB; 2 U/uL) 2.5 microliters (100 U) Taq DNA Ligase (NEB; 40 U/uL); and 2.5 microliters 100 millimolar DTT. The tube was then incubated at 50° C. for 5 minutes, then held at 4° C. The reaction was then purified with 0.7× volume (21 microliters) Ampure XP Beads (Agencourt; as per manufacturer's instructions), and eluted in 30 microliters H$_2$O, and quantitated spectrophotometrically.

To a new PCR tube was add 25.0 microliters of the eluate, plus 10.0 microliters 5× Phusion HF buffer (NEB), plus 1.0 microliters 10 millimolar deoxynucleotide triphosphate nucleotide mix, plus 2.0 microliters 10 uM SynTemp_PE2_B1_Short1 (SEQ ID NO: 277; a primer that is complementary to part of the extension products produced by the above steps; serves as a primer for the primer-extension and then PCR reactions described here), plus 0.5 uL Phusion Polymerase (NEB), plus water to final volume of 49.7 microliters. Of this reaction, a volume of 5.0 microliters was added to a new PCR tube, which was then incubated for 30 seconds at 55° C., 30 seconds 60° C., and 30 seconds 72° C., then followed by 10 cycles of: 98° C. then 65° C. then 72° C. for 30 seconds each, then held at 4° C. To each tube was then added 9.0 microliters 5× Phusion buffer, plus 1.0 microliters 10 millimolar deoxynucleotide triphosphate nucleotide mix, plus 1.75 microliters 10 uM SynTemp_PE2_B1_Short1 (SEQ ID NO: 277), plus 1.75 microliters 10 uM US_PCR_Prm_Only_02 (SEQ ID NO: 278), plus 0.5 microliters Phusion Polymerase (NEB), plus water to final volume of 50 microliters. The PCR tube was placed on a thermal cycler and amplified for 24 cycles of: 98° C. for 30 seconds, then 72° C. for 30 seconds; then held at 4° C., then purified with 1.2× volume (60 microliters) Ampure XP Beads (Agencourt; as per manufacturer's instructions), and eluted in 30 microliters H$_2$O, and quantitated spectrophotometrically.

The resulting library was then barcoded for sample identification by a PCR-based method, amplified, and sequenced by standard methods using a 150-cycle, mid-output NextSeq flowcell (Illumina), and demultiplexed informatically for further analysis.

Method 9: Barcoding Genomic DNA Loci with Multimeric Barcoding Reagents Containing Barcoded Oligonucleotides This method describes a framework for barcoding targets within specific genomic loci (e.g. barcoding a number of exons within a specific gene) using multimeric barcoding reagents that contain barcoded oligonucleotides. First, a solution of Multimeric Barcode Molecules was produced by In Vitro Transcription and cDNA Synthesis (as described in Method 3). Then, solutions of multimeric barcoding reagents containing barcoded oligonucleotides was produced as described in Method 4, with a modification made such that instead of using an adapter oligonucleotide targeting a synthetic DNA template (i.e. DS_ST_05, SEQ ID NO: 273, as used in Method 4), adapter oligonucleotides targeting the specific genomic loci were included at that step. Specifically, a solution of multimeric barcoding reagents containing appropriate barcoded oligonucleotides was produced individually for each of three different human genes: BRCA1 (containing 7 adapter oligonucleotides, SEQ ID NOs 279-285), HLA-A (containing 3 adapter oligonucleotides, SEQ ID NOs 286-288), and DQB1 (containing 2 adapter oligonucleotides, SEQ ID NOs 289-290). The process of Method 4 was conducted for each of these three solutions as described above. These three solutions were then merged together, in equal volume, and diluted to a final, total concentration all barcoded oligonucleotides of approximately 50 nanomolar.

In a PCR tube were plus 2.0 microliters 5× Phusion HF buffer (NEB), plus 1.0 microliter of 100 nanogram/microliter human genomic DNA (NA12878 from Coriell Institute) to final volume of 9.0 microliters. In certain variant versions of this protocol, the multimeric barcoding reagents (containing barcoded oligonucleotides) were also added at this step, prior to the high-temperature 98° C. incubation. The reaction was incubated at 98° C. for 120 seconds, then held at 4° C. To the tube was added 1.0 microliters of the above 50 nanomolar solution of multimeric barcode reagents, and then the reaction was incubated for 1 hour at 55° C., then 1 hour at 50° C., then 1 hour at 45° C., then held at 4° C. (Note that for certain samples, this last annealing process was extended to occur overnight, for a total of approximately 4 hours per temperature step).

In order to add a reverse universal priming sequence to each amplicon sequence (and thus to enable subsequent amplification of the entire library at once, using just one forward and one reverse amplification primer), the reaction was diluted 1:100, and 1.0 microliter of the resulting solution was added in a new PCR tube to 20.0 microliters 5× Phusion HF buffer (NEB), plus 2.0 microliters 10 millimolar deoxynucleotide triphosphate nucleotide mix, plus 1.0 microliters a reverse-primer mixture (equimolar concentration of SEQ ID Nos 291-303, each primer at 5 micromolar concentration), plus 1.0 uL Phusion Polymerase (NEB), plus water to final volume of 100 microliters. The reaction was incubated at 53° C. for 30 seconds, 72° C. for 45 seconds, 98° C. for 90 seconds, then 68° C. for 30 seconds, then 64° C. for 30 seconds, then 72° C. for 30 seconds; then held at 4° C. The reaction was then purified with 0.8× volume (80 microliters) Ampure XP Beads (Agencourt; as per manufacturer's instructions), and eluted in 30 microliters H$_2$O, and quantitated spectrophotometrically.

The resulting library was then barcoded for sample identification by a PCR-based method, amplified, and sequenced by standard methods using a 150-cycle, mid-output NextSeq flowcell (Illumina), and demultiplexed informatically for further analysis.

Method 10—Sequencing the Library of Multimeric Barcode Molecules

Preparing Amplified Selected Molecules for Assessment with High-Throughput Sequencing To a PCR tube was added 1.0 microliters of the amplified selected molecule solution, plus 1.0 microliters of 100 micromolar CS_SQ_AMP_REV1 (SEQ ID NO: 16), plus 1.0 microliters of 100 micromolar US_PCR_Prm_Only_02 (SEQ ID NO: 17), plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) plus 84.0 microliters H$_2$O to final volume of 100 microliters. The PCR tube was placed on a thermal cycler and amplified for 3 cycles of: 95° C. for 30 seconds, then 56° C. for 30 seconds, then 72° C. for 3 minutes; then held at 4° C. The solution was then purified with 0.8× volume (80 microliters) Ampure XP Beads (Agencourt; as per manufacturer's instructions), and eluted in 85 microliters H$_2$O.

This solution was then added to a new PCR tube, plus 1.0 microliters of 100 micromolar Illumina_PE1, plus 1.0 microliters of 100 micromolar Illumina_PE2, plus 10 microliters of 10× Thermopol Buffer (NEB) plus 2.0 microliter of 10 millimolar deoxynucleotide triphosphate nucleotide mix (Invitrogen), plus 1.0 microliters Vent Exo-Minus Polymerase (New England Biolabs, at 2 U/uL) to final volume of 100 microliters. The PCR tube was placed on a thermal cycler and amplified for 4 cycles of: 95° C. for 30 seconds, then 64° C. for 30 seconds, then 72° C. for 3 minutes; then 18 cycles of: 95° C. for 30 seconds, then 67° C. for 30 seconds, then 72° C. for 3 minutes; then held at 4° C. The solution was then purified with 0.8× volume (80 microliters) Ampure XP Beads (Agencourt; as per manufacturer's instructions), and eluted in 40 microliters H$_2$O.

High-throughput Illumina sequencing was then performed on this sample using a MiSeq sequencer with paired-end, 250-cycle V2 sequencing chemistry.

Figure 17:
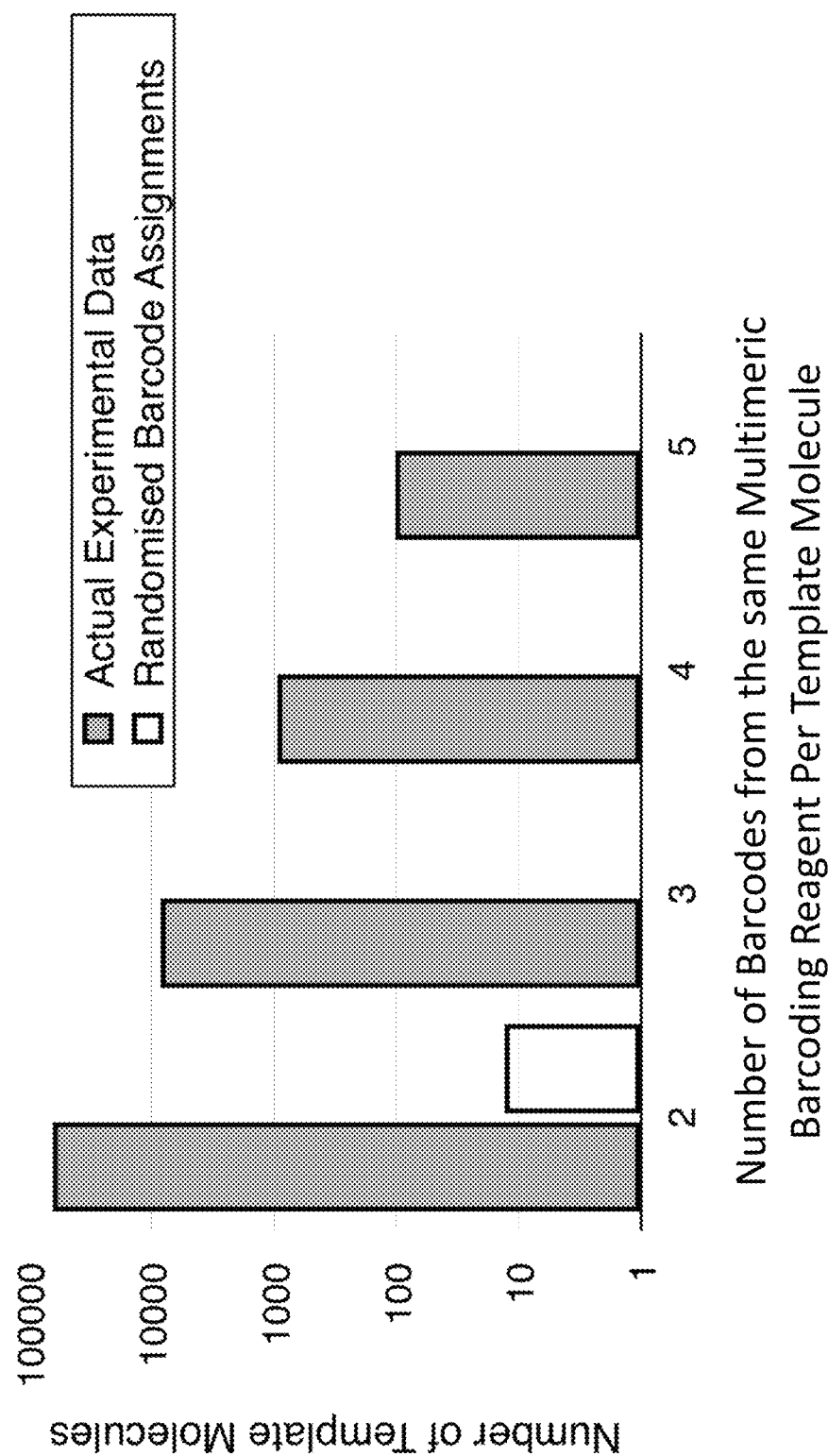
FIG. 17 is a graph showing the number of barcodes from the same multimeric barcoding reagent that labelled sequences on the same synthetic template molecule against the number of synthetic template molecules.

Method 11—Assessment of Multimeric Nature of Barcodes Annealed and Extended Along Single Synthetic Template DNA Molecules A library of barcoded synthetic DNA templates was created using a solution of multimeric barcoding reagents produced according to a protocol as described generally in Method 3 and Method 4, and using a solution of synthetic DNA templates as described in Method 5, and using a laboratory protocol as described in Method 6; the resulting library was then barcoded for sample identification by a PCR-based method, amplified, and sequenced by standard methods using a 150-cycle, mid-output NextSeq flowcell (Illumina), and demultiplexed informatically for further analysis. The DNA sequencing results from this method were then compared informatically with data produced from Method 10 to assess the degree of overlap between the multimeric barcoding of synthetic DNA templates and the arrangement of said barcodes on individual multimeric barcoding reagents (the results are shown in FIG. 17).

Results

Structure and Expected Sequence Content of Each Sequence Multimeric Barcoding Reagent Molecule The library of multimeric barcode molecules synthesised as described in Methods 1 to 3 was prepared for high-throughput sequencing, wherein each molecule sequenced includes a contiguous span of a specific multimeric barcode molecule (including one or more barcode sequences, and one or more associate upstream adapter sequences and/or downstream adapter sequences), all co-linear within the sequenced molecule. This library was then sequenced with paired-end 250 nucleotide reads on a MiSeq sequencer (Illumina) as described. This yielded approximately 13.5 million total molecules sequenced from the library, sequenced once from each end, for a total of approximately 27 million sequence reads.

Each forward read is expected to start with a six nucleotide sequence, corresponding to the 3' end of the upstream adapter: TGACCT This forward read is followed by the first barcode sequence within the molecule (expected to be 20 nt long).

This barcode is then followed by an 'intra-barcode sequence' (in this case being sequenced in the 'forward' direction (which is 82 nucleotides including both the downstream adapter sequence and upstream adapter sequence in series):

ATACCTGACTGCTCGTCAGTTGAGCGAATTCCGTATGGTGGTACACACCT

ACACTACTCGGACGCTCTTCCGATCTTGACCT

Within the 250 nucleotide forward read, this will then be followed by a second barcode, another intra-barcode sequence, and then a third barcode, and then a fraction of another intra-barcode sequence.

Each reverse read is expected to start with a sequence corresponding to the downstream adapter sequence: GCTCAACTGACGAGCAGTCAGGTAT This reverse read is then followed by the first barcode coming in from the opposite end of the molecule (also 20 nucleotides long, but sequenced from the opposite strand of the molecule and thus of the inverse orientation to those sequenced by the forward read)

This barcode is then followed by the 'intra-barcode sequence' but in the inverse orientation (as it is on the opposite strand):

AGGTCAAGATCGGAAGAGCGTCCGAGTAGTGTAGGTGTGTACCACCATAC

GGAATTCGCTCAACTGACGAGCAGTCAGGTAT

Likewise this 250 nucleotide reverse read will then be followed by a second barcode, another intra-barcode sequence, and then a third barcode, and then a fraction of another intra-barcode sequence.

Sequence Extraction and Analysis

With scripting in Python, each associated pair of barcode and flanking upstream-adapter and downstream-adapter sequence were isolated, with each individual barcode sequence of each barcode molecule then isolated, and each barcode sequence that was sequenced within the same molecule being annotated as belonging to the same multimeric barcode molecule in the library of multimeric barcode molecules. A simple analysis script (Networkx; Python) was employed to determine overall multimeric barcode molecule barcode groups, by examining overlap of barcode-barcode pairs across different sequenced molecules. Several metrics of this data were made, including barcode length, sequence content, and the size and complexity of the multimeric barcode molecules across the library of multimeric barcode molecules.

Number of Nucleotides within Each Barcode Sequence

Figure 1:
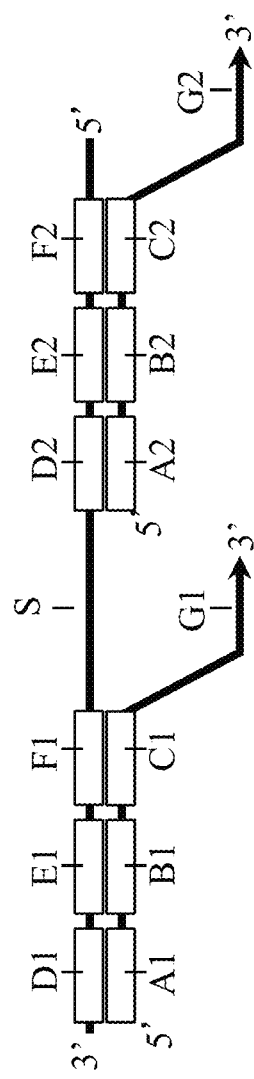
FIG. 1 illustrates a multimeric barcoding reagent that may be used in the method illustrated in FIG. 3 or FIG. 4.
Figure 2:
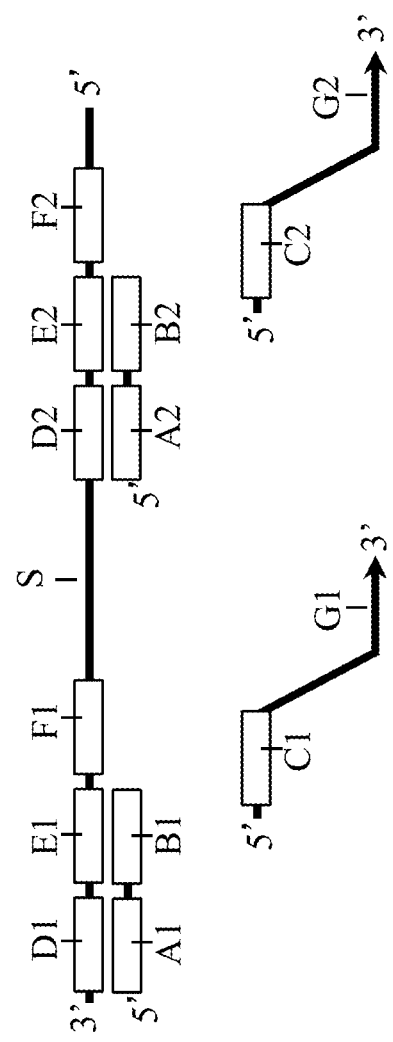
FIG. 2 illustrates a kit comprising a multimeric barcoding reagent and adapter oligonucleotides for labelling a target nucleic acid.
Figure 3:
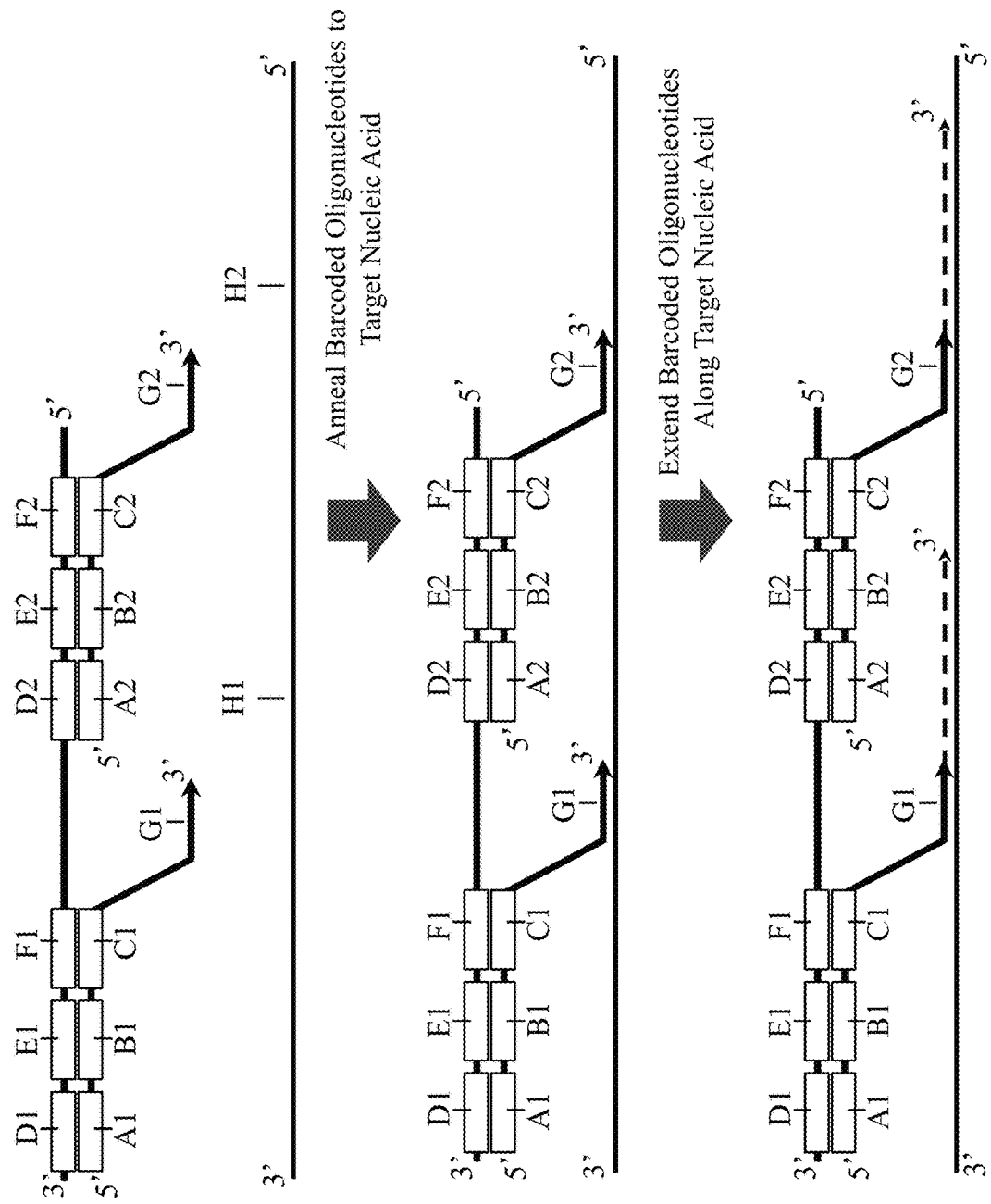
FIG. 3 illustrates a first method of preparing a nucleic acid sample for sequencing using a multimeric barcoding reagent.
Figure 4:
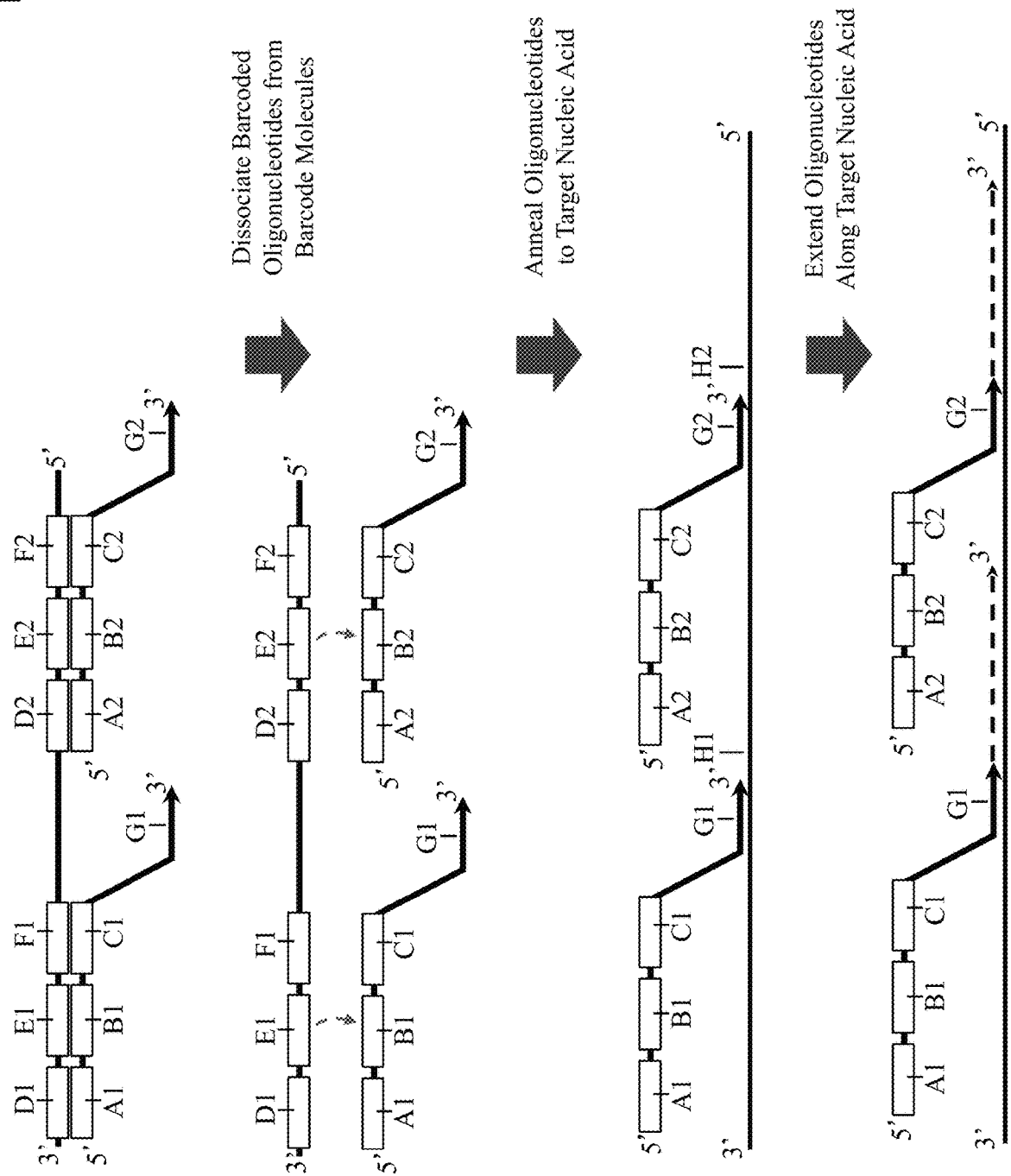
FIG. 4 illustrates a second method of preparing a nucleic acid sample for sequencing using a multimeric barcoding reagent.
Figure 5:
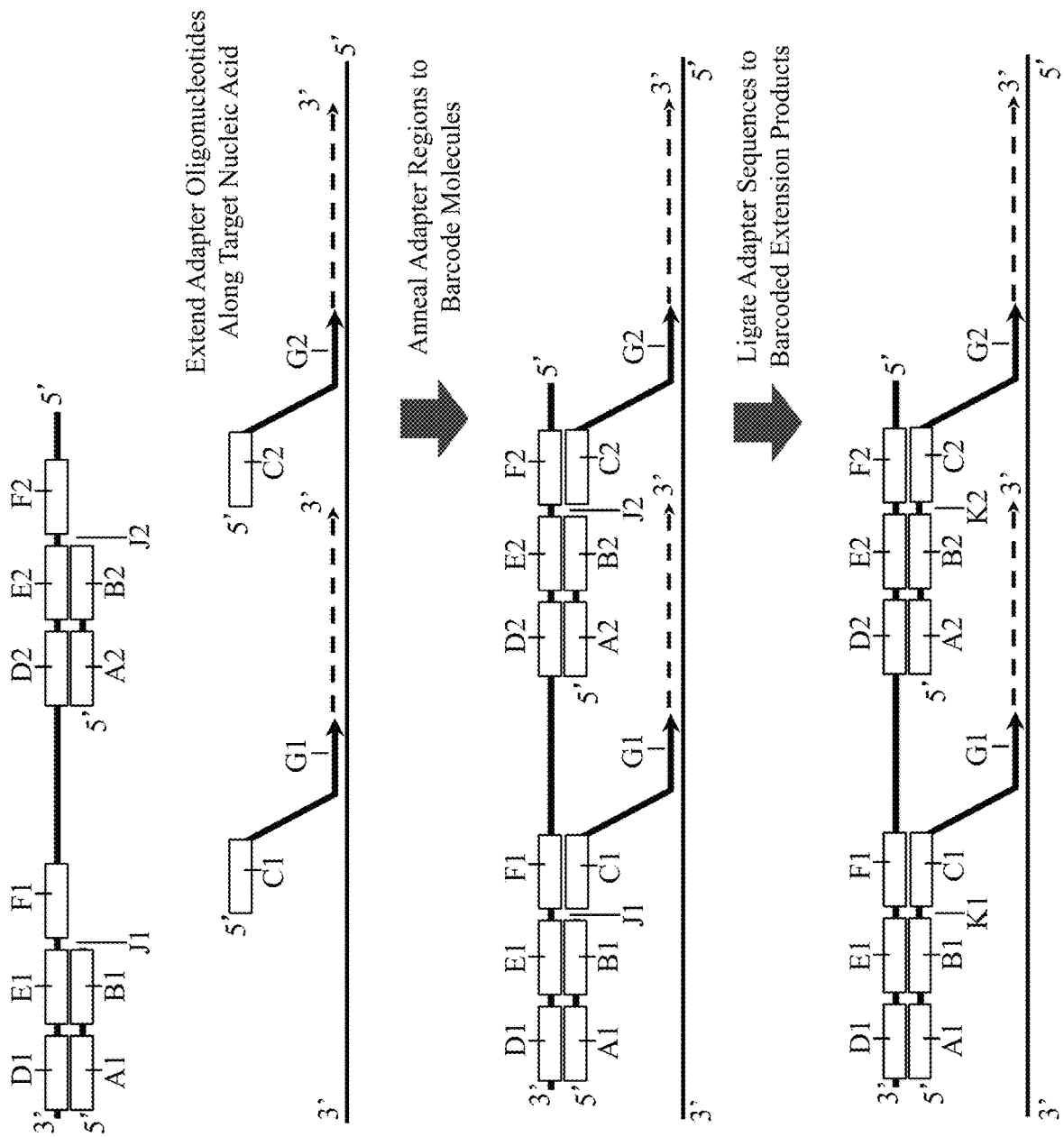
FIG. 5 illustrates a method of preparing a nucleic acid sample for sequencing using a multimeric barcoding reagent and adapter oligonucleotides.
Figure 6:
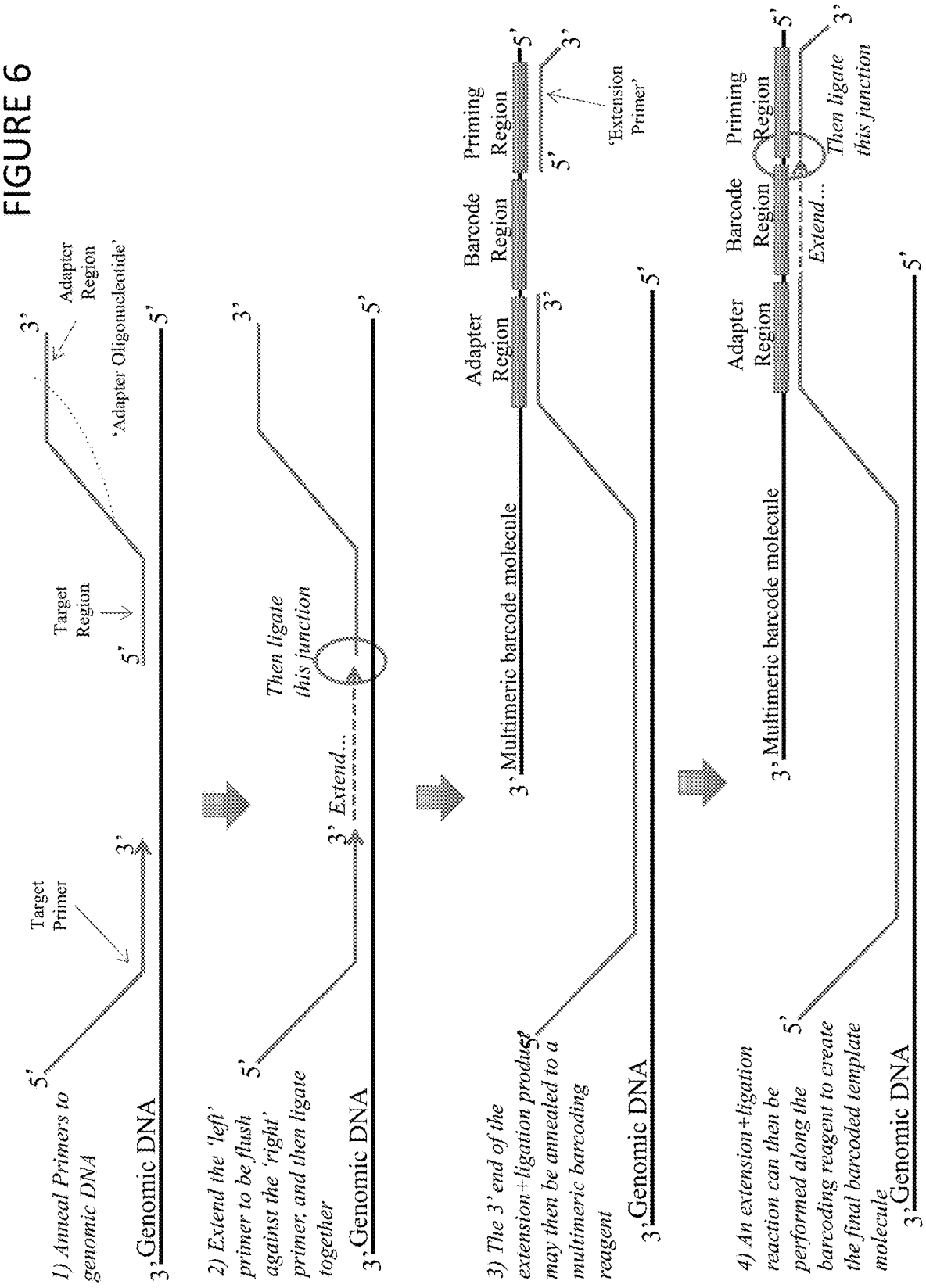
FIG. 6 illustrates a method of preparing a nucleic acid sample for sequencing using a multimeric barcoding reagent, adapter oligonucleotides and target oligonucleotides.
Figure 7:
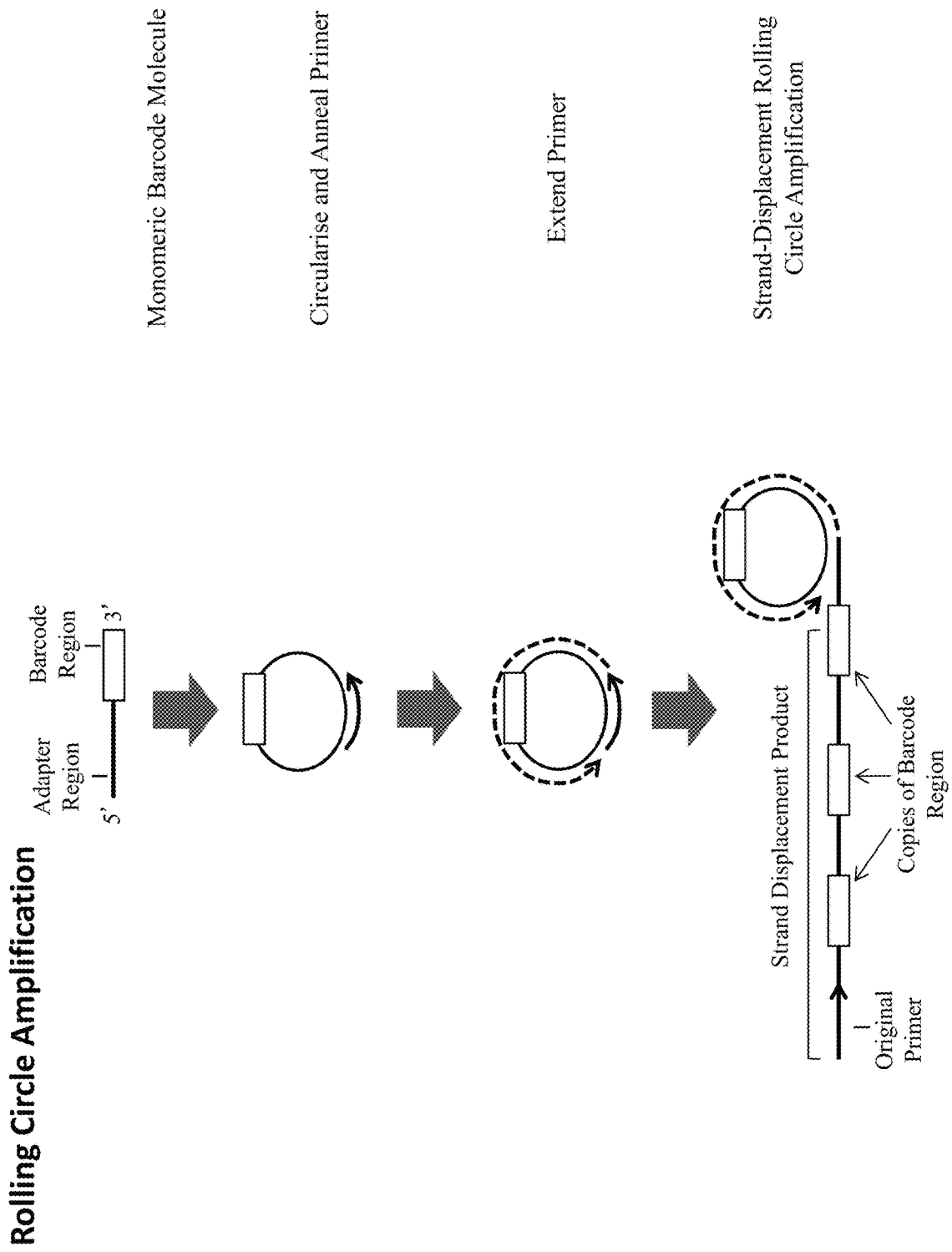
FIG. 7 illustrates a method of assembling a multimeric barcode molecule using a rolling circle amplification process.
Figure 8:
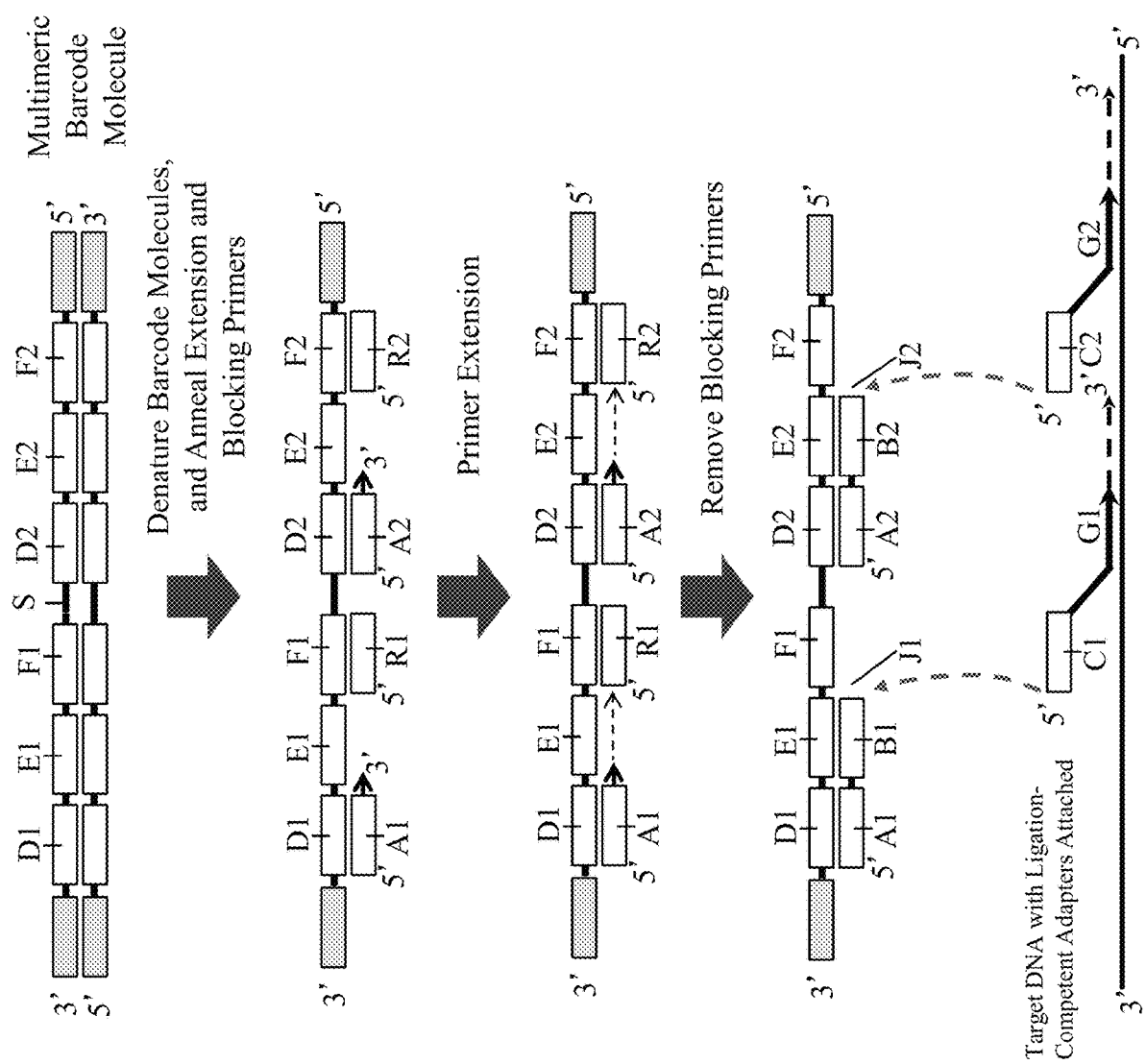
FIG. 8 illustrates a method of synthesizing multimeric barcoding reagents for labeling a target nucleic acid that may be used in the methods illustrated in FIG. 3, FIG. 4 and/or FIG. 5.
Figure 9:
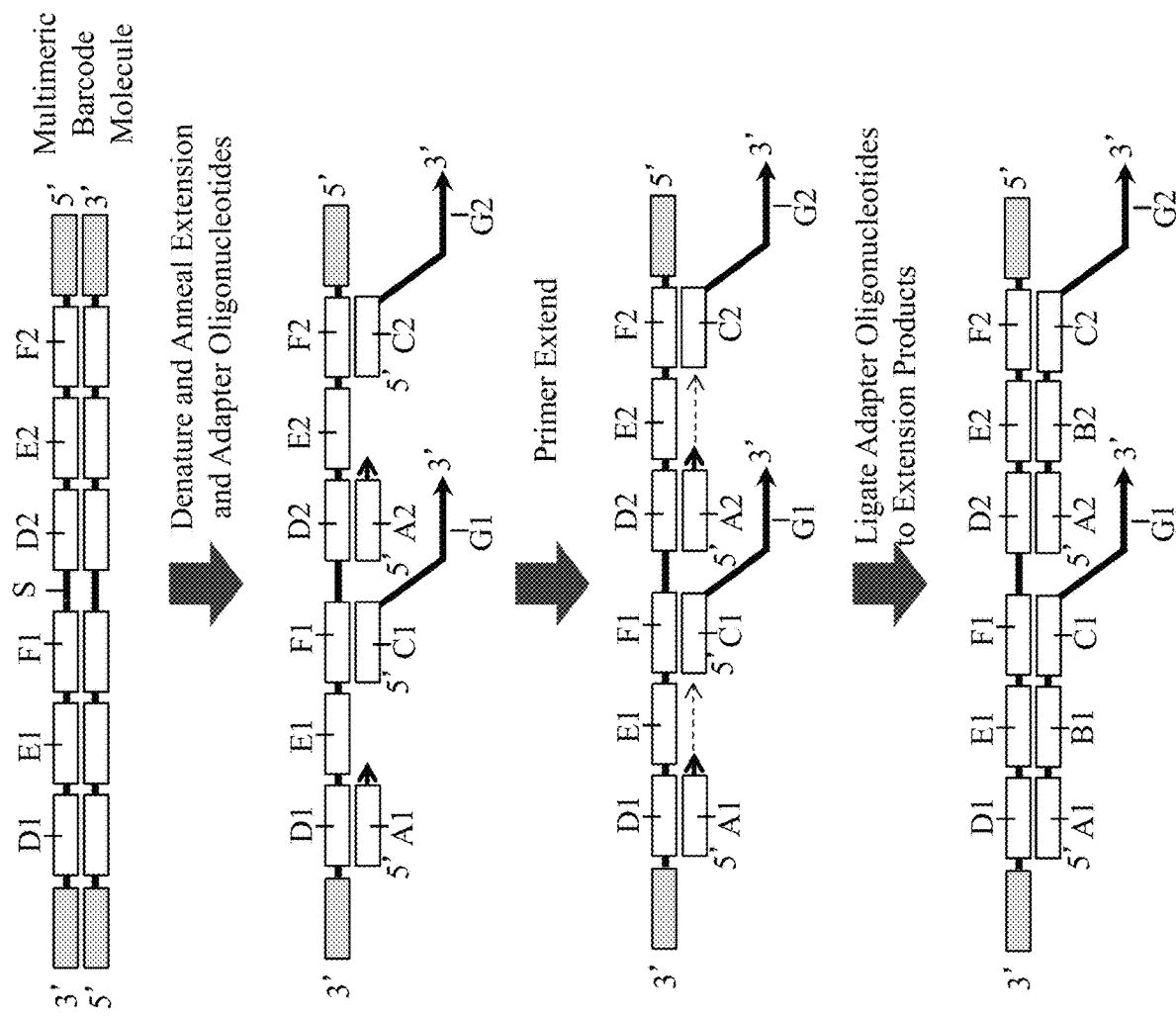
FIG. 9 illustrates an alternative method of synthesizing multimeric barcoding reagents (as illustrated in FIG. 1) for labeling a target nucleic acid that may be used in the method illustrated in FIG. 3 and/or FIG. 4.
Figure 10:
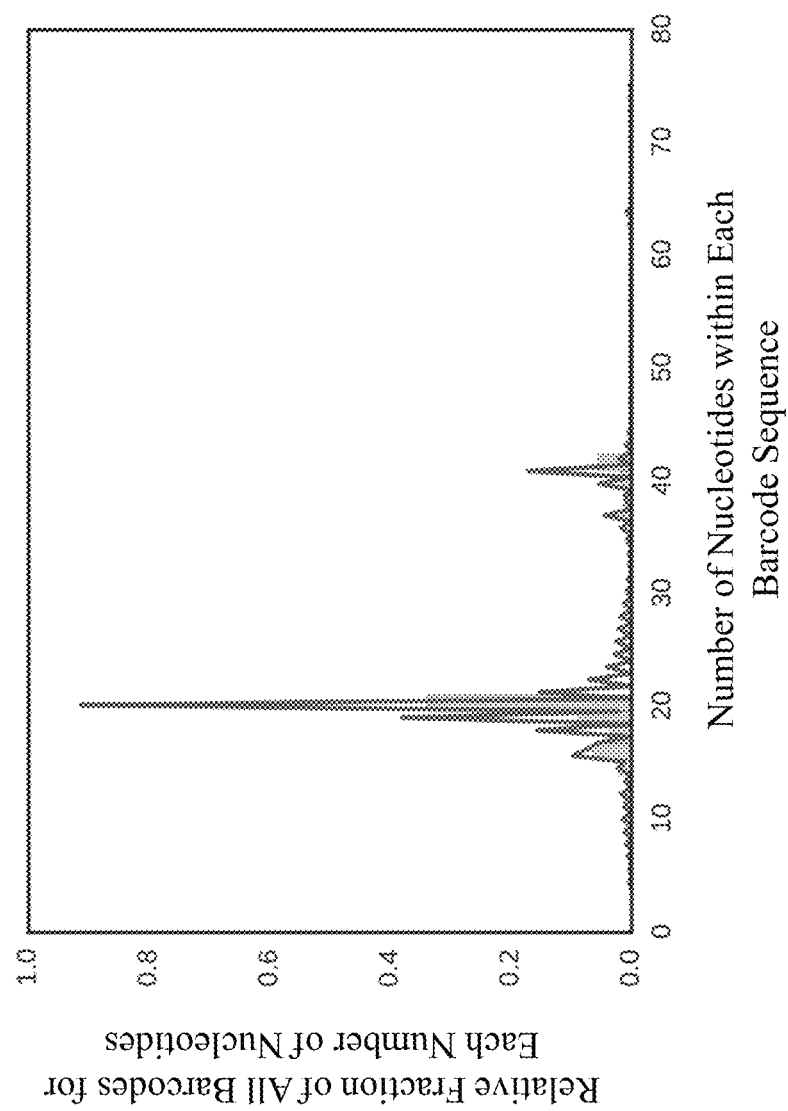
FIG. 10 is a graph showing the total number of nucleotides within each barcode sequence.

Each individual barcode sequence from each barcode molecule, contained within each Illumina-sequenced molecule was isolated, and the total length of each such barcode was determined by counting the number of nucleotides between the upstream adapter molecule sequence, and the downstream adapter molecule sequence. The results are shown in FIG. 10.

The overwhelming majority of barcodes are 20 nucleotides long, which corresponds to five additions of our four-nucleotide-long sub-barcode molecules from our double-stranded sub-barcode library. This is thus the expected and desired result, and indicates that each 'cycle' of: Ligation of Sub-Barcode Library to MlyI-Cleaved Solution, PCR Amplification of the Ligated Library, Uracil Glycosylase Enzyme Digestion, and MlyI Restriction Enzyme Cleavage, was successful and able to efficiently add new four-nucleotide sub-barcode molecules at each cycle, and then was successfully able to amplify and carry these molecules forward through the protocol for continued further processing, including through the five total cycles of sub-barcode addition, to make the final, upstream-adapter-ligated libraries.

We also used this sequence analysis method to quantitate the total number of unique barcodes in total, across all sequenced multimeric barcode molecules: this amounted to 19,953,626 total unique barcodes, which is essentially identical to the 20 million barcodes that would be expected, given that we synthesised 2 million multimeric barcode molecules, each with approximately 10 individual barcode molecules.

Together, this data and analysis thus shows that the methods of creating complex, combinatoric barcodes from sub-barcode sequences is effective and useful for the purpose of synthesising multimeric barcode molecules.

Total Number of Unique Barcode Molecules in Each Multimeric Barcode Molecule

Figure 11:
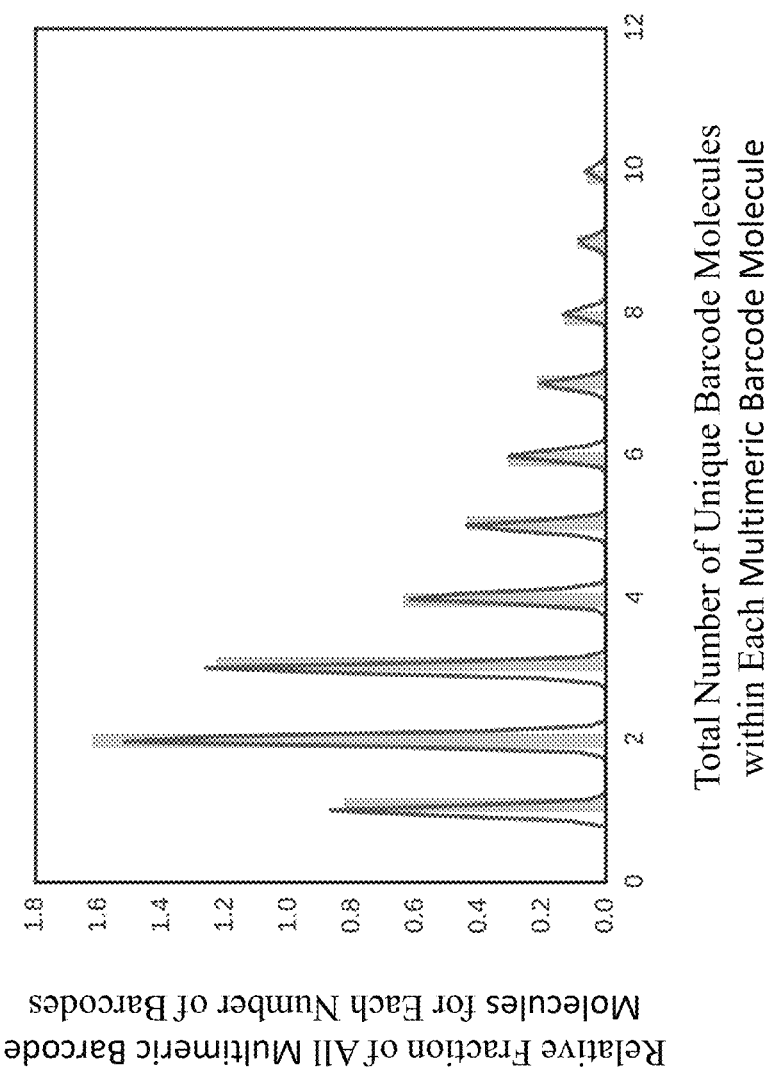
FIG. 11 is a graph showing the total number of unique barcode molecules in each sequenced multimeric barcode molecule.

FIG. 11 shows the results of the quantification of the total number of unique barcode molecules (as determined by their respective barcode sequences) in each sequenced multimeric barcode molecule. As described above, to do this we examined, in the first case, barcode sequences which were present and detected within the same individual molecules sequenced on the sequencer. We then employed an additional step of clustering barcode sequences further, wherein we employed a simple network analysis script (Networkx) which can determine links between individual barcode sequences based both upon explicit knowledge of links (wherein the barcodes are found within the same, contiguous sequenced molecule), and can also determine 'implicit' links, wherein two or more barcodes, which are not sequenced within the same sequenced molecule, instead both share a direct link to a common, third barcode sequence (this shared, common link thus dictating that the two first barcode sequences are in fact located on the same multimeric barcode molecule).

This figure shows that the majority of multimeric barcode molecules sequenced within our reaction have two or more unique barcodes contained therein, thus showing that, through our Overlap-Extension PCR linking process, we are able to link together multiple barcode molecules into multimeric barcode molecules. Whilst we would expect to see more multimeric barcode molecules exhibiting closer to the expected number of barcode molecules (10), we expect that this observed effect is due to insufficiently high sequencing depth, and that with a greater number of sequenced molecules, we would be able to observe a greater fraction of the true links between individual barcode molecules. This data nonetheless suggest that the fundamental synthesis procedure we describe here is efficacious for the intended purpose.

Representative Multimeric Barcode Molecules

Figure 12:
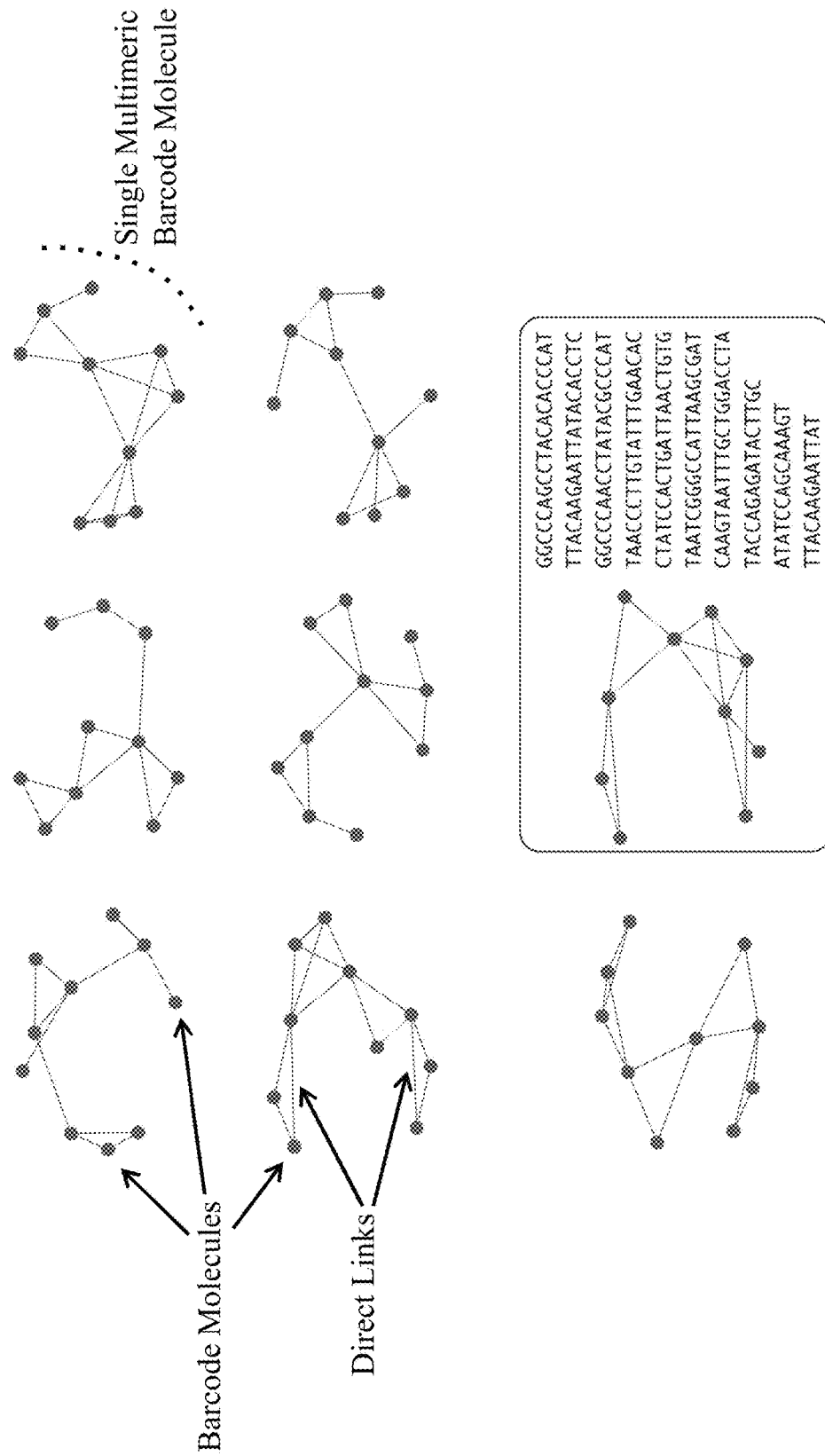
FIG. 12 shows representative multimeric barcode molecules that were detected by the analysis script.

FIG. 12 shows representative multimeric barcode molecules that have been detected by our analysis script. In this figure, each 'node' is a single barcode molecule (from its associated barcode sequence), each line is a 'direct link' between two barcode molecules that have been sequenced at least once in the same sequenced molecule, and each cluster of nodes is an individual multimeric barcode molecule, containing both barcodes with direct links and those within implicit, indirect links as determined by our analysis script. The inset figure includes a single multimeric barcode molecule, and the sequences of its constituent barcode molecules contained therein.

This figure illustrates the our multimeric barcode molecule synthesis procedure: that we are able to construct barcode molecules from sub-barcode molecule libraries, that we are able to link multiple barcode molecules with an overlap-extension PCR reaction, that we are able to isolate a quantitatively known number of individual multimeric barcode molecules, and that we are able to amplify these and subject them to downstream analysis and use.

Barcoding Synthetic DNA Templates of Known Sequence with (i) Multimeric Barcoding Reagents Containing Barcoded Oligonucleotides, and (ii) Multimeric Barcoding Reagents and Separate Adapter Oligonucleotides Sequence Extraction and Analysis With scripting in Python and implemented in an Amazon Web Services (AWS) framework, for each sequence read following sample-demultiplexing, each barcode region from the given multimeric barcode reagent was isolated from its flanking upstream-adapter and downstream-adapter sequence. Likewise, each molecular sequence identifier region from the given synthetic DNA template molecule was isolated from its flanking upstream and downstream sequences. This process was repeated for each molecule in the sample library; a single filtering step was performed in which individual barcodes and molecular sequence identifiers that were present in only a single read (thus likely to represent either sequencing error or error from the enzymatic sample-preparation process) were censored from the data. For each molecular sequence identifier, the total number of unique (ie with different sequences) barcode regions found associated therewith within single sequence reads was quantitated. A histogram plot was then created to visualize the distribution of this number across all molecular sequence identifiers found in the library.

DISCUSSION

Figure 13:
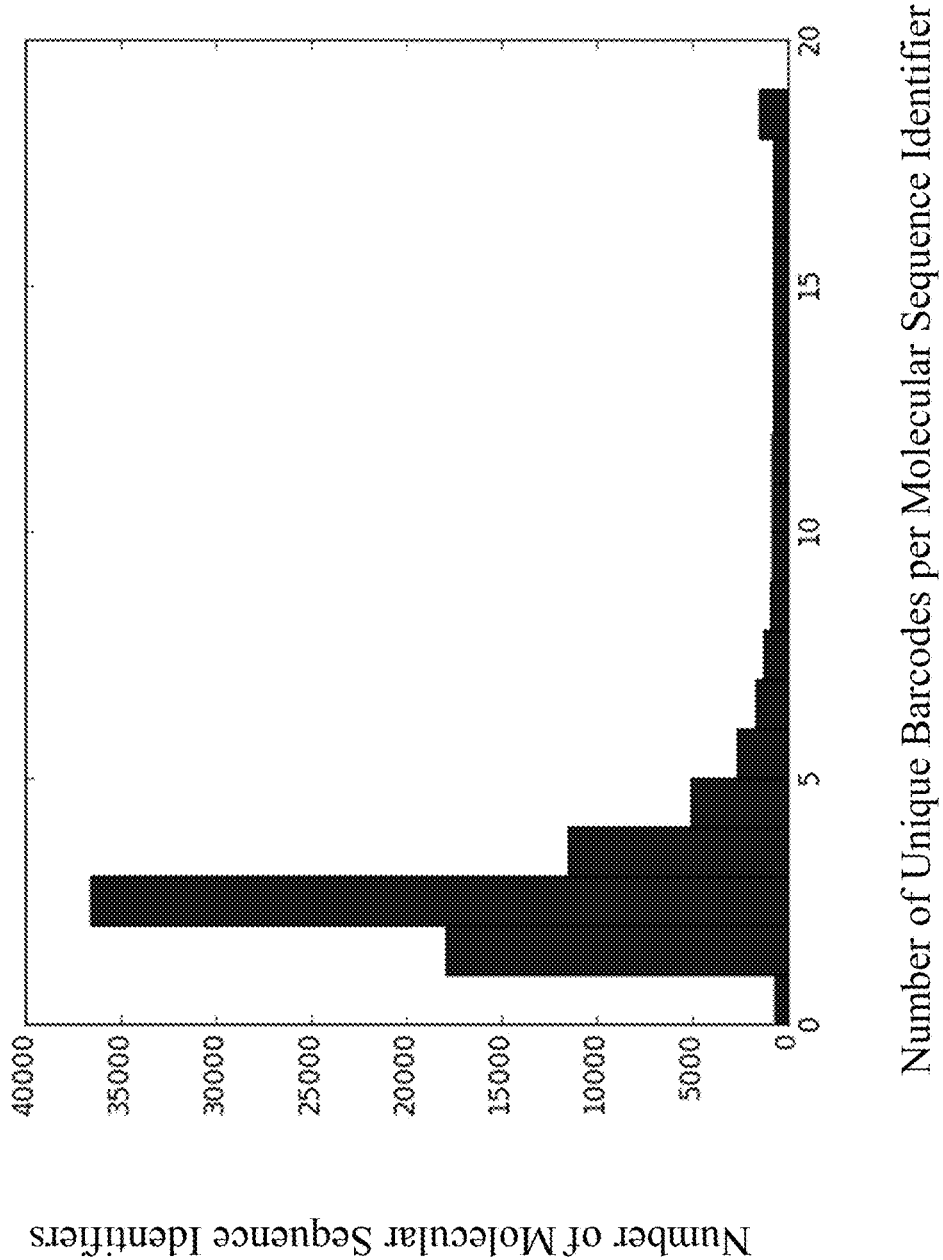
FIG. 13 is a graph showing the number of unique barcodes per molecular sequence identifier against the number of molecular sequence identifiers following the barcoding of synthetic DNA templates of known sequence with multimeric barcoding reagents containing barcoded oligonucleotides.

FIG. 13 shows the results of this analysis for Method 6 (Barcoding Synthetic DNA Templates of Known Sequence with Multimeric Barcoding Reagents Containing Barcoded Oligonucleotides). This figure makes clear that the majority of multimeric barcoding reagents are able to successfully label two or more of the tandemly-repeated copies of each molecular sequence identifier with which they are associated. A distribution from 1 to approximately 5 or 6 'labelling events' is observed, indicating that there may be a degree of stochastic interactions that occur with this system, perhaps due to incomplete enzymatic reactions, or steric hindrance at barcode reagent/synthetic template interface, or other factors.

Figure 14:
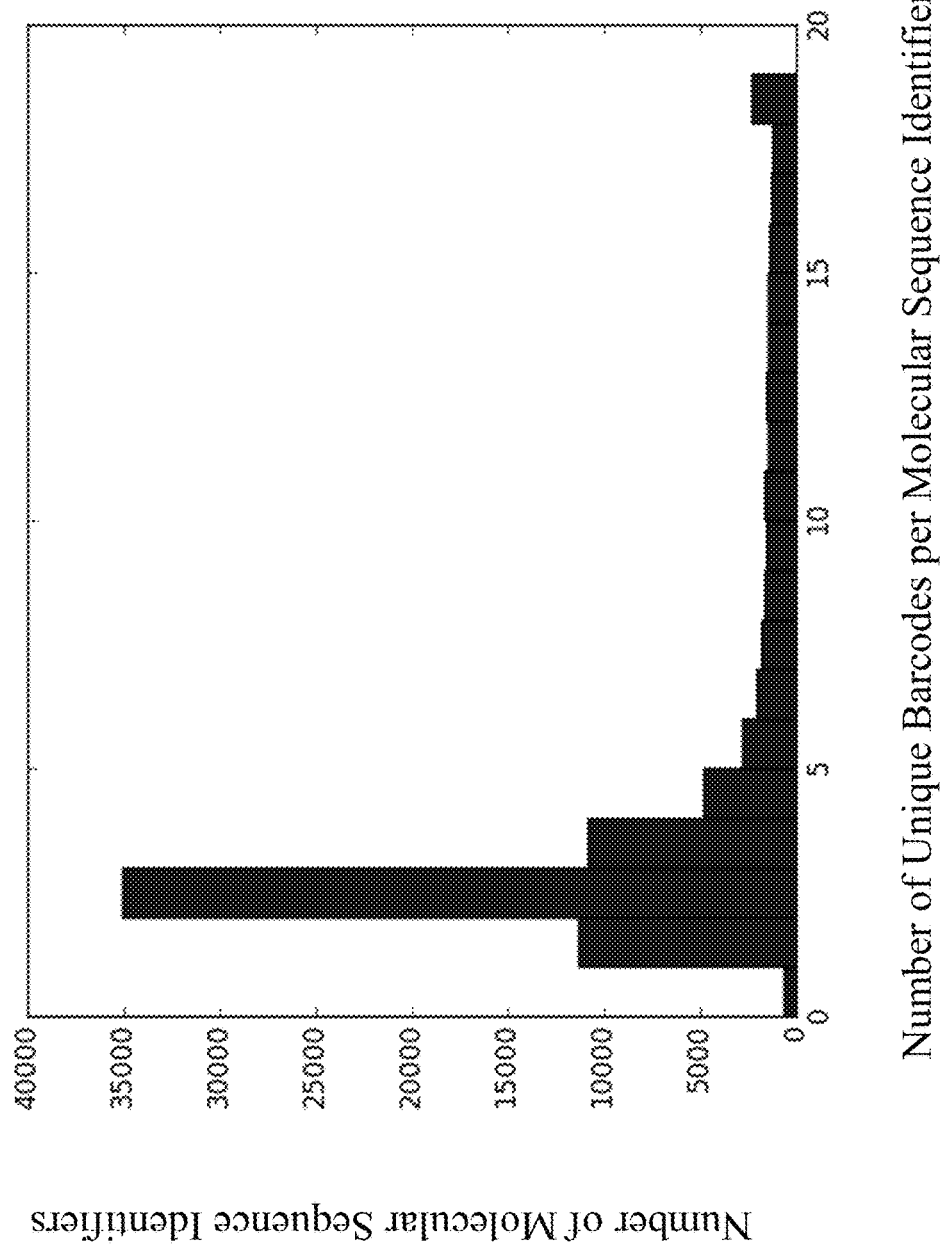
FIG. 14 is a graph showing the number of unique barcodes per molecular sequence identifier against the number of molecular sequence identifiers following the barcoding of synthetic DNA templates of known sequence with multimeric barcoding reagents and separate adapter oligonucleotides.

FIG. 14 shows the results of this same analysis conducted using Method 7 (Barcoding Oligonucleotides Synthetic DNA Templates of Known Sequence with Multimeric Barcode Molecules and Separate Adapter Oligonucleotides). This figure also clearly shows that the majority of multimeric barcoding reagents are able to successfully label two or more of the tandemly-repeated copies of each molecular sequence identifier with which they are associated, with a similar distribution to that observed for the previous analysis.

Together, these two figures show that this framework for multimeric molecular barcoding is an effective one, and furthermore that the framework can be configured in different methodologic ways. FIG. 13 shows results based on a method in which the framework is configured such that the multimeric barcode reagents already contain barcoded oligonucleotides, prior to their being contacted with a target (synthetic) DNA template. In contrast, FIG. 14 shows results based on an alternative method in which the adapter oligonucleotides first contact the synthetic DNA template, and then in a subsequent step the adapter oligonucleotides are barcoded through contact with a multimeric barcode reagent. Together these figures demonstrate both the multimeric barcoding ability of these reagents, and their versatility in different key laboratory protocols.

To analyse whether, and the extent to which, individual multimeric barcoding reagents successfully label two or more sub-sequences of the same synthetic DNA template, the groups of different barcodes on each individual multimeric barcoding reagent in the library (as predicted from the Networkx analysis described in the preceding paragraph and as illustrated in FIG. 12) was compared with the barcodes annealed and extended along single synthetic DNA templates (as described in Method 11). Each group of barcodes found on individual multimeric barcoding reagents was given a numeric 'reagent identifier label'. For each synthetic DNA template molecular sequence identifier (i.e., for each individual synthetic DNA template molecule) that was represented in the sequencing data of Method 11 by two or more barcodes (i.e., wherein two or more sub-sequences of the synthetic template molecule were annealed and extended by a barcoded oligonucleotide), the corresponding 'reagent identifier label' was determined. For each such synthetic template molecule, the total number of multimeric barcodes coming from the same, single multimeric barcoding reagent was then calculated (i.e., the number of different sub-sequences in the synthetic template molecule that were labeled by a different barcoded oligonucleotide but from the same, single multimeric barcoding reagent was calculated). This analysis was then repeated and compared with a 'negative control' condition, in which the barcodes assigned to each 'reagent identifier label' were randomized (i.e. the same barcode sequences remain present in the data, but they no longer correspond to the actual molecular linkage of different barcode sequences across the library of multimeric barcoding reagents).

The data from this analysis is shown in FIG. 17, for both the actual experimental data and for the control data with randomized barcode assignments (note the logarithmic scale of the vertical axis). As this figure shows, though the number of unique barcoding events per target synthetic DNA template molecule is small, they overlap almost perfectly with the known barcode content of individual multimeric barcoding reagents. That is, when compared with the randomized barcode data (which contains essentially no template molecules that appear to be 'multivalently barcoded'), the overwhelming majority (over 99.9%) of template molecules in the actual experiment that appear to be labeled by multiple barcoded oligonucleotides from the same, individual multimeric barcoding reagent, are in fact labeled multiply by the same, single reagents in solution. By contrast, if there were no non-random association between the different barcodes that labelled individual synthetic DNA templates (that is, if FIG. 17 showed no difference between the actual experimental data and the randomized data), then this would have indicated that the barcoding had not occurred in a spatially-constrained manner as directed by the multimeric barcoding reagents. However, as explained above, the data indicates convincingly that the desired barcoding reactions did occur, in which sub-sequences found on single synthetic DNA templates interacted with (and were then barcoded by) only single, individual multimeric barcoding reagents.

Figure 16:
FIG. 16 is a schematic illustration of a sequence read obtained from barcoding genomic DNA loci with multimeric barcoding reagents containing barcoded oligonucleotides.

Barcoding Genomic DNA Loci with Multimeric Barcoding Reagents Containing Barcoded Oligonucleotides Sequence Extraction and Analysis As with other analysis, scripting was composed in Python and implemented in an Amazon Web Services (AWS) framework. For each sequence read following sample-demultiplexing, each barcode region from the given multimeric barcode reagent was isolated from its flanking upstream-adapter and downstream-adapter sequence and recorded independently for further analysis. Likewise, each sequence to the 3' end of the downstream region (representing sequence containing the barcoded oligonucleotide, and any sequences that the oligonucleotide had primed along during the experimental protocol) was isolated for further analysis. Each downstream sequence of each read was analysed for the presence of expected adapter oligonucleotide sequences (i.e. from the primers corresponding to one of the three genes to which the oligonucleotides were directed) and relevant additional downstream sequences. Each read was then recorded as being either 'on-target' (with sequence corresponding to one of the expected, targeted sequence) or 'off-target'. Furthermore, for each of the targeted regions, the total number of unique multimeric barcodes (i.e. with identical but duplicate barcodes merged into a single-copy representation) was calculated. A schematic of each expected sequence read, and the constituent components thereof, is shown in FIG. 16.

DISCUSSION

FIG. 15 shows the results of this analysis for this method, for four different independent samples. These four samples represent a method wherein the process of annealing the multimeric barcode reagents took place for either 3 hours, or overnight (approximately 12 hours). Further, for each of these two conditions, the method was performed either with the multimeric barcode reagents retained intact as originally synthesized, or with a modified protocol in which the barcoded oligonucleotides are first denatured away from the barcode molecules themselves (through a high-temperature melting step). Each row represents a different amplicon target as indicated, and each cell represents the total number of unique barcode found associated with each amplicon in each of the four samples. Also listed is the total proportion of on-target reads, across all targets summed together, for each sample.

As seen in the figure, the majority of reads across all samples are on-target; however there is seen a large range in the number of unique barcode molecules observed for each amplicon target. These trends across different amplicons seem to be consistent across the different experimental conditions, and could be due to different priming (or mispriming) efficiencies of the different oligonucleotides, or different amplification efficiencies, or different mapping efficiencies, plus potential other factors acting independently or in combination. Furthermore, it is clear that the samples that were annealed for longer have a larger number of barcodes observed, likely due to more complete overall annealing of the multimeric reagents to their cognate genomic targets. And furthermore, the samples where the barcoded oligonucleotides were first denatured from the barcode molecules show lower overall numbers of unique barcodes, perhaps owing to an avidity effect wherein fully assembled barcode molecules can more effectively anneal clusters of primers to nearby genomic targets at the same locus. In any case, taken together, this figure illustrates the capacity of multimeric reagents to label genomic DNA molecules, across a large number of molecules simultaneously, and to do so whether the barcoded oligonucleotides remain bound on the multimeric barcoding reagents or whether they have been denatured therefrom and thus potentially able to diffuse more readily in solution.

Example 2

Materials and Methods for Linking Sequences from Microparticles

All experimental steps are conducted in a contamination-controlled laboratory environment, including the use of standard physical laboratory separations (E.g. pre-PCR and post-PCR laboratories).

Protocol for Isolating a Microparticle Specimen

A standard blood sample (e.g. 5-15 mL in total) is taken from a subject, and processed with a blood fractionation method using EDTA-containing tubes to isolate the plasma fraction, using centrifugation at 800×G for 10 minutes. Then a cellular plasma fraction is then carefully isolated and centrifuged at 800×G for 10 minutes to pellet remaining intact cells. The supernatant is then carefully isolated for further processing. The supernatant is then centrifuged at 3000×G for 30 minutes to pellet a microparticle fraction (a high-speed centrifugation mode at 20,000×G for 30 minutes is used to pellet a higher-concentration microparticle specimen); then the resulting supernatant is carefully removed, and the pellet is resuspended in an appropriate buffer for the following processing step. An aliquot from the resuspended pellet is taken and used to quantitate the concentration of DNA in the resuspended pellet (e.g. using a standard fluorescent nucleic acid staining method such as PicoGreen, ThermoFisher Scientific). The specimen is adjusted in volume to achieve an appropriate concentration for subsequent processing steps.

Protocol for Partitioning and PCR-Amplification

Following the process of isolating a microparticle specimen as above, the pellet is resuspended in a PCR buffer comprising a full solution of 1×PCR buffer, PCR polymerase enzyme, dNTPs, and a set of primer pairs; a polymerase and PCR buffer appropriate for direct PCR is employed. This resuspending step is performed such that each 5 microliters of the resuspended solution contains approximately 0.1 picograms of DNA from the microparticle specimen itself. A panel of 5-10 primer pairs (a greater number is used for larger amplicon panels) covering one or more gene targets is designed using a multiplex PCR design algorithm (e.g. PrimerPlex; PREMIER Biosoft) to minimise cross-priming and to achieve approximately equal annealing temperatures across all primers; each amplicon length is locked between 70 and 120 nucleotides; each forward primer has a constant forward adapter sequence at its 5' end, and each reverse primer has a constant reverse adapter sequence at its 5' end, and the primers are included in the polymerase reaction at equimolar concentrations. The resuspended sample is then spread across a set of PCR tubes (or individual wells in a 384-well plate format) with 5.0 microliters of the reaction solution included in each tube/well; up to 384 or more individual reactions are performed as the total amount of DNA in the microparticle specimen allows; 10-15 PCR cycles are performed for subsequent barcoding with barcoded oligonucleotides; 22-28 PCR cycles are performed for subsequent barcoding with multimeric barcoding reagents.

Protocol for Barcoding with Barcoded Oligonucleotides

Following the protocol of PCR amplification as above, barcoded oligonucleotides are added to each well, with each forward barcoded oligonucleotide comprising the forward adapter sequence at its 3' end, a forward (read 1) Illumina sequencing primer sequence on its 5' end, and a 6-nucleotide barcode sequence between the two; a reverse primer containing a reverse (read 2) Illumina amplification sequence on its 5' end and the reverse adapter sequence at its 3' end is used. A different single barcoded oligonucleotide (i.e. containing a different barcode sequence) is used for each well. The PCR reaction volume is adjusted to 50 microliters to dilute the target-specific primers, and 8-12 PCR cycles are performed to append barcode sequences to the sequences within each tube/well. The amplification products from each well are purified using a SPRI cleanup/size-selection step (Agencourt Ampure XP, Beckman-Coulter Genomics), and the resulting purified products from all wells are merged into a single solution. A final PCR reaction using the full-length Illumina amplification primers (PE PCR Primer 1.0/2.0) is performed for 7-12 cycles to amplify the merged products to the appropriate concentration for loading onto an Illumina flowcell, and the resulting reaction is SPRI purified/size-selected and quantitated.

Protocol for Barcoding with Multimeric Barcoding Reagents

To append barcode sequences with multimeric barcoding reagents, following the process of PCR amplification as above, PCR amplification products from individual wells are purified with a SPRI purification step, and then resuspended in 1×PCR reaction buffer (with dNTPs) in individual wells without merging or cross-contaminating the samples from different wells. From a library of at least 10 million different multimeric barcoding reagents, an aliquot containing approximately 5 multimeric barcoding reagents is then added to each well, wherein each multimeric barcoding reagent is a contiguous multimeric barcode molecule made of 10-30 individual barcode molecules, with each barcode molecule comprising a barcode region with a different sequence from the other barcode molecules, and with a barcoded oligonucleotide annealed to each barcode molecule. Each barcoded oligonucleotide contains a forward (read 1) Illumina sequencing primer sequence on its 5' end, and the forward adapter sequence (also contained in the forward PCR primers) at its 3' end, with its barcode sequence within the middle section. A reverse primer containing a reverse (read 2) Illumina amplification sequence on its 5' end and the reverse adapter sequence at its 3' end is also included in the reaction mixture. A hot-start polymerase is used for this barcode-appending reaction. The polymerase is first activated at its activation temperature, and then 5-10 PCR cycles are performed with the annealing step performed at the forward/reverse adapter annealing temperature to extend the barcoded oligonucleotides along the PCR-amplified products, and to extend the reverse Illumina amplification sequence to these primer-extension products. The resulting products from each well are purified using a SPRI cleanup/size-selection, and the resulting purified products from all wells are merged into a single solution. A final PCR reaction using the full-length Illumina amplification primers (PE PCR Primer 1.0/2.0) is performed for 7-12 cycles to amplify the merged products to the appropriate concentration for loading onto an Illumina flowcell, and the resulting reaction is SPRI purified/size-selected and quantitated.

Protocol for Sequencing and Informatic Analysis

Following barcoding and amplification protocols, amplified samples are quantitated and sequenced on Illumina sequencers (e.g. HiSeq 2500). Prior to loading, samples are combined with sequencer-ready phiX genomic DNA libraries such that phiX molecules comprise 50-70% of the final molar fraction of the combined libraries. Combined samples are then each loaded onto one or more lanes of the flowcell at the recommended concentration for clustering. Samples are sequenced to a read depth wherein each individual barcoded sequence is sequenced on average by 5-10 reads, using paired-end 2×100 sequencing cycles. Raw sequences are then quality-trimmed and length-trimmed, constant adapter/primer sequences are trimmed away, and the genomic DNA sequences and barcode sequences from each retained sequence read are isolated informatically. Linked sequences are determined by detecting genomic DNA sequences that are appended to the same barcode sequence, or appended to different barcode sequences from the same set of barcode sequences (i.e. from the same multimeric barcoding reagent).

Protocol for Barcoding Fragments of Genomic DNA using Barcoded Oligonucleotides

To isolate circulating microparticles from whole blood, 1.0 milliliters of whole human blood (collected with K2 EDTA tubes) were added to each of two 1.5 milliliter Eppendorf DNA Lo-Bind tubes, and centrifuged in a desktop microcentrifuge for 5 minutes at 500×G; the resulting top (supernatant) layer (approximately 400 microliters from each tube) were then added to new 1.5 milliliter Eppendorf DNA Lo-Bind tubes, and again centrifuged in a desktop microcentrifuge for 5 minutes at 500×G; the resulting top (supernatant) layer (approximately 300 microliters from each tube) were then added to new 1.5 milliliter Eppendorf DNA Lo-Bind tubes, and centrifuged in a desktop microcentrifuge for 15 minutes at 3000×G; the resulting supernatant layer was fully and carefully aspirated, and the pellet in each tube was resuspend in 10 microliters Phosphate-Buffered Saline (PBS) and then the two 10 microliter resuspended samples were merged into a single 20 microliter sample (producing the sample for 'Variant A' of the present method).

In a related variant of the method (Variant C'), an aliquot of this original 20 microliter sample was transferred to a new 1.5 milliliter Eppendorf DNA Lo-Bind tube, and centrifuged for 5 minutes at 1500×G, with the resulting pellet then resuspended in PBS and aliquoted into low-concentration solutions as described below.

Circulating microparticles within the aforementioned 20 microliter sample (and/or from the resuspend 'Variant C' sample) were then partitioned prior to appending barcoded oligonucleotides. To partition low numbers of circulating microparticles per partition, the 20-microliter sample was aliquoted into solutions containing lower microparticle concentrations; 8 solutions with different concentrations were used, with the first being the original (undiluted) 20-microliter sample, and each of the subsequent 7 solutions having a 2.5-fold lower microparticle concentration (in PBS) relative to the preceding solution. A 0.5 microliter aliquot of each solution was then added to 9.5 microliters of 1.22× 'NEBNext Ultra II End Prep Reaction Buffer' (New England Biolabs) in $H_2O$ in 200 microliter PCR tubes (Flat cap; from Axygen) and mixed gently. To permeabilise the microparticles, tubes were heated at 65 degrees Celsius for 30 minutes on a thermal cycler with a heated lid. To each tube was added 0.5 microliters 'NEBNext Ultra II End Prep Enzyme Mix' and mixed the solutions were mixed gently; the solutions were incubated at 20 degrees Celsius for 30 minutes and then 65 degrees Celsius for 30 minutes on a thermal cycler.

To each tube was added 5.0 microliters 'NEBNext Ultra II Ligation Master Mix', and 0.33 microliters 0.5× (in $H_2O$) 'NEBNext Ligation Enhancer', and 0.42 microliters 0.04× (in 0.1× NEBuffer 3) 'NEBNext Adapter', and the solutions were mixed gently; the solutions were then incubated at 20 degrees Celsius for 15 minutes (or for 2 hours in "Variant B" of this method) on a thermal cycler with the heated lid turned off. To each tube was added 0.5 microliters 'NEBNext USER Enzyme', and the solutions were mixed gently; the solutions were then incubated at 20 degrees Celsius for 20 minutes at 37 degrees Celsius for 30 minutes on a thermal cycler with a heated lid set to 50 degrees Celsius, and then held at 4 degrees Celsius. Each reaction was then purified with 1.1×-volume Ampure XP SPRI beads (Agencourt; as per manufacturer's instructions) and eluted in 21.0 microliters H2O. This process of ligating 'NEBNext Adapter' sequences to fragments of genomic DNA from partitioned circulating microparticles provides a process of appending a coupling sequence to said fragments (wherein the 'NEBNext Adapter' itself, which comprises partially double-stranded and partially single-stranded sequences, comprises said coupling sequences, wherein the process of appending coupling sequence is performed with a ligation reaction). In a subsequent step of the process, barcoded oligonucleotides are appended to fragments of genomic DNA from partitioned circulating microparticles with an annealing and extension process (performed via a PCR reaction).

In 'Variant B' of this method, following the above USER enzyme step but prior to Ampure XP purification, the USER-digested samples were added to 50.0 microliters 'NEBNext Ultra II Q5 Master Mix', and 2.5 microliters 'Universal PCR Primer for Illumina', and 2.5 microliters of a specific 'NEBNext Index Primer' [from NEBNext Multiplex Oligos Index Primers Set 1 or Index Primers Set 2], and 28.2 microliters H2O, and the solutions were mixed gently, and then amplified by 5 cycles PCR in a thermal cycler, with each cycle being: 98 degrees Celsius for 20 seconds, and 65 degrees Celsius for 3 minutes. Each reaction was then purified with 0.95×-volume Ampure XP SPRI beads (Agencourt; as per manufacturer's instructions) and eluted in 21.0 microliters H2O.

Ampure XP-purified solutions (either following USER-digestion or following the initial PCR amplification process for 'Variant B' of the methods) (20.0 microliters each) were then added to 25.0 microliters 'NEBNext Ultra II Q5 Master Mix', and 2.5 microliters 'Universal PCR Primer for Illumina', and 2.5 microliters of a specific 'NEBNext Index Primer', and the solutions were mixed gently, and then amplified by 28 (Or 26 cycles for Variant B) cycles PCR in a thermal cycler, with each cycle being: 98 degrees Celsius for 10 seconds, and 65 degrees Celsius for 75 seconds; with a single final extension step of 75 degrees Celsius for 5 minutes. Each reaction was then purified with 0.9×-volume Ampure XP SPRI beads (Agencourt; as per manufacturer's instructions) and eluted in 25.0 microliters H2O. These steps of PCR append barcode sequences to the sequences of fragments of genomic DNA from circulating microparticles, wherein the barcode sequences are comprised within barcoded oligonucleotides (i.e. comprised within the specific 'NEBNext Index Primer' employed within each PCR reaction). In each primer-binding and extension step of the PCR reactions, the barcoded oligonucleotides hybridise to coupling sequences (e.g. the sequences within the 'NEBNext Adapter') and then are used to prime an extension step, wherein the 3' end of the barcoded oligonucleotide is extended to produce a sequence comprising both the barcode sequence and a sequence of a fragment of genomic DNA from a circulating microparticle. One barcoded oligonucleotide (and thus one barcode sequence) was employed per PCR reaction, with different barcode sequences used for each of the different PCR reactions. Therefore, sequences of fragments of genomic DNA from circulating microparticles in each partition were appended to a single barcode sequence, which links the set of sequences from the partition. The set of sequences in each of the partitions was linked by a different barcode sequence.

To create a negative-control sample, a separate 20-microliter sample of circulating microparticles was prepared as in the first paragraph above, but then the fragments of genomic DNA therein were isolated and purified with a Qiagen DNEasy purification kit (using the spin-column and centrifugation protocol as per the Qiagen manufacturer's instructions), and eluted in 50 microliters H2O, and then being processed with the NEBNext End Prep, Ligation, USER, and PCR processing steps as described above. This negative-control sample was employed to analyse the sequencing signals and readouts wherein fragments of genomic DNA from a very large number of circulating microparticles are analysed (i.e. wherein no linking of sequences from one or a small number of circulating microparticles has been performed).

Following the above steps of centrifuging and partitioning circulating microparticles, and then appending coupling sequences, appending barcode sequences, and PCR amplification and purification, several barcoded libraries comprising sequences from fragments of genomic DNA from circulating microparticles were then merged and sequenced on a Mid-Output Illumina NextSeq 500 flowcell for 150 cycles performed with paired-end reads (100×50), plus a separate (forward-direction) Index Read (to determine the barcode sequences appended with the barcoded oligonucleotides). Typically, between 6 and 12 barcoded libraries (i.e. comprising one barcoded set of linked sequences per library) were merged and sequenced per flowcell; coverage of at least several million total reads were achieved per barcoded library. Sequence reads were demultiplexed according to the barcode within the index read, sequences from each barcoded partition were mapped with Bowtie2 to the reference human genome sequence (hg38), and then mapped (and de-duplicated) sequences were imported into Seqmonk (version 1.39.0) for visualisation, quantitation, and analysis. In typical representative analyses, reads were mapped into sliding windows of 500 Kb along each human chromosome and then the total number of reads across each such window were quantitated and visualised.

Figure 25:
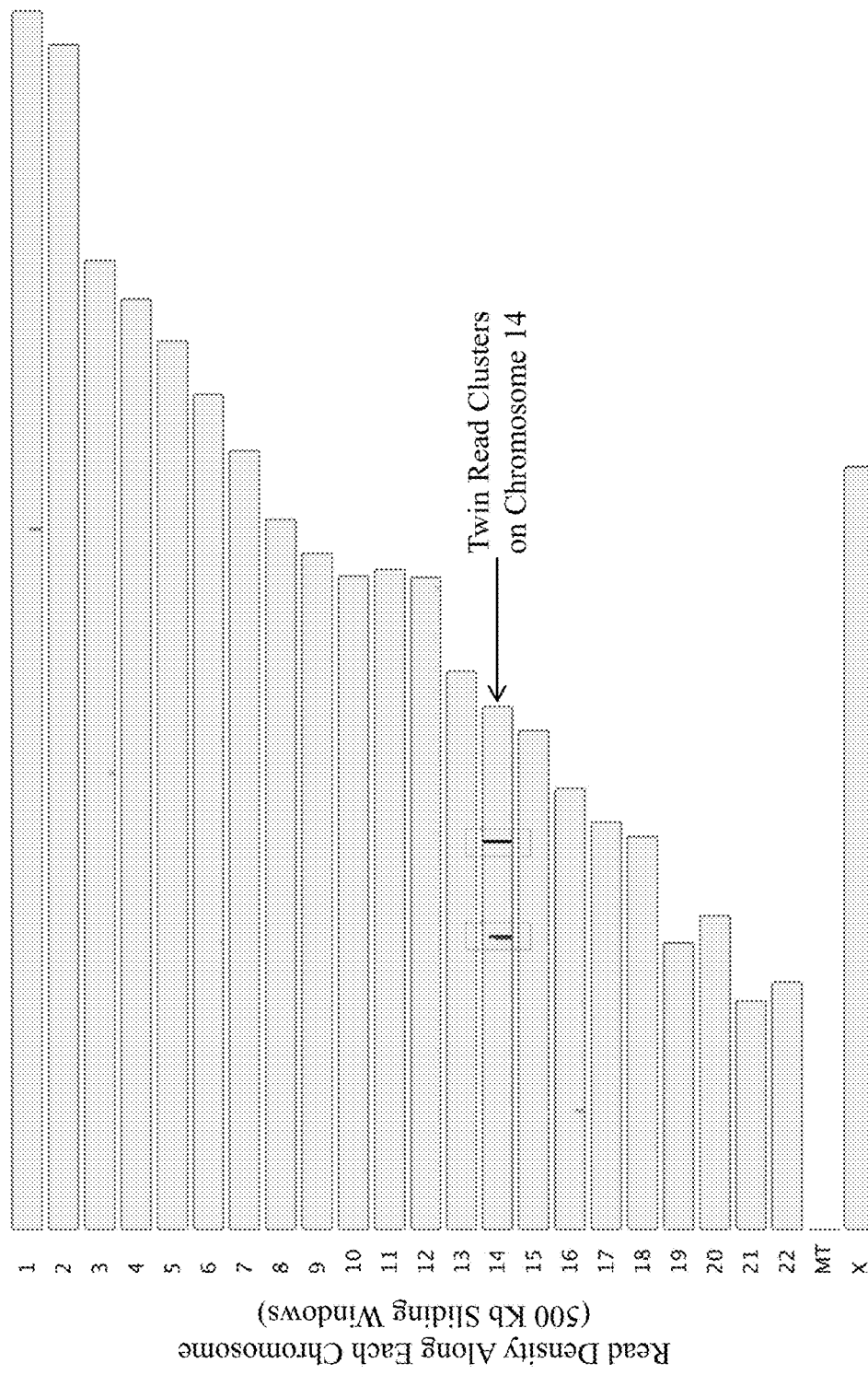
FIG. 25 illustrates the linkage of sequences of fragments of genomic DNA within a circulating microparticle, as produced by a method of appending barcoded oligonucleotides (from the 'Variant A' version of the example protocol). Shown is the density of sequence reads across all chromosomes in the human genome, with clear clustering of reads within singular chromosomal segments.

Key experimental results of these barcoded oligonucleotide methods are shown in FIGS. 25-29, and described in further detail here:

FIG. 25 illustrates the linkage of sequences of fragments of genomic DNA within a representative circulating microparticle, as produced by a method of appending barcoded oligonucleotides (from the 'Variant A' version of the example protocol). Shown is the density of sequence reads across all chromosomes in the human genome within 500 kilobase (Kb) sliding windows tiled across each chromosome. Two clear, self-contained clusters of reads are observed, approximately 200 Kb and 500 Kb in total span respectively. Notably, both of the two read clusters are on the same chromosome, and furthermore are from nearby portions of the same chromosome arm (on chromosome 14), thus confirming the suspicion that, indeed, multiple intramolecular chromosomal structures may be packaged into singular circulating microparticles, whereupon fragments of genomic DNA derived therefrom circulate within the human vasculature.

Figure 26:
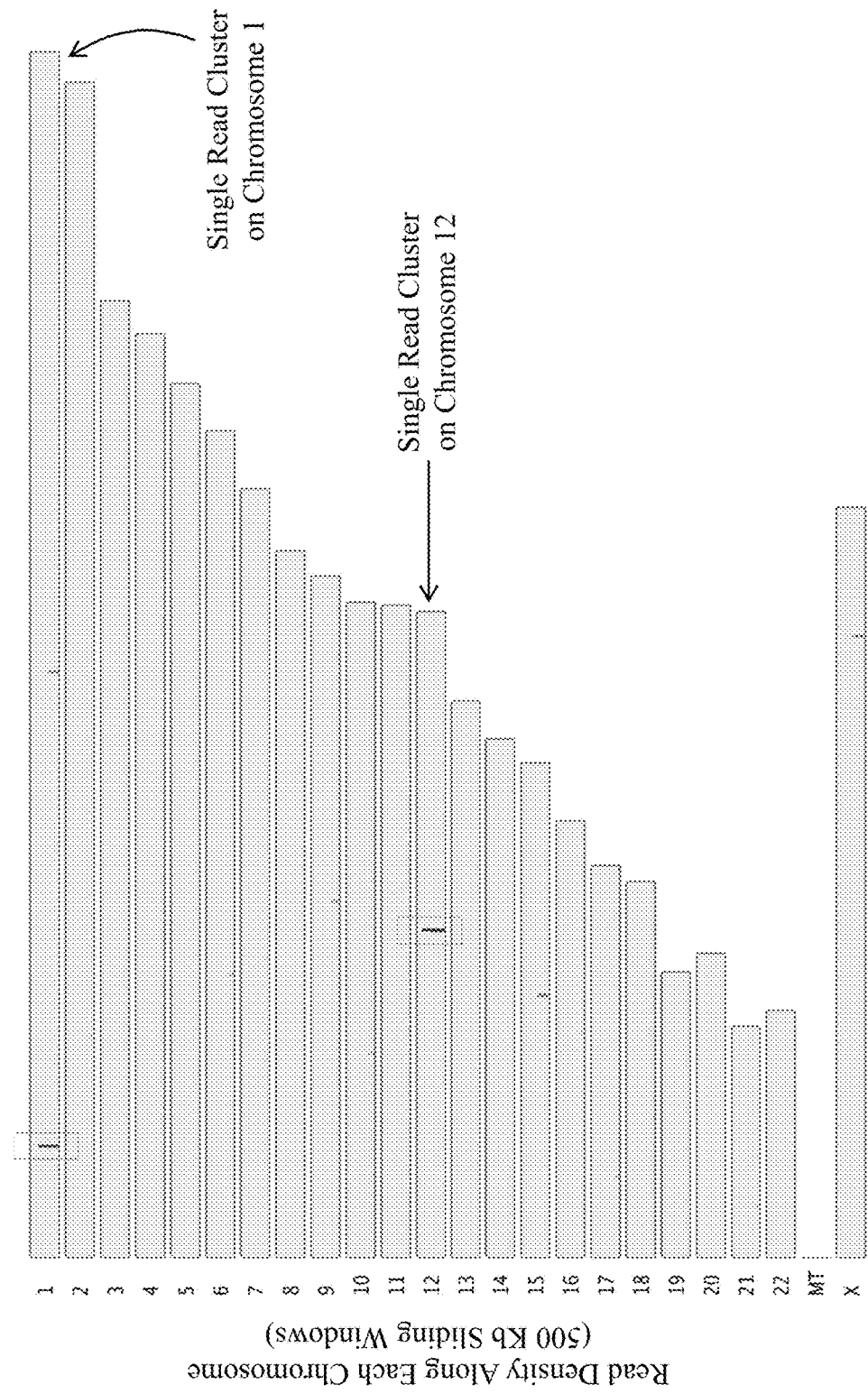
FIG. 26 illustrates the linkage of sequences of fragments of genomic DNA within a circulating microparticle, as produced by a method of appending barcoded oligonucleotides (from the 'Variant B' version of the example protocol). Shown is the density of sequence reads across all chromosomes in the human genome, with clear clustering of reads within singular chromosomal segments.

FIG. 26 also illustrates the linkage of sequences of fragments of genomic DNA within a circulating microparticle, but as produced by a variant method of appending barcoded oligonucleotides (from the 'Variant B' version of the example protocol) wherein the duration of ligation is increased relative to 'Variant A'. Shown again is the density of sequence reads across all chromosomes in the human genome, with clear clustering of reads within singular chromosomal segments (on chromosome 1 and chromosome 12 respectively). It is possible that the partition employed in this experiment comprised two different microparticles, in which case it is likely that one read cluster arose from each microparticle; alternatively, it is possible that a single microparticle contained a read cluster from each of chromosomes 1 and 12, which would thus demonstrate that inter-molecular chromosomal structures may also be packaged into singular circulating microparticles which then circulate through the blood.

Figure 27:
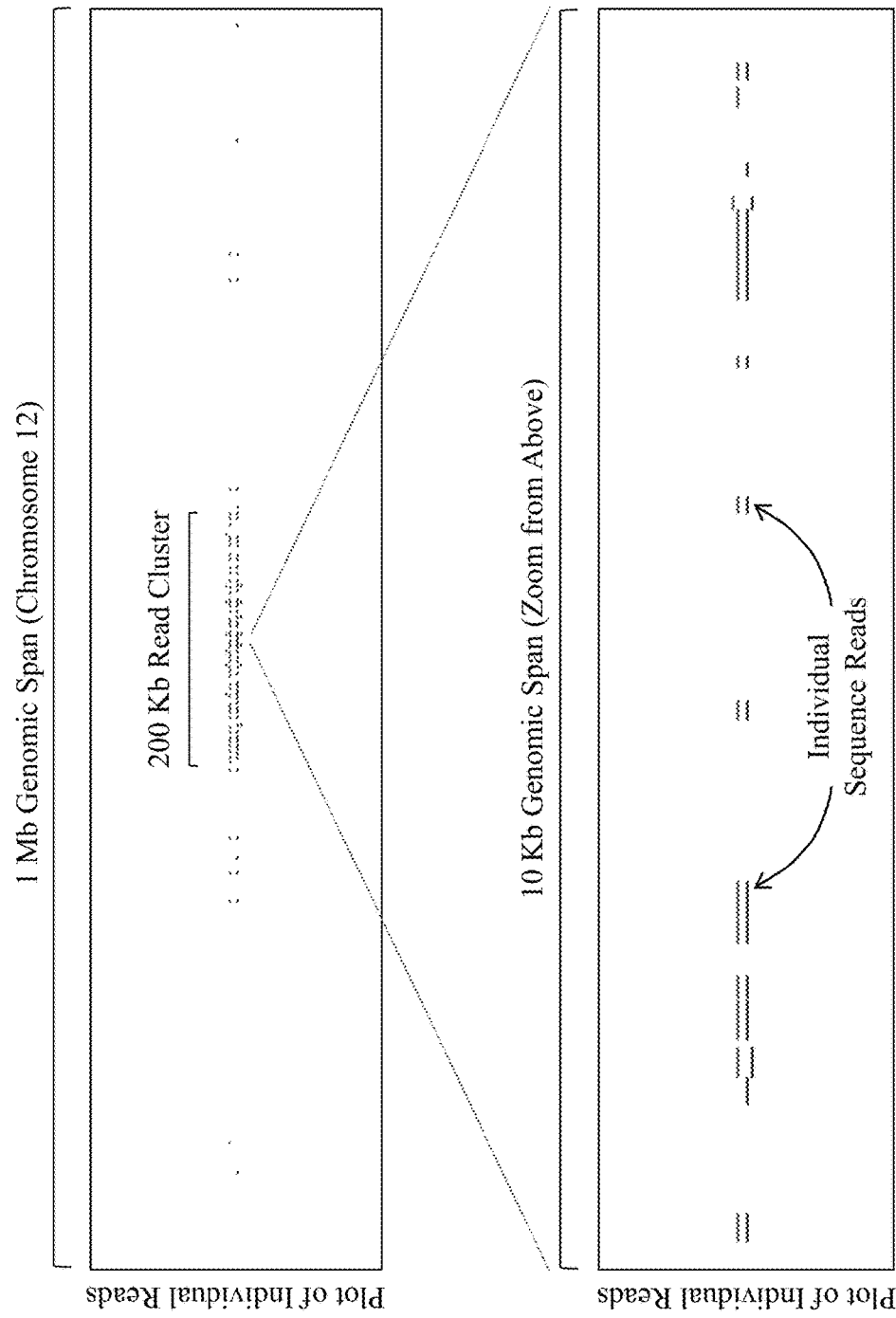
FIG. 27 illustrates the linkage of sequences of fragments of genomic DNA within a circulating microparticle, as produced by a method of appending barcoded oligonucleotides (from the 'Variant B' version of the example protocol). Shown is the density of sequence reads zoomed in within a specific chromosomal segment, to show the focal, high-density nature of these linked reads.

FIG. 27 illustrates the linkage of sequences of fragments of genomic DNA within a circulating microparticle, as produced by a method of appending barcoded oligonucleotides (from the 'Variant B' version of the example protocol). Shown are the actual sequence reads (of the read cluster from chromosome 12 from FIG. 26) zoomed in within a large and then within a small chromosomal segment, to show the focal, high-density nature of these linked reads, and to demonstrate the fact that the read clusters comprise clear, contiguous clusters of sequences from individual chromosome molecules from single cells, even down to the level of demonstrating immediately adjacent, non-overlapping, nucleosomally-positioned fragments.

Figure 28:
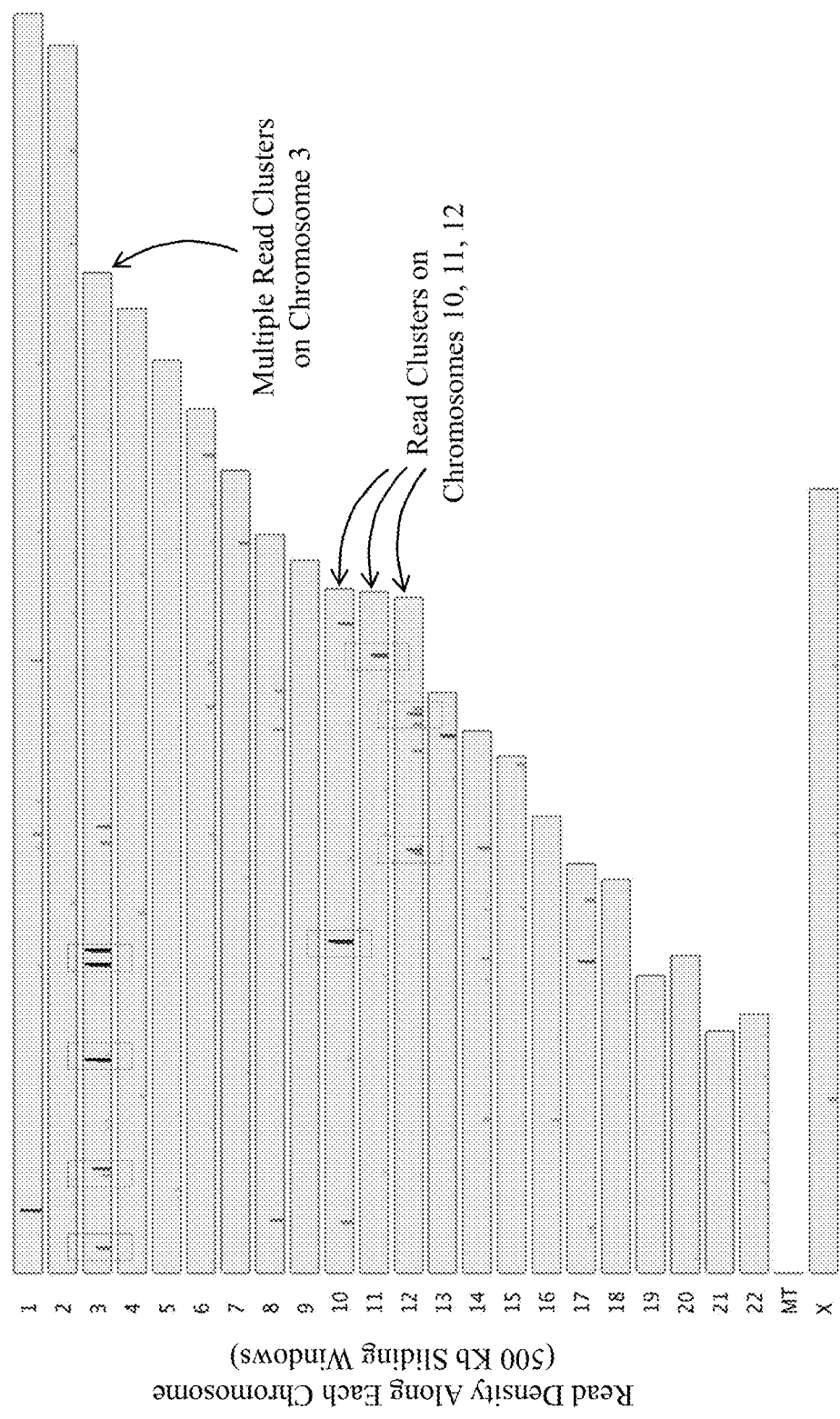
FIG. 28 illustrates the linkage of sequences of fragments of genomic DNA within a circulating microparticle, as produced by a method of appending barcoded oligonucleotides (from the 'Variant C' version of the example protocol). Shown is the density of sequence reads across all chromosomes in the human genome, with clear clustering of reads within singular chromosomal segments, though with such segments being larger in chromosomal span than in the other Variant methods (due to the larger microparticles being pelleted within Variant C compared with Variants A or B).

FIG. 28 illustrates the linkage of sequences of fragments of genomic DNA within a circulating microparticle, as produced by a method of appending barcoded oligonucleotides (from the 'Variant C' version of the example protocol). In contrast to Variant A and Variant B, this Variant C experiment employed a lower-speed centrifugation process to isolate a different, larger population of circulating microparticles compared with the other two variants. Shown is the density of sequence reads across all chromosomes in the human genome, from this experiment, again with clear clustering of reads observed within singular chromosomal segments. However, such segments are clearly larger in chromosomal span than in the other Variant methods (due to the larger microparticles being pelleted within Variant C compared with Variants A or B).

FIG. 29 illustrates a negative-control experiment, wherein fragments of genomic DNA are purified with a cleanup kit (Qiagen DNEasy Spin Column Kit) (i.e. therefore being unlinked) before being appending to barcoded oligonucleotides as in the 'Variant A' protocol. As would be expected given the input sample of unlinked reads, no clustering of reads is observed at all (rather, what reads do exist are dispersed randomly and essentially evenly throughout all chromosomal regions of the genome), validating that circulating microparticles comprise fragments of genomic DNA from focal, contiguous genomic regions within individual chromosomes. Even with further random sampling/sub-sampling of reads from said control library, no read clusters are observed.

The invention claimed is:

1. A method of analysing a sample comprising a cell-free microparticle, wherein the cell-free microparticle contains at least two fragments of genomic DNA, wherein the cell-free microparticle contains at least one fragment of genomic DNA comprising a maternal sequence and at least one fragment of genomic DNA comprising a paternal sequence, and wherein the method comprises:
(a) linking at least two of the at least two fragments of genomic DNA to produce a set of at least two linked fragments of genomic DNA; and
(b) sequencing each of the linked fragments in the set to produce at least two linked sequence reads.

2. The method of claim 1, wherein at least 3, at least 4, at least 5, at least 10, at least 50, at least 100, at least 500, at least 1000, at least 5000, at least 10,000, at least 100,000, or at least 1,000,000 fragments of genomic DNA of the cell-free microparticle are linked and then sequenced to produce at least 3, at least 4, at least 5, at least 10, at least 50, at least 100, at least 500, at least 1000, at least 5000, at least 10,000, at least 100,000, or at least 1,000,000 linked sequence reads.

3. The method of claim 1, wherein the sample comprises first and second cell-free microparticles, wherein each cell-free microparticle contains at least two fragments of genomic DNA, wherein each cell-free microparticle contains at least one fragment of genomic DNA comprising a maternal sequence and at least one fragment of genomic DNA comprising a paternal sequence, and wherein the method comprises performing step (a) to produce a first set of linked fragments of genomic DNA for the first cell-free microparticle and a second set of linked fragments of genomic DNA for the second cell-free microparticle, and performing step (b) to produce a first set of linked sequence reads for the first cell-free microparticle and a second set of linked sequence reads for the second cell-free microparticle.

4. The method of claim 3, wherein prior to step (a), the method further comprises the step of partitioning the sample into at least two different reaction volumes.

5. The method of claim 1, wherein the sample comprises n cell-free microparticles, wherein each cell-free microparticle contains at least two fragments of genomic DNA, wherein each cell-free microparticle contains at least one fragment of genomic DNA comprising a maternal sequence and at least one fragment of genomic DNA comprising a paternal sequence, and wherein the method comprises performing step (a) to produce n sets of linked fragments of genomic DNA, one set for each of the n cell-free microparticles, and performing step (b) to produce n sets of linked sequence reads, one for each of the n cell-free microparticles, wherein n is at least 3, at least 5, at least 10, at least 50, at least 100, at least 1000, at least 10,000, at least 100,000, at least 1,000,000, at least 10,000,000, or at least 100,000,000 cell-free microparticles.

6. The method of claim 1, wherein the method comprises:
(a) preparing the sample for sequencing comprising appending the at least two fragments of genomic DNA of the cell-free microparticle to a barcode sequence to produce a set of linked fragments of genomic DNA; and (b) sequencing each of the linked fragments in the set to produce at least two linked sequence reads, wherein the at least two linked sequence reads are linked by the barcode sequence.

7. The method of claim 6, wherein prior to the step of appending the at least two fragments of genomic DNA of the cell-free microparticle to a barcode sequence, the method comprises appending a coupling sequence to each of the fragments of genomic DNA of the cell-free microparticle, wherein the coupling sequences are then appended to the barcode sequence to produce the set of linked fragments of genomic DNA.

8. The method of claim 6, wherein the sample comprises first and second cell-free microparticles, wherein each cell-free microparticle contains at least two fragments of genomic DNA, wherein each cell-free microparticle contains at least one fragment of genomic DNA comprising a maternal sequence and at least one fragment of genomic DNA comprising a paternal sequence, and wherein the method comprises performing step (a) to produce a first set of linked fragments of genomic DNA for the first cell-free microparticle and a second set of linked fragments of genomic DNA for the second cell-free microparticle, and performing step (b) to produce a first set of linked sequence reads for the first cell-free microparticle and a second set of linked sequence reads for the second cell-free microparticle, wherein the at least two linked sequence reads for the first cell-free microparticle are linked by a different barcode sequence to the at least two linked sequence reads of the second cell-free microparticle.

9. The method of claim 1, wherein the method comprises: (a) preparing the sample for sequencing comprising appending each of the at least two fragments of genomic DNA of the cell-free microparticle to a different barcode sequence of a set of barcode sequences to produce a set of linked fragments of genomic DNA; and (b) sequencing each of the linked fragments in the set to produce at least two linked sequence reads, wherein the at least two linked sequence reads are linked by the set of barcode sequences.

10. The method of claim 9, wherein prior to the step of appending each of the at least two fragments of genomic DNA of the cell-free microparticle to a different barcode sequence, the method comprises appending a coupling sequence to each of the fragments of genomic DNA of the cell-free microparticle, wherein each of the at least two fragments of genomic DNA of the cell-free microparticle is appended to a different barcode sequence of the set of barcode sequences by its coupling sequence.

11. The method of claim 9, wherein the sample comprises first and second cell-free microparticles, wherein each cell-free microparticle contains at least two fragments of genomic DNA, wherein each cell-free microparticle contains at least one fragment of genomic DNA comprising a maternal sequence and at least one fragment of genomic DNA comprising a paternal sequence, and wherein the method comprises performing step (a) to produce a first set of linked fragments of genomic DNA for the first cell-free microparticle and a second set of linked fragments of genomic DNA for the second cell-free microparticle, and performing step (b) to produce a first set of linked sequence reads for the first cell-free microparticle and a second set of linked sequence reads for the second cell-free microparticle, wherein the first set of linked sequence reads are linked by a different set of barcode sequences to the second set of linked sequence reads.

12. The method of claim 11, wherein prior to the step of appending, the method further comprises the step of partitioning the sample into at least two different reaction volumes.

13. The method of claim 1, wherein the method comprises: (a) preparing the sample for sequencing comprising: (i) contacting the sample with a multimeric barcoding reagent comprising first and second barcode regions linked together, wherein each barcode region comprises a nucleic acid sequence, and (ii) appending barcode sequences to each of the at least two fragments of genomic DNA of the cell-free microparticle to produce first and second different barcoded target nucleic acid molecules, wherein the first barcoded target nucleic acid molecule comprises the nucleic acid sequence of the first barcode region and the second barcoded target nucleic acid molecule comprises the nucleic acid sequence of the second barcode region; and (b) sequencing each of the barcoded target nucleic acid molecules to produce at least two linked sequence reads; and optionally wherein prior to the step of appending barcode sequences to each of the at least two fragments of genomic DNA of the cell-free microparticle, the method comprises appending a coupling sequence to each of the fragments of genomic DNA of the cell-free microparticle, wherein a barcode sequence is then appended to the coupling sequence of each of the at least two fragments of genomic DNA of the cell-free microparticle to produce the first and second different barcoded target nucleic acid molecules.

14. The method of claim 13, wherein the method comprises analysing a sample comprising at least two cell-free microparticles, wherein each cell-free microparticle contains at least two fragments of genomic DNA, wherein each cell-free microparticle contains at least one fragment of genomic DNA comprising a maternal sequence and at least one fragment of genomic DNA comprising a paternal sequence, and wherein the method comprises the steps of: (a) preparing the sample for sequencing comprising: (i) contacting the sample with a library of multimeric barcoding reagents comprising a multimeric barcoding reagent for each of the two or more cell-free microparticles, wherein each multimeric barcoding reagent is as defined in claim 13; and (ii) appending barcode sequences to each of the at least two fragments of genomic DNA of each cell-free microparticle, wherein at least two barcoded target nucleic acid molecules are produced from each of the at least two cell-free microparticles, and wherein the at least two barcoded target nucleic acid molecules produced from a single cell-free microparticle each comprise the nucleic acid sequence of a barcode region from the same multimeric barcoding reagent; and (b) sequencing each of the barcoded target nucleic acid molecules to produce at least two linked sequence reads for each cell-free microparticle.

15. The method of claim 14, wherein prior to the step of appending, the method further comprises the step of partitioning the sample into at least two different reaction volumes.

16. The method of claim 1, wherein the cell-free microparticle is selected from the group consisting of: an exosome, an apoptotic body, and an extracellular microvesicle.

17. A method of preparing a sample for sequencing, wherein the sample comprises a cell-free microparticle, wherein the cell-free microparticle contains at least two fragments of genomic DNA, wherein the cell-free microparticle contains at least one fragment of genomic DNA comprising a maternal sequence and at least one fragment of genomic DNA comprising a paternal sequence, and wherein the method comprises appending the at least two fragments of genomic DNA of the cell-free microparticle to a barcode sequence, or to different barcode sequences of a set of barcode sequences, to produce a set of linked fragments of genomic DNA.

18. The method of claim 17, wherein prior to the step of appending the at least two fragments of genomic DNA of the cell-free microparticle to a barcode sequence, or to different barcode sequences of a set of barcode sequences, the method comprises appending a coupling sequence to each of the fragments of genomic DNA of the cell-free microparticle, wherein the coupling sequences are then appended to the barcode sequence, or to the different barcode sequences of a set of barcode sequences, to produce the set of linked fragments of genomic DNA.

19. The method of claim 17, wherein the sample comprises first and second cell-free microparticles, wherein each cell-free microparticle contains at least two fragments of genomic DNA, wherein each cell-free microparticle contains at least one fragment of genomic DNA comprising a maternal sequence and at least one fragment of genomic DNA comprising a paternal sequence, and wherein the method comprises appending the at least two fragments of genomic DNA of the first cell-free microparticle to a first barcode sequence, or to different barcode sequences of a first set of barcode sequences, to produce a first set of linked fragments of genomic DNA and appending the at least two fragments of genomic DNA of the second cell-free microparticle to a second barcode sequence, or to different barcode sequences of a second set of barcode sequences, to produce a second set of linked fragments of genomic DNA.

20. The method of claim 19, wherein prior to the step of appending, the method further comprises the step of partitioning the sample into at least two different reaction volumes.

21. The method of claim 17, wherein the cell-free microparticle is selected from the group consisting of: an exosome, an apoptotic body, and an extracellular microvesicle.

* * * * *

SEQUENCE LISTING

```
<160> NUMBER OF SEQ ID NOS: 303

<210> SEQ ID NO 1
<211> LENGTH: 38
<212> TYPE: DNA
<213> ORGANISM: Artificial Sequence
<220> FEATURE:
<223> OTHER INFORMATION: Primer

<400> SEQUENCE: 1
ctcgatgcta cgtgactact gcgtcgagga gtctatcc            38

<210> SEQ ID NO 2
<211> LENGTH: 96
<212> TYPE: DNA
<213> ORGANISM: Artificial Sequence
<220> FEATURE:
<223> OTHER INFORMATION: Primer

<400> SEQUENCE: 2
atacctgact gctcgtcagt tgagcgaatt ccgtatgggt agcaaggtcc aagagaggct      60
ccatcctcac tcgcctgact acgacaagac ctactg                               96

<210> SEQ ID NO 3
<211> LENGTH: 98
<212> TYPE: DNA
<213> ORGANISM: Artificial Sequence
<220> FEATURE:
<223> OTHER INFORMATION: Primer

<400> SEQUENCE: 3
tccagtaggt cttgtcgtag tcaggcgagt gaggatggag cctctcttgg accttgctac      60
ccatacggaa ttcgctcaac tgacgagcag tcaggtat                             98

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ctcgatgcta cgtgactact gc                             22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
cagtaggtct tgtcgtagtc ag                             22

<210> SEQ ID NO 6
<211> LENGTH: 45
```

```
<212> TYPE: DNA
<213> ORGANISM: Artificial Sequence
<220> FEATURE:
<223> OTHER INFORMATION: Primer

<400> SEQUENCE: 6
atggtacaca cctacactac tcggacgctc ttccgatctt gacct          45

<210> SEQ ID NO 7
<211> LENGTH: 44
<212> TYPE: DNA
<213> ORGANISM: Artificial Sequence
<220> FEATURE:
<223> OTHER INFORMATION: Primer

<400> SEQUENCE: 7
aggtcaagat cggaagagcg tccgagtagt gtaggtgtgt acca            44

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tggtacacac ctacactact cg                                    22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccatacggaa ttcgctcaac                                       20

<210> SEQ ID NO 10
<211> LENGTH: 42
<212> TYPE: DNA
<213> ORGANISM: Artificial Sequence
<220> FEATURE:
<223> OTHER INFORMATION: Primer

<400> SEQUENCE: 10
gttgagcgaa ttccgtatgg tggtacacac ctacactact cg              42

<210> SEQ ID NO 11
<211> LENGTH: 46
<212> TYPE: DNA
<213> ORGANISM: Artificial Sequence
<220> FEATURE:
<223> OTHER INFORMATION: Primer

<400> SEQUENCE: 11
taggacgata cgagtgtgta ctcgtggtac acacctacac tactcg          46

<210> SEQ ID NO 12
<211> LENGTH: 42
<212> TYPE: DNA
<213> ORGANISM: Artificial Sequence
<220> FEATURE:
<223> OTHER INFORMATION: Primer

<400> SEQUENCE: 12
```

```
cgagtagtgt aggtgtgtac caccatacgg aattcgctca ac                    42
```

<210> SEQ ID NO 13
<211> LENGTH: 44
<212> TYPE: DNA
<213> ORGANISM: Artificial Sequence
<220> FEATURE:
<223> OTHER INFORMATION: Primer

<400> SEQUENCE: 13

```
ctgtcaaggt agactagcat gctcccatac ggaattcgct caac                  44
```

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14

```
taggacgata cgagtgtgta ctcg                                        24
```

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15

```
ctgtcaaggt agactagcat gctc                                        24
```

<210> SEQ ID NO 16
<211> LENGTH: 56
<212> TYPE: DNA
<213> ORGANISM: Artificial Sequence
<220> FEATURE:
<223> OTHER INFORMATION: Primer

<400> SEQUENCE: 16

```
ctcggcattc ctgctgaacc gctcttccga tctgctcaac tgacgagcag tcaggt     56
```

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17

```
acactctttc cctacacgac gctcttccga tcttgacct                        39
```

<210> SEQ ID NO 18
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 18

```
aaacggatag actcctcgac                                             20
```

<210> SEQ ID NO 19
<211> LENGTH: 20
<212> TYPE: DNA

```
<213> ORGANISM: Artificial Sequence
<220> FEATURE:
<223> OTHER INFORMATION: Sequence used in the synthesis of sub-barcode
      molecule library

<400> SEQUENCE: 19
aaagggatag actcctcgac                                                   20

<210> SEQ ID NO 20
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 20
aaatggatag actcctcgac                                                   20

<210> SEQ ID NO 21
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 21
aacaggatag actcctcgac                                                   20

<210> SEQ ID NO 22
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 22
aaccggatag actcctcgac                                                   20

<210> SEQ ID NO 23
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 23
aacgggatag actcctcgac                                                   20

<210> SEQ ID NO 24
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 24
aactggatag actcctcgac                                                   20

<210> SEQ ID NO 25
<211> LENGTH: 20
<212> TYPE: DNA
<213> ORGANISM: Artificial Sequence
```

```
<220> FEATURE:
<223> OTHER INFORMATION: Sequence used in the synthesis of sub-barcode
      molecule library

<400> SEQUENCE: 25
aagaggatag actcctcgac                                                   20

<210> SEQ ID NO 26
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 26
aagcggatag actcctcgac                                                   20

<210> SEQ ID NO 27
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 27
aaggggatag actcctcgac                                                   20

<210> SEQ ID NO 28
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 28
aagtggatag actcctcgac                                                   20

<210> SEQ ID NO 29
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 29
aataggatag actcctcgac                                                   20

<210> SEQ ID NO 30
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 30
aatcggatag actcctcgac                                                   20

<210> SEQ ID NO 31
<211> LENGTH: 20
<212> TYPE: DNA
<213> ORGANISM: Artificial Sequence
<220> FEATURE:
```

<223> OTHER INFORMATION: Sequence used in the synthesis of sub-barcode
      molecule library

<400> SEQUENCE: 31
aatgggatag actcctcgac                                              20

<210> SEQ ID NO 32
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 32
aattggatag actcctcgac                                              20

<210> SEQ ID NO 33
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 33
acaaggatag actcctcgac                                              20

<210> SEQ ID NO 34
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 34
acacggatag actcctcgac                                              20

<210> SEQ ID NO 35
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 35
acagggatag actcctcgac                                              20

<210> SEQ ID NO 36
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 36
acatggatag actcctcgac                                              20

<210> SEQ ID NO 37
<211> LENGTH: 20
<212> TYPE: DNA
<213> ORGANISM: Artificial Sequence
<220> FEATURE:
<223> OTHER INFORMATION: Sequence used in the synthesis of sub-barcode -continued molecule library

<400> SEQUENCE: 37
accaggatag actcctcgac                                               20

<210> SEQ ID NO 38
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 38
acccggatag actcctcgac                                               20

<210> SEQ ID NO 39
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 39
accgggatag actcctcgac                                               20

<210> SEQ ID NO 40
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 40
acctggatag actcctcgac                                               20

<210> SEQ ID NO 41
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 41
acgaggatag actcctcgac                                               20

<210> SEQ ID NO 42
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 42
acgcggatag actcctcgac                                               20

<210> SEQ ID NO 43
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 43
acggggatag actcctcgac                                              20

<210> SEQ ID NO 44
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 44
acgtggatag actcctcgac                                              20

<210> SEQ ID NO 45
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 45
actaggatag actcctcgac                                              20

<210> SEQ ID NO 46
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 46
actcggatag actcctcgac                                              20

<210> SEQ ID NO 47
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 47
actgggatag actcctcgac                                              20

<210> SEQ ID NO 48
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 48
acttggatag actcctcgac                                              20

<210> SEQ ID NO 49
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

```
<400> SEQUENCE: 49
agaaggatag actcctcgac                                                   20

<210> SEQ ID NO 50
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 50
agacggatag actcctcgac                                                   20

<210> SEQ ID NO 51
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 51
agagggatag actcctcgac                                                   20

<210> SEQ ID NO 52
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 52
agatggatag actcctcgac                                                   20

<210> SEQ ID NO 53
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 53
agcaggatag actcctcgac                                                   20

<210> SEQ ID NO 54
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 54
agccggatag actcctcgac                                                   20

<210> SEQ ID NO 55
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 55
```
agcgggatag actcctcgac                                                    20

<210> SEQ ID NO 56
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 56
agctggatag actcctcgac                                                    20

<210> SEQ ID NO 57
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 57
aggaggatag actcctcgac                                                    20

<210> SEQ ID NO 58
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 58
aggcggatag actcctcgac                                                    20

<210> SEQ ID NO 59
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 59
agggggatag actcctcgac                                                    20

<210> SEQ ID NO 60
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 60
aggtggatag actcctcgac                                                    20

<210> SEQ ID NO 61
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 61
agtaggatag actcctcgac                                                    20

<210> SEQ ID NO 62
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 62
agtcggatag actcctcgac                                                    20

<210> SEQ ID NO 63
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 63
agtgggatag actcctcgac                                                    20

<210> SEQ ID NO 64
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 64
agttggatag actcctcgac                                                    20

<210> SEQ ID NO 65
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 65
ataaggatag actcctcgac                                                    20

<210> SEQ ID NO 66
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 66
atacggatag actcctcgac                                                    20

<210> SEQ ID NO 67
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 67
atagggatag actcctcgac                                                    20

<210> SEQ ID NO 68
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 68
atatggatag actcctcgac                                              20

<210> SEQ ID NO 69
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 69
atcaggatag actcctcgac                                              20

<210> SEQ ID NO 70
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 70
atccggatag actcctcgac                                              20

<210> SEQ ID NO 71
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 71
atcgggatag actcctcgac                                              20

<210> SEQ ID NO 72
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 72
atctggatag actcctcgac                                              20

<210> SEQ ID NO 73
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 73
atgaggatag actcctcgac                                              20

<210> SEQ ID NO 74
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 74
atgcggatag actcctcgac                                              20

<210> SEQ ID NO 75
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 75
atggggatag actcctcgac                                              20

<210> SEQ ID NO 76
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 76
atgtggatag actcctcgac                                              20

<210> SEQ ID NO 77
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 77
attaggatag actcctcgac                                              20

<210> SEQ ID NO 78
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 78
attcggatag actcctcgac                                              20

<210> SEQ ID NO 79
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 79
attgggatag actcctcgac                                              20

```
<210> SEQ ID NO 80
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 80
atttggatag actcctcgac                                              20

<210> SEQ ID NO 81
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 81
caaaggatag actcctcgac                                              20

<210> SEQ ID NO 82
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 82
caacggatag actcctcgac                                              20

<210> SEQ ID NO 83
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 83
caagggatag actcctcgac                                              20

<210> SEQ ID NO 84
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 84
caatggatag actcctcgac                                              20

<210> SEQ ID NO 85
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 85
cacaggatag actcctcgac                                              20

<210> SEQ ID NO 86
```

```
<210> SEQ ID NO 86
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 86
caccggatag actcctcgac                                                   20

<210> SEQ ID NO 87
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 87
cacgggatag actcctcgac                                                   20

<210> SEQ ID NO 88
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 88
cactggatag actcctcgac                                                   20

<210> SEQ ID NO 89
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 89
cagaggatag actcctcgac                                                   20

<210> SEQ ID NO 90
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 90
cagcggatag actcctcgac                                                   20

<210> SEQ ID NO 91
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 91 cagggatag actcctcgac                                                    20

<210> SEQ ID NO 92
<211> LENGTH: 20
```

```
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 92
cagtggatag actcctcgac                                                   20

<210> SEQ ID NO 93
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 93
cataggatag actcctcgac                                                   20

<210> SEQ ID NO 94
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 94
catcggatag actcctcgac                                                   20

<210> SEQ ID NO 95
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 95
catgggatag actcctcgac                                                   20

<210> SEQ ID NO 96
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 96
cattggatag actcctcgac                                                   20

<210> SEQ ID NO 97
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 97
ccaaggatag actcctcgac                                                   20

<210> SEQ ID NO 98
<211> LENGTH: 20
<212> TYPE: DNA
```

```
<213> ORGANISM: Artificial Sequence
<220> FEATURE:
<223> OTHER INFORMATION: Sequence used in the synthesis of sub-barcode
      molecule library

<400> SEQUENCE: 98
ccacggatag actcctcgac                                                  20

<210> SEQ ID NO 99
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 99
ccagggatag actcctcgac                                                  20

<210> SEQ ID NO 100
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 100
ccatggatag actcctcgac                                                  20

<210> SEQ ID NO 101
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 101
cccaggatag actcctcgac                                                  20

<210> SEQ ID NO 102
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 102
cccgggatag actcctcgac                                                  20

<210> SEQ ID NO 103
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 103
ccctggatag actcctcgac                                                  20

<210> SEQ ID NO 104
<211> LENGTH: 20
<212> TYPE: DNA
<213> ORGANISM: Artificial Sequence
```

```
<220> FEATURE:
<223> OTHER INFORMATION: Sequence used in the synthesis of sub-barcode
      molecule library

<400> SEQUENCE: 104
ccgaggatag actcctcgac                                               20

<210> SEQ ID NO 105
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 105
ccgcggatag actcctcgac                                               20

<210> SEQ ID NO 106
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 106
ccggggatag actcctcgac                                               20

<210> SEQ ID NO 107
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 107
ccgtggatag actcctcgac                                               20

<210> SEQ ID NO 108
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 108
cctaggatag actcctcgac                                               20

<210> SEQ ID NO 109
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 109
cctcggatag actcctcgac                                               20

<210> SEQ ID NO 110
<211> LENGTH: 20
<212> TYPE: DNA
<213> ORGANISM: Artificial Sequence
<220> FEATURE:
```

<223> OTHER INFORMATION: Sequence used in the synthesis of sub-barcode
      molecule library

<400> SEQUENCE: 110
cctgggatag actcctcgac                                                    20

<210> SEQ ID NO 111
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 111
ccttggatag actcctcgac                                                    20

<210> SEQ ID NO 112
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 112
cgaaggatag actcctcgac                                                    20

<210> SEQ ID NO 113
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 113
cgacggatag actcctcgac                                                    20

<210> SEQ ID NO 114
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 114
cgagggatag actcctcgac                                                    20

<210> SEQ ID NO 115
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 115
cgatggatag actcctcgac                                                    20

<210> SEQ ID NO 116
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 116
cgcaggatag actcctcgac                                               20

<210> SEQ ID NO 117
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 117
cgccggatag actcctcgac                                               20

<210> SEQ ID NO 118
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 118
cgcgggatag actcctcgac                                               20

<210> SEQ ID NO 119
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 119
cgctggatag actcctcgac                                               20

<210> SEQ ID NO 120
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 120
cggaggatag actcctcgac                                               20

<210> SEQ ID NO 121
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 121
cggcggatag actcctcgac                                               20

<210> SEQ ID NO 122
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 122
cgggggatag actcctcgac                                              20

<210> SEQ ID NO 123
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 123
cggtggatag actcctcgac                                              20

<210> SEQ ID NO 124
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 124
cgtaggatag actcctcgac                                              20

<210> SEQ ID NO 125
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 125
cgtcggatag actcctcgac                                              20

<210> SEQ ID NO 126
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 126
cgtgggatag actcctcgac                                              20

<210> SEQ ID NO 127
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 127
cgttggatag actcctcgac                                              20

<210> SEQ ID NO 128
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

```
<400> SEQUENCE: 128
ctaaggatag actcctcgac                                                    20

<210> SEQ ID NO 129
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 129
ctacggatag actcctcgac                                                    20

<210> SEQ ID NO 130
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 130
ctagggatag actcctcgac                                                    20

<210> SEQ ID NO 131
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 131
ctatggatag actcctcgac                                                    20

<210> SEQ ID NO 132
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 132
ctcaggatag actcctcgac                                                    20

<210> SEQ ID NO 133
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 133
ctccggatag actcctcgac                                                    20

<210> SEQ ID NO 134
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 134
```
ctcgggatag actcctcgac                                               20

<210> SEQ ID NO 135
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 135
ctctggatag actcctcgac                                               20

<210> SEQ ID NO 136
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 136
ctgaggatag actcctcgac                                               20

<210> SEQ ID NO 137
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 137
ctgcggatag actcctcgac                                               20

<210> SEQ ID NO 138
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 138
ctggggatag actcctcgac                                               20

<210> SEQ ID NO 139
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 139
ctgtggatag actcctcgac                                               20

<210> SEQ ID NO 140
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 140
cttaggatag actcctcgac                                              20

<210> SEQ ID NO 141
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 141
cttcggatag actcctcgac                                              20

<210> SEQ ID NO 142
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 142
cttgggatag actcctcgac                                              20

<210> SEQ ID NO 143
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 143
ctttggatag actcctcgac                                              20

<210> SEQ ID NO 144
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 144
gaaaggatag actcctcgac                                              20

<210> SEQ ID NO 145
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 145
gaacggatag actcctcgac                                              20

<210> SEQ ID NO 146
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 146
gaagggatag actcctcgac                                              20

<210> SEQ ID NO 147
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 147
gaatggatag actcctcgac                                          20

<210> SEQ ID NO 148
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 148
gacaggatag actcctcgac                                          20

<210> SEQ ID NO 149
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 149
gaccggatag actcctcgac                                          20

<210> SEQ ID NO 150
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 150
gacgggatag actcctcgac                                          20

<210> SEQ ID NO 151
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 151
gactggatag actcctcgac                                          20

<210> SEQ ID NO 152
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 152
gagaggatag actcctcgac                                          20

```
<210> SEQ ID NO 153
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 153
gagcggatag actcctcgac                                             20

<210> SEQ ID NO 154
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 154 gagggatag actcctcgac                                              20

<210> SEQ ID NO 155
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 155
gagtggatag actcctcgac                                             20

<210> SEQ ID NO 156
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 156
gataggatag actcctcgac                                             20

<210> SEQ ID NO 157
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 157
gatcggatag actcctcgac                                             20

<210> SEQ ID NO 158
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 158
gatgggatag actcctcgac                                             20
```

<210> SEQ ID NO 159
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 159
gattggatag actcctcgac                                                    20

<210> SEQ ID NO 160
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 160
gcaaggatag actcctcgac                                                    20

<210> SEQ ID NO 161
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 161
gcacggatag actcctcgac                                                    20

<210> SEQ ID NO 162
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 162
gcagggatag actcctcgac                                                    20

<210> SEQ ID NO 163
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 163
gcatggatag actcctcgac                                                    20

<210> SEQ ID NO 164
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 164
gccaggatag actcctcgac                                                    20

<210> SEQ ID NO 165

```
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 165
gcccggatag actcctcgac                                               20

<210> SEQ ID NO 166
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 166
gccgggatag actcctcgac                                               20

<210> SEQ ID NO 167
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 167
gcctggatag actcctcgac                                               20

<210> SEQ ID NO 168
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 168
gcgaggatag actcctcgac                                               20

<210> SEQ ID NO 169
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 169
gcgcggatag actcctcgac                                               20

<210> SEQ ID NO 170
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 170
gcggggatag actcctcgac                                               20

<210> SEQ ID NO 171
<211> LENGTH: 20
```

```
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 171
gcgtggatag actcctcgac                                               20

<210> SEQ ID NO 172
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 172
gctaggatag actcctcgac                                               20

<210> SEQ ID NO 173
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 173
gctcggatag actcctcgac                                               20

<210> SEQ ID NO 174
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 174
gctgggatag actcctcgac                                               20

<210> SEQ ID NO 175
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 175
gcttggatag actcctcgac                                               20

<210> SEQ ID NO 176
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 176
ggaaggatag actcctcgac                                               20

<210> SEQ ID NO 177
<211> LENGTH: 20
<212> TYPE: DNA
```

```
<213> ORGANISM: Artificial Sequence
<220> FEATURE:
<223> OTHER INFORMATION: Sequence used in the synthesis of sub-barcode
      molecule library

<400> SEQUENCE: 177
ggacggatag actcctcgac                                               20

<210> SEQ ID NO 178
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 178
ggagggatag actcctcgac                                               20

<210> SEQ ID NO 179
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 179
ggatggatag actcctcgac                                               20

<210> SEQ ID NO 180
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 180
ggcaggatag actcctcgac                                               20

<210> SEQ ID NO 181
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 181
ggccggatag actcctcgac                                               20

<210> SEQ ID NO 182
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 182
ggcgggatag actcctcgac                                               20

<210> SEQ ID NO 183
<211> LENGTH: 20
<212> TYPE: DNA
<213> ORGANISM: Artificial Sequence
```

```
<220> FEATURE:
<223> OTHER INFORMATION: Sequence used in the synthesis of sub-barcode
      molecule library

<400> SEQUENCE: 183
ggctggatag actcctcgac                                                     20

<210> SEQ ID NO 184
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 184
gggaggatag actcctcgac                                                     20

<210> SEQ ID NO 185
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 185
gggcggatag actcctcgac                                                     20

<210> SEQ ID NO 186
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 186
gggtggatag actcctcgac                                                     20

<210> SEQ ID NO 187
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 187
ggtaggatag actcctcgac                                                     20

<210> SEQ ID NO 188
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 188
ggtcggatag actcctcgac                                                     20

<210> SEQ ID NO 189
<211> LENGTH: 20
<212> TYPE: DNA
<213> ORGANISM: Artificial Sequence
<220> FEATURE:
```

<223> OTHER INFORMATION: Sequence used in the synthesis of sub-barcode
      molecule library

<400> SEQUENCE: 189
ggtgggatag actcctcgac                                            20

<210> SEQ ID NO 190
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 190
ggttggatag actcctcgac                                            20

<210> SEQ ID NO 191
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 191
gtaaggatag actcctcgac                                            20

<210> SEQ ID NO 192
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 192
gtacggatag actcctcgac                                            20

<210> SEQ ID NO 193
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 193
gtagggatag actcctcgac                                            20

<210> SEQ ID NO 194
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 194
gtatggatag actcctcgac                                            20

<210> SEQ ID NO 195
<211> LENGTH: 20
<212> TYPE: DNA
<213> ORGANISM: Artificial Sequence
<220> FEATURE:
<223> OTHER INFORMATION: Sequence used in the synthesis of sub-barcode molecule library

<400> SEQUENCE: 195
gtcaggatag actcctcgac                    20

<210> SEQ ID NO 196
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 196
gtccggatag actcctcgac                    20

<210> SEQ ID NO 197
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 197
gtcgggatag actcctcgac                    20

<210> SEQ ID NO 198
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 198
gtctggatag actcctcgac                    20

<210> SEQ ID NO 199
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 199
gtgaggatag actcctcgac                    20

<210> SEQ ID NO 200
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 200
gtgcggatag actcctcgac                    20

<210> SEQ ID NO 201
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

```
<400> SEQUENCE: 201
gtggggatag actcctcgac                                              20

<210> SEQ ID NO 202
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 202
gtgtggatag actcctcgac                                              20

<210> SEQ ID NO 203
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 203
gttaggatag actcctcgac                                              20

<210> SEQ ID NO 204
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 204
gttcggatag actcctcgac                                              20

<210> SEQ ID NO 205
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 205
gttgggatag actcctcgac                                              20

<210> SEQ ID NO 206
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 206
gtttggatag actcctcgac                                              20

<210> SEQ ID NO 207
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library
```

```
<400> SEQUENCE: 207
taaaggatag actcctcgac                                               20

<210> SEQ ID NO 208
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 208
taacggatag actcctcgac                                               20

<210> SEQ ID NO 209
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 209
taagggatag actcctcgac                                               20

<210> SEQ ID NO 210
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 210
taatggatag actcctcgac                                               20

<210> SEQ ID NO 211
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 211
tacaggatag actcctcgac                                               20

<210> SEQ ID NO 212
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 212
taccggatag actcctcgac                                               20

<210> SEQ ID NO 213
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 213
```
tacgggatag actcctcgac                     20

<210> SEQ ID NO 214
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 214
tactggatag actcctcgac                     20

<210> SEQ ID NO 215
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 215
tagaggatag actcctcgac                     20

<210> SEQ ID NO 216
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 216
tagcggatag actcctcgac                     20

<210> SEQ ID NO 217
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 217
taggggatag actcctcgac                     20

<210> SEQ ID NO 218
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 218
tagtggatag actcctcgac                     20

<210> SEQ ID NO 219
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 219
tataggatag actcctcgac                                              20

<210> SEQ ID NO 220
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 220
tatcggatag actcctcgac                                              20

<210> SEQ ID NO 221
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 221
tatgggatag actcctcgac                                              20

<210> SEQ ID NO 222
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 222
tattggatag actcctcgac                                              20

<210> SEQ ID NO 223
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 223
tcaaggatag actcctcgac                                              20

<210> SEQ ID NO 224
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 224
tcacggatag actcctcgac                                              20

<210> SEQ ID NO 225
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 225
tcagggatag actcctcgac                                              20

```
<210> SEQ ID NO 226
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 226
tcatggatag actcctcgac                                                   20

<210> SEQ ID NO 227
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 227
tccaggatag actcctcgac                                                   20

<210> SEQ ID NO 228
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 228
tcccggatag actcctcgac                                                   20

<210> SEQ ID NO 229
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 229
tccgggatag actcctcgac                                                   20

<210> SEQ ID NO 230
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 230
tcctggatag actcctcgac                                                   20

<210> SEQ ID NO 231
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 231
tcgaggatag actcctcgac                                                   20
```

```
<210> SEQ ID NO 232
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 232
tcgcggatag actcctcgac                                              20

<210> SEQ ID NO 233
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 233
tcggggatag actcctcgac                                              20

<210> SEQ ID NO 234
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 234
tcgtggatag actcctcgac                                              20

<210> SEQ ID NO 235
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 235
tctaggatag actcctcgac                                              20

<210> SEQ ID NO 236
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 236
tctcggatag actcctcgac                                              20

<210> SEQ ID NO 237
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 237
tctgggatag actcctcgac                                              20
```

```
<210> SEQ ID NO 238
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 238
tcttggatag actcctcgac                                                    20

<210> SEQ ID NO 239
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 239
tgaaggatag actcctcgac                                                    20

<210> SEQ ID NO 240
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 240
tgacggatag actcctcgac                                                    20

<210> SEQ ID NO 241
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 241
tgagggatag actcctcgac                                                    20

<210> SEQ ID NO 242
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 242
tgatggatag actcctcgac                                                    20

<210> SEQ ID NO 243
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 243
tgcaggatag actcctcgac                                                    20

<210> SEQ ID NO 244
```

```
<210> SEQ ID NO 244
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 244
tgccggatag actcctcgac                                                   20

<210> SEQ ID NO 245
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 245
tgcgggatag actcctcgac                                                   20

<210> SEQ ID NO 246
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 246
tgctggatag actcctcgac                                                   20

<210> SEQ ID NO 247
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 247
tggaggatag actcctcgac                                                   20

<210> SEQ ID NO 248
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 248
tggcggatag actcctcgac                                                   20

<210> SEQ ID NO 249
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 249
tgggggatag actcctcgac                                                   20

<210> SEQ ID NO 250
<211> LENGTH: 20
```

```
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 250
tggtggatag actcctcgac                                              20

<210> SEQ ID NO 251
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 251
tgtaggatag actcctcgac                                              20

<210> SEQ ID NO 252
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 252
tgtcggatag actcctcgac                                              20

<210> SEQ ID NO 253
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 253
tgtgggatag actcctcgac                                              20

<210> SEQ ID NO 254
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 254
tgttggatag actcctcgac                                              20

<210> SEQ ID NO 255
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 255
ttaaggatag actcctcgac                                              20

<210> SEQ ID NO 256
<211> LENGTH: 20
<212> TYPE: DNA
```

<213> ORGANISM: Artificial Sequence
<220> FEATURE:
<223> OTHER INFORMATION: Sequence used in the synthesis of sub-barcode
      molecule library

<400> SEQUENCE: 256
ttacggatag actcctcgac                                                  20

<210> SEQ ID NO 257
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 257
ttagggatag actcctcgac                                                  20

<210> SEQ ID NO 258
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 258
ttatggatag actcctcgac                                                  20

<210> SEQ ID NO 259
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 259
ttcaggatag actcctcgac                                                  20

<210> SEQ ID NO 260
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 260
ttccggatag actcctcgac                                                  20

<210> SEQ ID NO 261
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 261
ttcgggatag actcctcgac                                                  20

<210> SEQ ID NO 262
<211> LENGTH: 20
<212> TYPE: DNA
<213> ORGANISM: Artificial Sequence

```
<220> FEATURE:
<223> OTHER INFORMATION: Sequence used in the synthesis of sub-barcode
      molecule library

<400> SEQUENCE: 262
ttctggatag actcctcgac                                                   20

<210> SEQ ID NO 263
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 263
ttgaggatag actcctcgac                                                   20

<210> SEQ ID NO 264
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 264
ttgcggatag actcctcgac                                                   20

<210> SEQ ID NO 265
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 265
ttggggatag actcctcgac                                                   20

<210> SEQ ID NO 266
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 266
ttgtggatag actcctcgac                                                   20

<210> SEQ ID NO 267
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 267
tttaggatag actcctcgac                                                   20

<210> SEQ ID NO 268
<211> LENGTH: 20
<212> TYPE: DNA
<213> ORGANISM: Artificial Sequence
<220> FEATURE:
```

<223> OTHER INFORMATION: Sequence used in the synthesis of sub-barcode
      molecule library

<400> SEQUENCE: 268
tttcggatag actcctcgac                                              20

<210> SEQ ID NO 269
<211> LENGTH: 20
<212> TYPE: DNA
<213> ORGANISM: Artificial Sequence
<220> FEATURE:
<223> OTHER INFORMATION: Sequence used in the synthesis of sub-barcode
      molecule library

<400> SEQUENCE: 269
tttgggatag actcctcgac                                              20

<210> SEQ ID NO 270
<211> LENGTH: 47
<212> TYPE: DNA
<213> ORGANISM: Artificial Sequence
<220> FEATURE:
<223> OTHER INFORMATION: Primer

<400> SEQUENCE: 270
taatacgact cactataggg agataggacg atacgagtgt gtactcg                47

<210> SEQ ID NO 271
<211> LENGTH: 31
<212> TYPE: DNA
<213> ORGANISM: Artificial Sequence
<220> FEATURE:
<223> OTHER INFORMATION: Primer

<400> SEQUENCE: 271
ctgtcaaggt agactagcat gctcccatac g                                 31

<210> SEQ ID NO 272
<211> LENGTH: 24
<212> TYPE: DNA
<213> ORGANISM: Artificial Sequence
<220> FEATURE:
<223> OTHER INFORMATION: Primer

<400> SEQUENCE: 272
ctgtcaaggt agactagcat gctc                                         24

<210> SEQ ID NO 273
<211> LENGTH: 60
<212> TYPE: DNA
<213> ORGANISM: Artificial Sequence
<220> FEATURE:
<223> OTHER INFORMATION: Adaptor oligonucleotide

<400> SEQUENCE: 273
cctgactgct cgtcagttga ttaagtactc tgtgagatga tgatcagtag agcgagtcgt  60

<210> SEQ ID NO 274
<211> LENGTH: 50
<212> TYPE: DNA
<213> ORGANISM: Artificial Sequence
<220> FEATURE:
<223> OTHER INFORMATION: Primer

<400> SEQUENCE: 274
caccgagatc tacactcttt ccctacacga cgctcttccg atcttgacct              50

<210> SEQ ID NO 275
<211> LENGTH: 59
<212> TYPE: DNA
<213> ORGANISM: Artificial Sequence
<220> FEATURE:
<223> OTHER INFORMATION: Synthetic template
<220> FEATURE:
<221> NAME/KEY: misc_feature
<222> LOCATION: (22)..(39)
<223> OTHER INFORMATION: n is a, c, g, or t

<400> SEQUENCE: 275
atgatcagta gagcgagtcg tnnnnnnnnn nnnnnnnnnt gctacgactt ccgagtcca    59

<210> SEQ ID NO 276
<211> LENGTH: 27
<212> TYPE: DNA
<213> ORGANISM: Artificial Sequence
<220> FEATURE:
<223> OTHER INFORMATION: Primer

<400> SEQUENCE: 276
gctctactga tcattggact cggaagt                                       27

<210> SEQ ID NO 277
<211> LENGTH: 28
<212> TYPE: DNA
<213> ORGANISM: Artificial Sequence
<220> FEATURE:
<223> OTHER INFORMATION: Primer

<400> SEQUENCE: 277
tccgatcttg gactcggaag tcgtagca                                      28

<210> SEQ ID NO 278
<211> LENGTH: 39
<212> TYPE: DNA
<213> ORGANISM: Artificial Sequence
<220> FEATURE:
<223> OTHER INFORMATION: Primer

<400> SEQUENCE: 278
acactctttc cctacacgac gctcttccga tcttgacct                          39

<210> SEQ ID NO 279
<211> LENGTH: 59
<212> TYPE: DNA
<213> ORGANISM: Artificial Sequence
<220> FEATURE:
<223> OTHER INFORMATION: BRCA1 adaptor oligonucleotide

<400> SEQUENCE: 279
cctgactgct cgtcagttga ttaagtactc tgtgagatgc ttggcccctc ttcggtaac    59

<210> SEQ ID NO 280
<211> LENGTH: 60
<212> TYPE: DNA
<213> ORGANISM: Artificial Sequence
<220> FEATURE:
<223> OTHER INFORMATION: BRCA1 adaptor oligonucleotide

<400> SEQUENCE: 280
cctgactgct cgtcagttga ttaagtactc tgtgagatgc tgggagctca aaagatggct   60

<210> SEQ ID NO 281

<211> LENGTH: 58
<212> TYPE: DNA
<213> ORGANISM: Artificial Sequence
<220> FEATURE:
<223> OTHER INFORMATION: BRCA1 adaptor oligonucleotide

<400> SEQUENCE: 281
cctgactgct cgtcagttga ttaagtactc tgtgagatgc agctgggctc aaaggacc    58

<210> SEQ ID NO 282
<211> LENGTH: 60
<212> TYPE: DNA
<213> ORGANISM: Artificial Sequence
<220> FEATURE:
<223> OTHER INFORMATION: BRCA1 adaptor oligonucleotide

<400> SEQUENCE: 282
cctgactgct cgtcagttga ttaagtactc tgtgagatgc agacaaattc cccagcaggt    60

<210> SEQ ID NO 283
<211> LENGTH: 58
<212> TYPE: DNA
<213> ORGANISM: Artificial Sequence
<220> FEATURE:
<223> OTHER INFORMATION: BRCA1 adaptor oligonucleotide

<400> SEQUENCE: 283
cctgactgct cgtcagttga ttaagtactc tgtgagatgc atggtgtgaa cccgggag    58

<210> SEQ ID NO 284
<211> LENGTH: 60
<212> TYPE: DNA
<213> ORGANISM: Artificial Sequence
<220> FEATURE:
<223> OTHER INFORMATION: BRCA1 adaptor oligonucleotide

<400> SEQUENCE: 284
cctgactgct cgtcagttga ttaagtactc tgtgagatgc ccaaatccca agtcgtgtgt    60

<210> SEQ ID NO 285
<211> LENGTH: 60
<212> TYPE: DNA
<213> ORGANISM: Artificial Sequence
<220> FEATURE:
<223> OTHER INFORMATION: BRCA1 adaptor oligonucleotide

<400> SEQUENCE: 285
cctgactgct cgtcagttga ttaagtactc tgtgagatgc tcatccctgg ttccttgagg    60

<210> SEQ ID NO 286
<211> LENGTH: 60
<212> TYPE: DNA
<213> ORGANISM: Artificial Sequence
<220> FEATURE:
<223> OTHER INFORMATION: HLA-A adaptor oligonucleotide

<400> SEQUENCE: 286
cctgactgct cgtcagttga ttaagtactc tgtgaaaacg gcctctgtgg ggagaagcaa    60

<210> SEQ ID NO 287
<211> LENGTH: 59
<212> TYPE: DNA
<213> ORGANISM: Artificial Sequence
<220> FEATURE:
<223> OTHER INFORMATION: HLA-A adaptor oligonucleotide

<400> SEQUENCE: 287

```
cctgactgct cgtcagttga ttaagtactc tgtgagatgc actgggctga ccgtggggt    59
```

<210> SEQ ID NO 288
<211> LENGTH: 60
<212> TYPE: DNA
<213> ORGANISM: Artificial Sequence
<220> FEATURE:
<223> OTHER INFORMATION: HLA-A adaptor oligonucleotide

<400> SEQUENCE: 288

```
cctgactgct cgtcagttga ttaagtactc tgcctgaatg wtctgactct tcccgtmaga    60
```

<210> SEQ ID NO 289
<211> LENGTH: 60
<212> TYPE: DNA
<213> ORGANISM: Artificial Sequence
<220> FEATURE:
<223> OTHER INFORMATION: DQB1 adaptor oligonucleotide

<400> SEQUENCE: 289

```
cctgactgct cgtcagttga ttaagtactc tgggatcccc gcagaggatt tcgtgtacca    60
```

<210> SEQ ID NO 290
<211> LENGTH: 60
<212> TYPE: DNA
<213> ORGANISM: Artificial Sequence
<220> FEATURE:
<223> OTHER INFORMATION: DQB1 adaptor oligonucleotide

<400> SEQUENCE: 290

```
cctgactgct cgtcagttga ttaagtactc tgtgagatgg agcccacagt gaccatctcc    60
```

<210> SEQ ID NO 291
<211> LENGTH: 60
<212> TYPE: DNA
<213> ORGANISM: Artificial Sequence
<220> FEATURE:
<223> OTHER INFORMATION: BRCA1 reverse primer

<400> SEQUENCE: 291

```
cggtctcggc attcctgctg aaccgctctt ccgatctgtt ctgagacacc tgatgacctg    60
```

<210> SEQ ID NO 292
<211> LENGTH: 57
<212> TYPE: DNA
<213> ORGANISM: Artificial Sequence
<220> FEATURE:
<223> OTHER INFORMATION: BRCA1 reverse primer

<400> SEQUENCE: 292

```
cggtctcggc attcctgctg aaccgctctt ccgatcttga acccaggagt ttgaggc    57
```

<210> SEQ ID NO 293
<211> LENGTH: 60
<212> TYPE: DNA
<213> ORGANISM: Artificial Sequence
<220> FEATURE:
<223> OTHER INFORMATION: BRCA1 reverse primer

<400> SEQUENCE: 293

```
cggtctcggc attcctgctg aaccgctctt ccgatcttgg agctttatct gctctgtgat    60
```

<210> SEQ ID NO 294
<211> LENGTH: 57
<212> TYPE: DNA

```
<213> ORGANISM: Artificial Sequence
<220> FEATURE:
<223> OTHER INFORMATION: BRCA1 reverse primer

<400> SEQUENCE: 294
cggtctcggc attcctgctg aaccgctctt ccgatctttc actgtgatgg ccaggat       57

<210> SEQ ID NO 295
<211> LENGTH: 57
<212> TYPE: DNA
<213> ORGANISM: Artificial Sequence
<220> FEATURE:
<223> OTHER INFORMATION: BRCA1 reverse primer

<400> SEQUENCE: 295
cggtctcggc attcctgctg aaccgctctt ccgatcttga cccaagcaag cctaaag       57

<210> SEQ ID NO 296
<211> LENGTH: 57
<212> TYPE: DNA
<213> ORGANISM: Artificial Sequence
<220> FEATURE:
<223> OTHER INFORMATION: BRCA1 reverse primer

<400> SEQUENCE: 296
cggtctcggc attcctgctg aaccgctctt ccgatcttgc cacagtagat gctcagt       57

<210> SEQ ID NO 297
<211> LENGTH: 58
<212> TYPE: DNA
<213> ORGANISM: Artificial Sequence
<220> FEATURE:
<223> OTHER INFORMATION: BRCA1 reverse primer

<400> SEQUENCE: 297
cggtctcggc attcctgctg aaccgctctt ccgatctccc agcaaccatt tcatttca      58

<210> SEQ ID NO 298
<211> LENGTH: 60
<212> TYPE: DNA
<213> ORGANISM: Artificial Sequence
<220> FEATURE:
<223> OTHER INFORMATION: HLA-A reverse primer

<400> SEQUENCE: 298
cggtctcggc attcctgctg aaccgctctt ccgatcttgg atctcggacc cggagactgt    60

<210> SEQ ID NO 299
<211> LENGTH: 58
<212> TYPE: DNA
<213> ORGANISM: Artificial Sequence
<220> FEATURE:
<223> OTHER INFORMATION: HLA-A reverse primer

<400> SEQUENCE: 299
cggtctcggc attcctgctg aaccgctctt ccgatctccc tggtaccvgt gcgctgca      58

<210> SEQ ID NO 300
<211> LENGTH: 60
<212> TYPE: DNA
<213> ORGANISM: Artificial Sequence
<220> FEATURE:
<223> OTHER INFORMATION: HLA-A reverse primer

<400> SEQUENCE: 300
cggtctcggc attcctgctg aaccgctctt ccgatctgac cctgctaaag gtctccagag    60
```

```
<210> SEQ ID NO 301
<211> LENGTH: 57
<212> TYPE: DNA
<213> ORGANISM: Artificial Sequence
<220> FEATURE:
<223> OTHER INFORMATION: HLA-A reverse primer

<400> SEQUENCE: 301
cggtctcggc attcctgctg aaccgctctt ccgatctgac cctgctaaag gtcagag        57

<210> SEQ ID NO 302
<211> LENGTH: 60
<212> TYPE: DNA
<213> ORGANISM: Artificial Sequence
<220> FEATURE:
<223> OTHER INFORMATION: DQB1 reverse primer

<400> SEQUENCE: 302
cggtctcggc attcctgctg aaccgctctt ccgatctagg acgctcacct ctccgctgca        60

<210> SEQ ID NO 303
<211> LENGTH: 57
<212> TYPE: DNA
<213> ORGANISM: Artificial Sequence
<220> FEATURE:
<223> OTHER INFORMATION: DQB1 reverse primer

<400> SEQUENCE: 303
cggtctcggc attcctgctg aaccgctctt ccgatctctg gggtgctcca cgtggca        57
```